United States Patent
Hitchcock et al.

(10) Patent No.: US 9,487,526 B2
(45) Date of Patent: Nov. 8, 2016

(54) QUINOXALINE DERIVATIVES AS GPR6 MODULATORS

(71) Applicant: ENVOY THERAPEUTICS, INC., San Diego, CA (US)

(72) Inventors: Stephen Hitchcock, San Diego, CA (US); Holger Monenschein, San Diego, CA (US); Holly Reichard, San Diego, CA (US); Huikai Sun, San Diego, CA (US); Shota Kikuchi, San Diego, CA (US); Todd Macklin, San Diego, CA (US); Maria Hopkins, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/421,516

(22) PCT Filed: Aug. 13, 2013

(86) PCT No.: PCT/US2013/054715
§ 371 (c)(1),
(2) Date: Feb. 13, 2015

(87) PCT Pub. No.: WO2014/028479
PCT Pub. Date: Feb. 20, 2014

(65) Prior Publication Data
US 2015/0232469 A1 Aug. 20, 2015

Related U.S. Application Data

(60) Provisional application No. 61/682,704, filed on Aug. 13, 2012, provisional application No. 61/696,748, filed on Sep. 4, 2012.

(51) Int. Cl.
| | | |
|---|---|---|
| C07D 487/04 | (2006.01) | |
| C07D 241/44 | (2006.01) | |
| C07D 405/12 | (2006.01) | |
| C07D 471/04 | (2006.01) | |

(52) U.S. Cl.
CPC .......... *C07D 487/04* (2013.01); *C07D 241/44* (2013.01); *C07D 405/12* (2013.01); *C07D 471/04* (2013.01)

(58) Field of Classification Search
None
See application file for complete search history.

(56) References Cited

FOREIGN PATENT DOCUMENTS

| | | |
|---|---|---|
| WO | 2006/039718 A2 | 4/2006 |
| WO | 2007/023186 A1 | 3/2007 |
| WO | 2007/125405 A2 | 11/2007 |
| WO | 2008/127594 A2 | 10/2008 |
| WO | 2008/149163 A2 | 12/2008 |
| WO | 2009/021083 A1 | 2/2009 |
| WO | 2010/143170 A2 | 12/2010 |
| WO | 2011/150156 A2 | 12/2011 |
| WO | 2012/167423 A1 | 12/2012 |
| WO | 2012/167733 A1 | 12/2012 |
| WO | 2013/169964 A1 | 11/2013 |

OTHER PUBLICATIONS

U.S. Appl. No. 14/577,480, Hitchcock et al.
Sekhar, et al., Design, synthesis, and preliminary in vitro and in vivo pharmacological evaluation of 4-{4-[2-(4-(2-substitutedquinoxalin-3-yl)piperazin-1-yl)ethyl]phenyl}thiazoles as atypical antipsychotic agents, Med Chem Res (2013) 22:1660-1673.

*Primary Examiner* — Paul V Ward
(74) *Attorney, Agent, or Firm* — Matthew J. Russo; David M. Stemerick

(57) ABSTRACT

The present invention provides compounds of Formula (I):

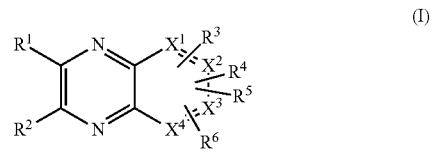

that are GPR6 modulators and are therefore useful for the treatment of diseases treatable by modulation of GPR6, in particular treating Parkinson disease, levodopa induced dyskinesias, Huntington's disease, other dyskinesias, akinesias, and motor disorders involving dysfunction of the striatum, schizophrenia and drug addiction. Also provided are pharmaceutical compositions containing such compounds and processes for preparing such compounds.

21 Claims, No Drawings

QUINOXALINE DERIVATIVES AS GPR6 MODULATORS

FIELD OF INVENTION

The present invention provides compounds that are G-protein-coupled receptor 6 (hereinafter referred to as GPR6) modulators and are therefore useful for the treatment of diseases treatable by modulation of GPR6, in particular treating Parkinson disease, levodopa induced dyskinesias, Huntington's disease, other dyskinesias, akinesias, and motor disorders involving dysfunction of the striatum, schizophrenia and drug addiction. Also provided are pharmaceutical compositions containing such compounds and processes for preparing such compounds.

BACKGROUND

Parkinson disease (PD) is a degenerative disorder of the central nervous system. The motor symptoms of Parkinson's disease result from the death of dopamine-generating cells in the substantia nigra, a region of the midbrain. Degeneration of the nigrostriatal pathway causes reduction in the striatal concentration of dopamine Dopamine is a neurotransmitter or chemical messenger in the body which affects brain processes controlling movement, balance, walking, emotional response, and ability to experience pleasure and pain. The major striatal targets of dopaminergic innervation reside in the medium spiny neurons (MSNs) of the striatopallidal (indirect) and striatonigral (direct) output pathways. The MSNs of the direct output pathway express D1 dopamine receptors whereas those in the indirect pathway express D2 receptors. Currently, there is no cure for Parkinson's disease, but drugs can relieve at least some of the symptoms. Modern treatments are effective at managing the early motor symptoms of the disease, mainly through the use of levodopa. About 75% of Parkinson's disease patients are treated with levodopa, a prodrug for dopamine discovered over 50 years ago (Dopamine Replacement Therapy).

Levodopa has common serious side effects including induced dyskinesia (LID), impulsive control disorders (ICD), psychotic symptoms and sleep disturbances. LID is progressive (90% of PD patients develop LID within 10 yrs). Accordingly there is a need for new treatments that are effective in treating PD. The present invention can fulfill this and related needs.

SUMMARY

Irreversible adaptations occur in D1 receptor signaling in MSNs in rodent models of LID including reduced desensitization leading of hypersensitivity in the direct pathway. Genetic inactivation of D1 but not D2 receptors abolishes LID in mice. However blockade of D1 receptor signaling does not affect the antiparkinsonian efficacy of L-DOPA. cAMP pathways modulated by D1/D2 dopamine receptors in MSN have been implicated in LID. Dopamine D2 receptors in MSN are Gi coupled, i.e., an agonist of D2 decreases the level of intracellular cAMP.

The GPR6 receptor exhibits high expression in the central nervous system (CNS) with minimal expression in peripheral tissues. GPR6 is highly selectively enriched in D2 receptor expressing MSNs in the striatum. The striatum plays a central role in modulating important behaviors including movement, reward, and motivational processes. GPR6 is GPCR that exhibits receptor signaling via the Gs pathway. Thus, GPR6 agonist activity results in an increase in intracellular cAMP levels whereas antagonists or inverse agonists cause a decrease in cAMP levels. GPR6 activity is therefore functionally opposed to D2 receptor signaling. Therefore, antagonism or inverse agonism of Gs coupled GPR6 should decrease cAMP in MSNs—a functional alternative to dopamine mediated activation of D2 receptors. As such, compounds that modulate the activity of GPR6 have utility in a variety of neurological and psychiatric disorders, for example movement disorders including Parkinson's disease, levodopa induced dyskinesias, and Huntington's disease either alone or in combination with other agents are approved for the treatment of Parkinson's disease including L-DOPA, dopaminergic agonists, MAO B inhibitors, DOPA decarboxylase inhibitors and COMT inhibitors. Other potential disease indications that could be treated by modulation of GPR6 include non-levodopa induced dyskinesias, akinesias, and motor disorders involving dysfunction of the striatum drug addiction and eating disorders, cognitive disorders, schizophrenia, bipolar disorders, and depression.

Accordingly, in a first aspect, provided is a compound of Formula (I):

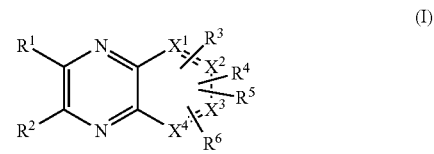

wherein:
  $R^1$ is a heterocycloamino ring substituted with $R^a$, $R^b$, and $R^c$ wherein:
    $R^a$ is —Z—Ar where Z is $C_{1-6}$ alkylene, $C_{1-6}$ haloalkylene, —O—, —C(O)—, —NH—, or —S(O)n- wherein n is 0, 1, or 2; and Ar is $C_{3-10}$ cycloalkyl, $C_{3-7}$ heterocycloalkyl, $C_{3-7}$ heterocycloalkenyl, $C_{6-10}$ aryl, or $C_{1-9}$ heteroaryl wherein $C_{3-10}$ cycloalkyl, $C_{3-7}$ heterocycloalkenyl, $C_{3-7}$ heterocycloalkyl, $C_{6-10}$ aryl, and $C_{1-9}$ heteroaryl are optionally substituted with 1 to 3 substituents independently selected from $C_{1-6}$ alkyl, halo, hydroxy, oxo, $C_{1-6}$ alkoxy, $C_{1-6}$ thioalkoxy, $C_{1-6}$ haloalkyl, $C_{1-6}$ hydroxyalkyl, $C_{1-6}$ haloalkoxy, $C_{1-6}$ alkylcarbonyl, $C_{1-6}$ alkylsulphonyl, cyano, $C_{2-12}$ alkoxyalkyloxy, $C_{1-9}$ amide, or $C_{1-6}$ hydroxyalkyloxy; and
    $R^b$ and $R^c$ are independently hydrogen, $C_{1-6}$ alkyl, hydroxy, or halo;
  $R^2$ is —$OR^e$ or —$NR^dR^e$ wherein $R^d$ is hydrogen or $C_{1-6}$ alkyl and $R^e$ is $C_{1-6}$ alkyl, $C_{1-6}$ haloalkyl, $C_{1-6}$ hydroxyalkyl, $C_{2-12}$ alkoxyalkyl, $C_{1-12}$ aminoalkyl, $C_{3-10}$ cycloalkyl, $C_{4-16}$ cycloalkylalkyl, $C_{6-10}$ aryl, $C_{1-9}$ heteroaryl, $C_{3-7}$ heterocyclyl, or $C_{3-7}$ heterocycloalkenyl wherein $C_{6-10}$ aryl, $C_{1-9}$ heteroaryl, $C_{3-7}$ heterocyclyl, and $C_{3-7}$ heterocycloalkenyl are optionally substituted with 1 to 3 substituents independently selected from $C_{1-6}$ alkyl, halo, hydroxy, oxo, $C_{1-6}$ alkoxy, $C_{1-6}$ haloalkyl or $C_{1-6}$ haloalkoxy, or cyano;
  all $X^1$-$X^4$ are carbon or one or two of $X^1$-$X^4$ are N and the rest of $X^1$-$X^4$ are carbon;
  $R^3$, $R^4$, $R^5$, and $R^6$ are independently absent, hydrogen, $C_{1-6}$ alkyl, halo, hydroxy, $C_{1-6}$ alkoxy, $C_{1-6}$ alkoxycarbonyl, $C_{1-6}$ haloalkyl, $C_{1-6}$ haloalkoxy, $C_{1-9}$ amide, $C_{3-7}$ heterocyclyl, $C_{1-8}$ alkylamino, or cyano;
  or a pharmaceutically acceptable salt thereof.

In a second aspect, provided is a pharmaceutical composition comprising a compound of Formula (I) (or embodiments thereof disclosed herein) or a pharmaceutically acceptable salt thereof and a pharmaceutically acceptable excipient.

In a third aspect, provided is a method of treating a disease treatable by administration of an antagonist and/or inverse agonist of GPR6 which method comprises administrating to the patient in need thereof a therapeutically effective amount of a compound of Formula (I) (or embodiments thereof disclosed herein) or a pharmaceutically acceptable salt thereof.

The method of third aspect wherein the disease is Parkinson disease, levodopa induced dyskinesia, non-levodopa induced dyskinesias, akinesias, motor disorders involving dysfunction of the striatum, drug addiction, eating disorders, cognitive disorders, schizophrenia, bipolar disorders, or depression. The method of third aspect wherein the compound of Formula (I) is administered in combination with an antipsychotic drug. The method of third aspect wherein the compound of Formula (I) is administered in combination with a dopamine agonist (e.g., Levodopa).

In a fourth aspect, provided is a compound of Formula (I) (or any embodiments thereof) or a pharmaceutically acceptable salt thereof for use as medicament. In one aspect of the fourth aspect, provided is the use of a compound of Formula (I) (or any embodiments thereof) or the pharmaceutical salts thereof for the treatment of a disease treatable by administration of an antagonist and/or inverse agonist of GPR6 such as Parkinson disease, levodopa induced dyskinesia, non-levodopa induced dyskinesias, akinesias, motor disorders involving dysfunction of the striatum, drug addiction, eating disorders, cognitive disorders, schizophrenia, bipolar disorders, or depression. Also, one aspect of the fourth aspect, provided is the use of a compound of Formula (I) (or any embodiments thereof) or the pharmaceutical salts thereof in combination with an antipsychotic drug. Also, one aspect of the fourth aspect, provided is the use of a compound of Formula (I) (or any embodiments thereof) or the pharmaceutical salts thereof in combination with a dopamine agonist (e.g., Levodopa).

DETAILED DESCRIPTION

Definitions

Unless otherwise stated, the following terms used in the specification and claims are defined for the purposes of this Application and have the following meaning:

"$C_{1-6}$ alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"$C_{1-4}$ alkyl" means a linear saturated monovalent hydrocarbon radical of one to four carbon atoms or a branched saturated monovalent hydrocarbon radical of three to four carbon atoms.

"$C_{1-8}$ alkylamino" means a —NR'R" where R' is hydrogen or $C_{1-4}$ alkyl and R" is $C_{1-4}$ alkyl.

"$C_{1-6}$ alkylene" means a linear saturated divalent hydrocarbon radical of one to six carbon atoms or a branched saturated divalent hydrocarbon radical of two to six carbon atoms unless otherwise stated e.g., methylene, ethylene, propylene, 1-methylpropylene, 2-methylpropylene, butylene, pentylene, and the like.

"$C_{1-6}$ alkylsulfonyl" means a —$SO_2R$ radical where R is $C_{1-6}$ alkyl as defined above, e.g., methylsulfonyl, ethylsulfonyl, and the like.

"$C_{1-9}$ amide" refers to a —C(O)NRR' group in which R is selected from the group consisting of hydrogen and $C_{1-4}$ alkyl, and R' is selected from the group consisting of hydrogen, $C_{1-4}$ alkyl, or R and R' together with the nitrogen to which they are attached form a 4 to 8 membered, saturated, ring optionally having an additional ring heteroatom selected from the group N, O, and S, in particular, an azetinyl, pyrrolidinyl, piperidinyl, piperazinyl, 4-methylpiperazin-1-yl, or morpholinlyl ring.

"$C_{1-12}$ aminoalkyl" means a linear monovalent hydrocarbon radical of one to six carbon atoms or a branched monovalent hydrocarbon radical of three to six carbons substituted with at least one, preferably one or two, —NRR' where R is hydrogen, $C_{1-6}$ alkyl, or —C(O)R" where R" is $C_{1-6}$ alkyl, each as defined above, and R' is selected from hydrogen, $C_{1-6}$ alkyl, $C_{1-6}$ hydroxyalkyl, or $C_{2-12}$ alkoxyalkyl, each as defined herein, e.g., aminomethyl, methylaminoethyl, 2-ethylamino-2-methylethyl, 1,3-diaminopropyl, dimethylaminomethyl, diethylaminoethyl, acetylaminopropyl, and the like.

"$C_{1-6}$ alkoxy" means a —OR radical where R is $C_{1-6}$ alkyl as defined above, e.g., methoxy, ethoxy, propoxy, or 2-propoxy, n-, iso-, or tert-butoxy, and the like.

"$C_{2-12}$ alkoxyalkyl" means $C_{1-6}$ alkyl radical as defined above that is substituted with one or two $C_{1-6}$ alkoxy group as defined above, e.g., methoxymethyl, ethoxymethyl, 2-methoxyethyl, and the like.

"$C_{2-12}$ alkoxyalkyloxy" means —OR radical where R is $C_{2-12}$ alkoxyalkyl as defined above, e.g., methoxymethyloxy, 2-methoxyethyloxy, ethoxymethyloxy, and the like.

"$C_{1-6}$ alkylcarbonyl" means a —C(O)R radical where R is $C_{1-6}$ alkyl as defined above, e.g., methylcarbonyl, ethylcarbonyl, and the like.

"$C_{1-6}$ alkoxycarbonyl" means a —C(O)OR radical where R is $C_{1-6}$ alkyl as defined above, e.g., methoxycarbonyl, ethoxycarbonyl, and the like.

"$C_{6-10}$ aryl" means a monovalent monocyclic or bicyclic aromatic hydrocarbon radical of 6 to 10 ring atoms e.g., phenyl or naphthyl.

"$C_{3-10}$ cycloalkyl" means a cyclic saturated monovalent hydrocarbon radical of three to ten carbon atoms, e.g., cyclopropyl, cyclobutyl, cyclopentyl, or cyclohexyl, and the like.

"$C_{4-16}$ cycloalkylalkyl" means -(alkylene)-R where R is $C_{3-10}$ cycloalkyl as defined above, e.g., cyclopropylmethyl, cyclobutylmethyl, cyclopentylmethyl, or cyclohexylmethyl, and the like.

"Carbonyl" means —C=(O) group.

"Halo" means fluoro, chloro, bromo, or iodo, preferably fluoro or chloro.

"$C_{1-6}$ haloalkyl" means $C_{1-6}$ alkyl radical as defined above, which is substituted with one or more halogen atoms, preferably one to five halogen atoms, preferably fluorine or chlorine, including those substituted with different halogens, e.g., —$CH_2Cl$, —$CF_3$, —$CHF_2$, —$CH_2CF_3$, —$CF_2CF_3$, and the like. When the $C_{1-6}$ alkyl is substituted with only fluoro, it is referred to in this Application as $C_{1-6}$ fluoroalkyl.

"$C_{1-6}$ haloalkylene" means $C_{1-6}$ alkylene as defined above wherein one to three hydrogen atoms have been replaced by halo, preferably fluoro. e.g., fluoromethylene, difluoromethylene, 1, 2, or 3-fluoroethylene, —CH($CHF_2$)—, —CH($CF_3$)—, and the like.

"$C_{1-6}$ haloalkoxy" means a —OR radical where R is $C_{1-6}$ haloalkyl as defined above e.g., —OCF$_3$, —OCHF$_2$, and the like. When R is $C_{1-6}$ haloalkyl where the $C_{1-6}$ alkyl is substituted with only fluoro, it is referred to in this Application as fluoroalkoxy.

"$C_{1-6}$ hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"$C_{1-6}$ hydroxyalkoxy" or "$C_{1-6}$ hydroxyalkyloxy" means a —OR radical where R is hydroxyalkyl as defined above.

"$C_{3-7}$ heterocycloalkyl" or "$C_{3-7}$ heterocyclyl" means a saturated monovalent monocyclic group of 4 to 8 ring atoms in which one or two ring atoms are heteroatom selected from N, O, or S(O)n, where n is an integer from 0 to 2, the remaining ring atoms being C, unless stated otherwise. More specifically the term $C_{3-7}$ heterocyclyl includes, but is not limited to, pyrrolidinyl, piperidinyl, homopiperidinyl, morpholinyl, piperazinyl, tetrahydropyranyl, thiomorpholinyl, and the like.

The term "heterocyclamino" means a saturated monocyclic group of 4 to 8 ring atoms in which one or two ring atoms are heteroatom selected from N, O, or S(O)n where n is an integer from 0 to 2, provided that at least one ring member is N. More specifically the term heterocycloamino includes, but is not limited to, azetidinyl, pyrrolidinyl, piperidinyl, homopiperidinyl, morpholinyl, thiomorpholinyl, piperazinyl, homopiperazinyl, and the like.

"$C_{3-7}$ heterocycloalkenyl" or "$C_{3-7}$ heterocyclylalkenyl" means a nonaromatic, unsaturated monovalent monocyclic group of 4 to 8 ring atoms in which one or two ring atoms are heteroatom selected from N, O, or S(O)n, where n is an integer from 0 to 2, the remaining ring atoms being C. Additionally, one or two ring carbon atoms in the heterocyclalkenyl ring can optionally be replaced by a —C(O)— group. More specifically the term heterocycloalkenyl includes, but is not limited to, dihydropiperidinyl, and the like.

"$C_{1-9}$ heteroaryl" means a monovalent monocyclic or bicyclic fully unsaturated radical of 5 to 10 ring atoms where one or more, preferably one, two, or three, ring atoms are heteroatom selected from N, O, or S, the remaining ring atoms being carbon, unless stated otherwise. Representative examples include, but are not limited to, furyl, thienyl, pyrrolyl, imidazolyl, isothiazolyl, isoxazolyl, oxadiazolyl, oxazolyl, thiazolyl, thiadiazolyl, triazolyl, tetrazolyl, pyrazinyl, pyrazolyl, pyridazinyl, pyridyl, pyrimidyl, azepinyl, diazepinyl, benzazepinyl, benzodiazepinyl, benzofuryl, benzothienyl, indolyl, isoindolyl, benzimidazolyl, benzisothiazolyl, benzisoxazolyl, benzoxadiazolyl, benzoxazolyl, benzopyrazinyl, benzopyrazolyl, imidazopyridyl, pyrazolopyridyl, pyrrolopyridyl, quinazolyl, thienopyridyl, imidazopyridyl, quinolyl, isoquinolyl benzothiazolyl, and the like.

"$C_{1-6}$ thioalkoxy" means a —SR radical where R is $C_{1-6}$ alkyl as defined above, e.g., thiomethoxy, thioethoxy, and the like.

"GPR6 modulators" as used herein means that the compounds of the invention are antagonists i.e., block the action of a GPR6 agonist by competitive binding to the GPR6 receptor or are inverse agonists of GPR6 i.e., bind to the GPR6 receptor and induces a pharmacological response opposite to its agonist thereby reducing its baseline intracellular activity. A GPR6 modulator may possess both antagonist and inverse agonist activity within the same compound.

The present invention also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to, esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this invention.

The present invention also includes protected derivatives of compounds of Formula (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. (1999), the disclosure of which is incorporated herein by reference in its entirety. The protected derivatives of compounds of Formula (I) can be prepared by methods well known in the art.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, meso, racemic forms are within the scope of this invention, unless the specific stereochemistry or isomeric form is specifically indicated.

Additionally, as used herein the term $C_{1-6}$ alkyl and terms derived therefrom includes all the possible isomeric forms of said $C_{1-6}$ alkyl group. Furthermore, the cyclic groups such as $C_{6-10}$ aryl, $C_{1-9}$ heteroaryl, $C_{3-6}$ heterocycloalkyl include all the positional isomers. Furthermore, all polymorphic forms and hydrates of a compound of Formula (I) are within the scope of this invention.

The terms "compound" and "a compound of the invention" and "compound of the present invention" and the like, and their plural expressions include the embodiment of Formula (I) and the other more particular embodiments encompassed by Formula (I) described herein and exemplified compounds described herein and a pharmaceutically acceptable salt of each of these embodiments. All references to compounds, include all isotopes of the atoms contained therein, including isotopically-labeled compounds.

The compounds of the present invention may exist as tautomers. All tautomeric forms the compounds of the invention are contemplated to be within the scope of the present invention.

"Optional" or "optionally" means that the subsequently described event or circumstance may but need not occur, and that the description includes instances where the event or circumstance occurs and instances in which it does not. For example, "$C_{3-6}$ heterocycloalkyl group optionally substituted with an $C_{1-6}$ alkyl group" means that the alkyl may but need not be present, and the description includes situations where the heterocycloalkyl group is substituted with an alkyl group and situations where the heterocycloalkyl group is not substituted with alkyl.

The terms "pharmaceutically acceptable carrier" or "pharmaceutically acceptable excipient" mean a carrier or an excipient that is useful in preparing a pharmaceutical composition that is generally safe, non-toxic in the amounts used, and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient. Pharmaceutically acceptable excipients are well known in the art, such as those in Remington's Pharmaceutical Sciences, 17th ed., Mack Publishing Company, Easton, Pa., 1985.

The terms "condition," "disorder," and "disease" relate to any unhealthy or abnormal state.

"Treat," "treating," or "treatment" of a disease includes:
(1) preventing the disease, i.e. causing the clinical symptoms of the disease not to develop in a mammal that may be exposed to or predisposed to the disease but does not yet experience or display symptoms of the disease;
(2) inhibiting the disease, i.e., arresting, controlling, slowing, stopping, or reducing the development of the disease or its clinical symptoms; or
(3) relieving the disease, i.e., causing regression of the disease or its clinical symptoms or improvement of the disease or its clinical symptoms The terms "treat," "treating," and "treatment," do not necessarily indicate a total elimination of any or all symptoms or a cure of the disease.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated. A "therapeutically effective amount" means the amount of a compound of Formula (I) or a pharmaceutically acceptable salt thereof that, when administered in single or multiple doses, to a mammal for treating a disease, is sufficient to effect such treatment for the disease. The "therapeutically effective amount" will vary depending on the compound, the disease and its severity and the age, weight, etc., of the mammal to be treated, the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances.

The term "disease treatable by administration of an antagonist and/or inverse agonist of GPR6" includes Parkinson Disease, levodopa induced dyskinesia, non-levodopa induced dyskinesias, akinesias, motor disorders involving dysfunction of the striatum, drug addiction, eating disorders, cognitive disorders, schizophrenia, bipolar disorders, or depression.

Representative compounds of Formula (I) having the structure where $R^b$ and $R^c$ are hydrogen and $R^*$ represents $R^3$, $R^4$, $R^5$, and $R^6$ and when other than hydrogen are identified at the positions indicated in Table 1 below are:

Compound Table 1

| Cpd | X | Z | Ar | $R^e$ | $R^*$ | Salt | MSCalc | MSObs |
|---|---|---|---|---|---|---|---|---|
| 1 | N | $CH_2$ | 3-methylphenyl | cyclopropyl | | TFA | 373.494 | 374.3 |
| 4 | N | C(O) | 3-$CF_3$phenyl | cyclopropyl | | TFA | 441.4489 | 442.3 |
| 5 | N | $CH_2$ | 3-chlorophenyl | cyclopropyl | | TFA | 393.9124 | 394.2 |
| 6 | N | C(O) | 4-methylsulfonylphenyl | cyclopropyl | | TFA | 451.5413 | 452.2 |

-continued

Compound Table 1

| Cpd | X | Z | Ar | R$^e$ | R* | Salt | MSCalc | MSObs |
|---|---|---|---|---|---|---|---|---|
| 7 | N | C(O) | 2,5-dichlorophenyl | cyclopropyl | | TFA | 442.341 | 442.2 |
| 8 | N | C(O) | 3,4-dichlorophenyl | cyclopropyl | | TFA | 442.341 | 442.2 |
| 9 | N | C(O) | 3-chloro-4-methoxyphenyl | cyclopropyl | | TFA | 437.922 | 438.2 |
| 10 | N | C(O) | 3,5-dichlorophenyl | cyclopropyl | | TFA | 442.341 | 442.2 |
| 11 | N | C(O) | 3-chlorophenyl | cyclopropyl | | TFA | 407.896 | 408.2 |
| 12 | N | C(O) | 4-chlorophenyl | cyclopropyl | | TFA | 407.896 | 408.2 |
| 13 | N | CH$_2$ | pyridin-3-yl | cyclopropyl | | TFA | 360.4555 | 361.3 |
| 14 | N | C(O) | 2,3-dichlorophenyl | cyclopropyl | | TFA | 442.341 | 442.2 |
| 15 | N | C(O) | 2-chlorophenyl | cyclopropyl | | TFA | 407.896 | 408.2 |
| 16 | N | C(O) | 3-methylphenyl | cyclopropyl | | TFA | 387.4775 | 388.3 |
| 17 | N | CH$_2$ | pyridin-4-yl | cyclopropyl | | TFA | 360.4555 | 361.2 |
| 18 | N | CH$_2$ | 3-CF$_3$phenyl | cyclopropyl | | TFA | 427.4654 | 428.3 |
| 19 | N | CH$_2$ | 4-chlorophenyl | cyclopropyl | | TFA | 393.9124 | 394.2 |
| 20 | N | CH$_2$ | pyridin-2-yl | cyclopropyl | | TFA | 360.4555 | 361.2 |
| 21 | N | CH$_2$ | 3-chlorophenyl | 4-bromophenyl | | TFA | 508.8406 | 509.2 |
| 24 | N | CH$_2$ | 3-chlorophenyl | phenyl | | TFA | 429.9445 | 430.2 |
| 25 | N | CH$_2$ | 3-chlorophenyl | 4-trifluoromethoxyphenyl | | TFA | 513.942 | 514.3 |
| 26 | N | CH$_2$ | 3-chlorophenyl | 4-n-propylphenyl | | TFA | 472.0243 | 472.3 |
| 27 | N | C(O) | 4-CF$_3$phenyl | cyclopropyl | | TFA | 441.4489 | 442.3 |
| 28 | N | CH$_2$ | 2-chlorophenyl | cyclopropyl | | TFA | 393.9124 | 394.3 |
| 29 | N | CH$_2$ | 4-methylsulfonylphenyl | cyclopropyl | | TFA | 437.5578 | 438.3 |
| 30 | N | CH$_2$ | 3-chlorophenyl | 4-methyl-phenyl | | TFA | 443.9711 | 444.25 |
| 31 | N | CH$_2$ | 3-chlorophenyl | 4-methoxy-phenyl | | TFA | 459.9706 | 560.3 |
| 32 | N | CH$_2$ | 3-chlorophenyl | 2-methoxy-phenyl | | TFA | 459.9706 | 460.3 |
| 33 | N | CH$_2$ | 2,5-dichlorophenyl | cyclopropyl | | TFA | 428.3575 | 428.2 |
| 34 | N | CH$_2$ | 4-CF$_3$phenyl | cyclopropyl | | TFA | 427.4654 | 428.3 |
| 35 | N | CH$_2$ | 3-chlorophenyl | 3-methoxy-phenyl | | TFA | 459.9706 | 460.3 |
| 36 | N | CH$_2$ | 3-chlorophenyl | 4-tert-butyl-phenyl | | TFA | 486.0509 | 486.3 |
| 37 | N | CH$_2$ | 3-chlorophenyl | 4-isopropoxy-phenyl | | TFA | 488.0237 | 488.3 |
| 38 | N | CH$_2$ | 3-chlorophenyl | 4-fluorophenyl | | TFA | 447.935 | 448.3 |
| 39 | N | C(O) | 2,5-dichlorophenyl | cyclopentyl | | TFA | 470.3942 | 470.3 |
| 40 | N | CH$_2$ | 2,5-dichlorophenyl | cyclopentyl | | TFA | 456.4107 | 456.2 |
| 41 | N | C(O) | 2,5-dichlorophenyl | phenyl | | TFA | 478.3731 | 478.2 |
| 42 | N | CH$_2$ | 2,5-dichlorophenyl | cyclopropyl-methyl | | TFA | 442.3841 | 442.2 |
| 43 | N | CH$_2$ | 2,5-dichlorophenyl | phenyl | | TFA | 464.3896 | 464.2 |
| 45 | N | CH$_2$ | 2,5-dichlorophenyl | cyclopropyl | 7-Br | TFA | 507.2536 | 508.15 |
| 46 | N | CH$_2$ | 2,5-dichlorophenyl | cyclopropyl | 6-Br | TFA | 507.2536 | 508.1 |
| 47 | N | CH$_2$ | 2,5-dichlorophenyl | cyclopropyl | 7-OCH$_3$ | TFA | 458.3835 | 458.2 |
| 48 | N | CH$_2$ | 2,3-dichlorophenyl | cyclopropyl | | TFA | 428.3575 | 428.2 |
| 49 | N | CH$_2$ | 2,4-dichlorophenyl | cyclopropyl | | TFA | 428.3575 | 428.2 |
| 50 | N | CH$_2$ | 2,6-dichlorophenyl | cyclopropyl | | TFA | 428.3575 | 428.2 |
| 51 | N | CH$_2$ | 3-chlorophenyl | 3-bromophenyl | | TFA | 508.8406 | 509.9 |
| 52 | N | CH$_2$ | 3-chlorophenyl | 2-bromophenyl | | TFA | 508.8406 | 510 |
| 53 | N | CH$_2$ | 3-chlorophenyl | pyridin-3-yl | | TFA | 430.9326 | 431 |
| 54 | N | C(O) | 2,5-dichlorothien-3-yl | cyclopropyl | | | 448.3688 | 448.2 |
| 55 | N | CH$_2$ | 2,5-dichlorophenyl | cyclopropyl | 7-F | | 446.348 | 446.2 |
| 56 | N | CH$_2$ | 2,5-dichlorophenyl | 3-methoxy-phenyl | | | 494.4156 | 494.2 |
| 57 | N | CH$_2$ | 2,5-dichlorophenyl | 4-methoxy-phenyl | | | 494.4156 | 494.2 |
| 58 | N | CH$_2$ | 2,5-dichlorophenyl | 4-cyanophenyl | | | 489.3991 | 489.2 |
| 59 | N | CH$_2$ | 2,5-dichlorophenyl | cyclopropyl | 6-CN | | 453.367 | 453.2 |
| 60 | N | CH$_2$ | 2,5-dichlorophenyl | 2-methoxy-phenyl | | | 494.4156 | 494.2 |
| 61 | N | CH$_2$ | 2,5-dichlorophenyl | 4-fluorophenyl | | | 482.3801 | 482.2 |
| 62 | N | C(CCH$_3$) | 2,5-dichlorophenyl | cyclopropyl | | TFA | 442.3841 | 443.2 |

Compound Table 1

| Cpd | X | Z | Ar | R$^e$ | R* | Salt | MSCalc | MSObs |
|---|---|---|---|---|---|---|---|---|
| 64 | N | CH$_2$ | 2,5-dichlorophenyl | 4-bromophenyl | | | 543.2857 | 544.15 |
| 65 | N | CH$_2$ | 3-bromophenyl | cyclopropyl | | | 438.3635 | 438.2/440.2 |
| 66 | N | CH$_2$ | 2,5-dichlorophenyl | 3-methoxypropyl | | | 460.3994 | 461.2 |
| 67 | N | CO(O) | 2-chloro-4-methylsulfonylphenyl | cyclopropyl | | | 485.9864 | 486.2 |
| 68 | N | C(O) | 3,6-dichloropyridin-2-yl | cyclopropyl | | | 443.3291 | 443.2 |
| 69 | N | C(O) | benzofuran-3-yl | cyclopropyl | | TFA | 413.4717 | 414.30 |
| 70 | N | CH$_2$ | 3-chlorophenyl | pyridin-4-yl | | TFA | 430.9326 | 431.1 |
| 71 | N | CH$_2$ | 3-chlorophenyl | thia[1,3,4]diazol-2-yl | | TFA | 437.9484 | 438 |
| 72 | N | C(O) | 3,4-dimethylphenyl | cyclopropyl | | TFA | 401.5041 | 402.1 |
| 73 | N | CH$_2$ | 3,4-dimethylphenyl | cyclopropyl | | TFA | 387.5206 | 388.1 |
| 74 | N | C(O) | 2,4-dichlorophenyl | cyclopropyl | | TFA | 442.341 | 442 |
| 75 | N | C(O) | 4-cyanophenyl | cyclopropyl | | TFA | 398.4604 | 399.1 |
| 76 | N | CH$_2$ | 4-cyanophenyl | cyclopropyl | | TFA | 384.4769 | 384.9 |
| 77 | N | C(O) | 4-ethylphenyl | cyclopropyl | | TFA | 401.5041 | 402.1 |
| 78 | N | CH$_2$ | 4-ethylphenyl | cyclopropyl | | TFA | 387.5206 | 388.1 |
| 79 | N | CH$_2$ | 3,4-dichlorophenyl | cyclopropyl | | TFA | 428.3575 | 427.9 |
| 80 | N | C(O) | 2,5-difluorophenyl | cyclopropyl | | TFA | 409.4319 | 410 |
| 81 | N | CH$_2$ | 2,5-difluorophenyl | cyclopropyl | | TFA | 395.4483 | 396 |
| 82 | N | C(O) | naphth-2-yl | cyclopropyl | | TFA | 423.5096 | 424.1 |
| 83 | N | CH$_2$ | naphth-2-yl | cyclopropyl | | TFA | 409.5261 | 410 |
| 84 | N | C(O) | 4-tert-butylphenyl | cyclopropyl | | TFA | 429.5573 | 430.3 |
| 85 | N | C(O) | 2-bromo-5-methoxyphenyl | cyclopropyl | | TFA | 482.373 | 482 |
| 86 | N | C(O) | 3-bromo-4-methoxyphenyl | cyclopropyl | | TFA | 482.373 | 482 |
| 87 | N | C(O) | 4-bromo-2-chlorophenyl | cyclopropyl | | TFA | 486.7921 | 488 |
| 88 | N | C(O) | 5-fluoro-2-methylphenyl | cyclopropyl | | TFA | 405.468 | 406 |
| 89 | N | C(O) | 3-bromo-4-fluorophenyl | cyclopropyl | | TFA | 470.3374 | 472 |
| 90 | N | C(O) | 4-bromo-2-fluorophenyl | cyclopropyl | | TFA | 470.3374 | 470 |
| 91 | N | C(O) | 5-bromo-2-fluorophenyl | cyclopropyl | | TFA | 470.3374 | 470 |
| 92 | N | C(O) | 4-ethoxyphenyl | cyclopropyl | | TFA | 417.5035 | 418.1 |
| 93 | N | C(O) | 3-isopropylphenyl | cyclopropyl | | TFA | 415.5307 | 416.1 |
| 94 | N | CH$_2$ | 4-bromophenyl | cyclopropyl | | TFA | 438.3635 | 439.7 |
| 95 | N | CH$_2$ | 3-cyanophenyl | cyclopropyl | | TFA | 384.4769 | 385 |
| 96 | N | CH$_2$ | 4-fluorophenyl | cyclopropyl | | TFA | 377.4579 | 378 |
| 97 | N | CH$_2$ | 4-isopropylphenyl | cyclopropyl | | TFA | 401.5471 | 402.1 |
| 98 | N | C(O) | 5-methylisoxazol-3-yl | cyclopropyl | | | 378.4277 | 379.3 |
| 99 | N | CH$_2$ | 2,5-dichlorothien-3-yl | cyclopropyl | | TFA | 434.3853 | 434.1 |
| 100 | N | CH$_2$ | benzofuran-3-yl | cyclopropyl | | | 399.4882 | 400.30 |
| 101 | N | CH$_2$ | 3,6-dichloropyridin-yl | cyclopropyl | | TFA | 429.3456 | 429.3 |
| 102 | N | C(O) | cyclohexyl | cyclopropyl | | | 379.4986 | 380.3 |
| 103 | N | CH$_2$ | 2,5-dichlorophenyl | cyclopropyl | 5-CH$_3$ 7-CH$_3$ | | 456.4107 | 456.25 |
| 104 | N | CH$_2$ | 2,5-dichlorophenyl | cyclopropyl | 6-CH$_3$ 8-CH$_3$ | | 456.4107 | 456.2 |
| 105 | N | SO$_2$ | phenyl | cyclopropyl | | | 409.5046 | 410.3 |
| 106 | N | (CH$_2$)$_2$ | phenyl | cyclopropyl | | | 373.494 | 374.30 |
| 107 | N | (CH$_2$)$_2$ | 4-chlorophenyl | cyclopropyl | | | 407.939 | 408.30 |
| 108 | N | (CH$_2$)$_2$ | 4-methoxyphenyl | cyclopropyl | | | 403.52 | 404.35 |
| 109 | N | CH$_2$ | cyclohexyl | cyclopropyl | | | 365.515 | 366.4 |
| 110 | N | CH$_2$ | 2,5-dichlorophenyl | isobutyl | | TFA | 444.4 | 444 |
| 111 | N | CH$_2$ | 2,5-dichlorophenyl | isopropyl | | TFA | 430.3734 | 430.1 |
| 112 | N | CH$_2$ | 2,5-dichlorophenyl | 2-ethylbutyl | | TFA | 472.4531 | 472.1 |
| 113 | N | CH$_2$ | 2,5-dichlorophenyl | 4-methylpentan-2-yl | | TFA | 472.4531 | 472.2 |
| 114 | N | CH$_2$ | 2,5-dichlorophenyl | 2,2-dimethylpropyl | | TFA | 458.4266 | 458.2 |
| 115 | N | CH$_2$ | 2,5-dichlorophenyl | 3-methylbutyl | | TFA | 458.4266 | 458.1 |
| 116 | N | CH$_2$ | 2,5-dichlorophenyl | but-2-yl | | TFA | 444.4 | 444.1 |
| 117 | N | CH$_2$ | 2,5-dichlorophenyl | n-propyl | | TFA | 430.3734 | 430 |

-continued

Compound Table 1

| Cpd | X | Z | Ar | R$^e$ | R* | Salt | MSCalc | MSObs |
|---|---|---|---|---|---|---|---|---|
| 118 | N | CH$_2$ | 2,5-dichlorophenyl | 2-methoxyethyl | | TFA | 446.3728 | 446 |
| 119 | N | CH$_2$ | 2,5-dichlorophenyl | cyclobutyl | | TFA | 442.3841 | 441.9 |
| 120 | N | CH$_2$ | 2,5-dichlorophenyl | cyclopropyl | 5-Br | | 507.2536 | 508.1 |
| 121 | N | C(O) | 4-isopropylphenyl | cyclopropyl | | TFA | 415.5307 | 416.1 |
| 122 | N | C(O) | 4-bromo-2-methylphenyl | cyclopropyl | | TFA | 466.3736 | 468 |
| 123 | N | C(O) | 2-chloro-3,6-difluorophenyl | cyclopropyl | | TFA | 443.8769 | 444 |
| 124 | N | SO$_2$ | 4-OCF$_3$phenyl | cyclopropyl | | | 493.502 | 494.2 |
| 125 | N | CH$_2$ | 3-chlorophenyl | thiazol-2-yl | | TFA | 436.9603 | 437 |
| 126 | N | CH$_2$ | 3-chlorophenyl | pyrimidin-2-yl | | TFA | 431.9207 | 432 |
| 127 | N | CH$_2$ | 3-chlorophenyl | primidin-5-yl | | TFA | 431.9207 | 432 |
| 128 | N | SO$_2$ | cyclopentyl | cyclopropyl | | | 401.5257 | 402.3 |
| 129 | N | CH$_2$ | 5-fluoro-2-methylphenyl | cyclopropyl | | TFA | 391.4844 | 391.9 |
| 130 | N | C(O) | 2-chloro-5-iodophenyl | cyclopropyl | | TFA | 533.7925 | 533.94 |
| 131 | N | C(O) | 5-bromo-2-methylphenyl | cyclopropyl | | TFA | 466.3736 | 468.2 |
| 132 | N | C(O) | 4-OCF$_3$phenyl | cyclopropyl | | TFA | 457.4483 | 458.04 |
| 134 | N | CH$_2$ | 2,5-dichlorophenyl | cyclopropyl | 8-Br | TFA | 507.2536 | 508.1 |
| 135 | N | C(O) | indol-6-yl | cyclopropyl | | TFA | 412.487 | 413 |
| 136 | N | C(O) | 5-chloro-2-methylphenyl | cyclopropyl | | TFA | 421.9225 | 422.03 |
| 137 | N | C(O) | 4-chloro-2-methylphenyl | cyclopropyl | | TFA | 421.9225 | 422.04 |
| 138 | N | C(O) | 2,4-dimethylphenyl | cyclopropyl | | TFA | 401.5041 | 402.04 |
| 139 | N | C(O) | 2-chloro-5-methoxyphenyl | cyclopropyl | | TFA | 437.922 | 438 |
| 140 | N | C(O) | 3-cyano-4-isopropoxyphenyl | cyclopropyl | | TFA | 456.5395 | 457.07 |
| 141 | N | C(O) | 2-methoxy-5-trifluoromethoxy-phenyl | cyclopropyl | | TFA | 487.4743 | 488.04 |
| 142 | N | C(O) | 2,3,5-trichlorophenyl | cyclopropyl | | TFA | 476.7861 | 476.01 |
| 143 | N | C(O) | 2-chloro-6-trifluoromethylphenyl | cyclopropyl | | TFA | 475.894 | 476 |
| 144 | N | (CH$_2$)$_2$ | 2,5-dichlorophenyl | cyclopropyl | | | 442.3841 | 443.25 |
| 145 | N | CH$_2$ | 2,5-dichlorophenyl | pyridin-3-yl | | | 465.3777 | 466.25 |
| 146 | N | C(O) | 4-chloromethylphenyl | cyclopropyl | | TFA | 421.9225 | 422 |
| 147 | N | C(O) | indol-5-yl | cyclopropyl | | TFA | 412.487 | 413.1 |
| 148 | N | C(O) | 4-bromo-3-methylphenyl | cyclopropyl | | TFA | 466.3736 | 468 |
| 149 | N | CH$_2$ | 2-chloro-4-methylsulfonylphenyl | cyclopropyl | | TFA | 472.0028 | 472.2 |
| 151 | N | CH$_2$ | 2,5-dichlorophenyl | cyclopropyl | 7-CN | TFA | 453.367 | 453.2 |
| 152 | N | C(O) | 4-fluoro-3-methoxyphenyl | cyclopropyl | | TFA | 421.4674 | 422.1 |
| 153 | N | C(O) | 3-bromo-4-methylphenyl | cyclopropyl | | TFA | 466.3736 | |
| 154 | N | C(O) | 4-chloro-3-methylphenyl | cyclopropyl | | TFA | 421.9225 | 422 |
| 155 | N | C(O) | 4-fluoro-2-methylphenyl | cyclopropyl | | | 405.468 | 406 |
| 156 | N | CH$_2$ | 4-fluoro-2-methylphenyl | cyclopropyl | | TFA | 391.4844 | 392 |
| 157 | N | CH$_2$ | 5-methylisoxazol-3-yl | cyclopropyl | | TFA | 364.4442 | 365.3 |
| 158 | N | CH$_2$ | 2,5-dichlorophenyl | pyridin-3-yl | 7-CN | | 490.3871 | 490.2 |
| 159 | N | C(O) | 4-chlorophenyl | cyclopropyl | 6-CN | | 432.9054 | 433.25 |
| 160 | N | C(O) | 4-chlorophenyl | cyclopropyl | 6-F | | 425.8864 | 426.20 |
| 161 | N | SO$_2$ | phenyl | cyclopropyl | 6-CN | | 434.5141 | 435.30 |
| 162 | N | SO$_2$ | phenyl | pyridin-3-yl | H | | 446.5248 | 447.30 |
| 163 | N | CH$_2$ | 3-chlorophenyl | cyclopropyl | 6-CN | | 418.9219 | 419.25 |
| 164 | N | CH$_2$ | 2,5-dichlorophenyl | tert-butyl | | TFA | 444.4 | 444 |
| 165 | N | CH$_2$ | 2,5-dichlorophenyl | 3,3-dimethylbutyl | | TFA | 472.4531 | 472.1 |
| 166 | N | CH$_2$ | 2,5-dichlorophenyl | 2-ethoxyethyl | | TFA | 460.3994 | 460 |
| 167 | N | CH$_2$ | 2,5-dichlorophenyl | 2-isopropoxyethyl | | TFA | 474.426 | 474.1 |

-continued

Compound Table 1

| Cpd | X | Z | Ar | R^e | R* | Salt | MSCalc | MSObs |
|---|---|---|---|---|---|---|---|---|
| 168 | N | CH$_2$ | 2,5-dichlorophenyl | 3-ethoxypropyl | | TFA | 474.426 | 474.1 |
| 169 | N | CH$_2$ | 2,5-dichlorophenyl | cyclohexyl | | TFA | 470.4373 | 470.1 |
| 170 | N | CH$_2$ | 2,5-dichlorophenyl | tetrahydropyran-4-yl | | TFA | 472.4101 | 472 |
| 171 | N | CH$_2$ | 2,5-dichlorophenyl | (R)-3-hydroxyprop-2-yl | | TFA | 446.3728 | 446 |
| 172 | N | CH$_2$ | 2,5-dichlorophenyl | pyrazin-2-yl | | TFA | 466.3658 | 466 |
| 173 | N | CH$_2$ | 2,5-dichlorophenyl | pyrimidin-4-yl | | TFA | 466.3658 | 466 |
| 174 | N | CH$_2$ | 2,5-dichlorophenyl | pyridazin-3-yl | | TFA | 466.3658 | 466 |
| 175 | N | CH$_2$ | 2,5-dichlorophenyl | pyridin-3-yl | 6-F | TFA | 483.3681 | 483.25 |
| 176 | N | CH$_2$ | 2,5-dichlorophenyl | 1,2,4-triazin-3-yl | | TFA | 467.3538 | 467.1 |
| 177 | N | CH$_2$ | 2,5-dichlorophenyl | 5,6-dimethyl-1,2,4-triazin-3-yl | | TFA | 495.407 | 495.3 |
| 178 | N | CH$_2$ | 2,5-dichlorophenyl | 3,4-dimethylisoxazol-5-yl | | TFA | 483.393 | 483 |
| 179 | N | C(O) | 3-bromo-2-methylphenyl | cyclopropyl | | TFA | 466.3736 | 468.1 |
| 180 | N | C(O) | 3,5-difluorophenyl | cyclopropyl | | TFA | 409.4319 | 410.1 |
| 181 | N | C(O) | 4-bromophenyl | cyclopropyl | | TFA | 452.347 | 454 |
| 182 | N | C(O) | 3-cyanophenyl | cyclopropyl | | TFA | 398.4604 | 399.1 |
| 183 | N | C(O) | 3-bromophenyl | cyclopropyl | | TFA | 452.347 | 453.6 |
| 184 | N | C(O) | 2,6-dichlorophenyl | cyclopropyl | | TFA | 442.341 | 441.8 |
| 185 | N | C(O) | 2-bromo-4-methyl-phenyl | cyclopropyl | | TFA | 466.3736 | 468 |
| 186 | N | C(O) | 4-cyano-2-fluoro-phenyl | cyclopropyl | | TFA | 416.4508 | 417.1 |
| 187 | N | C(O) | benzo[d][1,2,3]thiadiazol 5-yl | cyclopropyl | | TFA | 431.5134 | 432 |
| 188 | N | C(O) | 2-chloro-5-fluoro-phenyl | cyclopropyl | | TFA | 425.8864 | 425.9 |
| 189 | N | C(O) | 2,6-difluorophenyl-3-methylphenyl | cyclopropyl | | TFA | 423.4584 | 424.2 |
| 190 | N | C(O) | 2-methoxy-5-trifluoromethylphenyl | cyclopropyl | | TFA | 471.4749 | 471.9 |
| 191 | N | C(O) | 4-bromo-3-trifluoromethylphenyl | cyclopropyl | | | 520.345 | 521.8 |
| 192 | N | CH$_2$ | 3,5-difluorophenyl | cyclopropyl | | TFA | 395.4483 | 395.9 |
| 193 | N | CH$_2$ | 4-chloro-3-methyl-phenyl | cyclopropyl | | TFA | 407.939 | 407.9 |
| 194 | N | CH$_2$ | 2,3-dimethylphenyl | cyclopropyl | | TFA | 387.5206 | 388.1 |
| 195 | N | CH$_2$ | 2-bromo-5-methoxyphenyl | cyclopropyl | | TFA | 468.3894 | 469.8 |
| 196 | N | CH$_2$ | 3-bromo-4-methoxyphenyl | cyclopropyl | | TFA | 468.3894 | 469.7 |
| 197 | N | CH$_2$ | 4-bromo-2-chlorophenyl | cyclopropyl | | TFA | 472.8085 | 473.7 |
| 198 | N | CH$_2$ | 3-bromo-4-fluorophenyl | cyclopropyl | | TFA | 456.3539 | 455.8 |
| 199 | N | CH$_2$ | 4-bromo-2-fluorophenyl | cyclopropyl | | TFA | 456.3539 | 457.8 |
| 200 | N | CH$_2$ | 5-bromo-2-fluorophenyl | cyclopropyl | | TFA | 456.3539 | 457.6 |
| 201 | N | CH$_2$ | 5-bromo-2-methylphenyl | cyclopropyl | | TFA | 452.39 | 453.7 |
| 202 | N | CH$_2$ | indol-6-yl | cyclopropyl | | TFA | 398.5034 | 398.9 |
| 203 | N | CH$_2$ | 5-chloro-2-methyl-phenyl | cyclopropyl | | TFA | 407.939 | 407.9 |
| 204 | N | CH$_2$ | 4-chloro-2-methyl-phenyl | cyclopropyl | | TFA | 407.939 | 408.1 |
| 205 | N | CH$_2$ | 2-chloro-3,6-difluorophenyl | cyclopropyl | | TFA | 429.8934 | 429.9 |
| 206 | N | CH$_2$ | 2,4-dimethylphenyl | cyclopropyl | | TFA | 387.5206 | 388 |
| 207 | N | CH$_2$ | 2-chloro-5-methoxyphenyl | cyclopropyl | | TFA | 423.9384 | 423.9 |
| 208 | N | CH$_2$ | 2-chloro-5-fluoro-phenyl | cyclopropyl | | TFA | 411.9029 | 411.9 |
| 209 | N | CH$_2$ | 2-chloro-6-trifluoromethylphenyl | cyclopropyl | | TFA | 461.9104 | 462.1 |

-continued

Compound Table 1

| Cpd | X | Z | Ar | R$^e$ | R* | Salt | MSCalc | MSObs |
|---|---|---|---|---|---|---|---|---|
| 210 | N | CH$_2$ | 3-isopropylphenyl | cyclopropyl | | TFA | 401.5471 | 401.9 |
| 211 | N | SO$_2$ | phenyl | cyclopropyl | 6-F | | 427.4951 | 428.25 |
| 112 | N | CH$_2$ | 2,5-difluorophenyl | cyclopropyl | 6-F | | 413.4388 | 414.30 |
| 213 | N | CH$_2$ | 2,5-dichlorophenyl | pyridin-4-yl | | TFA | 465.3777 | 465 |
| 214 | N | CH$_2$ | 2,5-difluorophenyl | cyclopropyl | 6-F 7-F | TFA | 431.4293 | 432 |
| 215 | N | CH$_2$ | 3-chloro-4-methoxyphenyl | cyclopropyl | | TFA | 423.9384 | 423.9 |
| 216 | N | CH$_2$ | 4-bromo-3-methylphenyl | cyclopropyl | | TFA | 452.39 | 451.9 |
| 217 | N | CH$_2$ | 4-bromo-2-methylphenyl | cyclopropyl | | TFA | 452.39 | 453.9 |
| 218 | N | CH$_2$ | 2-chloro-5-iodophenyl | cyclopropyl | | TFA | 519.809 | 519.8 |
| 219 | N | CH$_2$ | 2-methoxy-5-trifluoromethoxy-phenyl | cyclopropyl | | TFA | 473.4908 | 473.9 |
| 220 | N | CH$_2$ | 2,3,5-trichlorophenyl | cyclopropyl | | TFA | 462.8026 | 463.6 |
| 221 | N | CH$_2$ | 2-chloro-5-fluoropyridin-3-yl | cyclopropyl | | TFA | 412.891 | 413 |
| 222 | N | C(O) | 4-chlorophenyl | pyridin-3-yl | 6-CN | TFA | 444.9161 | 445.20 |
| 223 | N | SO$_2$ | 3-chlorophenyl | cyclopropyl | 6-CN | | 468.9591 | 469.20 |
| 224 | N | SO$_2$ | 3-chlorophenyl | cyclopropyl | 6-F | | 461.9402 | 462.20 |
| 225 | N | SO$_2$ | 2,5-dichlorophenyl | cyclopropyl | 6-CN | | 503.4042 | 504.20 |
| 226 | N | SO$_2$ | 4-chlorophenyl | cyclopropyl | 6-CN | TFA | 468.9591 | 469.2 |
| 227 | N | CH$_2$ | 2,5-dichlorophenyl | pyridin-2-yl | | TFA | 465.3777 | 465 |
| 228 | N | CH$_2$ | 2,5-difluorophenyl | pyridin-3-yl | | TFA | 432.4685 | 433.1 |
| 229 | N | C(O) | 4-chloro-3-methylphenyl | pyridin-3-yl | | TFA | 458.9427 | 459.1 |
| 230 | N | CH$_2$ | 2,5-dichlorophenyl | cyclopropyl | 6-F 7-F | TFA | 464.3384 | 464 |
| 231 | N | C(O) | 3-bromoo-4-fluorophenyl | cyclopropyl | 6-F 7-F | TFA | 506.3184 | 507.8 |
| 232 | N | CH$_2$ | 2-bromo-5-chlorophenyl | cyclopropyl | | TFA | 472.8085 | 473.8 |
| 233 | N | CH$_2$ | 5-chloro-2-trifluoromethylphenyl | cyclopropyl | | TFA | 461.9104 | 462.1 |
| 234 | N | CH$_2$ | 2,6-difluoro-3-methylphenyl | cyclopropyl | | TFA | 409.4749 | 410.1 |
| 235 | N | CH$_2$ | 2-methoxy-5-trifluoromethylphenyl | cyclopropyl | | TFA | 457.4914 | 458.1 |
| 236 | N | SO$_2$ | 2-methylphenyl | cyclopropyl | 6-CN | | 448.5406 | 449.30 |
| 237 | N | SO$_2$ | 3-fluorophenyl | cyclopropyl | 6-CN | TFA | 452.5045 | 453.1 |
| 238 | N | SO$_2$ | 3-methylphenyl | cyclopropyl | 6-CN | | 448.5406 | 449.30 |
| 239 | N | SO$_2$ | 4-methylphenyl | cyclopropyl | 6-CN | | 448.5406 | 449.30 |
| 240 | N | SO$_2$ | 2-fluorophenyl | cyclopropyl | 6-CN | TFA | 452.5045 | 453.2 |
| 241 | N | CH$_2$ | 2,5-dichlorophenyl | cyclopropyl | 5-CN | TFA | 453.367 | 453.25 |
| 242 | N | C(O) | 4-chlorophenyl | cyclopropyl | 6-F 7-F | | 443.8769 | 444.2 |
| 243 | N | SO$_2$ | 2-chlorophenyl | cyclopropyl | 6-CN | TFA | 468.9591 | 469.2 |
| 244 | N | SO$_2$ | 4-fluorophenyl | cyclopropyl | 6-CN | TFA | 452.5045 | 453.3 |
| 245 | N | CH$_2$ | 3-chlorophenyl | cyclopropyl | 6-F 7-F | TFA | 429.8934 | 430.3 |
| 246 | N | C(O) | 4-bromo-3-fluorophenyl | cyclopropyl | 6-F | | 488.3279 | 489.25 |
| 247 | N | CH$_2$ | 2,5-dichlorophenyl | cyclopropyl | 8-CN | TFA | 453.367 | 453.2 |
| 248 | N | SO$_2$ | 2-bromophenyl | cyclopropyl | 6-CN | | 513.4102 | 514.20 |
| 249 | N | SO$_2$ | 3-bromophenyl | cyclopropyl | 6-CN | | 513.4102 | 514.10 |
| 250 | N | SO$_2$ | 4-bromophenyl | cyclopropyl | 6-CN | | 513.4102 | 514.20 |
| 251 | N | SO$_2$ | 2-cyanophenyl | cyclopropyl | 6-CN | TFA | 459.5235 | 460.3 |
| 252 | N | SO$_2$ | 3-cyanophenyl | cyclopropyl | 6-CN | TFA | 459.5235 | 460.3 |
| 253 | N | SO$_2$ | 4-cyanophenyl | cyclopropyl | 6-CN | TFA | 459.5235 | 460.3 |
| 254 | N | CH$_2$ | 4-fluorophenyl | cyclopropyl | 6-CN | | 402.4673 | 403.30 |
| 255 | N | C(O) | 3-bromo-4-fluorophenyl | cyclopropyl | 6-CN | TFA | 495.3469 | 496.8 |
| 256 | N | CH$_2$ | 2,5-difluorophenyl | cyclopropyl | 6-CN | TFA | 420.4578 | 420.9 |
| 257 | N | CH$_2$ | 2,5-dichlorophenyl | isopropyl | 6-CN | TFA | 455.3829 | 455 |
| 258 | N | CH$_2$ | 2,5-difluorophenyl | isopropyl | 6-CN | TFA | 422.4737 | 423 |
| 259 | N | C(O) | 3-bromo-4-fluorophenyl | isopropyl | 6-CN | TFA | 497.3628 | 498.8 |
| 260 | N | CH$_2$ | 2,5-difluorophenyl | cyclobutyl | 6-CN | TFA | 434.4844 | 435.1 |
| 261 | N | C(O) | 3-bromo-4-fluorophenyl | cyclobutyl | 6-CN | TFA | 509.3735 | 508.8 |
| 264 | N | C(O) | 2,5-dichloropyridin-yl | cyclopropyl | 6-CN | | 468.3386 | 468.2 |

-continued

Compound Table 1

| Cpd | X | Z | Ar | R$^e$ | R* | Salt | MSCalc | MSObs |
|---|---|---|---|---|---|---|---|---|
| 265 | N | C(O) | 4-chlorophenyl | cyclobutyl | 6-CN | | 446.932 | 447.30 |
| 266 | N | C(O) | 4-chlorophenyl | isopropyl | 6-CN | | 434.9213 | 435.30 |
| 268 | N | CH$_2$ | 2,5-dichlorophenyl | 2,2,2-trifluoroethyl | | TFA | 470.3182 | 469.8 |
| 269 | N | SO$_2$ | 3,5-dimethylisoxazol-4-yl | cyclopropyl | 6-CN | TFA | 453.5174 | 454 |
| 270 | N | SO$_2$ | 2,5-dimethylphenyl | cyclopropyl | 6-CN | TFA | 462.5672 | 463.1 |
| 271 | N | SO$_2$ | 4-methoxyphenyl | cyclopropyl | 6-CN | TFA | 464.5401 | 465.1 |
| 272 | N | SO$_2$ | 2-methoxyphenyl | cyclopropyl | 6-CN | TFA | 464.5401 | 465.1 |
| 273 | N | SO$_2$ | 3-methoxyphenyl | cyclopropyl | 6-CN | TFA | 464.5401 | 465.1 |
| 274 | N | SO$_2$ | 5-chlorothien-2-yl | cyclopropyl | 6-CN | TFA | 474.9868 | 474.9 |
| 275 | N | SO$_2$ | 2,4,6-trimethylphenyl | cyclopropyl | 6-CN | TFA | 476.5938 | 477.1 |
| 276 | N | SO$_2$ | 2-methoxy-4-methylphenyl | cyclopropyl | 6-CN | TFA | 478.5667 | 479 |
| 277 | N | SO$_2$ | 5-chloro-1,3-dimethylpyrazol-4-yl | cyclopropyl | 6-CN | TFA | 486.9777 | 487.1 |
| 278 | N | SO$_2$ | 2,3,4-trifluorophenyl | cyclopropyl | 6-CN | TFA | 488.4855 | 489.1 |
| 279 | N | SO$_2$ | 4-tert-butylphenyl | cyclopropyl | 6-CN | TFA | 490.6204 | 491.1 |
| 280 | N | SO$_2$ | 4-chloro-2-5-dimethylphenyl | cyclopropyl | 6-CN | TFA | 497.0123 | 497.1 |
| 281 | N | SO$_2$ | 3-chloro-5-fluoro-2-methylphenyl | cyclopropyl | 6-CN | TFA | 500.9762 | 501 |
| 282 | N | SO$_2$ | 4-trifluoro-methoxyphenyl | cyclopropyl | 6-CN | TFA | 518.5115 | 519.3 |
| 283 | N | SO$_2$ | 5-bromothien-2-yl | cyclopropyl | 6-CN | TFA | 519.4379 | 520.8 |
| 284 | N | SO$_2$ | 4-bromo-2-fluorophenyl | cyclopropyl | 6-CN | TFA | 531.4006 | 532.7 |
| 285 | N | SO$_2$ | 2-chloro-5-trifluoro-methylphenyl | cyclopropyl | 6-CN | TFA | 536.9571 | 537 |
| 286 | N | SO$_2$ | 4-bromo-2-chlorophenyl | cyclopropyl | 6-CN | TFA | 547.8552 | 548.9 |
| 293 | N | CH$_2$ | 2,6-dichlorophenyl | cyclopropyl | 6-CN | TFA | 453.367 | 453.2 |
| 294 | N | C(O) | 4-chlorophenyl | cyclobutylmethyl | 6-CN | | | |
| 295 | N | C(O) | 2,5-dichlorophenyl | cyclobutylmethyl | 6-CN | | | |
| 296 | N | C(O) | 2,5-dichloropyridin-3-yl | cyclopropyl | 6-CN | TFA | 468.3386 | 468.2 |
| 297 | N | C(O) | 4-chlorophenyl | oxetan-3-yl | 6-CN | | 429.3456 | 429.2 |
| 299 | N | CH$_2$ | 2,5-dichlorophenyl | oxetan-3-yl | 6-CN | | | |
| 302 | N | C(O) | 4-chlorophenyl | cyclopropyl | 7-CN | TFA | 432.9054 | 433.2 |
| 304 | N | CH$_2$ | 2,5-difluorophenyl | cyclopropyl | 7-CN | TFA | 420.4578 | 421.3 |
| 307 | N | SO$_2$ | 4-fluorophenyl | cyclopropyl | 7-CN | TFA | 452.5045 | 453.2 |
| 308 | N | CH$_2$ | 2,5-dichlorophenyl | pyridin-3-yl | 6-CN | TFA | 490.3871 | 490.2 |
| 310 | N | CH$_2$ | 2,5-difluorophenyl | pyridine-3-yl | 6-CN | | 457.4779 | 458.3 |
| 312 | N | CH$_2$ | 2,5-difluorophenyl | 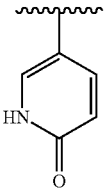 | 6-CN | | | |
| 313 | N | CH$_2$ | 2,5-dichlorophenyl | 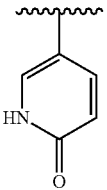 | 6-CN | | | |
| 319 | N | CH$_2$ | 2,5-difluorophenyl | 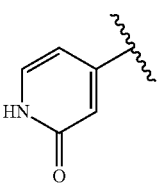 [SMILES: *c1cc[nH]c(=O)c1] | 6-CN | | | |
| 320 | N | SO$_2$ | 4-ethylphenyl | cyclopropyl | 6-CN | TFA | 462.5672 | 462.9 |

-continued

Compound Table 1

| Cpd | X | Z | Ar | R^e | R* | Salt | MSCalc | MSObs |
|---|---|---|---|---|---|---|---|---|
| 321 | N | CH$_2$ | 2,5-difluorophenyl | 6-membered HN-C(=O) pyridinone (attached at 6-position) | 6-CN | | | |
| 322 | N | SO$_2$ | 2-fluoro-5-methyl-phenyl | cyclopropyl | 6-CN | TFA | 466.5311 | 467.2 |
| 323 | N | C(O) | 4-chlorophenyl | 6-membered HN-C(=O) pyridinone (attached at 6-position) | 6-CN | | | |
| 324 | N | CH$_2$ | 2,5-difluorophenyl | HN-C(=O) pyridinone (attached at 3-position) | 6-CN | | | |
| 325 | N | SO$_2$ | 3,4-difluorophenyl | cyclopropyl | 6-CN | TFA | 470.495 | 470.9 |
| 326 | N | C(O) | 4-chlorophenyl | HN-C(=O) pyridinone (attached at 3-position) | 6-CN | | | |
| 327 | N | C(O) | 4-chlorophenyl | pyridin-3-yl | 6-CN | | 469.9256 | 470.2 |
| 328 | N | SO$_2$ | 2,5-dimethoxyphenyl | cyclopropyl | 6-CN | TFA | 494.566 | 495.1 |
| 329 | N | SO$_2$ | 2-chloro-4-trifluoro-methylphenyl | cyclopropyl | 6-CN | TFA | 536.9571 | 537 |
| 332 | N | CH$_2$ | 2,5-difluorophenyl | 6-methoxypyridin-3-yl | 6-CN | TFA | 487.5039 | 488.30 |
| 333 | N | CH$_2$ | 2,5-dichlorophenyl | 1-oxocyclobut-3-yl | 6-CN | TFA | 481.3771 | 481.2 |
| 334 | N | CH$_2$ | 2,5-difluorophenyl | 1-oxocyclobut-3-yl | 6-CN | TFA | 448.4679 | 449.3 |
| 335 | N | CH$_2$ | 2,5-dichlorophenyl | cyclobutyl | 6-CN | TFA | 467.3936 | 467 |
| 336 | N | C(O) | 4-chlorophenyl | 2-fluoroethyl | 6-CN | TFA | 438.8852 | 438.8 |
| 337 | N | CH$_2$ | 2,5-dichlorophenyl | 2,2-difluoroethyl | 6-CN | | 477.3372 | 476.8 |
| 338 | N | C(O) | 4-chlorophenyl | 2,2-difluoroethyl | | | 456.8757 | 457.1 |
| 339 | N | CH$_2$ | 2,5-dichlorophenyl | isoxazol-3-yl | 6-CN | TFA | 480.3493 | 479.8 |
| 340 | N | C(O) | 4-chlorophenyl | isoxazol-3-yl | 6-CN | TFA | 459.8877 | 460 |
| 341 | N | SO$_2$ | 3-cyano-4-fluoro-phenyl | cyclopropyl | 6-CN | TFA | 477.514 | 478 |
| 342 | N | CH$_2$ | 2,4-difluorophenyl | cyclopropyl | 6-CN | TFA | 420.4578 | 421.3 |
| 343 | N | SO$_2$ | 5-chloro-2-methoxyphenyl | cyclopropyl | 6-CN | TFA | 498.9851 | 499 |
| 344 | N | SO$_2$ | 5-chloro-2,4-difluorophenyl | cyclopropyl | 6-CN | TFA | 504.9401 | 505 |
| 345 | N | SO$_2$ | 5-bromo-6-chloropyridin-3-yl | cyclopropyl | 6-CN | TFA | 548.8433 | 549.9 |
| 346 | N | SO$_2$ | 4-bromo-2,5-difluorophenyl | cyclopropyl | 6-CN | TFA | 549.3911 | 550.8 |
| 347 | N | CH$_2$ | 2,5-dichlorophenyl | 2-fluoroethyl | 6-CN | TFA | 459.3467 | 459 |
| 348 | N | CH$_2$ | 2,5-difluorophenyl | 2-fluoroethyl | 6-CN | TFA | 426.4376 | 426.9 |
| 349 | N | CH$_2$ | 2,5-difluorophenyl | 2,2-difluoroethyl | 6-CN | TFA | 444.428 | 444.9 |

Compound Table 1

| Cpd | X | Z | Ar | R$^e$ | R* | Salt | MSCalc | MSObs |
|---|---|---|---|---|---|---|---|---|
| 352 | N | CH$_2$ | 2,4,5-trifluorophenyl | cyclopropyl | 6-CN | TFA | 438.4482 | 439.2 |
| 357 | N | SO$_2$ | 2,4-dimethoxyphenyl | cyclopropyl | 6-CN | | 494.566 | 494.9 |
| 367 | N | CH$_2$ | 5-chloro-2-fluoro-phenyl | cyclopropyl | 6-CN | TFA | 436.9124 | 437.2 |
| 371 | N | CH$_2$ | 2,4-difluorophenyl | pyridin-3-yl | 6-CN | TFA | 457.4779 | 458.30 |
| 373 | N | CH$_2$ | 2,4-difluorophenyl | cyclopropyl | 7-CN | TFA | 420.4578 | 421.25 |
| 374 | N | CH$_2$ | 5-chloro-2-fluoro-phenyl | cyclopropyl | 7-CN | TFA | 436.9124 | 437.20 |
| 375 | N | CH$_2$ | 2,4,5-trifluorophenyl | cyclopropyl | 7-CN | TFA | 438.4482 | 439.30 |
| 376 | N | CH$_2$ | 2,4,5-trifluorophenyl | pyridin-3-yl | 6-CN | TFA | 475.4684 | 476.30 |
| 377 | N | C(O) | 4-chloro-2-fluoro-phenyl | pyridin-3-yl | 6-CN | TFA | 487.9161 | 488.20 |
| 378 | N | CH$_2$ | 2,5-difluorophenyl | isoxazol-3-yl | 6-CN | | 447.4401 | 448 |
| 399 | N | CH$_2$ | 2,5-difluorophenyl | 3,3,3-trifluoropropyl | 6-CN | TFA | 476.4451 | 477.3 |
| 400 | N | CH$_2$ | 2,4-difluorophenyl | 3,3,3-trifluoropropyl | 6-CN | TFA | 476.4451 | 477.2 |
| 401 | N | CH$_2$ | 2,5-difluorophenyl | cyclopropyl | 6-Br | TFA | 474.3444 | 474.2/476.2 |
| 402 | N | CH$_2$ | 5-chloro-2-fluorophenyl | cyclopropyl | 6-Br | TFA | 490.799 | 490.1/492.1 |
| 403 | N | CH$_2$ | 2,4-difluorophenyl | cyclopropyl | 6-Br | TFA | 474.3444 | 474.2/476.2 |
| 404 | N | CH$_2$ | 2,4-difluorophenyl | 2,2-difluoroethyl | 6-CN | | 444.428 | 445.2 |
| 407 | N | CH$_2$ | 2,4-difluorophenyl | 2-methoxyethyl | 6-CN | TFA | 438.4731 | 439.3 |
| 408 | CH | CH$_2$ | 5-methyloxazol-2-yl | cyclopropyl | | TFA | 363.4561 | 364.3 |
| 409 | CH | CH$_2$ | 3-methyl-[1,2,4]-oxadiazol-5-yl | cyclopropyl | | TFA | 364.4442 | 365.3 |
| 410 | CH | CH$_2$ | phenyl | phenyl | | TFA | 394.5114 | 395.1 |
| 411 | CH | O | phenyl | cyclopropyl | | | 360.4521 | 361.30 |
| 412 | CH | NH | 4-chlorophenyl | cyclopropyl | | TFA | 393.9124 | 394.3 |
| 414 | CH | CH$_2$ | 2,4-difluorophenyl | pyridin-3-yl | 6-CN | TFA | 456.4899 | 457.30 |
| 415 | CH | CH$_2$ | 2,4-difluorophenyl | cyclopropyl | 6-CN | TFA | 419.4697 | 420.3 |
| 462 | CH | CH$_2$ | 2,4-difluorophenyl | isopropyl | 6-CN | | 421.4856 | 422.3 |
| 463 | CH | CH$_2$ | 2,4-difluorophenyl | cyclobutyl | 6-CN | | 433.4963 | 434.3 |
| 466 | CH | O | 4-chloro-2-fluorophenyl | cyclopropyl | 6-CN | TFA | 437.8972 | 438.20 |
| 467 | CH | O | 4-chloro-2-fluorophenyl | isopropyl | 6-CN | TFA | 439.913 | 440.20 |
| 469 | CH | O | 2,4-difluorophenyl | cyclopropyl | 6-CN | TFA | 421.4425 | 422.20 |
| 470 | CH | C(O) | 5-chloro-2-fluorophenyl | cyclopropyl | 6-CN | TFA | 449.9078 | 450.20 |
| 471 | CH | CHF | 2,5-difluorophenyl | cyclopropyl | 6-CN | TFA | 437.4602 | 438.3 |
| 472 | CH | CH$_2$ | 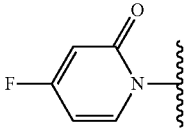 [SMILES: *n1ccc(F)cc1=O] | cyclopropyl | 6-CN | TFA | 418.4667 | 419.2 |
| 473 | CH | C(O) | 2,5-difluorophenyl | cyclopropyl | 6-CN | TFA | 433.4532 | 434.2 |
| 475 | CH | O | 4-chloro-2-fluorophenyl | cyclopropyl | 7-CN | TFA | 437.8972 | 438.20 |
| 479 | CH | CH$_2$ | 2,4-difluorophenyl | cyclopropyl | 6-F 7-F | TFA | 430.4412 | 431.25 |
| 480 | CH | CH$_2$ | 2,4-difluorophenyl | cyclopropyl | 6-F | TFA | 412.4507 | 413.30 |
| 481 | CH | CHF | 2,4-difluorophenyl | cyclopropyl | 6-CN | TFA | 437.4602 | 438.20 |
| 482 | CH | CHF | 2,4-difluorophenyl | isopropyl | 6-CN | TFA | 439.4761 | 440.30 |
| 483 | CH | CHF | 2,5-difluorophenyl | cyclobutyl | 6-CN | TFA | 451.4868 | 452.3 |
| 485 | CH | CHF | 2,5-difluorophenyl | cyclopropyl | 7-CN | TFA | 437.4602 | 438.3 |
| 486 | CH | CHF | 2,5-difluorophenyl | isopropyl | 6-CN | TFA | 439.4761 | 440.3 |
| 488 | CH | CHF | 2,4-difluorophenyl | cyclopropyl | 7-CN | TFA | 437.4602 | 438.30 |
| 492 | CH | (R)—CHF | 2,4-difluorophenyl | cyclopropyl | 6-CN | TFA | 437.4602 | 438.20 |
| 496 | CH | CH$_2$ | 2,4-difluorophenyl | cyclopropyl | 6-Br | TFA | 473.3563 | 473.3/475.2 |
| 497 | CH | CH$_2$ | 2,4-difluorophenyl | 3,3,3-trifluoropropyl | 6-CN | TFA | 475.457 | 476.3 |
| 499 | CH | CHF | 2,5-difluorophenyl | 3,3,3-trifluoropropyl | 6-CN | TFA | 493.4474 | 494.3 |
| 500 | CH | O | 2,4-difluorophenyl | 3,3,3-trifluoropropyl | 6-CN | TFA | 477.4298 | 478.2 |

-continued

Compound Table 1

| Cpd | X | Z | Ar | R$^e$ | R* | Salt | MSCalc | MSObs |
|---|---|---|---|---|---|---|---|---|
| 501 | CH | CHF | 2,5-difluorophenyl | cyclopropyl | 6-Br | TFA | 491.3468 | 491.2/493.2 |
| 502 | CH | O | 2,4-fluorophenyl | cyclopropyl | 6-Br | TFA | 475.3291 | 475.2/477.2 |
| 504 | CH | (S)—CHF | 2,5-difluorophenyl | isopropyl | 6-CN | | 439.4761 | 440.1 |
| 505 | CH | (R)—CHF | 2,5-difluorophenyl | isopropyl | 6-CN | | 439.4761 | 440.1 |
| 506 | CH | (S)—CHF | 2,4-difluorophenyl | cyclopropyl | 6-CN | | 437.4602 | 438.2 |
| 507 | CH | (R)—CHF | 2,4-difluorophenyl | cyclopropyl | 6-CN | | 437.4602 | 438.1 |
| 508 | CH | (S)—CHF | 2,4-difluorophenyl | isopropyl | 6-CN | | 439.4761 | 440.1 |
| 509 | CH | (R)—CHF | 2,4-difluorophenyl | isopropyl | 6-CN | | 439.4761 | 440 |
| 510 | CH | (S)—CHF | 2,4-difluorophenyl | cyclopropyl | 7-CN | | 437.4602 | 438.1 |
| 511 | CH | (R)—CHF | 2,4-difluorophenyl | cyclopropyl | 7-CN | | 437.4602 | 438.1 |
| 512 | CH | CHF | 2,4-difluorophenyl | 2,2-difluoroethyl | 6-CN | | 461.4304 | 462.2 |
| 513 | CH | CH$_2$ | 2,4-difluorophenyl | 2,2-difluoroethyl | 6-CN | | 443.4399 | 444.2 |
| 514 | CH | O | 2,4-difluorophenyl | 2,2-difluoroethyl | 6-CN | | 445.4128 | 446.2 |
| 515 | CH | (S)—CHF | 2,4-difluorophenyl | cyclopropyl | 6-CN | TFA | 437.4602 | 438.3 |
| 519 | CH | CH$_2$ | 2,4-difluorophenyl | 2-methoxyethyl, | 6-CN | | 437.485 | 438.3 |
| 522 | CH | O | 2,4-difluorophenyl | 2-methoxyethyl, | 6-CN | | 439.4578 | 440.25 |
| 523 | CH | CHF | 2,4-difluorophenyl | 2-methoxyethyl, | 6-CN | | 455.4755 | 456.3 |
| 527 | CH | CH$_2$ | 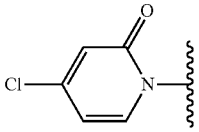 [SMILES: *n1ccc(Cl)cc1=O] | cyclopropyl | 6-CN | | 434.9213 | 435.2 |
| 530 | CH | CH$_2$ | 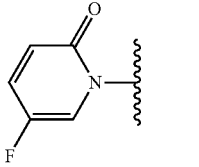 [SMILES: *n1cc(F)ccc1=O] | cyclopropyl | 6-CN | | 418.4667 | 419.3 |
| 534 | CH | CF$_2$ | 5-chloro-2-fluorophenyl | cyclopropyl | 6-CN | | 471.9052 | 472.2 |
| 536 | CH | CH$_2$ | 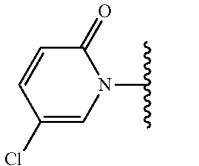 [SMILES: *n1cc(Cl)ccc1=O] | cyclopropyl | 6-CN | | 434.9213 | 435.3 |
| 546 | CH | CF$_2$ | 2,4-difluorophenyl | cyclopropyl | 6-CN | | 455.4507 | 456.2 |
| 548 | CH | CF$_2$ | 2,5-difluorophenyl | cyclopropyl | 6-CN | | 455.4507 | 456.3 |
| 627 | CH | O | 2-fluoro-4-chlorophenyl | isopropyl | | HCl | 438.373 | 439.8 |
| 628 | CH | C(O) | 3-isopropylamino-5-chlorophenyl | isopropyl | 7-CN | | 491.027 | 491.0 |

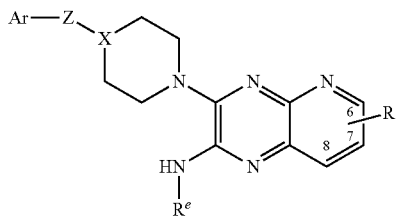

| 3 | N | CH$_2$ | 3-methylphenyl | cyclopropyl | | | 374.482 | 375.3 |
| 23 | N | CH$_2$ | 3-chlorophenyl | phenyl | | TFA | 430.9326 | 431.2 |

-continued

Compound Table 1

| Cpd | X | Z | Ar | R$^e$ | R* | Salt | MSCalc | MSObs |
|---|---|---|---|---|---|---|---|---|
| 63 | N | CH$_2$ | 2,5-dichlorophenyl | cyclopropyl | | | 429.3456 | 429.2 |
| 150 | N | CH$_2$ | 2,5-dichlorophenyl | pyridin-3-yl | | TFA | 466.3658 | 466.2 |

[Structure: Ar—Z—X—piperazine—N attached to pyrazine-fused pyridine ring with positions 5, 7, 8 labeled and N—R* substituent; HN—R$^e$ group]

| Cpd | X | Z | Ar | R$^e$ | R* | Salt | MSCalc | MSObs |
|---|---|---|---|---|---|---|---|---|
| 133 | N | CH$_2$ | 2,5-dichlorophenyl | cyclopropyl | | TFA | 429.3456 | 429.2 |
| 262 | N | C(O) | 4-chlorophenyl | cyclopropyl | | | 408.884 | 409.25 |
| 263 | N | CH$_2$ | 2,5-difluorophenyl | cyclopropyl | | TFA | 396.4364 | 397.3 |
| 267 | N | C(O) | 4-trifluoromethyl-phenyl | cyclopropyl | | TFA | 442.437 | 443.3 |
| 287 | N | SO$_2$ | 4-fluorophenyl | cyclopropyl | | TFA | 428.4832 | 429.3 |
| 288 | N | C(O) | 4-difluoromethyl-phenyl | cyclopropyl | | TFA | 424.4465 | 425.3 |
| 289 | N | CH$_2$ | 5-chloro-2-difluoro-methoxyphenyl | cyclopropyl | | TFA | 460.9074 | 461.3 |
| 290 | N | CH$_2$ | 4-fluorophenyl | cyclopropyl | | TFA | 378.4459 | 379.3 |
| 298 | N | CH$_2$ | 2,6-dichlorophenyl | cyclopropyl | | TFA | 429.3456 | 429.2 |
| 300 | N | CH$_2$ | 5-chloro-2-propoxy-phenyl | cyclopropyl | | TFA | 452.9796 | 453.3 |
| 301 | N | SO$_2$ | 4-trifluoromethyl-phenyl | cyclopropyl | | TFA | 478.4907 | 479.3 |
| 305 | N | CH$_2$ | 2-methoxy-5-tert-butylphenyl | cyclopropyl | | TFA | 446.5878 | 447.4 |
| 306 | N | CH$_2$ | 2,5-dimethylphenyl | cyclopropyl | | TFA | 388.5086 | 389.3 |
| 311 | N | CH$_2$ | 2,6-difluorophenyl | cyclopropyl | | TFA | 396.4364 | 397.3 |
| 314 | N | CH$_2$ | 3-chloro-4-fluoro-phenyl | cyclopropyl | | TFA | 412.891 | 413.3 |
| 315 | N | CH$_2$ | 2,4,5-trifluorophenyl | cyclopropyl | | TFA | 414.4268 | 415.3 |
| 316 | N | CH$_2$ | 4-chloro-3-fluoro-phenyl | cyclopropyl | | TFA | 412.891 | 413.3 |
| 317 | N | CH$_2$ | 3,4-difluorophenyl | cyclopropyl | | TFA | 396.4364 | 397.3 |
| 318 | N | CH$_2$ | 2,4-difluorophenyl | cyclopropyl | | TFA | 396.4364 | 397.3 |
| 330 | N | CH$_2$ | 5-chloro-2-fluoro-phenyl | cyclopropyl | | TFA | 412.891 | 413.3 |
| 331 | N | CH$_2$ | 2-chloro-5-fluoro-phenyl | cyclopropyl | | TFA | 412.891 | 413.2 |
| 350 | N | CH$_2$ | 5-chloro-2-fluoro-phenyl | cyclopropyl | 8-Cl | TFA | 447.336 | 448.20 |
| 351 | N | CH$_2$ | 2,5-difluorophenyl | cyclopropyl | 8-Cl | TFA | 430.8814 | 431.20 |
| 353 | N | CH$_2$ | 2,4-difluorophenyl | cyclopropyl | 8-Cl | TFA | 430.8814 | 431.20 |
| 354 | N | CH$_2$ | 2,4,5-trifluorophenyl | cyclopropyl | 8-Cl | TFA | 448.8719 | 449.20 |
| 358 | N | C(O) | 4-chloro-3-fluoro-phenyl | cyclopropyl | | TFA | 426.8745 | 427.2 |
| 359 | N | C(O) | 3,4-difluorophenyl | cyclopropyl | | TFA | 410.4199 | 411.3 |
| 360 | N | C(O) | 3-chloro-4-fluoro-phenyl | cyclopropyl | | TFA | 426.8745 | 427.2 |
| 361 | N | C(O) | 4-chloro-2-fluoro-phenyl | cyclopropyl | | TFA | 426.8745 | 427.2 |
| 362 | N | C(O) | 2-chloro-4-fluoro-phenyl | cyclopropyl | | TFA | 426.8745 | 427.2 |
| 365 | N | CH$_2$ | 2,4-difluorophenyl | 2,2-difluoroethyl | | TFA | 420.4066 | 421.20 |
| 366 | N | CH$_2$ | 5-chloro-2-fluoro-phenyl | 2,2-difluoroethyl | | TFA | 436.8612 | 437.20 |
| 368 | N | C(O) | 4-chloro-2-fluoro-phenyl | 2,2-difluoroethyl | | TFA | 450.8447 | 451.20 |
| 370 | N | CH$_2$ | 2,4,5-trifluorophenyl | 2,2 difluoroethyl | | TFA | 438.3971 | 439.20 |
| 372 | N | C(O) | 4-chloro-2-hydroxy-phenyl | cyclopropyl | | TFA | 424.8835 | 425.2 |

-continued

Compound Table 1

| Cpd | X | Z | Ar | R$^e$ | R* | Salt | MSCalc | MSObs |
|---|---|---|---|---|---|---|---|---|
| 380 | N | C(O) | 4-chloro-2-methoxy-phenyl | cyclopropyl | | TFA | 438.91 | 439.2 |
| 381 | N | C(O) | 2-fluoro-4-trifluoro-methylphenyl | cyclopropyl | | TFA | 460.4274 | 461.3 |
| 382 | N | C(O) | 3-fluoro-5-chloropyridin-2-yl | cyclopropyl | | TFA | 427.8625 | 428.3 |
| 383 | N | C(O) | 2-fluoro-4-methyl-phenyl | cyclopropyl | | TFA | 406.456 | 407.3 |
| 384 | N | C(O) | 2-fluoro-4-methoxy-phenyl | cyclopropyl | | TFA | 422.4554 | 423.2 |
| 385 | N | C(O) | 4-chloro-2-methyl-phenyl | cyclopropyl | | TFA | 422.9106 | 423.3 |
| 386 | N | C(O) | 4-cyano-2-fluoro-phenyl | cyclopropyl | | TFA | 417.4389 | 418.3 |
| 387 | N | C(O) | 4-fluoro-2-hydoxy-phenyl | cyclopropyl | | TFA | 408.4288 | 409.3 |
| 388 | N | C(O) | 4-chloro-2,6-difluorophenyl | cyclopropyl | | TFA | 444.865 | 445.2 |
| 389 | N | C(O) | 3-fluoropyridin-2-yl | cyclopropyl | | TFA | 393.4175 | 394.3 |
| 391 | N | C(O) | 4-chloro-2-trifluoro-methylphenyl | cyclopropyl | | TFA | 476.882 | 477.3 |
| 393 | N | C(O) | 2,4,6-trifluorophenyl | cyclopropyl | | TFA | 428.4104 | 429.3 |
| 394 | N | C(O) | 2,4-difluoro-6-hydroxyphenyl | cyclopropyl | | TFA | 426.4193 | 427.3 |
| 395 | N | CH$_2$ | 2,4-difluorophenyl | cyclopropyl | 7-CH$_3$ | TFA | 410.463 | 411.3 |
| 396 | N | CH$_2$ | 5-chloro-2-fluorophenyl | cyclopropyl | 7-CH$_3$ | TFA | 426.9176 | 427.3 |
| 405 | N | CH$_2$ | 2,4-difluorophenyl | cyclopropyl | 7-Br | TFA | 475.3325 | 475.2/ 477.2 |
| 406 | N | CH$_2$ | 2,4-difluorophenyl | 2-methoxyethyl | | TFA | 414.4517 | 415.3 |
| 413 | CH | CH$_2$ | 2,4-difluorophenyl | cyclopropyl | | TFA | 395.4483 | 396.3 |
| 416 | CH | O | 2-chlorophenyl | cyclopropyl | | TFA | 395.8853 | 396.20 |
| 417 | CH | O | 2-fluorophenyl | cyclopropyl | | TFA | 379.4307 | 380.25 |
| 418 | CH | O | 3-fluorophenyl | cyclopropyl | | TFA | 379.4307 | 380.30 |
| 419 | CH | C(O) | 4-fluorophenyl | cyclopropyl | | TFA | 391.4414 | 392.30 |
| 420 | CH | CH$_2$ | 4-fluorophenyl | cyclopropyl | | TFA | 377.4579 | 378.30 |
| 421 | CH | C(O) | 3,4-difluorophenyl | cyclopropyl | | TFA | 409.4319 | 410.30 |
| 422 | CH | SO$_2$ | 4-fluorophenyl | cyclopropyl | | TFA | 427.4951 | 428.30 |
| 423 | CH | CH$_2$ | 4-chlorophenyl | cyclopropyl | | TFA | 393.9124 | 394.30 |
| 424 | CH | O | 4-chlorophenyl | cyclopropyl | | TFA | 395.8853 | 396.30 |
| 425 | CH | O | 3-chlorophenyl | cyclopropyl | | TFA | 395.8853 | 396.25 |
| 428 | CH | CH$_2$ | 2,4-difluorophenyl | cyclopropyl | 7-CH$_3$ | TFA | 409.47 | 410.3 |
| 429 | CH | C(O) | 4-chlorophenyl | cyclopropyl | | TFA | 407.896 | 408.30 |
| 430 | CH | O | 2,5-difluorophenyl | cyclopropyl | | TFA | 397.4211 | 398.30 |
| 431 | CH | O | 2,4,6-trifluorophenyl | cyclopropyl | | TFA | 415.4116 | 416.30 |
| 432 | CH | O | 4-fluorophenyl | cyclopropyl | | TFA | 379.4307 | 380.30 |
| 433 | CH | O | 2,4-difluorophenyl | cyclopropyl | | TFA | 397.4211 | 398.20 |
| 434 | CH | C(O) | 2-fluorophenyl | cyclopropyl | | TFA | 391.4414 | 392.25 |
| 435 | CH | C(O) | 2,5-difluorophenyl | cyclopropyl | | TFA | 409.4319 | 410.25 |
| 436 | CH | O | 5-chloro-2-fluorophenyl | cyclopropyl | | TFA | 413.8757 | 414.20 |
| 437 | CH | O | phenyl | cyclopropyl | | TFA | 361.4402 | 362.25 |
| 438 | CH | C(O) | 2,4-difluorophenyl | cyclopropyl | | TFA | 409.4319 | 410.30 |
| 440 | CH | C(O) | 2,5-difluorophenyl | cyclopropyl | 7-CH$_3$ | TFA | 423.4584 | 424.3 |
| 441 | CH | O | 2,4-difluorophenyl | cyclopropyl | 7-CH$_3$ | TFA | 411.4477 | 412.3 |
| 442 | CH | O | 4-chloro-2-fluorophenyl | cyclopropyl | | TFA | 413.8757 | 414.20 |
| 443 | CH | C(O) | 2,4,6-trifluorophenyl | cyclopropyl | | TFA | 427.4223 | 428.25 |
| 444 | CH | C(O) | 4-chloro-2,6-difluorophenyl | cyclopropyl | | TFA | 443.8769 | 444.20 |
| 445 | CH | CH$_2$ | 2,5-difluorophenyl | cyclopropyl | | TFA | 395.4483 | 396.3 |
| 446 | CH | C(O) | 4-chloro-2-fluorophenyl | cyclopropyl | | TFA | 425.8864 | 426.20 |
| 447 | CH | C(O) | 5-chloro-2-fluorophenyl | cyclopropyl | | TFA | 425.8864 | 426.20 |
| 448 | CH | CHF | 2,4-difluorophenyl | cyclopropyl | | | 413.4388 | 414.30 |
| 449 | CH | CHF | 4-fluorophenyl | cyclopropyl | | | 395.4483 | 396.30 |
| 450 | CH | CF—(CH$_3$) | 2,4-difluorophenyl | cyclopropyl | | TFA | | |

Compound Table 1 (continued)

| Cpd | X | Z | Ar | R^e | R* | Salt | MSCalc | MSObs |
|---|---|---|---|---|---|---|---|---|
| 451 | CH | C(O) | morphiolin-4-yl | cyclopropyl | | TFA | 396.4364 | 397.2 |
| 452 | CH | CH₂ | 2,4-difluorophenyl | cyclopropyl | | TFA | | |
| 453 | CH | CHF | 5-chloro-2-fluorophenyl | cyclopropyl | | | 429.8934 | 430.25 |
| 454 | CH | CHF | 2,5-difluorophenyl | cyclopropyl | 7-CH₃ | | 427.4654 | 428.30 |
| 455 | CH | C(O) | 3-methoxyazetidin-1-yl | cyclopropyl | | TFA | | |
| 456 | CH | C(O) | 4-methylpiperazin-1-yl | cyclopropyl | | TFA | | |
| 457 | CH | C(O) | pyrrolidin-1-yl | cyclopropyl | | TFA | | |
| 458 | CH | C(O) | piperidin-1-yl | cyclopropyl | | TFA | | |
| 459 | CH | NH | 2,4-difluorophenyl | cyclopropyl | | TFA | 396.4364 | 397.3 |
| 460 | CH | C(CH₃)F | 5-chloro-2-fluorophenyl | cyclopropyl | | | 443.92 | 444.20 |
| 461 | CH | CHF | 2,5-difluorophenyl | cyclopropyl | | | 413.4388 | 414.20 |
| 464 | CH | CH₂ | 2,4-difluorophenyl | cyclopropyl | 7-Br | TFA | 474.3444 | 474.2/476.2 |
| 465 | CH | (S)—CHF | 2,5-difluorophenyl | cyclopropyl | 7-CH₃ | | 427.4654 | 428.3 |
| 468 | CH | O | 4-chloro-2-fluorophenyl | cyclopropyl | 7-CH₃ | TFA | 427.9023 | 428.20 |
| 474 | CH | CH₂ | 4-fluoro-2-oxopyridin-1-yl | cyclopropyl | 7-CH₃ | TF | 408.4719 | 409.3 |
| 476 | CH | H₂ | 2,4-difluorophenyl | cyclopropyl | 7-CN | | 420.4578 | 421.25 |
| 477 | CH | O | 2,4-difluorophenyl | cyclopropyl | 7-Cl | TFA | 431.8662 | 432.2 |
| 478 | CH | (R)—CHF | 2,5-difluorophenyl | cyclopropyl | 7-CH₃ | HCl | 427.4654 | 427.9 |
| 484 | CH | CH₂ | 2,4-difluorophenyl | cyclopropyl | 7-OCH₃ | TFA | 425.4743 | 426.3 |
| 487 | CH | CHF | 2,5-difluorophenyl | cyclopropyl | 8-Cl | TFA | 447.8839 | 448.2 |
| 489 | CH | CHF | 2,4-difluorophenyl | cyclopropyl | 7-CH₃ | TFA | 427.4654 | 428.30 |
| 490 | CH | CHF | 2,4-difluorophenyl | cyclopropyl | 7-Cl | TFA | 447.8839 | 448.2 |
| 491 | CH | CH₂ | 2,4-difluorophenyl | cyclopropyl | 7-OH | TFA | 411.4477 | 412.3 |
| 493 | CH | CHF | 2,4-difluorophenyl | cyclopropyl | 5-CH₃ | TFA | 427.4654 | 428.30 |
| 494 | CH | CH₂ | 2,4-difluorophenyl | cyclopropyl | 5-CH₃ | TFA | 409.4749 | 410.30 |
| 495 | CH | O | 2,4-difluorophenyl | cyclopropyl | 5-CH₃ | TFA | 411.4477 | 412.30 |
| 498 | CH | (R)—CHF | 2,4-difluorophenyl | cyclopropyl | 7-CH₃ | TFA | 427.4654 | 428.30 |
| 503 | CH | (S)—CHF | 2,4-difluorophenyl | cyclopropyl | 7-CH₃ | TFA | 427.4654 | 428.30 |
| 516 | CH | CHF | 2,4-difluorophenyl | cyclopropyl | 7-Br | TFA | 492.3348 | 492.2/494.2 |
| 517 | CH | (S)—CHF | 2,4-difluorophenyl | cyclopropyl | 5-CH₃ | TFA | 427.4654 | 428.3 |
| 518 | CH | (S)—CHF | 2,4-difluorophenyl | cyclopropyl | | TFA | 413.4388 | 414.3 |
| 520 | CH | CH₂ | 2,4-difluorophenyl | 2-methoxyethyl, | | TFA | 413.4636 | 414.3 |
| 521 | CH | CHF | 2,4-difluorophenyl | 2-methoxyethyl, | | TFA | 431.4541 | 432.2 |
| 524 | CH | (R)—CHF | 2,4-difluorophenyl | cyclopropyl | 7-Cl | TFA | 447.8839 | 448.2 |
| 525 | CH | (S)—CHF | 2,4-difluorophenyl | cyclopropyl | 7-Cl | TFA | 447.8839 | 448.2 |
| 526 | CH | O | 2,4-difluorophenyl | 2-methoxyethyl | | TFA | 415.4364 | 416.3 |
| 528 | CH | CH₂ | 5-fluoro-2-oxopyridin-1-yl | cyclopropyl | 5-CH₃ | | 408.4719 | 409.3 |
| 529 | CH | CH₂ | 4-chloro-2-oxopyridin-1-yl | cyclopropyl | 5-CH₃ | | 424.9265 | 425.2 |

Compound Table 1

| Cpd | X | Z | Ar | R$^e$ | R* | Salt | MSCalc | MSObs |
|---|---|---|---|---|---|---|---|---|
| 531 | CH | CH$_3$ | 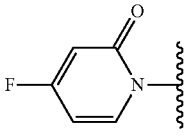 [SMILES: *n1ccc(F)cc1=O] | cyclopropyl | | | 394.4453 | 395.3 |
| 532 | CH | CH$_2$ | 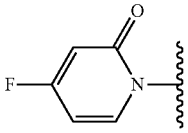 [SMILES: *n1ccc(F)cc1=O] | cyclopropyl | 5-CH$_3$ | | 408.4719 | 409.3 |
| 533 | CH | CH$_2$ | 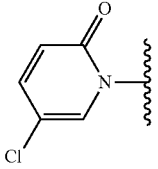 [SMILES: *n1cc(Cl)ccc1=O] | cyclopropyl | | | 410.8999 | 411.2 |
| 535 | CH | CF$_2$ | 5-chloro-2-fluorophenyl | cyclopropyl | 7-CH$_3$ | | 461.9104 | 462.2 |
| 537 | CH | CF$_2$ | 5-chloro-2-fluorophenyl | cyclopropyl | 5-CH$_3$ | | 461.9104 | 462.2 |
| 538 | CH | CH$_2$ | 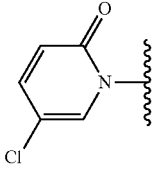 [SMILES: *n1cc(Cl)ccc1=O] | cyclopropyl | 5-CH$_3$ | | 424.9265 | 425.2 |
| 539 | CH | CH$_2$ | 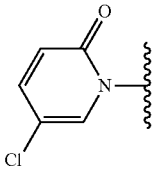 [SMILES: *n1cc(Cl)ccc1=O] | cyclopropyl | 7-CH$_3$ | | 424.9265 | 425.3 |
| 540 | CH | CF$_2$ | 5-chloro-2-fluorophenyl | cyclopropyl | | | 447.8839 | 448.2 |
| 541 | CH | CF$_2$ | 2,5-difluorophenyl | cyclopropyl | | | 431.4293 | 432.2 |
| 542 | CH | CF$_2$ | 2,5-difluorophenyl | cyclopropyl | 7-CH$_3$ | | 445.4558 | 446.3 |
| 543 | CH | (R)—CHF | 2,4-difluorophenyl | cyclopropyl | 7-CH$_3$ | | | |
| 544 | CH | CF$_2$ | 2,4-difluorophenyl | cyclopropyl | 5-CH$_3$ | | 445.4558 | 446.2 |
| 545 | CH | CF$_2$ | 2,5-difluorophenyl | cyclopropyl | 5-CH$_3$ | | 445.4558 | 446.3 |
| 547 | CH | CF$_2$ | 2,4-difluorophenyl | cyclopropyl | | | 431.4293 | 432.2 |
| 549 | CH | (S)—CHF | 2,4-difluorophenyl | cyclopropyl | 7-CN | | 438.178 | 439.3 |
| 550 | CH | (R)—CHF | 2,4-difluorophenyl | cyclopropyl | 7-CN | | 438.178 | 439.2 |
| 553 | CH | O | pyridin-3-yl | cyclopropyl | | | 362.1855 | 363.2 |
| 554 | CH | O | 4-methoxyphenyl | cyclopropyl | | | 391.2008 | 392.3 |
| 555 | CH | O | pyridin-2-yl | cyclopropyl | | | 362.1855 | 363.2 |
| 556 | CH | O | pyridin-4-yl | cyclopropyl | | | 362.1855 | 363.2 |
| 557 | CH | C(O) | 2-methoxyphenyl | cyclopropyl | | TFA | 403.2008 | 404.3 |
| 558 | CH | O | 4-cyanophenyl | cyclopropyl | | | 386.1855 | 387.2 |
| 559 | CH | C(O) | 2-chlorophenyl | cyclopropyl | | TFA | 407.1513 | 408.2 |
| 560 | CH | O | 3-methoxyphenyl | cyclopropyl | | TFA | 391.2008 | 392.3 |
| 561 | CH | O | 2-methoxyphenyl | cyclopropyl | | TFA | 391.2008 | 392.3 |
| 562 | CH | C(O) | phenyl | cyclopropyl | | | 373.1903 | 374.2 |
| 563 | CH | C(O) | 2,3-difluorophenyl | cyclopropyl | | TFA | 409.1714 | 410.2 |
| 564 | CH | C(O) | 3-chlorophenyl | cyclopropyl | | | 407.1513 | 408.2 |
| 565 | CH | O | 3-cyanophenyl | cyclopropyl | | | 386.1855 | 387.3 |
| 566 | CH | C(O) | 3-methoxyphenyl | cyclopropyl | | | 403.2008 | 404.3 |
| 567 | CH | C(O) | 2-mehylphenyl | cyclopropyl | | TFA | 387.2059 | 388.3 |
| 568 | CH | C(O) | 2,6-difluorophenyl | cyclopropyl | | TFA | 409.1714 | 410.3 |
| 569 | CH | C(O) | 2-chloro-5-fluorophenyl | cyclopropyl | | TFA | 425.1419 | 426.2 |
| 570 | CH | C(O) | 3-fluorophenyl | cyclopropyl | | TFA | 391.1808 | 392.3 |
| 571 | CH | C(O) | 2,3-difluoro-6- | cyclopropyl | | TFA | 443.877 | 444.2 |

Compound Table 1

| Cpd | X | Z | Ar | R$^e$ | R* | Salt | MSCalc | MSObs |
|---|---|---|---|---|---|---|---|---|
| 572 | CH | C(O) | 2-fluoro-4-chlorophenyl methoxyphenyl | cyclopropyl | | TFA | 409.457 | 410.2 |
| 573 | CH | C(O) | 3-fluoro-2-chlorophenyl | cyclopropyl | | HCl | 425.886 | 426.2 |
| 574 | CH | C(O) | 5-chlorothien-3-yl | cyclopropyl | | HCl | 413.924 | 414.2 |
| 575 | CH | C(O) | thien-2-yl | cyclopropyl | | TFA | 379.479 | 380.2 |
| 576 | CH | O | 2-cyanophenyl | cyclopropyl | | | 386.449 | 387.2 |
| 577 | CH | C(O) | 2-fluoro-6-chlorophenyl | cyclopropyl | | | 425.886 | 426.2 |
| 578 | CH | C(O) | 3-cyanophenyl | cyclopropyl | | TFA | 398.460 | 399.3 |
| 579 | CH | (S)—CHF | 2,4-difluorophenyl | cyclopropyl | 7-C(O)N(CH$_3$)$_2$ | TFA | 484.540 | 485.3 |
| 580 | CH | (R)—CHF | 2,4-difluorophenyl | cyclopropyl | 7-C(O)N(CH$_3$)$_2$ | TFA | 484.540 | 485.3 |
| 581 | CH | (S)—CHF | 2,4-difluorophenyl | cyclopropyl | 5-C(O)morpholin-4-yl | TFA | 526.5734 | 527.3 |
| 582 | CH | (R)—CHF | 2,4-difluorophenyl | cyclopropyl | 5-C(O)morpholin-4-yl | TFA | 526.5734 | 527.3 |
| 583 | CH | C(O) | 2-thiomethoxyphenyl | cyclopropyl | | TFA | 419.543 | 420.3 |
| 584 | CH | O | 4-(1-oxoethyl)phenyl | cyclopropyl | | TFA | 403.497 | 404.2 |
| 585 | CH | O | 4-(1-hydroxyethyl)phenyl | cyclopropyl | | TFA | 405.5128 | 406.3 |
| 586 | CH | C(O) | thien-3-yl | cyclopropyl | | TFA | 379.479 | 380.2 |
| 587 | CH | C(O) | 2-bromophenyl | cyclopropyl | | TFA | 451.367 | 452.1 |
| 588 | CH | C(O) | 2-bromopyrid-3-yl | cyclopropyl | | TFA | 453.355 | 453.2/455.2 |
| 589 | CH | C(O) | 2-fluoro-5-cyanophenyl | cyclopropyl | | TFA | 416.451 | 417.3 |
| 590 | CH | O | 4-(N,N-dimethylamide)phenyl | cyclopropyl | | TFA | 432.554 | 433.3 |
| 591 | CH | (R)—CHF | 2,4-difluorophenyl | cyclopropyl | 7-C(O)azetidin-1-yl | TFA | 496.527 | 497.3 |
| 592 | CH | (R)—CHF | 2,4-difluorophenyl | cyclopropyl | 7-C(O)(4-fluoroazetidin-1-yl) | | 514.5178 | 515.3 |
| 593 | CH | (S)—CHF | 2,4-difluorophenyl | cyclopropyl | 7-C(O)azetidin-1-yl | TFA | 496.527 | 497.3 |
| 594 | CH | CH$_2$ | 2,4-difluorophenyl | cyclopropyl | 7-Cl | | 429.893 | 430.3 |
| 595 | CH | C(O) | 6-fluoro-3-thiomethyoxyphenyl | cyclopropyl | | TFA | 437.553 | 438.3 |
| 597 | CH | C(O) | 6-chloro-3-cyanophenyl | cyclopropyl | 7-Cl | | 467.3505 | 467.2 |
| 598 | CH | C(O) | 2-(N,N-dimethylamide)-5-cyanophenyl | cyclopropyl | 7-C(O)N(CH$_3$)$_2$ | | 540.616 | 541.3 |
| 599 | CH | O | 2,4-difluorophenyl | cyclopropyl | 7-C(O)N(CH$_3$)$_2$ | | 468.499 | 469.3 |
| 602 | CH | O | 4-thiomethyoxyphenyl | cyclopropyl | | TFA | 407.552 | 408.3 |
| 603 | CH | O | 4-ethyoxyphenyl | cyclopropyl | | TFA | 405.513 | 406.3 |
| 604 | CH | C(O) | 6-fluoro-3-cyanophenyl | cyclopropyl | 7-C(O)(4-methylpiperazin-1-yl) | TFA | 495.346 | 495.2/497.2 |
| 606 | CH | O | 2-fluoro-4-methoxyphenyl | cyclopropyl | 5-C(O)N(CH$_3$)$_2$ | | 480.555 | 481.4 |
| 607 | CH | C(O) | 2-fluoro-4-methoxyphenyl | cyclopropyl | 5-CN | TFA | 434.489 | 435.3 |
| 608 | CH | C(O) | 2-fluoro-4-methoxyphenyl | cyclopropyl | 5-(morpholin-4-yl) | TFA | 494.581 | 495.4 |
| 610 | N | C(O) | 3-fluoro-6-chlorophenyl | cyclopropyl | 7-C(O)N(CH$_3$)$_2$ | | 497.952 | 498.3 |
| 612 | CH | O | 2-fluoro-4-methoxyphenyl | cyclopropyl | 5-(morpholin-4-yl) | TFA | 522.591 | 523.4 |
| 613 | N | CH$_2$ | 2-fluoro-4-methoxyphenyl | cyclopropyl | 7-(morpholin-4-yl) | TFA | 509.570 | 510.4 |

-continued

Compound Table 1

| Cpd | X | Z | Ar | R$^e$ | R* | Salt | MSCalc | MSObs |
|---|---|---|---|---|---|---|---|---|
| 614 | N | CH$_2$ | 2,4-difluorophenyl | cyclopropyl | 5-CN | TFA | 421.465 | 422.3 |
| 615 | N | CH$_2$ | 2-fluoro-4-methoxyphenyl | cyclopropyl | 5-CN | TFA | 433.501 | 434.4 |
| 616 | N | CH$_2$ | 2-fluoro-4-methoxyphenyl | cyclopropyl | 7-C(O)N(CH$_3$)$_2$ | TFA | 479.569 | 480.4 |
| 631 | CH | O | 2-fluoro-4-chlorophenyl | isopropyl | 7-C(O)N(CH$_3$)$_2$ | TFA | 486.989 | 487.3 |
| 632 | CH | C(O) | 3,5-difluorophenyl | isopropyl | 7-CN | TFA | 436.478 | 437.3 |
| 635 | N | CH$_2$ | 2,4-difluorophenyl | isopropyl | 7-C(O)N(CH$_3$)$_2$ | TFA | 469.551 | 470.4 |
| 636 | CH | C(O) | 3,5-difluorophenyl | isopropyl | 7-C(O)N(CH$_3$)$_2$ | TFA | 482.545 | 483.4 |
| 637 | CH | CH$_2$ | 2-fluoro-4-methoxyphenyl | isopropyl | 7-CN | TFA | 434.529 | 435.4 |
| 646 | CH | O | 2,4-difluorophenyl | tert-butyl | 7-CN |  | 438.473 | 439.4 |
| 647 | CH | O | 2-fluoro-4-hydroxyphenyl | isopropyl |  | TFA | 398.434 | 493.8 |
| 648 | CH | O | 2,4-difluorophenyl | 2,2-difluoroethyl | 7-C(O)N(CH$_3$)$_2$ | TFA | 492.469 | 493.8 |
| 653 | CH | SO$_2$ | 4-fluorophenyl | cyclopropyl | 7-CH$_3$ | TFA | 441.522 | 442.9 |

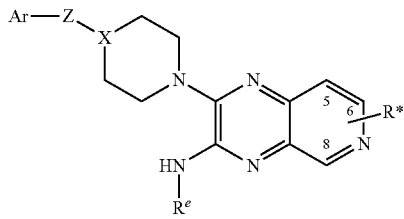

| Cpd | X | Z | Ar | R$^e$ | R* | Salt | MSCalc | MSObs |
|---|---|---|---|---|---|---|---|---|
| 291 | N | CH$_2$ | 2,5-difluorophenyl | cyclopropyl |  | TFA | 396.4364 | 397.3 |
| 292 | N | CH$_2$ | 2,5-dichlorophenyl | cyclopropyl |  | TFA | 429.3456 | 429.2 |
| 303 | N | C(O) | 4-chlorophenyl | cyclopropyl |  | TFA | 408.884 | 409.3 |
| 309 | N | SO$_2$ | 4-fluorophenyl | cyclopropyl |  | TFA | 428.4832 | 429.2 |
| 355 | N | CH$_2$ | 2,4,5-trifluorophenyl | cyclopropyl |  | TFA | 414.4268 | 415.3 |
| 356 | N | CH$_2$ | 2,4-difluorophenyl | cyclopropyl |  | TFA | 396.4364 | 397.3 |
| 363 | N | CH$_2$ | 2,4-difluorophenyl | 2,2-difluoroethyl |  | TFA | 420.4066 | 421.2 |
| 364 | N | CH$_2$, | 2,4,5-trifluorophenyl | 2,2 difluoroethyl |  | TFA | 438.3971 | 439.2 |
| 369 | N | CH$_2$ | 2,4,5-trifluorophenyl | pyridin-3-yl |  | TFA | 451.447 | 452.3 |
| 390 | N | CH$_2$ | 2,5-difluorophenyl | pyridin-3-yl | 6-CN | TFA | 433.4565 | 434.25 |
| 397 | N | CH$_2$ | 2,4-difluorophenyl | cyclopropyl | 6-Br | TFA | 475.3325 | 475.2/477.2 |
| 398 | N | CH$_2$ | 2,4-difluorophenyl | cyclopropyl | 6-CN | TFA | 421.4458 | 422.25 |
| 426 | CH | CH$_2$ | 2,4-difluorophenyl | cyclopropyl |  | TFA | 395.4483 | 396.3 |
| 427 | CH | CH$_2$ | 2,4-difluorophenyl | 2,2-difluoroethyl |  |  | 419.4185 | 320.3 |
| 439 | CH | CH$_2$ | 2,4-difluorophenyl | cyclopropyl | 6-CH$_3$ | TFA | 409.4749 | 410.3 |
| 551 | CH | (S)—CHF | 2,4-difluorophenyl | cyclopropyl | 6-CN |  | 438.178 | 439.2 |
| 552 | CH | (R)—CHF | 2,4-difluorophenyl | cyclopropyl | 6-CN |  | 438.178 | 439.2 |
| 611 | CH | O | 2-fluoro-4-methoxyphenyl | cyclopropyl |  | TFA | 409.477 | 410.3 |
| 617 | CH | O | 2-fluoro-4-hydroxyphenyl | cyclopropyl |  | TFA | 395.450 | 396.3 |
| 618 | CH | O | 2-fluoro-4-methoxyphenyl | isopropyl |  | TFA | 411.473 | 412.3 |
| 621 | CH | O | 2,4-difluorophenyl | isopropyl |  | TFA | 399.457 | 400.3 |
| 622 | CH | CHF | 2,4-difluorophenyl | isopropyl |  | TFA | 415.474 | 416.3 |
| 623 | CH | O | 2-fluoro-4-methoxyphenyl | ethyl |  | TFA | 397.466 | 398.3 |
| 655 | CH | O | 2,4-difluorophenyl | isopropyl |  |  | 399.437 | 400.0 |
| 656 | CH | O | 2,4-difluorophenyl | cyclobutyl |  |  | 411.448 | 412.0 |

Compound Table 1

| Cpd | X | Z | Ar | R$^e$ | R* | Salt | MSCalc | MSObs |
|---|---|---|---|---|---|---|---|---|

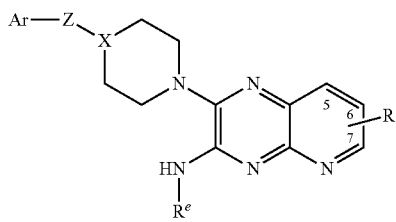

| 2 | N | CH$_2$ | 3-methylphenyl | cyclopropyl | | TFA | 374.482 | 375.3 |
| 22 | N | CH$_2$ | 3-chlorophenyl | phenyl | | TFA | 430.9326 | 431.25 |
| 44 | N | CH$_2$ | 2,5-dichlorophenyl | cyclopropyl | | TFA | 429.3456 | 429.2 |

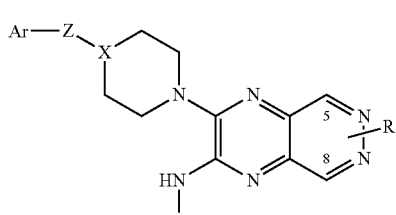

| 392 | N | CH$_2$ | 2,4-difluorophenyl | cyclopropyl | | TFA | 397.4244 | 398.25 |
| 452 | CH | CH$_2$ | 2,4-difluorophenyl | cyclopropyl | | TFA | 396.4364 | 397.2 |
| 596 | CH | (S)—CHF | 2,4-difluorophenyl | cyclopropyl | | TFA | 414.455 | 415.3 |
| 600 | CH | O | 2-fluoro-4-methoxyphenyl | cyclopropyl | | TFA | 410.469 | 411.3 |
| 601 | CH | (R)—CHF | 2,4-difluorophenyl | cyclopropyl | | TFA | 414.455 | 415.3 |
| 605 | CH | O | 2-fluoro-4-methoxyphenyl | cyclopropyl | | | 535.633 | 536.4 |
| 619 | CH | O | 2-fluoro-4-thiomethoxyphenyl | cyclopropyl | | TFA | 426.530 | 427.3 |
| 620 | CH | O | 2,4-difluorophenyl | cyclopropyl | | TFA | 398.429 | 399.3 |
| 624 | CH | O | 2-fluoro-4-hydroxyphenyl | cyclopropyl | | TFA | 396.418 | 397.3 |
| 625 | CH | O | 2-fluoro-4-methoxyphenyl | isopropyl | | TFA | 412.848 | 413.4 |
| 626 | CH | O | 2-fluoro-4-cyanophenyl | cyclopropyl | | TFA | 404.460 | 405.3 |
| 633 | CH | O | 2,4-difluorophenyl | isopropyl | | TFA | 400.445 | 401.3 |
| 634 | CH | CHF | 2,4-difluorophenyl | isopropyl | | TFA | 416.462 | 417.3 |
| 638 | CH | O | 2-fluoro-4-methoxyphenyl | (S)-sec-butyl | | TFA | 426.507 | 427.0 |
| 639 | CH | O | 2-fluoro-4-methoxyphenyl | (R)-sec-butyl | | TFA | 426.507 | 427.0 |
| 640 | CH | O | 2-fluoro-4-cyanophenyl | isopropyl | | TFA | 406.464 | 407.9 |
| 641 | CH | (R)—CHF | 2,4-difluorophenyl | isopropyl | | TFA | 415.463 | 416.9 |
| 642 | CH | C(O) | 2-fluoro-4-methoxyphenyl | isopropyl | | TFA | 424.491 | 425.0 |
| 643 | CH | CH$_2$ | 2-fluoro-4-methoxyphenyl | isopropyl | | TFA | 410.508 | 411.0 |
| 644 | CH | O | 2-fluoro-4-chlorophenyl | isopropyl | | TFA | 415.899 | 416.9 |
| 645 | CH | (R)—CHF | 2,4-difluorophenyl | 2-methylcyclopropyl | | TFA | 428.473 | 429.0 |
| 647 | CH | O | 2-fluoro-4-hydroxyphenyl | isopropyl | | TFA | 398.434 | 493.8 |
| 649 | N | CH$_2$ | 3-methoxyphenyl | isopropyl | | TFA | 399.440 | 400.0 |
| 650 | CH | O | 3-methoxyphenyl | isopropyl | | TFA | 397.470 | 395.0 |
| 651 | CH | O | 2,4-difluorophenyl | isopropyl | 5-CH$_3$ 7-CH$_3$ | TFA | 428.478 | 428.9 |
| 652 | CH | O | 2,4-difluorophenyl | isopropyl | 7-CH$_3$ | TFA | 414.452 | 415.0 |
| 654 | CH | O | 2-fluoro-4-chlorophenyl | cyclopropyl | | TFA | 414.864 | 414.9 |
| 657 | CH | O | 2-fluoro-4-fluoromethoxyphenyl | isopropyl | | TFA | 430.451 | 430.9 | and are named as

N-cyclopropyl-3-(4-(3-methylbenzyl)piperazin-1-yl)quinoxalin-2-amine, 2,2,2-trifluoroacetic acid salt
N-cyclopropyl-2-(4-(3-methylbenzyl)piperazin-1-yl)pyrido[2,3-b]pyrazin-3-amine, 2,2,2-trifluoroacetic acid salt
N-cyclopropyl-3-(4-(3-methylbenzyl)piperazin-1-yl)pyrido[2,3-b]pyrazin-2-amine
(4-(3-(cyclopropylamino)quinoxalin-2-yl)piperazin-1-yl)(3-(trifluoromethyl)phenyl)methanone, 2,2,2-trifluoroacetic acid salt
3-(4-(4-chlorobenzyl)piperazin-1-yl)-N-cyclopropylquinoxalin-2-amine, 2,2,2-trifluoroacetic acid salt
(4-(3-(cyclopropylamino)quinoxalin-2-yl)piperazin-1-yl)(4-(methylsulfonyl)phenyl)methanone, 2,2,2-trifluoroacetic acid salt
(4-(3-(cyclopropylamino)quinoxalin-2-yl)piperazin-1-yl)(2,5-dichlorophenyl)methanone, 2,2,2-trifluoroacetic acid salt
(4-(3-(cyclopropylamino)quinoxalin-2-yl)piperazin-1-yl)(3,4-dichlorophenyl)methanone, 2,2,2-trifluoroacetic acid salt
(3-chloro-4-methoxyphenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(3,5-dichlorophenyl)methanone, 2,2,2-trifluoroacetic acid salt
(3-chlorophenyl)(4-(3-(cyclopropylamino)quinoxalin-2-yl)piperazin-1-yl)methanone, 2,2,2-trifluoroacetic acid salt
(4-chlorophenyl)(4-(3-(cyclopropylamino)quinoxalin-2-yl)piperazin-1-yl)methanone, 2,2,2-trifluoroacetic acid salt
N-cyclopropyl-3-(4-(pyridin-3-ylmethyl)piperazin-1-yl)quinoxalin-2-amine, 2,2,2-trifluoroacetic acid salt
(4-(3-(cyclopropylamino)quinoxalin-2-yl)piperazin-1-yl)(2,3-dichlorophenyl)methanone, 2,2,2-trifluoroacetic acid salt
(2-chlorophenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(m-tolyl)methanone, 2,2,2-trifluoroacetic acid salt
N-cyclopropyl-3-(4-(pyridin-4-ylmethyl)piperazin-1-yl)quinoxalin-2-amine, 2,2,2-trifluoroacetic acid salt
N-cyclopropyl-3-(4-(3-(trifluoromethyl)benzyl)piperazin-1-yl)quinoxalin-2-amine, 2,2,2-trifluoroacetic acid salt
3-(4-(4-chlorobenzyl)piperazin-1-yl)-N-cyclopropylquinoxalin-2-amine, 2,2,2-trifluoroacetic acid salt
N-cyclopropyl-3-(4-(pyridin-2-ylmethyl)piperazin-1-yl)quinoxalin-2-amine, 22,2,2-trifluoroacetic acid salt
N-(4-bromophenyl)-3-(4-(3-chlorobenzyl)piperazin-1-yl)quinoxalin-2-amine, 2,2,2-trifluoroacetic acid salt
2-(4-(3-chlorobenzyl)piperazin-1-yl)-N-phenylpyrido[2,3-b]pyrazin-3-amine, 2,2,2-trifluoroacetic acid salt
3-(4-(3-chlorobenzyl)piperazin-1-yl)-N-phenylpyrido[2,3-b]pyrazin-2-amine, 2,2,2-trifluoroacetic acid salt
3-(4-(3-chlorobenzyl)piperazin-1-yl)-N-phenylquinoxalin-2-amine, 2,2,2-trifluoroacetic acid salt
3-(4-(3-chlorobenzyl)piperazin-1-yl)-N-(4-(trifluoromethoxy)phenyl)quinoxalin-2-amine, 2,2,2-trifluoroacetic acid salt
3-(4-(3-chlorobenzyl)piperazin-1-yl)-N-(4-propylphenyl)quinoxalin-2-amine, 2,2,2-trifluoroacetic acid salt
(4-(3-(cyclopropylamino)quinoxalin-2-yl)piperazin-1-yl)(4-(trifluoromethyl)phenyl)methanone, 2,2,2-trifluoroacetic acid salt
3-(4-(2-chlorobenzyl)piperazin-1-yl)-N-cyclopropylquinoxalin-2-amine, 2,2,2-trifluoroacetic acid salt
N-cyclopropyl-3-(4-(4-(methylsulfonyl)benzyl)piperazin-1-yl)quinoxalin-2-amine, 2,2,2-trifluoroacetic acid salt
3-(4-(3-chlorobenzyl)piperazin-1-yl)-N-(p-tolyl)quinoxalin-2-amine, 2,2,2-trifluoroacetic acid salt
3-(4-(3-chlorobenzyl)piperazin-1-yl)-N-(4-methoxyphenyl)quinoxalin-2-amine, 2,2,2-trifluoroacetic acid salt
3-(4-(3-chlorobenzyl)piperazin-1-yl)-N-(2-methoxyphenyl)quinoxalin-2-amine, 2,2,2-trifluoroacetic acid salt
N-cyclopropyl-3-(4-(2,5-dichlorobenzyl)piperazin-1-yl)quinoxalin-2-amine, 2,2,2-trifluoroacetic acid salt
N-cyclopropyl-3-(4-(4-(trifluoromethyl)benzyl)piperazin-1-yl)quinoxalin-2-amine, 2,2,2-trifluoroacetic acid salt
3-(4-(3-chlorobenzyl)piperazin-1-yl)-N-(3-methoxyphenyl)quinoxalin-2-amine, 2,2,2-trifluoroacetic acid salt
N-(4-(tert-butyl)phenyl)-3-(4-(3-chlorobenzyl)piperazin-1-yl)quinoxalin-2-amine, 2,2,2-trifluoroacetic acid salt
3-(4-(3-chlorobenzyl)piperazin-1-yl)-N-(4-isopropoxyphenyl)quinoxalin-2-amine, 2,2,2-trifluoroacetic acid salt
3-(4-(3-chlorobenzyl)piperazin-1-yl)-N-(4-fluorophenyl)quinoxalin-2-amine, 2,2,2-trifluoroacetic acid salt
(4-(3-(cyclopentylamino)quinoxalin-2-yl)piperazin-1-yl)(2,5-dichlorophenyl)methanone, 2,2,2-trifluoroacetic acid salt
N-cyclopentyl-3-(4-(2,5-dichlorobenzyl)piperazin-1-yl)quinoxalin-2-amine, 2,2,2-trifluoroacetic acid salt
(2,5-dichlorophenyl)(4-(3-(phenylamino)quinoxalin-2-yl)piperazin-1-yl)methanone, 2,2,2-trifluoroacetic acid salt
N-(cyclopropylmethyl)-3-(4-(2,5-dichlorobenzyl)piperazin-l-yl)quinoxalin-2-amine, 2,2,2-trifluoroacetic acid salt -continued 3-(4-(2,5-dichlorobenzyl)piperazin-1-yl)-N-phenylquinoxalin-2-amine, 2,2,2-trifluoroacetic acid salt
N-cyclopropyl-2-(4-(2,5-dichlorobenzyl)piperazin-1-yl)pyrido[2,3-b]pyrazin-3-amine, 2,2,2-trifluoroacetic acid salt
7-bromo-N-cyclopropyl-3-(4-(2,5-dichlorobenzyl)piperazin-1-yl)quinoxalin-2-amine, 2,2,2-trifluoroacetic acid salt
6-bromo-N-cyclopropyl-3-(4-(2,5-dichlorobenzyl)piperazin-1-yl)quinoxalin-2-amine, 2,2,2-trifluoroacetic acid salt
mixture of N-cyclopropyl-3-(4-(2,5-dichlorobenzyl)piperazin-1-yl)-7-methoxyquinoxalin-2-amine, 2,2,2-trifluoroacetic acid salt and
N-cyclopropyl-3-(4-(2,5-dichlorobenzyl)piperazin-1-yl)-7-methoxyquinoxalin-2-amine, 2,2,2-trifluoroacetic acid salt
N-cyclopropyl-3-(4-(2,3-dichlorobenzyl)piperazin-1-yl)quinoxalin-2-amine, 2,2,2-trifluoroacetic acid salt
N-cyclopropyl-3-(4-(2,4-dichlorobenzyl)piperazin-1-yl)quinoxalin-2-amine, 2,2,2-trifluoroacetic acid salt
N-cyclopropyl-3-(4-(2,6-dichlorobenzyl)piperazin-1-yl)quinoxalin-2-amine, 2,2,2-trifluoroacetic acid salt
N-(3-bromophenyl)-3-(4-(3-chlorobenzyl)piperazin-1-yl)quinoxalin-2-amine, 2,2,2-trifluoroacetic acid salt
N-(2-bromophenyl)-3-(4-(3-chlorobenzyl)piperazin-1-yl)quinoxalin-2-amine, 2,2,2-trifluoroacetic acid salt
3-(4-(3-chlorobenzyl)piperazin-1-yl)-N-(pyridin-3-yl)quinoxalin-2-amine, 2,2,2-trifluoroacetic acid salt
(4-(3-(cyclopropylamino)quinoxalin-2-yl)piperazin-1-yl)(2,5-dichlorothiophen-3-yl)methanone
mixture of N-cyclopropyl-3-(4-(2,5-dichlorobenzyl)piperazin-1-yl)-7-fluoroquinoxalin-2-amine and
N-cyclopropyl-3-(4-(2,5-dichlorobenzyl)piperazin-1-yl)-7-fluoroquinoxalin-2-amine
3-(4-(2,5-dichlorobenzyl)piperazin-1-yl)-N-(3-methoxyphenyl)quinoxalin-2-amine
3-(4-(2,5-dichlorobenzyl)piperazin-1-yl)-N-(4-methoxyphenyl)quinoxalin-2-amine
4-((3-(4-(2,5-dichlorobenzyl)piperazin-1-yl)quinoxalin-2-yl)amino)benzonitrile
2-(cyclopropylamino)-3-(4-(2,5-dichlorobenzyl)piperazin-1-yl)quinoxaline-6-carbonitrile
3-(4-(2,5-dichlorobenzyl)piperazin-1-yl)-N-(2-methoxyphenyl)quinoxalin-2-amine
3-(4-(2,5-dichlorobenzyl)piperazin-1-yl)-N-(4-fluorophenyl)quinoxalin-2-amine
N-cyclopropyl-3-(4-(1-(2,5-dichlorophenyl)ethyl)piperazin-1-yl)quinoxalin-2-amine, 2,2,2-trifluoroacetic acid salt
N-cyclopropyl-3-(4-(2,5-dichlorobenzyl)piperazin-1-yl)pyrido[2,3-b]pyrazin-2-amine
N-(4-bromophenyl)-3-(4-(2,5-dichlorobenzyl)piperazin-1-yl)quinoxalin-2-amine
3-(4-(3-bromobenzyl)piperazin-1-yl)-N-cyclopropylquinoxalin-2-amine
3-(4-(2,5-dichlorobenzyl)piperazin-1-yl)-N-(3-methoxypropyl)quinoxalin-2-amine
(2-chloro-4-(methylsulfonyl)phenyl)(4-(3-(cyclopropylamino)quinoxalin-2-yl)piperazin-1-yl)methanone
(4-(3-(cyclopropylamino)quinoxalin-2-yl)piperazin-1-yl)(3,6-dichloropyridin-2-yl)methanone
benzofuran-3-yl(4-(3-(cyclopropylamino)quinoxalin-2-yl)piperazin-1-yl)methanone, 2,2,2-trifluoroacetic acid salt
3-(4-(3-chlorobenzyl)piperazin-1-yl)-N-(pyridin-4-yl)quinoxalin-2-amine, 2,2,2-trifluoroacetic acid salt
N-(3-(4-(3-chlorobenzyl)piperazin-1-yl)quinoxalin-2-yl)-1,3,4-thiadiazol-2-amine, 2,2,2-trifluoroacetic acid salt
(4-(3-(cyclopropylamino)quinoxalin-2-yl)piperazin-1-yl)(3,4-dimethylphenyl)methanone, 2,2,2-trifluoroacetic acid salt
2,2,2-trifluoroacetic acid, N-cyclopropyl-3-(4-(3,4-dimethylbenzyl)piperazin-1-yl)quinoxalin-2-amine salt
(4-(3-(cyclopropylamino)quinoxalin-2-yl)piperazin-1-yl)(2,4-dichlorophenyl)methanone, 2,2,2-trifluoroacetic acid salt
4-(4-(3-(cyclopropylamino)quinoxalin-2-yl)piperazine-1-carbonyl)benzonitrile, 2,2,2-trifluoroacetic acid salt
4-((4-(3-(cyclopropylamino)quinoxalin-2-yl)piperazin-1-yl)methyl)benzonitrile, 2,2,2-trifluoroacetic acid salt
(4-(3-(cyclopropylamino)quinoxalin-2-yl)piperazin-1-yl)(4-ethylphenyl)methanone, 2,2,2-trifluoroacetic acid salt
N-cyclopropyl-3-(4-(4-ethylbenzyl)piperazin-1-yl)quinoxalin-2-amine, 2,2,2-trifluoroacetic acid salt
N-cyclopropyl-3-(4-(3,4-dichlorobenzyl)piperazin-1-yl)quinoxalin-2-amine, 2,2,2-trifluoroacetic acid salt
(4-(3-(cyclopropylamino)quinoxalin-2-yl)piperazin-1-yl)(2,5-difluorophenyl)methanone, 2,2,2-trifluoroacetic acid salt
N-cyclopropyl-3-(4-(2,5-difluorobenzyl)piperazin-1-yl)quinoxalin-2-amine, 2,2,2-trifluoroacetic acid salt
(4-(3-(cyclopropylamino)quinoxalin-2-yl)piperazin-1-yl)(naphthalen-2-yl)methanone, 2,2,2-trifluoroacetic acid salt
N-cyclopropyl-3-(4-(naphthalen-2-ylmethyl)piperazin-1-yl)quinoxalin-2-amine, 2,2,2-trifluoroacetic acid salt
(4-(tert-butyl)phenyl)(4-(3-(cyclopropylamino)quinoxalin-2-yl)piperazin-1-yl)methanone, 2,2,2-trifluoroacetic acid salt
(2-bromo-5-methoxyphenyl)(4-(3-(cyclopropylamino)quinoxalin-2-yl)piperazin-1-yl)methanone, 2,2,2-trifluoroacetic acid salt
(3-bromo-4-methoxyphenyl)(4-(3-(cyclopropylamino)quinoxalin-2-yl)piperazin-1-yl)methanone, 2,2,2-trifluoroacetic acid salt
(4-bromo-2-chlorophenyl)(4-(3-(cyclopropylamino)quinoxalin-2-yl)piperazin-1-yl)methanone, 2,2,2-trifluoroacetic acid salt -continued (4-(3-(cyclopropylamino)quinoxalin-2-yl)piperazin-1-yl)(5-fluoro-2-methylphenyl)methanone, 2,2,2-trifluoroacetic acid salt
(3-bromo-4-fluorophenyl)(4-(3-(cyclopropylamino)quinoxalin-2-yl)piperazin-1-yl)methanone, 2,2,2-trifluoroacetic acid salt
(4-bromo-2-fluorophenyl)(4-(3-(cyclopropylamino)quinoxalin-2-yl)piperazin-1-yl)methanone, 2,2,2-trifluoroacetic acid salt
(5-bromo-2-fluorophenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(4-ethoxyphenyl)methanone, 2,2,2-trifluoroacetic acid salt
(4-(3-(cyclopropylamino)quinoxalin-2-yl)piperazin-1-yl)(3-isopropylphenyl)methanone, 2,2,2-trifluoroacetic acid salt
3-(4-(4-bromobenzyl)piperazin-1-yl)-N-cyclopropylquinoxalin-2-amine, 2,2,2-trifluoroacetic acid salt
3-((4-(3-(cyclopropylamino)quinoxalin-2-yl)piperazin-1-yl)methyl)benzonitrile, 2,2,2-trifluoroacetic acid salt
N-cyclopropyl-3-(4-(4-fluorobenzyl)piperazin-1-yl)quinoxalin-2-amine, 2,2,2-trifluoroacetic acid salt
N-cyclopropyl-3-(4-(4-isopropylbenzyl)piperazin-1-yl)quinoxalin-2-amine, 2,2,2-trifluoroacetic acid salt
(4-(3-(cyclopropylamino)quinoxalin-2-yl)piperazin-1-yl)(5-methylisoxazol-3-yl)methanone
N-cyclopropyl-3-(4-((2,5-dichlorothiophen-3-yl)methyl)piperazin-1-yl)quinoxalin-2-amine, 2,2,2-trifluoroacetic acid salt
3-(4-(benzofuran-3-ylmethyl)piperazin-1-yl)-N-cyclopropylquinoxalin-2-amine
N-cyclopropyl-3-(4-((3,6-dichloropyridin-2-yl)methyl)piperazin-1-yl)quinoxalin-2-amine, 2,2,2-trifluoroacetic acid salt
cyclohexyl(4-(3-(cyclopropylamino)quinoxalin-2-yl)piperazin-1-yl)methanone
N-cyclopropyl-3-(4-(2,5-dichlorobenzyl)piperazin-1-yl)-5,7-dimethylquinoxalin-2-amine
N-cyclopropyl-3-(4-(2,5-dichlorobenzyl)piperazin-1-yl)-6,8-dimethylquinoxalin-2-amine
N-cyclopropyl-3-(4-(phenylsulfonyl)piperazin-1-yl)quinoxalin-2-amine
N-cyclopropyl-3-(4-phenethylpiperazin-1-yl)quinoxalin-2-amine
3-(4-(4-chlorophenethyl)piperazin-1-yl)-N-cyclopropylquinoxalin-2-amine
N-cyclopropyl-3-(4-(4-methoxyphenethyl)piperazin-1-yl)quinoxalin-2-amine
3-(4-(cyclohexylmethyl)piperazin-1-yl)-N-cyclopropylquinoxalin-2-amine
3-(4-(2,5-dichlorobenzyl)piperazin-1-yl)-N-isobutylquinoxalin-2-amine, 2,2,2-trifluoroacetic acid salt
3-(4-(2,5-dichlorobenzyl)piperazin-1-yl)-N-isopropylquinoxalin-2-amine, 2,2,2-trifluoroacetic acid salt
3-(4-(2,5-dichlorobenzyl)piperazin-1-yl)-N-(2-ethylbutyl)quinoxalin-2-amine, 2,2,2-trifluoroacetic acid salt
3-(4-(2,5-dichlorobenzyl)piperazin-1-yl)-N-(4-methylpentan-2-yl)quinoxalin-2-amine, 2,2,2-trifluoroacetic acid salt
3-(4-(2,5-dichlorobenzyl)piperazin-1-yl)-N-neopentylquinoxalin-2-amine, 2,2,2-trifluoroacetic acid salt
3-(4-(2,5-dichlorobenzyl)piperazin-1-yl)-N-isopentylquinoxalin-2-amine, 2,2,2-trifluoroacetic acid salt
N-(sec-butyl)-3-(4-(2,5-dichlorobenzyl)piperazin-1-yl)quinoxalin-2-amine, 2,2,2-trifluoroacetic acid salt
3-(4-(2,5-dichlorobenzyl)piperazin-1-yl)-N-propylquinoxalin-2-amine, 2,2,2-trifluoroacetic acid salt
3-(4-(2,5-dichlorobenzyl)piperazin-1-yl)-N-(2-methoxyethyl)quinoxalin-2-amine, 2,2,2-trifluoroacetic acid salt
N-cyclobutyl-3-(4-(2,5-dichlorobenzyl)piperazin-1-yl)quinoxalin-2-amine, 2,2,2-trifluoroacetic acid salt
5-bromo-N-cyclopropyl-3-(4-(2,5-dichlorobenzyl)piperazin-1-yl)quinoxalin-2-amine
(4-(3-(cyclopropylamino)quinoxalin-2-yl)piperazin-1-yl)(4-isopropylphenyl)methanone, 2,2,2-trifluoroacetic acid salt
(4-bromo-2-methylphenyl)(4-(3-(cyclopropylamino)quinoxalin-2-yl)piperazin-1-yl)methanone, 2,2,2-trifluoroacetic acid salt
(2-chloro-3,6-difluorophenyl)(4-(3-(cyclopropylamino)quinoxalin-2-yl)piperazin-1-yl)methanone, 2,2,2-trifluoroacetic acid salt
N-cyclopropyl-3-(4-((4-(trifluoromethoxy)phenyl)sulfonyl)piperazin-1-yl)quinoxalin-2-amine
N-(3-(4-(3-chlorobenzyl)piperazin-1-yl)quinoxalin-2-yl)thiazol-2-amine, 2,2,2-trifluoroacetic acid salt
3-(4-(3-chlorobenzyl)piperazin-1-yl)-N-(pyrimidin-2-yl)quinoxalin-2-amine, 2,2,2-trifluoroacetic acid salt
3-(4-(3-chlorobenzyl)piperazin-1-yl)-N-(pyrimidin-5-yl)quinoxalin-2-amine, 2,2,2-trifluoroacetic acid salt
3-(4-(cyclopentylsulfonyl)piperazin-1-yl)-N-cyclopropylquinoxalin-2-amine
N-cyclopropyl-3-(4-(5-fluoro-2-methylbenzyl)piperazin-1-yl)quinoxalin-2-amine, 2,2,2-trifluoroacetic acid salt
(2-chloro-5-iodophenyl)(4-(3-(cyclopropylamino)quinoxalin-2-yl)piperazin-1-yl)methanone, 2,2,2-trifluoroacetic acid salt
(5-bromo-2-methylphenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(4-(trifluoromethoxy)phenyl)methanone, 2,2,2-trifluoroacetic acid salt
8-bromo-N-cyclopropyl-3-(4-(2,5-dichlorobenzyl)piperazin-1-yl)quinoxalin-2-amine, 2,2,2-trifluoroacetic acid salt
N-cyclopropyl-3-(4-(2,5-dichlorobenzyl)piperazin-1-yl)pyrido[3,4-b]pyrazin-2-amine, 2,2,2-trifluoroacetic acid salt
8-bromo-N-cyclopropyl-3-(4-(2,5-dichlorobenzyl)piperazin-1-yl)quinoxalin-2-amine, 2,2,2-trifluoroacetic acid salt -continued (4-(3-(cyclopropylamino)quinoxalin-2-yl)piperazin-1-yl)(1H-indol-6-yl)methanone, 2,2,2-trifluoroacetic acid salt
(5-chloro-2-methylphenyl)(4-(3-(cyclopropylamino)quinoxalin-2-yl)piperazin-1-yl)methanone, 2,2,2-trifluoroacetic acid salt
(4-chloro-2-methylphenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(2,4-dimethylphenyl)methanone, 2,2,2-trifluoroacetic acid salt
(2-chloro-5-methoxyphenyl)(4-(3-(cyclopropylamino)quinoxalin-2-yl)piperazin-1-yl)methanone, 2,2,2-trifluoroacetic acid salt
5-(4-(3-(cyclopropylamino)quinoxalin-2-yl)piperazine-1-carbonyl)-2-isopropoxybenzonitrile, 2,2,2-trifluoroacetic acid salt
(4-(3-(cyclopropylamino)quinoxalin-2-yl)piperazin-1-yl)(2-methoxy-5-(trifluoromethoxy)phenyl)methanone, 2,2,2-trifluoroacetic acid salt
(4-(3-(cyclopropylamino)quinoxalin-2-yl)piperazin-1-yl)(2,3,5-trichlorophenyl)methanone, 2,2,2-trifluoroacetic acid salt
(2-chloro-6-(trifluoromethyl)phenyl)(4-(3-(cyclopropylamino)quinoxalin-2-yl)piperazin-1-yl)methanone, 2,2,2-trifluoroacetic acid salt
N-cyclopropyl-3-(4-(2,5-dichlorophenethyl)piperazin-1-yl)quinoxalin-2-amine
3-(4-(2,5-dichlorobenzyl)piperazin-1-yl)-N-(pyridin-3-yl)quinoxalin-2-amine
(4-(chloromethyl)phenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(1H-indol-5-yl)methanone, 2,2,2-trifluoroacetic acid salt
(4-bromo-3-methylphenyl)(4-(3-(cyclopropylamino)quinoxalin-2-yl)piperazin-1-yl)methanone, 2,2,2-trifluoroacetic acid salt
3-(4-(2-chloro-4-(methylsulfonyl)benzyl)piperazin-1-yl)-N-cyclopropylquinoxalin-2-amine, 2,2,2-trifluoroacetic acid salt
3-(4-(2,5-dichlorobenzyl)piperazin-1-yl)-N-(pyridin-3-yl)pyrido[2,3-b]pyrazin-2-amine, 2,2,2-trifluoroacetic acid salt
3-(cyclopropylamino)-2-(4-(2,5-dichlorobenzyl)piperazin-1-yl)quinoxaline-6-carbonitrile, 2,2,2-trifluoroacetic acid salt
(4-(3-(cyclopropylamino)quinoxalin-2-yl)piperazin-1-yl)(4-fluoro-3-methoxyphenyl)methanone, 2,2,2-trifluoroacetic acid salt
(3-bromo-4-methylphenyl)(4-(3-(cyclopropylamino)quinoxalin-2-yl)piperazin-1-yl)methanone, 2,2,2-trifluoroacetic acid salt
(4-chloro-3-methylphenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(4-fluoro-2-methylphenyl)methanone
N-cyclopropyl-3-(4-(4-fluoro-2-methylbenzyl)piperazin-1-yl)quinoxalin-2-amine, 2,2,2-trifluoroacetic acid salt
N-cyclopropyl-3-(4-((5-methylisoxazol-3-yl)methyl)piperazin-1-yl)quinoxalin-2-amine, 2,2,2-trifluoroacetic acid salt
2-(4-(2,5-dichlorobenzyl)piperazin-1-yl)-3-(pyridin-3-ylamino)quinoxaline-6-carbonitrile
3-(4-(4-chlorobenzoyl)piperazin-1-yl)-2-(cyclopropylamino)quinoxaline-6-carbonitrile
(4-chlorophenyl)(4-(3-(cyclopropylamino)-7-fluoroquinoxalin-2-yl)piperazin-1-yl)methanone
2-(cyclopropylamino)-3-(4-(phenylsulfonyl)piperazin-1-yl)quinoxaline-6-carbonitrile
3-(4-(phenylsulfonyl)piperazin-1-yl)-N-(pyridin-3-yl)quinoxalin-2-amine
3-(4-(3-chlorobenzyl)piperazin-1-yl)-2-(cyclopropylamino)quinoxaline-6-carbonitrile
N-(tert-butyl)-3-(4-(2,5-dichlorobenzyl)piperazin-1-yl)quinoxalin-2-amine, 2,2,2-trifluoroacetic acid salt
3-(4-(2,5-dichlorobenzyl)piperazin-1-yl)-N-(3,3-dimethylbutyl)quinoxalin-2-amine, 2,2,2-trifluoroacetic acid salt
3-(4-(2,5-dichlorobenzyl)piperazin-1-yl)-N-(2-ethoxyethyl)quinoxalin-2-amine, 2,2,2-trifluoroacetic acid salt
3-(4-(2,5-dichlorobenzyl)piperazin-1-yl)-N-(2-isopropoxyethyl)quinoxalin-2-amine, 2,2,2-trifluoroacetic acid salt
3-(4-(2,5-dichlorobenzyl)piperazin-1-yl)-N-(3-ethoxypropyl)quinoxalin-2-amine, 2,2,2-trifluoroacetic acid salt
N-cyclohexyl-3-(4-(2,5-dichlorobenzyl)piperazin-1-yl)quinoxalin-2-amine, 2,2,2-trifluoroacetic acid salt
3-(4-(2,5-dichlorobenzyl)piperazin-1-yl)-N-(tetrahydro-2H-pyran-4-yl)quinoxalin-2-amine, 2,2,2-trifluoroacetic acid salt
(R)-2-((3-(4-(2,5-dichlorobenzyl)piperazin-1-yl)quinoxalin-2-yl)amino)propan-1-ol, 2,2,2-trifluoroacetic acid salt
3-(4-(2,5-dichlorobenzyl)piperazin-1-yl)-N-(pyrazin-2-yl)quinoxalin-2-amine, 2,2,2-trifluoroacetic acid salt
3-(4-(2,5-dichlorobenzyl)piperazin-1-yl)-N-(pyrimidin-4-yl)quinoxalin-2-amine, 2,2,2-trifluoroacetic acid salt
3-(4-(2,5-dichlorobenzyl)piperazin-1-yl)-N-(pyridazin-3-yl)quinoxalin-2-amine, 2,2,2-trifluoroacetic acid salt
mixture of 3-(4-(2,5-dichlorobenzyl)piperazin-1-yl)-6-fluoro-N-(pyridin-3-yl)quinoxalin-2-amine, 2,2,2-trifluoroacetic acid salt and
3-(4-(2,5-dichlorobenzyl)piperazin-1-yl)-7-fluoro-N-(pyridin-3-yl)quinoxalin-2-amine, 2,2,2-trifluoroacetic acid salt
3-(4-(2,5-dichlorobenzyl)piperazin-1-yl)-N-(1,2,4-triazin-3-yl)quinoxalin-2-amine, 2,2,2-trifluoroacetic acid salt
3-(4-(2,5-dichlorobenzyl)piperazin-1-yl)-N-(5,6-dimethyl-1,2,4-triazin-3-yl)quinoxalin-2-amine, 2,2,2-trifluoroacetic acid salt N-(3-(4-(2,5-dichlorobenzyl)piperazin-1-yl)quinoxalin-2-yl)-3,4-dimethylisoxazol-5-amine, 2,2,2-trifluoroacetic acid salt
(3-bromo-2-methylphenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(3,5-difluorophenyl)methanone, 2,2,2-trifluoroacetic acid salt
(4-bromophenyl)(4-(3-(cyclopropylamino)quinoxalin-2-yl)piperazin-1-yl)methanone, 2,2,2-trifluoroacetic acid salt
3-(4-(3-(cyclopropylamino)quinoxalin-2-yl)piperazine-1-carbonyl)benzonitrile, 2,2,2-trifluoroacetic acid salt
(3-bromophenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(2,6-dichlorophenyl)methanone, 2,2,2-trifluoroacetic acid salt
(2-bromo-4-methylphenyl)(4-(3-(cyclopropylamino)quinoxalin-2-yl)piperazin-1-yl)methanone, 2,2,2-trifluoroacetic acid salt
4-(4-(3-(cyclopropylamino)quinoxalin-2-yl)piperazine-1-carbonyl)-3-fluorobenzonitrile, 2,2,2-trifluoroacetic acid salt
benzo[d][1,2,3]thiadiazol-5-yl(4-(3-(cyclopropylamino)quinoxalin-2-yl)piperazin-1-yl)methanone, 2,2,2-trifluoroacetic acid salt
(2-chloro-5-fluorophenyl)(4-(3-(cyclopropylamino)quinoxalin-2-yl)piperazin-1-yl)methanone, 2,2,2-trifluoroacetic acid salt
(4-(3-(cyclopropylamino)quinoxalin-2-yl)piperazin-1-yl)(2,6-difluoro-3-methylphenyl)methanone, 2,2,2-trifluoroacetic acid salt
(4-(3-(cyclopropylamino)quinoxalin-2-yl)piperazin-1-yl)(2-methoxy-5-(trifluoromethyl)phenyl)methanone, 2,2,2-trifluoroacetic acid salt
(4-bromo-3-(trifluoromethyl)phenyl)(4-(3-(cyclopropylamino)quinoxalin-2-yl)piperazin-1-yl)methanone
N-cyclopropyl-3-(4-(3,5-difluorobenzyl)piperazin-1-yl)quinoxalin-2-amine, 2,2,2-trifluoroacetic acid salt
3-(4-(4-chloro-3-methylbenzyl)piperazin-1-yl)-N-cyclopropylquinoxalin-2-amine, 2,2,2-trifluoroacetic acid salt
N-cyclopropyl-3-(4-(2,3-dimethylbenzyl)piperazin-1-yl)quinoxalin-2-amine, 2,2,2-trifluoroacetic acid salt
3-(4-(2-bromo-5-methoxybenzyl)piperazin-1-yl)-N-cyclopropylquinoxalin-2-amine, 2,2,2-trifluoroacetic acid salt
3-(4-(3-bromo-4-methoxybenzyl)piperazin-1-yl)-N-cyclopropylquinoxalin-2-amine, 2,2,2-trifluoroacetic acid salt
3-(4-(4-bromo-2-chlorobenzyl)piperazin-1-yl)-N-cyclopropylquinoxalin-2-amine, 2,2,2-trifluoroacetic acid salt
3-(4-(3-bromo-4-fluorobenzyl)piperazin-1-yl)-N-cyclopropylquinoxalin-2-amine, 2,2,2-trifluoroacetic acid salt
3-(4-(4-bromo-2-fluorobenzyl)piperazin-1-yl)-N-cyclopropylquinoxalin-2-amine, 2,2,2-trifluoroacetic acid salt
3-(4-(5-bromo-2-fluorobenzyl)piperazin-1-yl)-N-cyclopropylquinoxalin-2-amine, 2,2,2-trifluoroacetic acid salt
3-(4-(5-bromo-2-methylbenzyl)piperazin-1-yl)-N-cyclopropylquinoxalin-2-amine, 2,2,2-trifluoroacetic acid salt
3-(4-((1H-indol-6-yl)methyl)piperazin-1-yl)-N-cyclopropylquinoxalin-2-amine, 2,2,2-trifluoroacetic acid salt
3-(4-(5-chloro-2-methylbenzyl)piperazin-1-yl)-N-cyclopropylquinoxalin-2-amine, 2,2,2-trifluoroacetic acid salt
3-(4-(4-chloro-2-methylbenzyl)piperazin-1-yl)-N-cyclopropylquinoxalin-2-amine, 2,2,2-trifluoroacetic acid salt
3-(4-(2-chloro-3,6-difluorobenzyl)piperazin-1-yl)-N-cyclopropylquinoxalin-2-amine, 2,2,2-trifluoroacetic acid salt
N-cyclopropyl-3-(4-(2,4-dimethylbenzyl)piperazin-1-yl)quinoxalin-2-amine, 2,2,2-trifluoroacetic acid salt
3-(4-(2-chloro-5-methoxybenzyl)piperazin-1-yl)-N-cyclopropylquinoxalin-2-amine, 2,2,2-trifluoroacetic acid salt
3-(4-(2-chloro-5-fluorobenzyl)piperazin-1-yl)-N-cyclopropylquinoxalin-2-amine, 2,2,2-trifluoroacetic acid salt
3-(4-(2-chloro-6-(trifluoromethyl)benzyl)piperazin-1-yl)-N-cyclopropylquinoxalin-2-amine, 2,2,2-trifluoroacetic acid salt
N-cyclopropyl-3-(4-(3-isopropylbenzyl)piperazin-1-yl)quinoxalin-2-amine, 2,2,2-trifluoroacetic acid salt
N-cyclopropyl-6-fluoro-3-(4-(phenylsulfonyl)piperazin-1-yl)quinoxalin-2-amine
N-cyclopropyl-3-(4-(2,5-difluorobenzyl)piperazin-1-yl)-6-fluoroquinoxalin-2-amine
3-(4-(2,5-dichlorobenzyl)piperazin-1-yl)-N-(pyridin-4-yl)quinoxalin-2-amine, 2,2,2-trifluoroacetic acid salt
N-cyclopropyl-3-(4-(2,5-difluorobenzyl)piperazin-1-yl)-6,7-difluoroquinoxalin-2-amine, 2,2,2-trifluoroacetic acid salt
3-(4-(3-chloro-4-methoxybenzyl)piperazin-1-yl)-N-cyclopropylquinoxalin-2-amine, 2,2,2-trifluoroacetic acid salt
3-(4-(4-bromo-3-methylbenzyl)piperazin-1-yl)-N-cyclopropylquinoxalin-2-amine, 2,2,2-trifluoroacetic acid salt
3-(4-(4-bromo-2-methylbenzyl)piperazin-1-yl)-N-cyclopropylquinoxalin-2-amine, 2,2,2-trifluoroacetic acid salt -continued 3-(4-(2-chloro-5-iodobenzyl)piperazin-1-yl)-N-cyclopropylquinoxalin-2-amine, 2,2,2-trifluoroacetic acid salt
N-cyclopropyl-3-(4-(2-methoxy-5-(trifluoromethoxy)benzyl)piperazin-1-yl)quinoxalin-2-amine, 2,2,2-trifluoroacetic acid salt
N-cyclopropyl-3-(4-(2,3,5-trichlorobenzyl)piperazin-1-yl)quinoxalin-2-amine, 2,2,2-trifluoroacetic acid salt
3-(4-((2-chloro-5-fluoropyridin-3-yl)methyl)piperazin-1-yl)-N-cyclopropylquinoxalin-2-amine, 2,2,2-trifluoroacetic acid salt
(4-chlorophenyl)(4-(3-(pyridin-3-ylamino)quinoxalin-2-yl)piperazin-1-yl)methanone, 2,2,2-trifluoroacetic acid salt
3-(4-((3-chlorophenyl)sulfonyl)piperazin-1-yl)-2-(cyclopropylamino)quinoxaline-6-carbonitrile
3-(4-((3-chlorophenyl)sulfonyl)piperazin-1-yl)-N-cyclopropyl-6-fluoroquinoxalin-2-amine
2-(cyclopropylamino)-3-(4-((2,5-dichlorophenyl)sulfonyl)piperazin-1-yl)quinoxaline-6-carbonitrile
3-(4-((4-chlorophenyl)sulfonyl)piperazin-1-yl)-2-(cyclopropylamino)quinoxaline-6-carbonitrile, 2,2,2-trifluoroacetic acid salt
3-(4-(2,5-dichlorobenzyl)piperazin-1-yl)-N-(pyridin-2-yl)quinoxalin-2-amine, 2,2,2-trifluoroacetic acid salt
3-(4-(2,5-difluorobenzyl)piperazin-1-yl)-N-(pyridin-3-yl)quinoxalin-2-amine, 2,2,2-trifluoroacetic acid salt
(4-chloro-3-methylphenyl)(4-(3-(pyridin-3-ylamino)quinoxalin-2-yl)piperazin-1-yl)methanone, 2,2,2-trifluoroacetic acid salt
N-cyclopropyl-3-(4-(2,5-dichlorobenzyl)piperazin-1-yl)-6,7-difluoroquinoxalin-2-amine, 2,2,2-trifluoroacetic acid salt
(3-bromo-4-fluorophenyl)(4-(3-(cyclopropylamino)-6,7-difluoroquinoxalin-2-yl)piperazin-1-yl)methanone, 2,2,2-trifluoroacetic acid salt
3-(4-(2-bromo-5-chlorobenzyl)piperazin-1-yl)-N-cyclopropylquinoxalin-2-amine, 2,2,2-trifluoroacetic acid salt
3-(4-(5-chloro-2-(trifluoromethyl)benzyl)piperazin-1-yl)-N-cyclopropylquinoxalin-2-amine, 2,2,2-trifluoroacetic acid salt
N-cyclopropyl-3-(4-(2,6-difluoro-3-methylbenzyl)piperazin-1-yl)quinoxalin-2-amine, 2,2,2-trifluoroacetic acid salt
N-cyclopropyl-3-(4-(2-methoxy-5-(trifluoromethyl)benzyl)piperazin-1-yl)quinoxalin-2-amine, 2,2,2-trifluoroacetic acid salt
2-(cyclopropylamino)-3-(4-(o-tolylsulfonyl)piperazin-1-yl)quinoxaline-6-carbonitrile
2-(cyclopropylamino)-3-(4-((3-fluorophenyl)sulfonyl)piperazin-1-yl)quinoxaline-6-carbonitrile, 2,2,2-trifluoroacetic acid salt
2-(cyclopropylamino)-3-(4-(m-tolylsulfonyl)piperazin-1-yl)quinoxaline-6-carbonitrile
2-(cyclopropylamino)-3-(4-tosylpiperazin-1-yl)quinoxaline-6-carbonitrile
2-(cyclopropylamino)-3-(4-((2-fluorophenyl)sulfonyl)piperazin-1-yl)quinoxaline-6-carbonitrile, 2,2,2-trifluoroacetic acid salt
2-(cyclopropylamino)-3-(4-(2,5-dichlorobenzyl)piperazin-1-yl)quinoxaline-5-carbonitrile, 2,2,2-trifluoroacetic acid salt
(4-chlorophenyl)(4-(3-(cyclopropylamino)-6,7-difluoroquinoxalin-2-yl)piperazin-1-yl)methanone
3-(4-((2-chlorophenyl)sulfonyl)piperazin-1-yl)-2-(cyclopropylamino)quinoxaline-6-carbonitrile, 2,2,2-trifluoroacetic acid salt
2-(cyclopropylamino)-3-(4-((4-fluorophenyl)sulfonyl)piperazin-1-yl)quinoxaline-6-carbonitrile, 2,2,2-trifluoroacetic acid salt
3-(4-(3-chlorobenzyl)piperazin-1-yl)-N-cyclopropyl-6,7-difluoroquinoxalin-2-amine, 2,2,2-trifluoroacetic acid salt
(4-bromo-3-fluorophenyl)(4-(3-(cyclopropylamino)-7-fluoroquinoxalin-2-yl)piperazin-1-yl)methanone
3-(cyclopropylamino)-2-(4-(2,5-dichlorobenzyl)piperazin-1-yl)quinoxaline-5-carbonitrile, 2,2,2-trifluoroacetic acid salt
3-(4-((2-bromophenyl)sulfonyl)piperazin-1-yl)-2-(cyclopropylamino)quinoxaline-6-carbonitrile
3-(4-((3-bromophenyl)sulfonyl)piperazin-1-yl)-2-(cyclopropylamino)quinoxaline-6-carbonitrile
3-(4-((4-bromophenyl)sulfonyl)piperazin-1-yl)-2-(cyclopropylamino)quinoxaline-6-carbonitrile
3-(4-((2-cyanophenyl)sulfonyl)piperazin-1-yl)-2-(cyclopropylamino)quinoxaline-6-carbonitrile, 2,2,2-trifluoroacetic acid salt
3-(4-((3-cyanophenyl)sulfonyl)piperazin-1-yl)-2-(cyclopropylamino)quinoxaline-6-carbonitrile, 2,2,2-trifluoroacetic acid salt
3-(4-((4-cyanophenyl)sulfonyl)piperazin-1-yl)-2-(cyclopropylamino)quinoxaline-6-carbonitrile, 2,2,2-trifluoroacetic acid salt
2-(cyclopropylamino)-3-(4-(4-fluorobenzyl)piperazin-1-yl)quinoxaline-6-carbonitrile
3-(4-(3-bromo-4-fluorobenzoyl)piperazin-1-yl)-2-(cyclopropylamino)quinoxaline-6-carbonitrile, 2,2,2-trifluoroacetic acid salt
2-(cyclopropylamino)-3-(4-(2,5-difluorobenzyl)piperazin-1-yl)quinoxaline-6-carbonitrile, 2,2,2-trifluoroacetic acid salt
3-(4-(2,5-dichlorobenzyl)piperazin-1-yl)-2-(isopropylamino)quinoxaline-6-carbonitrile, 2,2,2-trifluoroacetic acid salt
3-(4-(2,5-difluorobenzyl)piperazin-1-yl)-2-(isopropylamino)quinoxaline-6-carbonitrile, 2,2,2-trifluoroacetic acid salt
3-(4-(3-bromo-4-fluorobenzoyl)piperazin-1-yl)-2-(isopropylamino)quinoxaline-6-carbonitrile, 2,2,2-trifluoroacetic acid salt
2-(cyclobutylamino)-3-(4-(2,5-difluorobenzyl)piperazin-1-yl)quinoxaline-6-carbonitrile, 2,2,2-trifluoroacetic acid salt
3-(4-(3-bromo-4-fluorobenzoyl)piperazin-1-yl)-2-(cyclobutylamino)quinoxaline-6-carbonitrile, 2,2,2-trifluoroacetic acid salt (4-chlorophenyl)(4-(2-(cyclopropylamino)pyrido[3,4-b]pyrazin-3-yl)piperazin-1-yl)methanone
N-cyclopropyl-3-(4-(2,5-difluorobenzyl)piperazin-1-yl)pyrido[3,4-b]pyrazin-2-amine, 2,2,2-trifluoroacetic acid salt
2-(cyclopropylamino)-3-(4-(2,5-dichloroisonicotinoyl)piperazin-1-yl)quinoxaline-6-carbonitrile
3-(4-(4-chlorobenzoyl)piperazin-1-yl)-2-(cyclobutylamino)quinoxaline-6-carbonitrile
3-(4-(4-chlorobenzoyl)piperazin-1-yl)-2-(isopropylamino)quinoxaline-6-carbonitrile
(4-(2-(cyclopropylamino)pyrido[3,4-b]pyrazin-3-yl)piperazin-1-yl)(4-(trifluoromethyl)phenyl)methanone, 2,2,2-trifluoroacetic acid salt
3-(4-(2,5-dichlorobenzyl)piperazin-1-yl)-N-(2,2,2-trifluoroethyl)quinoxalin-2-amine, 2,2,2-trifluoroacetic acid salt
2-(cyclopropylamino)-3-(4-((3,5-dimethylisoxazol-4-yl)sulfonyl)piperazin-1-yl)quinoxaline-6-carbonitrile, 2,2,2-trifluoroacetic acid salt
2-(cyclopropylamino)-3-(4-((2,5-dimethylphenyl)sulfonyl)piperazin-1-yl)quinoxaline-6-carbonitrile, 2,2,2-trifluoroacetic acid salt
2-(cyclopropylamino)-3-(4-((4-methoxyphenyl)sulfonyl)piperazin-1-yl)quinoxaline-6-carbonitrile, 2,2,2-trifluoroacetic acid salt
2-(cyclopropylamino)-3-(4-((2-methoxyphenyl)sulfonyl)piperazin-1-yl)quinoxaline-6-carbonitrile, 2,2,2-trifluoroacetic acid salt
2-(cyclopropylamino)-3-(4-((3-methoxyphenyl)sulfonyl)piperazin-1-yl)quinoxaline-6-carbonitrile, 2,2,2-trifluoroacetic acid salt
3-(4-((5-chlorothiophen-2-yl)sulfonyl)piperazin-1-yl)-2-(cyclopropylamino)quinoxaline-6-carbonitrile, 2,2,2-trifluoroacetic acid salt
2-(cyclopropylamino)-3-(4-(mesitylsulfonyl)piperazin-1-yl)quinoxaline-6-carbonitrile, 2,2,2-trifluoroacetic acid salt
2-(cyclopropylamino)-3-(4-((2-methoxy-4-methylphenyl)sulfonyl)piperazin-1-yl)quinoxaline-6-carbonitrile, 2,2,2-trifluoroacetic acid salt
3-(4-((5-chloro-1,3-dimethyl-1H-pyrazol-4-yl)sulfonyl)piperazin-1-yl)-2-(cyclopropylamino)quinoxaline-6-carbonitrile, 2,2,2-trifluoroacetic acid salt
2-(cyclopropylamino)-3-(4-((2,3,4-trifluorophenyl)sulfonyl)piperazin-1-yl)quinoxaline-6-carbonitrile, 2,2,2-trifluoroacetic acid salt
3-(4-((4-tert-butyl)phenyl)sulfonyl)piperazin-1-yl)-2-(cyclopropylamino)quinoxaline-6-carbonitrile, 2,2,2-trifluoroacetic acid salt
3-(4-((4-chloro-2,5-dimethylphenyl)sulfonyl)piperazin-1-yl)-2-(cyclopropylamino)quinoxaline-6-carbonitrile, 2,2,2-trifluoroacetic acid salt
3-(4-((3-chloro-5-fluoro-2-methylphenyl)sulfonyl)piperazin-1-yl)-2-(cyclopropylamino)quinoxaline-6-carbonitrile, 2,2,2-trifluoroacetic acid salt
2-(cyclopropylamino)-3-(4-((4-(trifluoromethoxy)phenyl)sulfonyl)piperazin-1-yl)quinoxaline-6-carbonitrile, 2,2,2-trifluoroacetic acid salt
3-(4-((5-bromothiophen-2-yl)sulfonyl)piperazin-1-yl)-2-(cyclopropylamino)quinoxaline-6-carbonitrile, 2,2,2-trifluoroacetic acid salt
3-(4-((4-bromo-2-fluorophenyl)sulfonyl)piperazin-1-yl)-2-(cyclopropylamino)quinoxaline-6-carbonitrile, 2,2,2-trifluoroacetic acid salt
3-(4-((2-chloro-5-(trifluoromethyl)phenyl)sulfonyl)piperazin-1-yl)-2-(cyclopropylamino)quinoxaline-6-carbonitrile, 2,2,2-trifluoroacetic acid salt
3-(4-((4-bromo-2-chlorophenyl)sulfonyl)piperazin-1-yl)-2-(cyclopropylamino)quinoxaline-6-carbonitrile, 2,2,2-trifluoroacetic acid salt
N-cyclopropyl-3-(4-((4-fluorophenyl)sulfonyl)piperazin-1-yl)pyrido[3,4-b]pyrazin-2-amine, 2,2,2-trifluoroacetic acid salt
(4-(2-(cyclopropylamino)pyrido[3,4-b]pyrazin-3-yl)piperazin-1-yl)(4-(difluoromethyl)phenyl)methanone, 2,2,2-trifluoroacetic acid salt
3-(4-(5-chloro-2-(difluoromethoxy)benzyl)piperazin-1-yl)-N-cyclopropylpyrido[3,4-b]pyrazin-2-amine, 2,2,2-trifluoroacetic acid salt
N-cyclopropyl-3-(4-(4-fluorobenzyl)piperazin-1-yl)pyrido[3,4-b]pyrazin-2-amine, 2,2,2-trifluoroacetic acid salt
N-cyclopropyl-2-(4-(2,5-difluorobenzyl)piperazin-1-yl)pyrido[3,4-b]pyrazin-3-amine, 2,2,2-trifluoroacetic acid salt
N-cyclopropyl-2-(4-(2,5-dichlorobenzyl)piperazin-1-yl)pyrido[3,4-b]pyrazin-3-amine, 2,2,2-trifluoroacetic acid salt
2-(cyclopropylamino)-3-(4-(2,6-dichlorobenzyl)piperazin-1-yl)quinoxaline-6-carbonitrile, 2,2,2-trifluoroacetic acid salt
3-(4-(3-chlorobenzoyl)piperazin-1-yl)-2-((cyclobutylmethyl)amino)quinoxaline-6-carbonitrile
2-((cyclobutylmethyl)amino)-3-(4-(2,5-dichlorobenzoyl)piperazin-1-yl)quinoxaline-6-carbonitrile
2-(cyclopropylamino)-3-(4-(2,5-dichloronicotinoyl)piperazin-1-yl)quinoxaline-6-carbonitrile, 2,2,2-trifluoroacetic acid salt
3-(4-(4-chlorobenzoyl)piperazin-1-yl)-2-(oxetan-3-ylamino)quinoxaline-6-carbonitrile
N-cyclopropyl-3-(4-(2,6-dichlorobenzyl)piperazin-1-yl)pyrido[3,4-b]pyrazin-2-amine, 2,2,2-trifluoroacetic acid salt
3-(4-(2,5-dichlorobenzyl)piperazin-1-yl)-2-(oxetan-3-ylamino)quinoxaline-6-carbonitrile
3-(4-(5-chloro-2-propoxybenzyl)piperazin-1-yl)-N-cyclopropylpyrido[3,4-b]pyrazin-2-amine, 2,2,2-trifluoroacetic acid salt
N-cyclopropyl-3-(4-((4-(trifluoromethyl)phenyl)sulfonyl)piperazin-1-yl)pyrido[3,4-b]pyrazin-2-amine, 2,2,2-trifluoroacetic acid salt
2-(4-(4-chlorobenzoyl)piperazin-1-yl)-3-(cyclopropylamino)quinoxaline-6-carbonitrile, 2,2,2-trifluoroacetic acid salt
(4-chlorophenyl)(4-(3-(cyclopropylamino)pyrido[3,4-b]pyrazin-2-yl)piperazin-1-yl)methanone, 2,2,2-trifluoroacetic acid salt
3-(cyclopropylamino)-2-(4-(2,5-difluorobenzyl)piperazin-1-yl)quinoxaline-6-carbonitrile, 2,2,2-trifluoroacetic acid salt 3-(4-(5-(tert-butyl)-2-methoxybenzyl)piperazin-1-yl)-N-cyclopropylpyrido[3,4-b]pyrazin-2-amine, 2,2,2-trifluoroacetic acid salt
N-cyclopropyl-3-(4-(2,5-dimethylbenzyl)piperazin-1-yl)pyrido[3,4-b]pyrazin-2-amine, 2,2,2-trifluoroacetic acid salt
3-(cyclopropylamino)-2-(4-((4-fluorophenyl)sulfonyl)piperazin-1-yl)quinoxaline-6-carbonitrile, 2,2,2-trifluoroacetic acid salt
3-(4-(2,5-dichlorobenzyl)piperazin-1-yl)-2-(pyridin-3-ylamino)quinoxaline-6-carbonitrile, 2,2,2-trifluoroacetic acid salt
N-cyclopropyl-2-(4-((4-fluorophenyl)sulfonyl)piperazin-1-yl)pyrido[3,4-b]pyrazin-3-amine, 2,2,2-trifluoroacetic acid salt
3-(4-(2,5-difluorobenzyl)piperazin-1-yl)-2-(pyridin-3-ylamino)quinoxaline-6-carbonitrile
N-cyclopropyl-3-(4-(2,6-difluorobenzyl)piperazin-1-yl)pyrido[3,4-b]pyrazin-2-amine, 2,2,2-trifluoroacetic acid salt
3-(4-(2,5-difluorobenzyl)piperazin-1-yl)-2-((6-oxo-1,6-dihydropyridin-3-yl)amino)quinoxaline-6-carbonitrile
3-(4-(2,5-dichlorobenzyl)piperazin-1-yl)-2-((6-oxo-1,6-dihydropyridin-3-yl)amino)quinoxaline-6-carbonitrile
3-(4-(3-chloro-4-fluorobenzyl)piperazin-1-yl)-N-cyclopropylpyrido[3,4-b]pyrazin-2-amine, 2,2,2-trifluoroacetic acid salt
N-cyclopropyl-3-(4-(2,4,5-trifluorobenzyl)piperazin-1-yl)pyrido[3,4-b]pyrazin-2-amine, 2,2,2-trifluoroacetic acid salt
3-(4-(4-chloro-3-fluorobenzyl)piperazin-1-yl)-N-cyclopropylpyrido[3,4-b]pyrazin-2-amine, 2,2,2-trifluoroacetic acid salt
N-cyclopropyl-3-(4-(3,4-difluorobenzyl)piperazin-1-yl)pyrido[3,4-b]pyrazin-2-amine, 2,2,2-trifluoroacetic acid salt
N-cyclopropyl-3-(4-(2,4-difluorobenzyl)piperazin-1-yl)pyrido[3,4-b]pyrazin-2-amine, 2,2,2-trifluoroacetic acid salt
3-(4-(2,5-difluorobenzyl)piperazin-1-yl)-2-((6-oxo-1,6-dihydropyridin-4-yl)amino)quinoxaline-6-carbonitrile
2-(cyclopropylamino)-3-(4-((4-ethylphenyl)sulfonyl)piperazin-1-yl)quinoxaline-6-carbonitrile, 2,2,2-trifluoroacetic acid salt
3-(4-(2,5-difluorobenzyl)piperazin-1-yl)-2-((6-oxo-1,6-dihydropyridin-2-yl)amino)quinoxaline-6-carbonitrile
2-(cyclopropylamino)-3-(4-((2-fluoro-5-methylphenyl)sulfonyl)piperazin-1-yl)quinoxaline-6-carbonitrile, 2,2,2-trifluoroacetic acid salt
3-(4-(4-chlorobenzoyl)piperazin-1-yl)-2-((6-oxo-1,6-dihydropyridin-2-yl)amino)quinoxaline-6-carbonitrile
3-(4-(2,5-difluorobenzyl)piperazin-1-yl)-2-((6-oxo-1,6-dihydropyridin-2-yl)amino)quinoxaline-6-carbonitrile
2-(cyclopropylamino)-3-(4-((3,4-difluorophenyl)sulfonyl)piperazin-1-yl)quinoxaline-6-carbonitrile, 2,2,2-trifluoroacetic acid salt
3-(4-(4-chlorobenzoyl)piperazin-1-yl)-2-((2-oxo-1,2-dihydropyridin-3-yl)amino)quinoxaline-6-carbonitrile
3-(4-(4-chlorobenzoyl)piperazin-1-yl)-2-(pyridin-3-ylamino)quinoxaline-6-carbonitrile
2-(cyclopropylamino)-3-(4-((2,5-dimethoxyphenyl)sulfonyl)piperazin-1-yl)quinoxaline-6-carbonitrile, 2,2,2-trifluoroacetic acid salt
3-(4-((2-chloro-4-(trifluoromethyl)phenyl)sulfonyl)piperazin-1-yl)-2-(cyclopropylamino)quinoxaline-6-carbonitrile, 2,2,2-trifluoroacetic acid salt
3-(4-(5-chloro-2-fluorobenzyl)piperazin-1-yl)-N-cyclopropylpyrido[3,4-b]pyrazin-2-amine, 2,2,2-trifluoroacetic acid salt
3-(4-(2-chloro-5-fluorobenzyl)piperazin-1-yl)-N-cyclopropylpyrido[3,4-b]pyrazin-2-amine, 2,2,2-trifluoroacetic acid salt
3-(4-(2,5-difluorobenzyl)piperazin-1-yl)-2-((6-methoxypyridin-3-yl)amino)quinoxaline-6-carbonitrile, 2,2,2-trifluoroacetic acid salt
3-(4-(2,5-dichlorobenzyl)piperazin-1-yl)-2-((3-oxocyclobutyl)amino)quinoxaline-6-carbonitrile, 2,2,2-trifluoroacetic acid salt
3-(4-(2,5-difluorobenzyl)piperazin-1-yl)-2-((3-oxocyclobutyl)amino)quinoxaline-6-carbonitrile, 2,2,2-trifluoroacetic acid salt
2-(cyclobutylamino)-3-(4-(2,5-dichlorobenzyl)piperazin-1-yl)quinoxaline-6-carbonitrile, 2,2,2-trifluoroacetic acid salt
3-(4-(4-chlorobenzoyl)piperazin-1-yl)-2-((2-fluoroethyl)amino)quinoxaline-6-carbonitrile, 2,2,2-trifluoroacetic acid salt
3-(4-(2,5-dichlorobenzyl)piperazin-1-yl)-2-((2,2-difluoroethyl)amino)quinoxaline-6-carbonitrile
3-(4-(4-chlorobenzoyl)piperazin-1-yl)-2-((2,2-difluoroethyl)amino)quinoxaline-6-carbonitrile
3-(4-(2,5-dichlorobenzyl)piperazin-1-yl)-2-(isoxazol-3-ylamino)quinoxaline-6-carbonitrile, 2,2,2-trifluoroacetic acid salt
3-(4-(4-chlorobenzoyl)piperazin-1-yl)-2-(isoxazol-3-ylamino)quinoxaline-6-carbonitrile, 2,2,2-trifluoroacetic acid salt
3-(4-((3-cyano-4-fluorophenyl)sulfonyl)piperazin-1-yl)-2-(cyclopropylamino)quinoxaline-6-carbonitrile, 2,2,2-trifluoroacetic acid salt
2-(cyclopropylamino)-3-(4-(2,4-difluorobenzyl)piperazin-1-yl)quinoxaline-6-carbonitrile, 2,2,2-trifluoroacetic acid salt
3-(4-((5-chloro-2-methoxyphenyl)sulfonyl)piperazin-1-yl)-2-(cyclopropylamino)quinoxaline-6-carbonitrile, 2,2,2-trifluoroacetic acid salt
3-(4-((5-chloro-2,4-difluorophenyl)sulfonyl)piperazin-1-yl)-2-(cyclopropylamino)quinoxaline-6-carbonitrile, 2,2,2-trifluoroacetic acid salt
3-(4-((5-bromo-6-chloropyridin-3-yl)sulfonyl)piperazin-1-yl)-2-(cyclopropylamino)quinoxaline-6-carbonitrile, 2,2,2-trifluoroacetic acid salt -continued 3-(4-((4-bromo-2,5-difluorophenyl)sulfonyl)piperazin-1-yl)-2-(cyclopropylamino)quinoxaline-6-carbonitrile, 2,2,2-trifluoroacetic acid salt
3-(4-(2,5-dichlorobenzyl)piperazin-1-yl)-2-((2-fluoroethyl)amino)quinoxaline-6-carbonitrile, 2,2,2-trifluoroacetic acid salt
3-(4-(2,5-difluorobenzyl)piperazin-1-yl)-2-((2-fluoroethyl)amino)quinoxaline-6-carbonitrile, 2,2,2-trifluoroacetic acid salt
3-(4-(2,5-difluorobenzyl)piperazin-1-yl)-2-((2,2-difluoroethyl)amino)quinoxaline-6-carbonitrile, 2,2,2-trifluoroacetic acid salt
8-chloro-3-(4-(5-chloro-2-fluorobenzyl)piperazin-1-yl)-N-cyclopropylpyrido[3,4-b]pyrazin-2-amine, 2,2,2-trifluoroacetic acid salt
8-chloro-N-cyclopropyl-3-(4-(2,5-difluorobenzyl)piperazin-1-yl)pyrido[3,4-b]pyrazin-2-amine, 2,2,2-trifluoroacetic acid salt
2-(cyclopropylamino)-3-(4-(2,4,5-trifluorobenzyl)piperazin-1-yl)quinoxaline-6-carbonitrile, 2,2,2-trifluoroacetic acid salt
8-chloro-N-cyclopropyl-3-(4-(2,4-difluorobenzyl)piperazin-1-yl)pyrido[3,4-b]pyrazin-2-amine, 2,2,2-trifluoroacetic acid salt
8-chloro-N-cyclopropyl-3-(4-(2,4,5-trifluorobenzyl)piperazin-1-yl)pyrido[3,4-b]pyrazin-2-amine, 2,2,2-trifluoroacetic acid salt
N-cyclopropyl-2-(4-(2,4,5-trifluorobenzyl)piperazin-1-yl)pyrido[3,4-b]pyrazin-3-amine, 2,2,2-trifluoroacetic acid salt
N-cyclopropyl-2-(4-(2,4-difluorobenzyl)piperazin-1-yl)pyrido[3,4-b]pyrazin-3-amine, 2,2,2-trifluoroacetic acid salt
2-(cyclopropylamino)-3-(4-((2,4-dimethoxyphenyl)sulfonyl)piperazin-1-yl)quinoxaline-6-carbonitrile
(4-chloro-3-fluorophenyl)(4-(2-(cyclopropylamino)pyrido[3,4-b]pyrazin-3-yl)piperazin-1-yl)methanone, 2,2,2-trifluoroacetic acid salt
(4-(2-(cyclopropylamino)pyrido[3,4-b]pyrazin-3-yl)piperazin-1-yl)(3,4-difluorophenyl)methanone, 2,2,2-trifluoroacetic acid salt
(3-chloro-4-fluorophenyl)(4-(2-(cyclopropylamino)pyrido[3,4-b]pyrazin-3-yl)piperazin-1-yl)methanone, 2,2,2-trifluoroacetic acid salt
(4-chloro-2-fluorophenyl)(4-(2-(cyclopropylamino)pyrido[3,4-b]pyrazin-3-yl)piperazin-1-yl)methanone, 2,2,2-trifluoroacetic acid salt
(2-chloro-4-fluorophenyl)(4-(2-(cyclopropylamino)pyrido[3,4-b]pyrazin-3-yl)piperazin-1-yl)methanone, 2,2,2-trifluoroacetic acid salt
2-(4-(2,4-difluorobenzyl)piperazin-1-yl)-N-(2,2-difluoroethyl)pyrido[3,4-b]pyrazin-3-amine, 2,2,2-trifluoroacetic acid salt
N-(2,2-difluoroethyl)-2-(4-(2,4,5-trifluorobenzyl)piperazin-1-yl)pyrido[3,4-b]pyrazin-3-amine, 2,2,2-trifluoroacetic acid salt
3-(4-(2,4-difluorobenzyl)piperazin-1-yl)-N-(2,2-difluoroethyl)pyrido[3,4-b]pyrazin-2-amine, 2,2,2-trifluoroacetic acid salt
3-(4-(5-chloro-2-fluorobenzyl)piperazin-1-yl)-N-(2,2-difluoroethyl)pyrido[3,4-b]pyrazin-2-amine, 2,2,2-trifluoroacetic acid salt
3-(4-(5-chloro-2-fluorobenzyl)piperazin-1-yl)-2-(cyclopropylamino)quinoxaline-6-carbonitrile, 2,2,2-trifluoroacetic acid salt
(4-chloro-2-fluorophenyl)(4-(2-((2,2-difluoroethyl)amino)pyrido[3,4-b]pyrazin-3-yl)piperazin-1-yl)methanone, 2,2,2-trifluoroacetic acid salt
N-(pyridin-3-yl)-2-(4-(2,4,5-trifluorobenzyl)piperazin-1-yl)pyrido[3,4-b]pyrazin-3-amine, 2,2,2-trifluoroacetic acid salt
N-(2,2-difluoroethyl)-3-(4-(2,4,5-trifluorobenzyl)piperazin-1-yl)pyrido[3,4-b]pyrazin-2-amine, 2,2,2-trifluoroacetic acid salt
3-(4-(2,4-difluorobenzyl)piperazin-1-yl)-2-(pyridin-3-ylamino)quinoxaline-6-carbonitrile, 2,2,2-trifluoroacetic acid salt
(4-chloro-2-hydroxyphenyl)(4-(2-(cyclopropylamino)pyrido[3,4-b]pyrazin-3-yl)piperazin-1-yl)methanone, 2,2,2-trifluoroacetic acid salt
3-(cyclopropylamino)-2-(4-(2,4-difluorobenzyl)piperazin-1-yl)quinoxaline-6-carbonitrile, 2,2,2-trifluoroacetic acid salt
2-(4-(5-chloro-2-fluorobenzyl)piperazin-1-yl)-3-(cyclopropylamino)quinoxaline-6-carbonitrile, 2,2,2-trifluoroacetic acid salt
3-(cyclopropylamino)-2-(4-(2,4,5-trifluorobenzyl)piperazin-1-yl)quinoxaline-6-carbonitrile, 2,2,2-trifluoroacetic acid salt
2-(pyridin-3-ylamino)-3-(4-(2,4,5-trifluorobenzyl)piperazin-1-yl)quinoxaline-6-carbonitrile, 2,2,2-trifluoroacetic acid salt
3-(4-(4-chloro-2-fluorobenzoyl)piperazin-1-yl)-2-(pyridin-3-ylamino)quinoxaline-6-carbonitrile, 2,2,2-trifluoroacetic acid salt
3-(4-(2,5-difluorobenzyl)piperazin-1-yl)-2-(isoxazol-3-ylamino)quinoxaline-6-carbonitrile
2-(4-(2,4-difluorobenzyl)piperazin-1-yl)-N-(pyridin-3-yl)pyrido[3,4-b]pyrazin-3-amine
(4-chloro-2-methoxyphenyl)(4-(2-(cyclopropylamino)pyrido[3,4-b]pyrazin-3-yl)piperazin-1-yl)methanone, 2,2,2-trifluoroacetic acid salt
(4-(2-(cyclopropylamino)pyrido[3,4-b]pyrazin-3-yl)piperazin-1-yl)(2-fluoro-4-(trifluoromethyl)phenyl)methanone, 2,2,2-trifluoroacetic acid salt
(5-chloro-3-fluoropyridin-2-yl)(4-(2-(cyclopropylamino)pyrido[3,4-b]pyrazin-3-yl)piperazin-1-yl)methanone, 2,2,2-trifluoroacetic acid salt
(4-(2-(cyclopropylamino)pyrido[3,4-b]pyrazin-3-yl)piperazin-1-yl)(2-fluoro-4-methylphenyl)methanone, 2,2,2-trifluoroacetic acid salt
(4-(2-(cyclopropylamino)pyrido[3,4-b]pyrazin-3-yl)piperazin-1-yl)(2-fluoro-4-methoxyphenyl)methanone, 2,2,2-trifluoroacetic acid salt
(4-chloro-2-methylphenyl)(4-(2-(cyclopropylamino)pyrido[3,4-b]pyrazin-3-yl)piperazin-1-yl)methanone, 2,2,2-trifluoroacetic acid salt
4-(4-(2-(cyclopropylamino)pyrido[3,4-b]pyrazin-3-yl)piperazine-1-carbonyl)-3-fluorobenzonitrile, 2,2,2-trifluoroacetic acid salt (4-(2-(cyclopropylamino)pyrido[3,4-b]pyrazin-3-yl)piperazin-1-yl)(4-fluoro-2-hydroxyphenyl)methanone, 2,2,2-trifluoroacetic acid salt
(4-chloro-2,6-difluorophenyl)(4-(2-(cyclopropylamino)pyrido[3,4-b]pyrazin-3-yl)piperazin-1-yl)methanone, 2,2,2-trifluoroacetic acid salt
(4-(2-(cyclopropylamino)pyrido[3,4-b]pyrazin-3-yl)piperazin-1-yl)(3-fluoropyridin-2-yl)methanone, 2,2,2-trifluoroacetic acid salt
2-(4-(2,5-difluorobenzyl)piperazin-1-yl)-N-(pyridin-3-yl)pyrido[3,4-b]pyrazin-3-amine, 2,2,2-trifluoroacetic acid salt
(4-chloro-2-(trifluoromethyl)phenyl)(4-(2-(cyclopropylamino)pyrido[3,4-b]pyrazin-3-yl)piperazin-1-yl)methanone, 2,2,2-trifluoroacetic acid salt
N-cyclopropyl-3-(4-(2,4-difluorobenzyl)piperazin-1-yl)pyrazino[2,3-d]pyridazin-2-amine, 2,2,2-trifluoroacetic acid salt
(4-(2-(cyclopropylamino)pyrido[3,4-b]pyrazin-3-yl)piperazin-1-yl)(2,4,6-trifluorophenyl)methanone, 2,2,2-trifluoroacetic acid salt
(4-(2-(cyclopropylamino)pyrido[3,4-b]pyrazin-3-yl)piperazin-1-yl)(2,4-difluoro-6-hydroxyphenyl)methanone, 2,2,2-trifluoroacetic acid salt
N-cyclopropyl-3-(4-(2,4-difluorobenzyl)piperazin-1-yl)-7-methylpyrido[3,4-b]pyrazin-2-amine, 2,2,2-trifluoroacetic acid salt
3-(4-(5-chloro-2-fluorobenzyl)piperazin-1-yl)-N-cyclopropyl-7-methylpyrido[3,4-b]pyrazin-2-amine, 2,2,2-trifluoroacetic acid salt
7-bromo-3-(cyclopropylmethyl)-2-(4-(2,4-difluorobenzyl)piperazin-1-yl)pyrido[3,4-b]pyrazine 2,2,2-trifluoroacetate
3-(cyclopropylamino)-2-(4-(2,4-difluorobenzyl)piperazin-1-yl)pyrido[3,4-b]pyrazine-7-carbonitrile, 2,2,2-trifluoroacetic acid salt
3-(4-(2,5-difluorobenzyl)piperazin-1-yl)-2-((3,3,3-trifluoropropyl)amino)quinoxaline-6-carbonitrile, 2,2,2-trifluoroacetic acid salt
3-(4-(2,4-difluorobenzyl)piperazin-1-yl)-2-((3,3,3-trifluoropropyl)amino)quinoxaline-6-carbonitrile, 2,2,2-trifluoroacetic acid salt
6-bromo-N-cyclopropyl-3-(4-(2,5-difluorobenzyl)piperazin-1-yl)quinoxalin-2-amine, 2,2,2-trifluoroacetic acid salt
6-bromo-3-(4-(5-chloro-2-fluorobenzyl)piperazin-1-yl)-N-cyclopropylquinoxalin-2-amine, 2,2,2-trifluoroacetic acid salt
6-bromo-N-cyclopropyl-3-(4-(2,4-difluorobenzyl)piperazin-1-yl)quinoxalin-2-amine, 2,2,2-trifluoroacetic acid salt
3-(4-(2,4-difluorobenzyl)piperazin-1-yl)-2-((2,2-difluoroethyl)amino)quinoxaline-6-carbonitrile
7-bromo-N-cyclopropyl-3-(4-(2,4-difluorobenzyl)piperazin-1-yl)pyrido[3,4-b]pyrazin-2-amine, 2,2,2-trifluoroacetic acid salt
3-(4-(2,4-difluorobenzyl)piperazin-1-yl)-N-(2-methoxyethyl)pyrido[3,4-b]pyrazin-2-amine, 2,2,2-trifluoroacetic acid salt
3-(4-(2,4-difluorobenzyl)piperazin-1-yl)-2-((2-methoxyethyl)amino)quinoxaline-6-carbonitrile
N-cyclopropyl-3-(4-((5-methyloxazol-2-yl)methyl)piperidin-1-yl)quinoxalin-2-amine, 2,2,2-trifluoroacetic acid salt
N-cyclopropyl-3-(4-((3-methyl-1,2,4-oxadiazol-5-yl)methyl)piperidin-1-yl)quinoxalin-2-amine, 2,2,2-trifluoroacetic acid salt
3-(4-benzylpiperidin-1-yl)-N-phenylquinoxalin-2-amine, 2,2,2-trifluoroacetic acid salt
N-cyclopropyl-3-(4-phenoxypiperidin-1-yl)quinoxalin-2-amine
3-(4-((4-chlorophenyl)amino)piperidin-1-yl)-N-cyclopropylquinoxalin-2-amine, 22,2,2-trifluoroacetic acid salt
N-cyclopropyl-3-(4-(2,4-difluorobenzyl)piperidin-1-yl)pyrido[3,4-b]pyrazin-2-amine, 2,2,2-trifluoroacetic acid salt
3-(4-(2,4-difluorobenzyl)piperidin-1-yl)-2-(pyridin-3-ylamino)quinoxaline-6-carbonitrile, 2,2,2-trifluoroacetic acid salt
2-(cyclopropylamino)-3-(4-(2,4-difluorobenzyl)piperidin-1-yl)quinoxaline-6-carbonitrile, 2,2,2-trifluoroacetic acid salt
3-(4-(2-chlorophenoxy)piperidin-1-yl)-N-cyclopropylpyrido[3,4-b]pyrazin-2-amine, 2,2,2-trifluoroacetic acid salt
N-cyclopropyl-3-(4-(2-fluorophenoxy)piperidin-1-yl)pyrido[3,4-b]pyrazin-2-amine, 2,2,2-trifluoroacetic acid salt
N-cyclopropyl-3-(4-(3-fluorophenoxy)piperidin-1-yl)pyrido[3,4-b]pyrazin-2-amine, 2,2,2-trifluoroacetic acid salt
(1-(2-(cyclopropylamino)pyrido[3,4-b]pyrazin-3-yl)piperidin-4-yl)(4-fluorophenyl)methanone, 2,2,2-trifluoroacetic acid salt
N-cyclopropyl-3-(4-(4-fluorobenzyl)piperidin-1-yl)pyrido[3,4-b]pyrazin-2-amine, 2,2,2-trifluoroacetic acid salt
(1-(2-(cyclopropylamino)pyrido[3,4-b]pyrazin-3-yl)piperidin-4-yl)(3,4-difluorophenyl)methanone, 2,2,2-trifluoroacetic acid salt
N-cyclopropyl-3-(4-((4-fluorophenyl)sulfonyl)piperidin-1-yl)pyrido[3,4-b]pyrazin-2-amine, 2,2,2-trifluoroacetic acid salt
3-(4-(4-chlorobenzyl)piperidin-1-yl)-N-cyclopropylpyrido[3,4-b]pyrazin-2-amine, 2,2,2-trifluoroacetic acid salt
3-(4-(4-chlorophenoxy)piperidin-1-yl)-N-cyclopropylpyrido[3,4-b]pyrazin-2-amine, 2,2,2-trifluoroacetic acid salt
3-(4-(3-chlorophenoxy)piperidin-1-yl)-N-cyclopropylpyrido[3,4-b]pyrazin-2-amine, 2,2,2-trifluoroacetic acid salt
N-cyclopropyl-2-(4-(2,4-difluorobenzyl)piperidin-1-yl)pyrido[3,4-b]pyrazin-3-amine, 2,2,2-trifluoroacetic acid salt
2-(4-(2,4-difluorobenzyl)piperidin-1-yl)-N-(2,2-difluoroethyl)pyrido[3,4-b]pyrazin-3-amine
N-cyclopropyl-3-(4-(2,4-difluorobenzyl)piperidin-1-yl)-7-methylpyrido[3,4-b]pyrazin-2-amine, 2,2,2-trifluoroacetic acid salt -continued (4-chlorophenyl)(1-(2-(cyclopropylamino)pyrido[3,4-b]pyrazin-3-yl)piperidin-4-yl)methanone, 2,2,2-trifluoroacetic acid salt
N-cyclopropyl-3-(4-(2,5-difluorophenoxy)piperidin-1-yl)pyrido[3,4-b]pyrazin-2-amine, 2,2,2-trifluoroacetic acid salt
N-cyclopropyl-3-(4-(2,4,6-trifluorophenoxy)piperidin-1-yl)pyrido[3,4-b]pyrazin-2-amine, 2,2,2-trifluoroacetic acid salt
N-cyclopropyl-3-(4-(4-fluorophenoxy)piperidin-1-yl)pyrido[3,4-b]pyrazin-2-amine, 2,2,2-trifluoroacetic acid salt
N-cyclopropyl-3-(4-(2,4-difluorophenoxy)piperidin-1-yl)pyrido[3,4-b]pyrazin-2-amine, 2,2,2-trifluoroacetic acid salt
(1-(2-(cyclopropylamino)pyrido[3,4-b]pyrazin-3-yl)piperidin-4-yl)(2-fluorophenyl)methanone, 2,2,2-trifluoroacetic acid salt
(1-(2-(cyclopropylamino)pyrido[3,4-b]pyrazin-3-yl)piperidin-4-yl)(2,5-difluorophenyl)methanone, 2,2,2-trifluoroacetic acid salt
3-(4-(5-chloro-2-fluorophenoxy)piperidin-1-yl)-N-cyclopropylpyrido[3,4-b]pyrazin-2-amine, 2,2,2-trifluoroacetic acid salt
N-cyclopropyl-3-(4-phenoxypiperidin-1-yl)pyrido[3,4-b]pyrazin-2-amine, 2,2,2-trifluoroacetic acid salt
(1-(2-(cyclopropylamino)pyrido[3,4-b]pyrazin-3-yl)piperidin-4-yl)(2,4-difluorophenyl)methanone, 2,2,2-trifluoroacetic acid salt
N-cyclopropyl-2-(4-(2,4-difluorobenzyl)piperidin-1-yl)-7-methylpyrido[3,4-b]pyrazin-3-amine, 2,2,2-trifluoroacetic acid salt
(1-(2-(cyclopropylamino)-7-methylpyrido[3,4-b]pyrazin-3-yl)piperidin-4-yl)(2,5-difluorophenyl)methanone, 2,2,2-trifluoroacetic acid salt
N-cyclopropyl-3-(4-(2,4-difluorophenoxy)piperidin-1-yl)-7-methylpyrido[3,4-b]pyrazin-2-amine, 2,2,2-trifluoroacetic acid salt
3-(4-(4-chloro-2-fluorophenoxy)piperidin-1-yl)-N-cyclopropylpyrido[3,4-b]pyrazin-2-amine, 2,2,2-trifluoroacetic acid salt
(1-(2-(cyclopropylamino)pyrido[3,4-b]pyrazin-3-yl)piperidin-4-yl)(2,4,6-trifluorophenyl)methanone, 2,2,2-trifluoroacetic acid salt
(4-chloro-2,6-difluorophenyl)(1-(2-(cyclopropylamino)pyrido[3,4-b]pyrazin-3-yl)piperidin-4-yl)methanone, 2,2,2-trifluoroacetic acid salt
N-cyclopropyl-3-(4-(2,5-difluorobenzyl)piperidin-1-yl)pyrido[3,4-b]pyrazin-2-amine, 2,2,2-trifluoroacetic acid salt
(4-chloro-2-fluorophenyl)(1-(2-(cyclopropylamino)pyrido[3,4-b]pyrazin-3-yl)piperidin-4-yl)methanone, 2,2,2-trifluoroacetic acid salt
(5-chloro-2-fluorophenyl)(1-(2-(cyclopropylamino)pyrido[3,4-b]pyrazin-3-yl)piperidin-4-yl)methanone, 2,2,2-trifluoroacetic acid salt
N-cyclopropyl-3-(4-((2,4-difluorophenyl)fluoromethyl)piperidin-1-yl)pyrido[3,4-b]pyrazin-2-amine
N-cyclopropyl-3-(4-(fluoro(4-fluorophenyl)methyl)piperidin-1-yl)pyrido[3,4-b]pyrazin-2-amine
N-cyclopropyl-3-(4-(2,4-difluorobenzyl)piperidin-1-yl)pyrazino[2,3-d]pyridazin-2-amine, 2,2,2-trifluoroacetic acid salt
3-(4-((5-chloro-2-fluorophenyl)fluoromethyl)piperidin-1-yl)-N-cyclopropylpyrido[3,4-b]pyrazin-2-amine
N-cyclopropyl-3-(4-((2,5-difluorophenyl)fluoromethyl)piperidin-1-yl)-7-methylpyrido[3,4-b]pyrazin-2-amine
(1-(2-(cyclopropylamino)pyrido[3,4-b]pyrazin-3-yl)piperidin-4-yl)(3-methoxyazetidin-1-yl)methanone
(1-(2-(cyclopropylamino)pyrido[3,4-b]pyrazin-3-yl)piperidin-4-yl)(4-methylpiperazin-1-yl)methanone
(1-(2-(cyclopropylamino)pyrido[3,4-b]pyrazin-3-yl)piperidin-4-yl)(pyrrolidin-1-yl)methanone
(1-(2-(cyclopropylamino)pyrido[3,4-b]pyrazin-3-yl)piperidin-4-yl)(piperidin-1-yl)methanone
N-cyclopropyl-3-(4-((2,4-difluorophenyl)amino)piperidin-1-yl)pyrido[3,4-b]pyrazin-2-amine, 22,2,2-trifluoroacetic acid salt
3-(4-(1-(5-chloro-2-fluorophenyl)-1-fluoroethyl)piperidin-1-yl)-N-cyclopropylpyrido[3,4-b]pyrazin-2-amine
N-cyclopropyl-3-(4-((2,5-difluorophenyl)fluoromethyl)piperidin-1-yl)pyrido[3,4-b]pyrazin-2-amine
3-(4-(2,4-difluorobenzyl)piperidin-1-yl)-2-(isopropylamino)quinoxaline-6-carbonitrile
2-(cyclobutylamino)-3-(4-(2,4-difluorobenzyl)piperidin-1-yl)quinoxaline-6-carbonitrile
7-bromo-N-cyclopropyl-3-(4-(2,4-difluorobenzyl)piperidin-1-yl)pyrido[3,4-b]pyrazin-2-amine, 2,2,2-trifluoroacetic acid salt
(S)-N-cyclopropyl-3-(4-((2,5-difluorophenyl)fluoromethyl)piperidin-1-yl)-7-methylpyrido[3,4-b]pyrazin-2-amine
3-(4-(4-chloro-2-fluorophenoxy)piperidin-1-yl)-2-(cyclopropylamino)quinoxaline-6-carbonitrile, 2,2,2-trifluoroacetic acid salt
3-(4-(4-chloro-2-fluorophenoxy)piperidin-1-yl)-2-(isopropylamino)quinoxaline-6-carbonitrile, 2,2,2-trifluoroacetic acid salt
3-(4-(4-chloro-2-fluorophenoxy)piperidin-1-yl)-N-cyclopropyl-7-methylpyrido[3,4-b]pyrazin-2-amine, 2,2,2-trifluoroacetic acid salt
2-(cyclopropylamino)-3-(4-(2,4-difluorophenoxy)piperidin-1-yl)quinoxaline-6-carbonitrile, 2,2,2-trifluoroacetic acid salt
3-(4-(5-chloro-2-fluorobenzoyl)piperidin-1-yl)-2-(cyclopropylamino)quinoxaline-6-carbonitrile, 2,2,2-trifluoroacetic acid salt
2-(cyclopropylamino)-3-(4-((2,5-difluorophenyl)fluoromethyl)piperidin-1-yl)quinoxaline-6-carbonitrile, 2,2,2-trifluoroacetic acid salt
2-(cyclopropylamino)-3-(4-((4-fluoro-2-oxopyridin-1(2H)-yl)methyl)piperidin-1-yl)quinoxaline-6-carbonitrile, 2,2,2-trifluoroacetic acid salt
2-(cyclopropylamino)-3-(4-(2,5-difluorobenzoyl)piperidin-1-yl)quinoxaline-6-carbonitrile, 2,2,2-trifluoroacetic acid salt -continued 1-((1-(2-(cyclopropylamino)-7-methylpyrido[3,4-b]pyrazin-3-yl)piperidin-4-yl)methyl)-4-fluoropyridin-2(1H)-one, 2,2,2-trifluoroacetic acid salt
2-(4-(4-chloro-2-fluorophenoxy)piperidin-1-yl)-3-(cyclopropylamino)quinoxaline-6-carbonitrile, 2,2,2-trifluoroacetic acid salt
2-(cyclopropylamino)-3-(4-(2,4-difluorobenzyl)piperidin-1-yl)pyrido[3,4-b]pyrazine-7-carbonitrile
7-chloro-N-cyclopropyl-3-(4-(2,4-difluorophenoxy)piperidin-1-yl)pyrido[3,4-b]pyrazin-2-amine, 2,2,2-trifluoroacetic acid salt
(R)-N-cyclopropyl-3-(4-((2,5-difluorophenyl)fluoromethyl)piperidin-1-yl)-7-methylpyrido[3,4-b]pyrazin-2-amine, hydrogen chloride salt
N-cyclopropyl-3-(4-(2,4-difluorobenzyl)piperidin-1-yl)-6,7-difluoroquinoxalin-2-amine, 2,2,2-trifluoroacetic acid salt
N-cyclopropyl-3-(4-(2,4-difluorobenzyl)piperidin-1-yl)-6-fluoroquinoxalin-2-amine, 2,2,2-trifluoroacetic acid salt
2-(cyclopropylamino)-3-(4-((2,4-difluorophenyl)fluoromethyl)piperidin-1-yl)quinoxaline-6-carbonitrile, 2,2,2-trifluoroacetic acid salt
3-(4-((2,4-difluorophenyl)fluoromethyl)piperidin-1-yl)-2-(isopropylamino)quinoxaline-6-carbonitrile, 2,2,2-trifluoroacetic acid salt
2-(cyclobutylamino)-3-(4-((2,5-difluorophenyl)fluoromethyl)piperidin-1-yl)quinoxaline-6-carbonitrile, 2,2,2-trifluoroacetic acid salt
N-cyclopropyl-3-(4-(2,4-difluorobenzyl)piperidin-1-yl)-7-methoxypyrido[3,4-b]pyrazin-2-amine, 2,2,2-trifluoroacetic acid salt
3-(cyclopropylamino)-2-(4-((2,5-difluorophenyl)fluoromethyl)piperidin-1-yl)quinoxaline-6-carbonitrile, 2,2,2-trifluoroacetic acid salt
3-(4-((2,5-difluorophenyl)fluoromethyl)piperidin-1-yl)-2-(isopropylamino)quinoxaline-6-carbonitrile, 2,2,2-trifluoroacetic acid salt
8-chloro-N-cyclopropyl-3-(4-((2,5-difluorophenyl)fluoromethyl)piperidin-1-yl)pyrido[3,4-b]pyrazin-2-amine, 2,2,2-trifluoroacetic acid salt
3-(cyclopropylamino)-2-(4-((2,4-difluorophenyl)fluoromethyl)piperidin-1-yl)quinoxaline-6-carbonitrile, 2,2,2-trifluoroacetic acid salt
N-cyclopropyl-3-(4-((2,4-difluorophenyl)fluoromethyl)piperidin-1-yl)-7-methylpyrido[3,4-b]pyrazin-2-amine, 2,2,2-trifluoroacetic acid salt
7-chloro-N-cyclopropyl-3-(4-((2,4-difluorophenyl)fluoromethyl)piperidin-1-yl)pyrido[3,4-b]pyrazin-2-amine, 2,2,2-trifluoroacetic acid salt
2-(cyclopropylamino)-3-(4-(2,4-difluorobenzyl)piperidin-1-yl)pyrido[3,4-b]pyrazin-7-ol, 2,2,2-trifluoroacetic acid salt
(R)-2-(cyclopropylamino)-3-(4-((2,4-difluorophenyl)fluoromethyl)piperidin-1-yl)quinoxaline-6-carbonitrile, 2,2,2-trifluoroacetic acid salt
N-cyclopropyl-3-(4-((2,4-difluorophenyl)fluoromethyl)piperidin-1-yl)-5-methylpyrido[3,4-b]pyrazin-2-amine, 2,2,2-trifluoroacetic acid salt
N-cyclopropyl-3-(4-(2,4-difluorobenzyl)piperidin-1-yl)-5-methylpyrido[3,4-b]pyrazin-2-amine, 2,2,2-trifluoroacetic acid salt
N-cyclopropyl-3-(4-(2,4-difluorophenoxy)piperidin-1-yl)-5-methylpyrido[3,4-b]pyrazin-2-amine, 2,2,2-trifluoroacetic acid salt
6-bromo-N-cyclopropyl-3-(4-(2,4-difluorobenzyl)piperidin-1-yl)quinoxalin-2-amine, 2,2,2-trifluoroacetic acid salt
3-(4-(2,4-difluorobenzyl)piperidin-1-yl)-2-((3,3,3-trifluoropropyl)amino)quinoxaline-6-carbonitrile, 2,2,2-trifluoroacetic acid salt
(R)-N-cyclopropyl-3-(4-((2,4-difluorophenyl)fluoromethyl)piperidin-1-yl)-7-methylpyrido[3,4-b]pyrazin-2-amine, 2,2,2-trifluoroacetic acid salt
3-(4-((2,5-difluorophenyl)fluoromethyl)piperidin-1-yl)-2-((3,3,3-trifluoropropyl)amino)quinoxaline-6-carbonitrile, 2,2,2-trifluoroacetic acid salt
3-(4-(2,4-difluorophenoxy)piperidin-1-yl)-2-((3,3,3-trifluoropropyl)amino)quinoxaline-6-carbonitrile, 2,2,2-trifluoroacetic acid salt
6-bromo-N-cyclopropyl-3-(4-((2,5-difluorophenyl)fluoromethyl)piperidin-1-yl)quinoxalin-2-amine, 2,2,2-trifluoroacetic acid salt
6-bromo-N-cyclopropyl-3-(4-(2,4-difluorophenoxy)piperidin-1-yl)quinoxalin-2-amine, 2,2,2-trifluoroacetic acid salt
(S)-N-cyclopropyl-3-(4-((2,4-difluorophenyl)fluoromethyl)piperidin-1-yl)-7-methylpyrido[3,4-b]pyrazin-2-amine, 2,2,2-trifluoroacetic acid salt
(S)-3-(4-((2,5-difluorophenyl)fluoromethyl)piperidin-1-yl)-2-(isopropylamino)quinoxaline-6-carbonitrile
(R)-3-(4-((2,5-difluorophenyl)fluoromethyl)piperidin-1-yl)-2-(isopropylamino)quinoxaline-6-carbonitrile
(S)-2-(cyclopropylamino)-3-(4-((2,4-difluorophenyl)fluoromethyl)piperidin-1-yl)quinoxaline-6-carbonitrile
(R)-2-(cyclopropylamino)-3-(4-((2,4-difluorophenyl)fluoromethyl)piperidin-1-yl)quinoxaline-6-carbonitrile
(S)-3-(4-((2,4-difluorophenyl)fluoromethyl)piperidin-1-yl)-2-(isopropylamino)quinoxaline-6-carbonitrile
(R)-3-(4-((2,4-difluorophenyl)fluoromethyl)piperidin-1-yl)-2-(isopropylamino)quinoxaline-6-carbonitrile
(S)-3-(cyclopropylamino)-2-(4-((2,4-difluorophenyl)fluoromethyl)piperidin-1-yl)quinoxaline-6-carbonitrile
(R)-3-(cyclopropylamino)-2-(4-((2,4-difluorophenyl)fluoromethyl)piperidin-1-yl)quinoxaline-6-carbonitrile
2-((2,2-difluoroethyl)amino)-3-(4-((2,4-difluorophenyl)fluoromethyl)piperidin-1-yl)quinoxaline-6-carbonitrile
3-(4-(2,4-difluorobenzyl)piperidin-1-yl)-2-((2,2-difluoroethyl)amino)quinoxaline-6-carbonitrile
2-((2,2-difluoroethyl)amino)-3-(4-(2,4-difluorophenoxy)piperidin-1-yl)quinoxaline-6-carbonitrile (S)-2-(cyclopropylamino)-3-(4-((2,4-difluorophenyl)fluoromethyl)piperidin-1-yl)quinoxaline-6-carbonitrile, 2,2,2-trifluoroacetic acid salt
7-bromo-N-cyclopropyl-3-(4-((2,4-difluorophenyl)fluoromethyl)piperidin-1-yl)pyrido[3,4-b]pyrazin-2-amine, 2,2,2-trifluoroacetic acid salt
(S)-N-cyclopropyl-3-(4-((2,4-difluorophenyl)fluoromethyl)piperidin-1-yl)-5-methylpyrido[3,4-b]pyrazin-2-amine, 2,2,2-trifluoroacetic acid salt
(S)-N-cyclopropyl-3-(4-((2,4-difluorophenyl)fluoromethyl)piperidin-1-yl)pyrido[3,4-b]pyrazin-2-amine, 2,2,2-trifluoroacetic acid salt
3-(4-(2,4-difluorobenzyl)piperidin-1-yl)-2-((2-methoxyethyl)amino)quinoxaline-6-carbonitrile
3-(4-(2,4-difluorobenzyl)piperidin-1-yl)-N-(2-methoxyethyl)pyrido[3,4-b]pyrazin-2-amine, 2,2,2-trifluoroacetic acid salt
3-(4-((2,4-difluorophenyl)fluoromethyl)piperidin-1-yl)-N-(2-methoxyethyl)pyrido[3,4-b]pyrazin-2-amine, 2,2,2-trifluoroacetic acid salt
3-(4-(2,4-difluorophenoxy)piperidin-1-yl)-2-((2-methoxyethyl)amino)quinoxaline-6-carbonitrile
3-(4-((2,4-difluorophenyl)fluoromethyl)piperidin-1-yl)-2-((2-methoxyethyl)amino)quinoxaline-6-carbonitrile
(R)-7-chloro-N-cyclopropyl-3-(4-((2,4-difluorophenyl)fluoromethyl)piperidin-1-yl)pyrido[3,4-b]pyrazin-2-amine, 2,2,2-trifluoroacetic acid salt
(S)-7-chloro-N-cyclopropyl-3-(4-((2,4-difluorophenyl)fluoromethyl)piperidin-1-yl)pyrido[3,4-b]pyrazin-2-amine, 2,2,2-trifluoroacetic acid salt
3-(4-(2,4-difluorophenoxy)piperidin-1-yl)-N-(2-methoxyethyl)pyrido[3,4-b]pyrazin-2-amine, 2,2,2-trifluoroacetic acid salt
3-(4-((4-chloro-2-oxopyridin-1(2H)-yl)methyl)piperidin-1-yl)-2-(cyclopropylamino)quinoxaline-6-carbonitrile
1-((1-(2-(cyclopropylamino)-5-methylpyrido[3,4-b]pyrazin-3-yl)piperidin-4-yl)methyl)-5-fluoropyridin-2(1H)-one
4-chloro-1-((1-(2-(cyclopropylamino)-5-methylpyrido[3,4-b]pyrazin-3-yl)piperidin-4-yl)methyl)pyridin-2(1H)-one
2-(cyclopropylamino)-3-(4-((5-fluoro-2-oxopyridin-1(2H)-yl)methyl)piperidin-1-yl)quinoxaline-6-carbonitrile
1-((1-(2-(cyclopropylamino)pyrido[3,4-b]pyrazin-3-yl)piperidin-4-yl)methyl)-4-fluoropyridin-2(1H)-one
1-((1-(2-(cyclopropylamino)-5-methylpyrido [3,4-b]pyrazin-3-yl)piperidin-4-yl)methyl)-4-fluoropyridin-2(1H)-one
5-chloro-1-((1-(2-(cyclopropylamino)pyrido[3,4-b]pyrazin-3-yl)piperidin-4-yl)methyl)pyridin-2(1H)-one
3-(4-((5-chloro-2-fluorophenyl)difluoromethyl)piperidin-1-yl)-2-(cyclopropylamino)quinoxaline-6-carbonitrile
3-(4-((5-chloro-2-fluorophenyl)difluoromethyl)piperidin-1-yl)-N-cyclopropyl-7-methylpyrido[3,4-b]pyrazin-2-amine
3-(4-((5-chloro-2-oxopyridin-1(2H)-yl)methyl)piperidin-1-yl)-2-(cyclopropylamino)quinoxaline-6-carbonitrile
3-(4-((5-chloro-2-fluorophenyl)difluoromethyl)piperidin-1-yl)-N-cyclopropyl-5-methylpyrido[3,4-b]pyrazin-2-amine
5-chloro-1-((1-(2-(cyclopropylamino)-5-methylpyrido[3,4-b]pyrazin-3-yl)piperidin-4-yl)methyl)pyridin-2(1H)-one
5-chloro-1-((1-(2-(cyclopropylamino)-7-methylpyrido[3,4-b]pyrazin-3-yl)piperidin-4-yl)methyl)pyridin-2(1H)-one
3-(4-((5-chloro-2-fluorophenyl)difluoromethyl)piperidin-1-yl)-N-cyclopropylpyrido[3,4-b]pyrazin-2-amine
N-cyclopropyl-3-(4-((2,5-difluorophenyl)difluoromethyl)piperidin-1-yl)pyrido[3,4-b]pyrazin-2-amine
N-cyclopropyl-3-(4-((2,5-difluorophenyl)difluoromethyl)piperidin-1-yl)-7-methylpyrido[3,4-b]pyrazin-2-amine
N-cyclopropyl-3-(4-((2,4-difluorophenyl)difluoromethyl)piperidin-1-yl)-5-methylpyrido[3,4-b]pyrazin-2-amine
N-cyclopropyl-3-(4-((2,5-difluorophenyl)difluoromethyl)piperidin-1-yl)-5-methylpyrido[3,4-b]pyrazin-2-amine
2-(cyclopropylamino)-3-(4-((2,4-difluorophenyl)difluoromethyl)piperidin-1-yl)quinoxaline-6-carbonitrile
N-cyclopropyl-3-(4-((2,4-difluorophenyl)difluoromethyl)piperidin-1-yl)pyrido[3,4-b]pyrazin-2-amine
2-(cyclopropylamino)-3-(4-((2,5-difluorophenyl)difluoromethyl)piperidin-1-yl)quinoxaline-6-carbonitrile
(S)-2-(cyclopropylamino)-3-(4-((2,4-difluorophenyl)fluoromethyl)piperidin-1-yl)pyrido[3,4-b]pyrazine-7-carbonitrile
(R)-2-(cyclopropylamino)-3-(4-((2,4-difluorophenyl)fluoromethyl)piperidin-1-yl)pyrido[3,4-b]pyrazine-7-carbonitrile
(R)-3-(cyclopropylamino)-2-(4-((2,4-difluorophenyl)fluoromethyl)piperidin-1-yl)pyrido[3,4-b]pyrazine-7-carbonitrile
(S)-3-(cyclopropylamino)-2-(4-((2,4-difluorophenyl)fluoromethyl)piperidin-1-yl)pyrido[3,4-b]pyrazine-7-carbonitrile
N-cyclopropyl-3-(4-(pyridin-3-yloxy)piperidin-1-yl)pyrido[3,4-b]pyrazin-2-amine
N-cyclopropyl-3-(4-(4-methoxyphenoxy)piperidin-1-yl)pyrido[3,4-b]pyrazin-2-amine
N-cyclopropyl-3-(4-(pyridin-2-yloxy)piperidin-1-yl)pyrido[3,4-b]pyrazin-2-amine
N-cyclopropyl-3-(4-(pyridin-4-yloxy)piperidin-1-yl)pyrido[3,4-b]pyrazin-2-amine
(1-(2-(cyclopropylamino)pyrido[3,4-b]pyrazin-3-yl)piperidin-4-yl)(2-methoxyphenyl)methanone, 2,2,2-trifluoroacetic acid salt
4-((1-(2-(cyclopropylamino)pyrido[3,4-b]pyrazin-3-yl)piperidin-4-yl)oxy)benzonitrile
(2-chlorophenyl)(1-(2-(cyclopropylamino)pyrido[3,4-b]pyrazin-3-yl)piperidin-4-yl)methanone, 2,2,2-trifluoroacetic acid salt -continued N-cyclopropyl-3-(4-(3-methoxyphenoxy)piperidin-1-yl)pyrido[3,4-b]pyrazin-2-amine, 2,2,2-trifluoroacetic acid salt
N-cyclopropyl-3-(4-(2-methoxyphenoxy)piperidin-1-yl)pyrido[3,4-b]pyrazin-2-amine, 2,2,2-trifluoroacetic acid salt
(1-(2-(cyclopropylamino)pyrido[3,4-b]pyrazin-3-yl)piperidin-4-yl)(phenyl)methanone
(1-(2-(cyclopropylamino)pyrido[3,4-b]pyrazin-3-yl)piperidin-4-yl)(2,3-difluorophenyl)methanone, 2,2,2-trifluoroacetic acid salt
(3-chlorophenyl)(1-(2-(cyclopropylamino)pyrido[3,4-b]pyrazin-3-yl)piperidin-4-yl)methanone
3-((1-(2-(cyclopropylamino)pyrido[3,4-b]pyrazin-3-yl)piperidin-4-yl)oxy)benzonitrile
(1-(2-(cyclopropylamino)pyrido[3,4-b]pyrazin-3-yl)piperidin-4-yl)(3-methoxyphenyl)methanone
(1-(2-(cyclopropylamino)pyrido[3,4-b]pyrazin-3-yl)piperidin-4-yl)(o-tolyl)methanone, 2,2,2-trifluoroacetic acid salt
(1-(2-(cyclopropylamino)pyrido[3,4-b]pyrazin-3-yl)piperidin-4-yl)(2,6-difluorophenyl)methanone, 2,2,2-trifluoroacetic acid salt
(2-chloro-5-fluorophenyl)(1-(2-(cyclopropylamino)pyrido[3,4-b]pyrazin-3-yl)piperidin-4-yl)methanone, 2,2,2-trifluoroacetic acid salt
(1-(2-(cyclopropylamino)pyrido[3,4-b]pyrazin-3-yl)piperidin-4-yl)(3-fluorophenyl)methanone, 2,2,2-trifluoroacetic acid salt
(6-chloro-2,3-difluorophenyl)(1-(2-(cyclopropylamino)pyrido[3,4-b]pyrazin-3-yl)piperidin-4-yl)methanone, 2,2,2-trifluoroacetic acid salt
N-cyclopropyl-3-(4-(2-fluoro-4-methoxyphenoxy)piperidin-1-yl)pyrido[3,4-b]pyrazin-2-amine, 2,2,2-trifluoroacetic acid salt
(2-chloro-3-fluorophenyl)(1-(2-(cyclopropylamino)pyrido[3,4-b]pyrazin-3-yl)piperidin-4-yl)methanone, hydrogen chloride salt
(2-chlorothiophen-3-yl)(1-(2-(cyclopropylamino)pyrido[3,4-b]pyrazin-3-yl)piperidin-4-yl)methanone, hydrogen chloride salt
(1-(2-(cyclopropylamino)pyrido[3,4-b]pyrazin-3-yl)piperidin-4-yl)(thiophen-2-yl)methanone, 2,2,2-trifluoroacetic acid salt
2-((1-(2-(cyclopropylamino)pyrido[3,4-b]pyrazin-3-yl)piperidin-4-yl)oxy)benzonitrile
(2-chloro-6-fluorophenyl)(1-(2-(cyclopropylamino)pyrido[3,4-b]pyrazin-3-yl)piperidin-4-yl)methanone
(S)-2-(cyclopropylamino)-3-(4-((2,4-difluorophenyl)fluoromethyl)piperidin-1-yl)-N,N-dimethylpyrido[3,4-b]pyrazine-7-carboxamide, 2,2,2-trifluoroacetic acid salt
(S)-2-(cyclopropylamino)-3-(4-((2,4-difluorophenyl)fluoromethyl)piperidin-1-yl)-N,N-dimethylpyrido[3,4-b]pyrazine-7-carboxamide, 2,2,2-trifluoroacetic acid salt
(R)-2-(cyclopropylamino)-3-(4-((2,4-difluorophenyl)fluoromethyl)piperidin-1-yl)-N,N-dimethylpyrido[3,4-b]pyrazine-7-carboxamide, 2,2,2-trifluoroacetic acid salt
(S)-(2-(cyclopropylamino)-3-(4-((2,4-difluorophenyl)fluoromethyl)piperidin-1-yl)pyrido[3,4-b]pyrazin-7-yl)(morpholino)methanone, 2,2,2-trifluoroacetic acid salt
(R)-(2-(cyclopropylamino)-3-(4-((2,4-difluorophenyl)fluoromethyl)piperidin-1-yl)pyrido[3,4-b]pyrazin-7-yl)(morpholino)methanone, 2,2,2-trifluoroacetic acid salt
(1-(2-(cyclopropylamino)pyrido[3,4-b]pyrazin-3-yl)piperidin-4-yl)(2-(methylthio)phenyl)methanone, 2,2,2-trifluoroacetic acid salt
1-(4-((1-(2-(cyclopropylamino)pyrido[3,4-b]pyrazin-3-yl)piperidin-4-yl)oxy)phenyl)ethanone, 2,2,2-trifluoroacetic acid salt
2,2,2-trifluoroacetic acid, 1-(4-((1-(2-(cyclopropylamino)pyrido[3,4-b]pyrazin-3-yl)piperidin-4-yl)oxy)phenyl)ethanol salt
(1-(2-(cyclopropylamino)pyrido[3,4-b]pyrazin-3-yl)piperidin-4-yl)(thiophen-3-yl)methanone, 2,2,2-trifluoroacetic acid salt
(2-bromophenyl)(1-(2-(cyclopropylamino)pyrido[3,4-b]pyrazin-3-yl)piperidin-4-yl)methanone, 2,2,2-trifluoroacetic acid salt
(2-bromopyridin-3-yl)(1-(2-(cyclopropylamino)pyrido[3,4-b]pyrazin-3-yl)piperidin-4-yl)methanone, 2,2,2-trifluoroacetic acid salt
3-(1-(2-(cyclopropylamino)pyrido[3,4-b]pyrazin-3-yl)piperidine-4-carbonyl)-4-fluorobenzonitrile, 2,2,2-trifluoroacetic acid salt
4-((1-(2-(cyclopropylamino)pyrido[3,4-b]pyrazin-3-yl)piperidin-4-yl)oxy)-N,N-dimethylbenzamide, 2,2,2-trifluoroacetic acid salt
(R)-azetidin-1-yl(2-(cyclopropylamino)-3-(4-((2,4-difluorophenyl)fluoromethyl)piperidin-1-yl)pyrido[3,4-b]pyrazin-7-yl)methanone
(R)-(2-(cyclopropylamino)-3-(4-((2,4-difluorophenyl)fluoromethyl)piperidin-1-yl)pyrido[3,4-b]pyrazin-7-yl)(3-fluoroazetidin-1-yl)methanone
(S)-azetidin-1-yl(2-(cyclopropylamino)-3-(4-((2,4-difluorophenyl)fluoromethyl)piperidin-1-yl)pyrido[3,4-b]pyrazin-7-yl)methanone
7-chloro-N-cyclopropyl-3-(4-(2,4-difluorobenzyl)piperidin-1-yl)pyrido[3,4-b]pyrazin-2-amine
(1-(2-(cyclopropylamino)pyrido[3,4-b]pyrazin-3-yl)piperidin-4-yl)(2-fluoro-5-(methylthio)phenyl)methanone, 2,2,2-trifluoroacetic acid salt
(S)-N-cyclopropyl-3-(4-((2,4-difluorophenyl)fluoromethyl)piperidin-1-yl)pyrazino[2,3-d]pyridazin-2-amine, 2,2,2-trifluoroacetic acid salt
4-chloro-3-(1-(7-chloro-2-(cyclopropylamino)pyrido[3,4-b]pyrazin-3-yl)piperidine-4-carbonyl)benzonitrile
3-(4-(5-cyano-2-(dimethylcarbamoyl)benzoyl)piperidin-1-yl)-2-(cyclopropylamino)-N,N-dimethylpyrido[3,4-b]pyrazine-7-carboxamide
2-(cyclopropylamino)-3-(4-(2,4-difluorophenoxy)piperidin-1-yl)-N,N-dimethylpyrido[3,4-b]pyrazine-7-carboxamide
N-cyclopropyl-3-(4-(2-fluoro-4-methoxyphenoxy)piperidin-1-yl)pyrazino[2,3-d]pyridazin-2-amine, 2,2,2-trifluoroacetic acid salt
(R)-N-cyclopropyl-3-(4-((2,4-difluorophenyl)fluoromethyl)piperidin-1-yl)pyrazino[2,3-d]pyridazin-2-amine, 2,2,2-trifluoroacetic acid salt N-cyclopropyl-3-(4-(4-(methylthio)phenoxy)piperidin-1-yl)pyrido[3,4-b]pyrazin-2-amine, 2,2,2-trifluoroacetic acid salt
N-cyclopropyl-3-(4-(4-ethoxyphenoxy)piperidin-1-yl)pyrido[3,4-b]pyrazin-2-amine, 2,2,2-trifluoroacetic acid salt
3-(1-(7-bromo-2-(cyclopropylamino)pyrido[3,4-b]pyrazin-3-yl)piperidine-4-carbonyl)-4-fluorobenzonitrile
(2-(cyclopropylamino)-3-(4-(2-fluoro-4-methoxyphenoxy)piperidin-1-yl)pyrido[3,4-b]pyrazin-7-yl)(4-methylpiperazin-1-yl)methanone
2-(cyclopropylamino)-3-(4-(2-fluoro-4-methoxyphenoxy)piperidin-1-yl)-N,N-dimethylpyrido[3,4-b]pyrazine-5-carboxamide
2-(cyclopropylamino)-3-(4-(2-fluoro-4-methoxyphenoxy)piperidin-1-yl)pyrido[3,4-b]pyrazine-5-carbonitrile, 2,2,2-trifluoroacetic acid salt
N-cyclopropyl-3-(4-(2-fluoro-4-methoxyphenoxy)piperidin-1-yl)-5-morpholinopyrido[3,4-b]pyrazin-2-amine, 2,2,2-trifluoroacetic acid salt
N2-cyclopropyl-3-(4-(2-fluoro-4-methoxyphenoxy)piperidin-1-yl)-N5,N5-dimethylpyrido[3,4-b]pyrazine-2,5-diamine, 2,2,2-trifluoroacetic acid salt
3-(4-(2-chloro-5-fluorobenzoyl)piperazin-1-yl)-2-(cyclopropylamino)-N,N-dimethylpyrido[3,4-b]pyrazine-7-carboxamide
N-cyclopropyl-2-(4-(2-fluoro-4-methoxyphenoxy)piperidin-1-yl)pyrido[3,4-b]pyrazin-3-amine, 2,2,2-trifluoroacetic acid salt
azetidin-1-yl(2-(cyclopropylamino)-3-(4-(2-fluoro-4-methoxyphenoxy)piperidin-1-yl)pyrido[3,4-b]pyrazin-5-yl)methanone, 2,2,2-trifluoroacetic acid salt
(2-(cyclopropylamino)-3-(4-(2,4-difluorobenzyl)piperazin-1-yl)pyrido[3,4-b]pyrazin-7-yl)(morpholino)methanone, 2,2,2-trifluoroacetic acid salt
2-(cyclopropylamino)-3-(4-(2,4-difluorobenzyl)piperazin-1-yl)pyrido[3,4-b]pyrazine-5-carbonitrile, 2,2,2-trifluoroacetic acid salt
2-(cyclopropylamino)-3-(4-(2-fluoro-4-methoxybenzyl)piperazin-1-yl)pyrido[3,4-b]pyrazine-5-carbonitrile, 2,2,2-trifluoroacetic acid salt
2-(cyclopropylamino)-3-(4-(2-fluoro-4-methoxybenzyl)piperazin-1-yl)-N,N-dimethylpyrido[3,4-b]pyrazine-7-carboxamide, 2,2,2-trifluoroacetic acid salt
4-((1-(2-(cyclopropylamino)pyrido[3,4-b]pyrazin-3-yl)piperidin-4-yl)oxy)-3-fluorophenol, 2,2,2-trifluoroacetic acid salt
3-(4-(2-fluoro-4-methoxyphenoxy)piperidin-1-yl)-N-isopropylpyrido[3,4-b]pyrazin-2-amine, 2,2,2-trifluoroacetic acid salt
3-(4-(2-fluoro-4-methoxyphenoxy)piperidin-1-yl)-N-isopropylpyrido[3,4-b]pyrazin-2-amine, 2,2,2-trifluoroacetic acid salt
N-cyclopropyl-3-(4-(2-fluoro-4-(methylthio)phenoxy)piperidin-1-yl)pyrazino[2,3-d]pyridazin-2-amine, 2,2,2-trifluoroacetic acid salt
N-cyclopropyl-3-(4-(2,4-difluorophenoxy)piperidin-1-yl)pyrazino[2,3-d]pyridazin-2-amine, 2,2,2-trifluoroacetic acid salt
3-(4-(2,4-difluorophenoxy)piperidin-1-yl)-N-isopropylpyrido[3,4-b]pyrazin-2-amine, 2,2,2-trifluoroacetic acid salt
3-(4-((2,4-difluorophenyl)fluoromethyl)piperidin-1-yl)-N-isopropylpyrido[3,4-b]pyrazin-2-amine, 2,2,2-trifluoroacetic acid salt
N-ethyl-3-(4-(2-fluoro-4-methoxyphenoxy)piperidin-1-yl)pyrido[3,4-b]pyrazin-2-amine, 2,2,2-trifluoroacetic acid salt
4-((1-(3-(cyclopropylamino)pyrazino[2,3-d]pyridazin-2-yl)piperidin-4-yl)oxy)-3-fluorophenol
3-(4-(2-fluoro-4-methoxyphenoxy)piperidin-1-yl)-N-isopropylpyrazino[2,3-d]pyridazin-2-amine, 2,2,2-trifluoroacetic acid salt
4-((1-(2-(cyclopropylamino)pyrido[3,4-b]pyrazin-3-yl)piperidin-4-yl)oxy)-3-fluorobenzonitrile, 22,2,2-trifluoroacetic acid salt
2-(4-(4-chloro-2-fluorophenoxy)piperidin-1-yl)-3-(isopropylamino)quinoxaline-6-carbonitrile, hydrogen chloride salt
2-(4-(2-chloro-5-(isopropylamino)benzoyl)piperidin-1-yl)-3-(isopropylamino)quinoxaline-6-carbonitrile
3-(4-(2-fluoro-4-methoxyphenoxy)piperidin-1-yl)-2-(isopropylamino)pyrido[3,4-b]pyrazine-7-carbonitrile, 2,2,2-trifluoroacetic acid salt
3-(4-(2,4-difluorophenoxy)piperidin-1-yl)-2-(isopropylamino)-N,N-dimethylpyrido[3,4-b]pyrazine-7-carboxamide, 2,2,2-trifluoroacetic acid salt
3-(4-(4-chloro-2-fluorophenoxy)piperidin-1-yl)-2-(isopropylamino)-N,N-dimethylpyrido[3,4-b]pyrazine-7-carboxamide, 2,2,2-trifluoroacetic acid salt
3-(4-(2,5-difluorobenzoyl)piperidin-1-yl)-2-(isopropylamino)pyrido[3,4-b]pyrazine-7-carbonitrile, 2,2,2-trifluoroacetic acid salt
3-(4-(2,4-difluorophenoxy)piperidin-1-yl)-N-isopropylpyrazino[2,3-d]pyridazin-2-amine, 2,2,2-trifluoroacetic acid salt
3-(4-(2,4-difluorophenoxy)piperidin-1-yl)-N-isopropylpyrazino[2,3-d]pyridazin-2-amine, 2,2,2-trifluoroacetic acid salt
3-(4-(2,4-difluorobenzyl)piperazin-1-yl)-2-(isopropylamino)-N,N-dimethylpyrido[3,4-b]pyrazine-7-carboxamide, 2,2,2-trifluoroacetic acid salt
3-(4-(2,5-difluorobenzoyl)piperidin-1-yl)-2-(isopropylamino)-N,N-dimethylpyrido[3,4-b]pyrazine-7-carboxamide, 2,2,2-trifluoroacetic acid salt
3-(4-(2-fluoro-4-methoxybenzyl)piperidin-1-yl)-2-(isopropylamino)pyrido[3,4-b]pyrazine-7-carbonitrile, 2,2,2-trifluoroacetic acid salt
(S)-N-(sec-butyl)-3-(4-(2-fluoro-4-methoxyphenoxy)piperidin-1-yl)pyrazino[2,3-d]pyridazin-2-amine, 2,2,2-trifluoroacetic acid salt
(R)-N-(sec-butyl)-3-(4-(2-fluoro-4-methoxyphenoxy)piperidin-1-yl)pyrazino[2,3-d]pyridazin-2-amine, 2,2,2-trifluoroacetic acid salt
3-fluoro-4-((1-(3-(isopropylamino)pyrazino[2,3-d]pyridazin-2-yl)piperidin-4-yl)oxy)benzonitrile, 2,2,2-trifluoroacetic acid salt -continued (R)-3-(4-((2,4-difluorophenyl)fluoromethyl)piperidin-1-yl)-N-isopropylpyrazino[2,3-d]pyridazin-2-amine, 2,2,2-trifluoroacetic acid salt (2-fluoro-4-methoxyphenyl)(1-(3-(isopropylamino)pyrazino[2,3-d]pyridazin-2-yl)piperidin-4-yl)methanone, 2,2,2-trifluoroacetic acid salt 3-(4-(2-fluoro-4-methoxybenzyl)piperidin-1-yl)-N-isopropylpyrazino[2,3-d]pyridazin-2-amine, 2,2,2-trifluoroacetic acid salt 3-(4-(4-chloro-2-fluorophenoxy)piperidin-1-yl)-N-isopropylpyrazino[2,3-d]pyridazin-2-amine, 2,2,2-trifluoroacetic acid salt 3-(4-(4-chloro-2-fluorophenoxy)piperidin-1-yl)-N-isopropylpyrazino[2,3-d]pyridazin-2-amine, 2,2,2-trifluoroacetic acid salt 3-(4-((R)-(2,4-difluorophenyl)fluoromethyl)piperidin-1-yl)-N-((1R,2R)-2-methylcyclopropyl)pyrazino[2,3-d]pyridazin-2-amine, 2,2,2-trifluoroacetic acid salt 2-((2,2-difluoroethyl)amino)-3-(4-(2,4-difluorophenoxy)piperidin-1-yl)pyrido[3,4-b]pyrazine-7-carbonitrile, 2,2,2-trifluoroacetic acid salt 2-(tert-butylamino)-3-(4-(2,4-difluorophenoxy)piperidin-1-yl)pyrido[3,4-b]pyrazine-7-carbonitrile 3-fluoro-4-((1-(3-(isopropylamino)pyrazino[2,3-d]pyridazin-2-yl)piperidin-4-yl)oxy)phenol, 2,2,2-trifluoroacetic acid salt 2-((2,2-difluoroethyl)amino)-3-(4-(2,4-difluorophenoxy)piperidin-1-yl)-N,N-dimethylpyrido[3,4-b]pyrazine-7-carboxamide, 2,2,2-trifluoroacetic acid salt 3-(4-(2,4-difluorobenzyl)piperazin-1-yl)-N-isopropylpyrazino[2,3-d]pyridazin-2-amine 2,2,2-trifluoroacetate N-isopropyl-3-(4-(3-methoxyphenoxy)piperidin-1-yl)pyrazino[2,3-d]pyridazin-2-amine 2,2,2-trifluoroacetate 3-(4-(2,4-difluorophenoxy)piperidin-1-yl)-N-isopropyl-5,8-dimethylpyrazino[2,3-d]pyridazin-2-amine 2,2,2-trifluoroacetate 3-(4-(2,4-difluorophenoxy)piperidin-1-yl)-N-isopropyl-8-methylpyrazino [2,3-d]pyridazin-2-amine N-cyclopropyl-3-(4-((4-fluorophenyl)sulfonyl)piperidin-1-yl)-7-methylpyrido[3,4-b]pyrazin-2-amine 2,2,2-trifluoroacetate 3-(4-(4-chloro-2-fluorophenoxy)piperidin-1-yl)-N-cyclopropylpyrazino[2,3-d]pyridazin-2-amine 2,2,2-trifluoroacetate 2-(4-(2,4-difluorophenoxy)piperidin-1-yl)-N-isopropylpyrido[3,4-b]pyrazin-3-amine N-cyclobutyl-2-(4-(2,4-difluorophenoxy)piperidin-1-yl)pyrido[3,4-b]pyrazin-3-amine 3-(4-(2-fluoro-4-(fluoromethoxy)phenoxy)piperidin-1-yl)-N-isopropylpyrazino[2,3-d]pyridazin-2-amine

COMPOUND TABLE 2

| | MS(obs) (M$^+$ + 1) |
|---|---|
| 1. N-cyclopropyl-3-(3-(thiazol-5-ylmethyl)piperidin-1-yl)quinoxalin-2-amine,2,2,2-trifluoroacetic acid salt | |
| 2. N-cyclopropyl-3-(3-(4-fluorobenzyl)piperidin-1-yl)pyrido[3,4-b]pyrazin-2-amine,2,2,2-trifluoroacetic acid salt | |
| 3. 2-(cyclopropylamino)-3-(1-(2,5-dichlorobenzyl)piperidin-4-yl)quinoxaline-6-carbonitrile,2,2,2-trifluoroacetic acid salt | 452.2 |
| 4. 2-(cyclopropylamino)-3-(1-(2,5-difluorobenzyl)piperidin-4-yl)quinoxaline-6-carbonitrile,2,2,2-trifluoroacetic acid salt | 420.3 |
| 5. 3-(1-(4-chlorobenzoyl)piperidin-4-yl)-2-(cyclopropylamino)quinoxaline-6-carbonitrile,2,2,2-trifluoroacetic acid salt | 432.25 |
| 6 N-cyclopropyl-3-(1-(2,4-difluorobenzyl)piperidin-4-yl)-7-methylpyrido[3,4-b]pyrazin-2-amine,2,2,2-trifluoroacetic acid salt | 410.3 |
| 7. N-cyclopropyl-3-(4-(2,5-dichlorobenzyl)-2-methylpiperazin-1-yl)quinoxalin-2-amine | 442.2 |
| 8. (4-(3-(cyclopropylamino)quinoxalin-2-yl)-3-methylpiperazin-1-yl)(2,5-dichlorophenyl)methanone,2,2,2-trifluoroacetic acid salt | 456.2 |
| 9. N-cyclopropyl-3-(4-(2,5-dichlorobenzyl)-3-isopropylpiperazin-1-yl)quinoxalin-2-amine | 470.3 |
| 10. N-cyclopropyl-3-(4-(2,5-dichlorobenzyl)-3-methylpiperazin-1-yl)quinoxalin-2-amine,2,2,2-trifluoroacetic acid salt | 442.25. |

It is understood that $R^3$, $R^4$, $R^5$, and $R^6$ are substituents on carbon such that each of $X^1$-$X^4$ that are carbon will have a substituent selected from $R^3$, $R^4$, $R^5$, and $R^6$ and that one or two of $X^1$-$X^4$ are N, then one or two of $R^3$, $R^4$, $R^5$, and $R^6$ are absent.

EMBODIMENTS

Embodiment (1)

A compound of Formula (I):

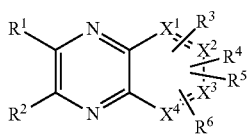

(I)

wherein:
$R^1$ is a heterocycloamino ring substituted with $R^a$, $R^b$, and $R^c$ wherein:
  $R^a$ is —Z—Ar where Z is $C_{1-6}$ alkylene, $C_{1-6}$ haloalkylene, —O—, —C(O)—, —NH—, or —S(O)n— wherein n is 0, 1, or 2; and Ar is $C_{3-10}$ cycloalkyl, $C_{3-7}$ heterocycloalkyl, $C_{3-7}$ heterocycloalkenyl, $C_{6-10}$ aryl, or $C_{1-9}$ heteroaryl wherein $C_{3-10}$ cycloalkyl, $C_{3-7}$ heterocycloalkenyl, $C_{3-7}$ heterocycloalkyl, $C_{6-10}$ aryl, and $C_{1-9}$ heteroaryl are optionally substituted with 1 to 3 substituents independently selected from $C_{1-6}$ alkyl, halo, hydroxy, oxo, $C_{1-6}$ alkoxy, $C_{1-6}$ thioalkoxy, $C_{1-6}$ haloalkyl, $C_{1-6}$ hydroxyalkyl, $C_{1-6}$ haloalkoxy, $C_{1-6}$ alkylcarbonyl, $C_{1-6}$ alkylsulphonyl, cyano, $C_{2-12}$ alkoxyalkyloxy, $C_{1-9}$ amide, or $C_{1-6}$ hydroxyalkyloxy; and
  $R^b$ and $R^c$ are independently hydrogen, $C_{1-6}$ alkyl, hydroxy, or halo;
$R^2$ is —$OR^e$ or —$NR^dR^e$ wherein $R^d$ is hydrogen or $C_{1-6}$ alkyl and $R^e$ is $C_{1-6}$ alkyl, $C_{1-6}$ haloalkyl, $C_{1-6}$ hydroxyalkyl, $C_{2-12}$ alkoxyalkyl, $C_{1-12}$ aminoalkyl, $C_{3-10}$ cycloalkyl, $C_{4-16}$ cycloalkylalkyl, $C_{6-10}$ aryl, $C_{1-9}$ heteroaryl, $C_{3-7}$ heterocyclyl, or $C_{3-7}$ heterocycloalkenyl wherein $C_{6-10}$ aryl, $C_{1-9}$ heteroaryl, $C_{3-7}$ heterocyclyl, and $C_{3-7}$ heterocycloalkenyl are optionally substituted with 1 to 3 substituents independently selected from $C_{1-6}$ alkyl, halo, hydroxy, oxo, $C_{1-6}$ alkoxy, $C_{1-6}$ haloalkyl or $C_{1-6}$ haloalkoxy, or cyano;
all $X^1$-$X^4$ are carbon or one or two of $X^1$-$X^4$ are N and the rest of $X^1$-$X^4$ are carbon;
$R^3$, $R^4$, $R^5$, and $R^6$ are independently absent, hydrogen, $C_{1-6}$ alkyl, halo, hydroxy, $C_{1-6}$ alkoxy, $C_{1-6}$ alkoxycarbonyl, $C_{1-6}$ haloalkyl, $C_{1-6}$ haloalkoxy, $C_{1-9}$ amide, $C_{3-7}$ heterocyclyl, $C_{1-8}$ alkylamino, or cyano;
or a pharmaceutically acceptable salt thereof Embodiment 2

The compound or pharmaceutically acceptable salt of embodiment 1, wherein:
$R^1$ is a heterocycloamino ring of formula:

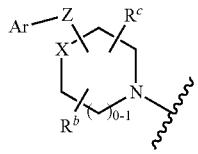

where X is carbon or nitrogen, and
$R^2$ is —$OR^e$ or —$NR^dR^e$ wherein $R^d$ is hydrogen or $C_{1-6}$ alkyl; and $R^e$ is $C_{1-6}$ alkyl, $C_{1-6}$ haloalkyl, $C_{1-6}$ hydroxyalkyl, $C_{2-12}$ alkoxyalkyl, $C_{1-12}$ aminoalkyl, $C_{3-10}$ cycloalkyl, $C_{3-10}$ oxocycloalkyl, phenyl, monocylic $C_{1-5}$ heteroaryl, or $C_{3-7}$ heterocyclylalkenyl wherein phenyl, $C_{1-9}$ heteroaryl, and $C_{3-7}$ heterocyclylalkenyl are optionally substituted with 1 to 3 substituents independently selected from $C_{1-6}$ alkyl, halo, hydroxy, oxo, $C_{1-6}$ alkoxy, $C_{1-6}$ haloalkyl or $C_{1-6}$ haloalkoxy, or cyano.

Within the compounds in embodiment 2, in one group of compounds, $R^1$ is a heterocycloamino ring of formula

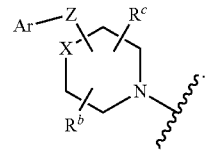

Embodiment 3

The compound or pharmaceutically acceptable salt of embodiment 1 or 2 or any groups contained therein, wherein $R^2$ is —$NR^dR^e$. Within the compounds in embodiment 3, in one group of compounds, $R^d$ is hydrogen.

Embodiment 4

The compound or pharmaceutically acceptable salt of any of the previous embodiments 1-3 and groups contained therein, wherein $R^1$ is a heterocycloamino ring of formula:

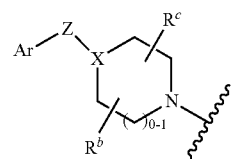

where X is carbon or nitrogen.

Within the compounds in embodiment 4, in one group of compounds, $R^1$ is a heterocycloamino ring of formula:

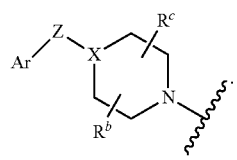

Embodiment 5

The compound or pharmaceutically acceptable salt of any of the previous embodiments 1-4 and groups contained therein, wherein all $X^1$-$X^4$ are carbon.

Embodiment 6

The compound or pharmaceutically acceptable salt of any of the previous embodiments 1-5 and groups contained therein, wherein $X^1$-$X^4$ are carbon and each of $R^3$, $R^4$, $R^5$, and $R^6$ are hydrogen.

Embodiment 7

The compound or pharmaceutically acceptable salt of any of the previous embodiments 1-4 and groups contained therein, wherein $X^1$, $X^3$ and $X^4$ are carbon and $X^2$ is $CR^3$ or $X^1$, $X^2$ and $X^4$ are carbon and $X^3$ is $CR^3$.

(a) Within the groups in embodiment 7, in one group of compounds each and $R^4$, $R^5$, and $R^6$ are hydrogen and $X^2$ is $CR^3$. Within groups of compounds in (a), in one group of compounds $R^3$ is halo, $C_{1-6}$ alkyl, $C_{1-6}$ alkoxy or cyano. Within groups of compounds in (a), in one group of compounds $R^3$ is cyano, methyl, methoxy, chloro or fluoro. Within groups of compounds in (a), in yet another group of compounds $R^3$ is halo or cyano. Within groups of compounds in (a), in one group of compounds $R^3$ is cyano or fluoro.

(b) Within the groups in embodiment 7, in another group of compounds each and $R^4$, $R^5$, and $R^6$ are hydrogen and $X^3$ is $CR^3$. Within groups of compounds in (b), in one group of compounds $R^3$ is halo, $C_{1-6}$ alkyl, $C_{1-6}$ alkoxy or cyano. Within groups of compounds in (b), in one group of compounds $R^3$ is cyano, methyl, methoxy, chloro or fluoro. Within groups of compounds in (b), in one group of compounds $R^3$ is cyano or fluoro.

Embodiment 8

The compound or pharmaceutically acceptable salt of any of the previous embodiments 1-4 and groups contained therein, wherein one or both of $X^2$ and $X^3$ are nitrogen and the remaining $X^1$-$X^4$ are carbon.

(a). Within groups in embodiment 8, in one group of compounds $X^2$ is N. Within groups of compounds in (a), in one group of compounds $X^2$ is N, $X^1$ is $CR^3$ where $R^3$ is hydrogen, halo, $C_{1-6}$ alkyl, $C_{1-6}$ alkoxy, cyano or hydroxy and $R^4$ is absent, and each of $R^5$ and $R^6$ are hydrogen. Within groups of compounds in (a), in another group of compounds $X^2$ is N, $X^1$ is $CR^3$ where $R^3$ is fluoro, chloro, methyl, ethyl, cyano, or methoxy and $R^4$ is absent, and each of $R^5$ and $R^6$ are hydrogen. Within groups of compounds in (a), in another group of compounds $X^2$ is N and $R^3$ is absent, and each of $R^4$, $R^5$, and $R^6$ are hydrogen.

(b). Within groups in embodiment 8, in another group of compounds $X^2$ is N, $X^3$ is $CR^3$ where $R^3$ is hydrogen, $C_{1-6}$ alkyl, $C_{1-6}$ alkoxy, halo, or cyano and $X^1$ and $X^4$ are carbon. Within groups of compounds in (b), in another group of compounds $X^2$ is N, $X^3$ is $CR^3$ where $R^3$ is cyano, fluoro, chloro, methyl, ethyl, or methoxy and $R^4$ is absent, and each of $R^5$ and $R^6$ are hydrogen. Within groups of compounds in (b), in another group of compounds $X^2$ is N, $X^3$ is $CR^3$ where $R^3$ is cyano, fluoro, chloro, methyl, or methoxy and $R^4$ is absent, and each of $R^5$ and $R^6$ are hydrogen.

(c). Within groups in embodiment 8, in another group of compounds $X^3$ is N. Within groups of compounds in (c), in one group of compounds $X^3$ is N, $X^2$ is $CR^3$ where $R^3$ is hydrogen, halo, $C_{1-6}$ alkyl, $C_{1-6}$ alkoxy, or cyano and $R^4$ is absent, and each of $R^5$ and $R^6$ are hydrogen. Within groups of compounds in (c), in another group of compounds $X^3$ is N, $X^2$ is $CR^3$ where $R^3$ is fluoro, chloro, methyl, ethyl, cyano, or methoxy and $R^4$ is absent, and each of $R^5$ and $R^6$ are hydrogen. Within groups of compounds in (c), in another group of compounds $X^3$ is N, $X^2$ is $CR^3$ where $R^3$ is fluoro, chloro, methyl, cyano, or methoxy and $X^1$ and $X^4$ are CH. Within groups of compounds in (c), in another group of compounds $X^3$ is N and each of $R^4$, $R^5$, and $R^6$ are hydrogen.

(d). Within groups in embodiment 8, in yet another group of compounds $X^2$ and $X^3$ are nitrogen. Within groups of compounds in (d), in one group of compounds and $R^4$ each of $R^5$ and $R^6$ are hydrogen.

Embodiment 9

The compound or pharmaceutically acceptable salt of any of the previous embodiments 1-8 and groups contained therein, wherein $R^2$ is —$NHR^e$.

Embodiment 10

The compound or pharmaceutically acceptable salt of any of the previous embodiments 1-8 and groups contained therein, wherein $R^2$ is —$NHR^e$ wherein $R^e$ is $C_{3-10}$ cycloalkyl. Within the groups in embodiment 10, in one group of compounds, $R^e$ is cyclopropyl, cyclobutyl, cyclopentyl or cyclohexyl. Within the groups in embodiment 10, in another group of compounds, $R^e$ is cyclopropyl.

Embodiment 11

The compound or pharmaceutically acceptable salt of any of the previous embodiments 1-8 and groups contained therein, wherein $R^2$ is —$NHR^e$ wherein $R^e$ is $C_{4-16}$ cycloalkylalkyl. Within the groups in embodiment 11, in one group of compounds, $R^e$ is cyclopropylmethyl, cyclobutylmethyl, cyclopentylmethyl or cyclohexylmethyl. Within the groups in embodiment 10, in another group of compounds, $R^e$ is cyclopropylmethyl.

Embodiment 12

The compound or pharmaceutically acceptable salt of any of the previous embodiments 1-8 and groups contained therein, wherein $R^2$ is —$NHR^e$ wherein $R^e$ is $C_{1-6}$ alkyl. Within the groups in embodiment 12, in one group of compounds, $R^e$ is isobutyl, tert-butyl, n-propyl, isopropyl, 2-ethylbutyl, 4-methylpent-2-yl, 2,2-dimethylpropyl, 3,3-dimethylbutyl, 3-methylbutyl, but-2-yl. Within the groups in embodiment 12, in another group of compounds, $R^e$ is isopropyl.

Embodiment 13

The compound or pharmaceutically acceptable salt of any of the previous embodiments 1-8 and groups contained therein, wherein $R^2$ is —$NHR^e$ wherein $R^e$ is hydroxyalkyl. Within the groups in embodiment 12, in one group of compounds, $R^e$ is 2-hydroxyethyl, 3-hydroxypropyl, or (R)-3-hydroxyprop-2-yl.

Embodiment 14

The compound or pharmaceutically acceptable salt of any of the previous embodiments 1-8 and groups contained therein, wherein $R^2$ is —$NHR^e$ wherein $R^e$ is $C_{2-12}$ alkoxyalkyl. Within the groups in embodiment 12, in one group of compounds, $R^e$ is 2-methoxyethyl, 3-methoxypropyl, 2-ethoxyethyl, 2-isopropoxyethyl, or 3-ethoxypropyl.

Embodiment 15

The compound or pharmaceutically acceptable salt of any of the previous embodiments 1-8 and groups contained therein, wherein $R^2$ is —$NHR^e$ wherein $R^e$ is $C_{1-12}$ aminoalkyl.

Embodiment 16

The compound or pharmaceutically acceptable salt of any of the previous embodiments 1-8 and groups contained therein, wherein $R^2$ is —$NHR^e$ wherein $R^e$ is $C_{1-6}$ haloalkyl. Within the groups in embodiment 12, in one group of compounds $R^e$ is 2,2,2-trifluoroethyl, 2-fluoroethyl, 2,2-difluoroethyl, or 3,3,3-trifluoropropyl.

Embodiment 17

The compound or pharmaceutically acceptable salt of any of the previous embodiments 1-8 and groups contained therein, wherein $R^2$ is —$NHR^e$ wherein $R^e$ is $C_{3-7}$ heterocyclyl or $C_{3-7}$ heterocycloalkenyloptionally substituted with 1 to 3 substituents independently selected from $C_{1-6}$ alkyl, halo, hydroxy, $C_{1-6}$ alkoxy, $C_{1-6}$ haloalkyl or $C_{1-6}$ haloalkoxy, or cyano. Within the groups in embodiment 12, in one group of compounds, $R^e$ is tetrahydropyran-4-yl, oxetan-3-yl, or of the formula:

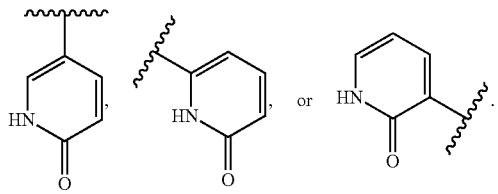

Embodiment 18

The compound or pharmaceutically acceptable salt of any of the previous embodiments 1-8 and groups contained therein, wherein $R^2$ is —$NHR^e$ wherein $R^e$ is monocylic $C_{1-9}$ heteroaryl optionally substituted with 1 to 3 substituents independently selected from $C_{1-6}$ alkyl, halo, hydroxy, $C_{1-6}$ alkoxy, haloalkyl or haloalkoxy, or cyano. Within the groups in embodiment 18, in one group of compounds, $R^e$ is pyridin-3-yl, pyridin-2-yl, pyridin-4-yl, thia[1,3,4]diazol-2-yl, thiazol-2-yl, pyrimidin-2-yl, pyrimidin-5-yl, pyrazin-2-yl, pyrimidin-6-yl, pyridazin-3-yl, 1,2,4-triazin-3-yl, 5,6-dimethyl-1,2,4-triazin-3-yl, 3,4-dimethylisoxazol-5-yl, 2-hydroxypyridin-5-yl (tautomeric form pyridin-2(1H)-one), 2-methoxypyridin-5-yl, or isoxazol-3-yl.

Embodiment 19

The compound or pharmaceutically acceptable salt of any of the previous embodiments 1-8 and groups contained therein, wherein $R^2$ is —$NHR^e$ wherein $R^e$ is phenyl optionally substituted with 1 to 3 substituents independently selected from $C_{1-6}$ alkyl, halo, hydroxy, $C_{1-6}$ alkoxy, haloalkyl or haloalkoxy, or cyano. Within the groups in embodiment 19, in one group of compounds, $R^e$ is 2-bromophenyl, 3-bromophenyl, 4-bromophenyl, 4-fluorophenyl, phenyl, 4-trifluoromethoxyphenyl, 4-n-propylphenyl, 4-methylphenyl, 4-tert-butylphenyl, 2-methoxyphenyl, 3-methoxyphenyl, 4-methoxyphenyl, 4-isopropoxyphenyl, or 4-cyanophenyl.

Embodiment 20

The compound or pharmaceutically acceptable salt of any of the previous embodiments 1-19 and groups contained therein, wherein $R^1$ is a heterocycloamino ring of formula:

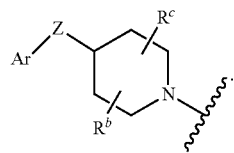

Within this group of compounds in another embodiment are compounds, wherein $R^1$ is a heterocycloamino ring of formula:

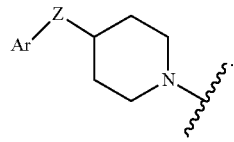

Embodiment 21

The compound or pharmaceutically acceptable salt of any of the previous embodiments 1-19 and groups contained therein, wherein $R^1$ is a heterocycloamino ring of formula:

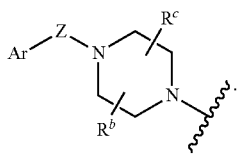

Within this group of compounds in another embodiment are compounds, wherein $R^1$ is a heterocycloamino ring of formula:

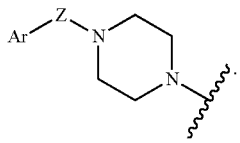

Embodiment 22

The compound or pharmaceutically acceptable salt of any of the previous embodiments 1-21 wherein Z is $C_{1-6}$ alkyene. Within the groups in embodiment 22, in one group of compounds Z is —$CH_2$—, —$CH(CH_3)$—, or —$(CH_2)_2$, more preferably —$CH_2$—.

Embodiment 23

The compound or pharmaceutically acceptable salt of any of the previous embodiments 1-20 wherein Z is $C_{1-6}$ haloalkylene. Within the groups in embodiment 23, in one group of compounds Z is —*CHF—; —*CF($CH_3$)—, or —$CF_2$— where the stereochemistry at *C is (RS), (R) or (S). Within the groups in embodiment 23, in one group of compounds Z is —*CHF— where the stereochemistry at *C is (RS), (R) or (S).

Embodiment 24

The compound or pharmaceutically acceptable salt of any of the previous embodiments 1-20 wherein Z is —O— provided Z is attached to a carbon atom in R¹.

Embodiment 25

The compound or pharmaceutically acceptable salt of any of the previous embodiments 1-21 wherein Z is —C(O)—.

Embodiment 26

The compound or pharmaceutically acceptable salt of any of the previous embodiments 1-21 wherein Z is $SO_2$.

Embodiment 27

The compound or pharmaceutically acceptable salt of any of the previous embodiments 1-20 wherein Z is —NH— provided Z is attached to a carbon atom in R¹.

Embodiment 28

The compound or pharmaceutically acceptable salt of any of the previous embodiments 1-27 wherein Ar is phenyl optionally substituted with 1 to 3 substituents independently selected from $C_{1-6}$ alkyl, halo, hydroxy, $C_{1-6}$ alkoxy, $C_{1-6}$ haloalkyl, $C_{1-6}$ haloalkoxy, $C_{1-6}$ alkylsulphonyl, $C_{1-6}$ alkylcarbonyl, cyano, $C_{2-12}$ alkoxyalkyloxy, or $C_{1-6}$ hydroxyalkyloxy. Within the groups in embodiment 28, in one group of compounds in one group of compounds Ar is phenyl optionally substituted with 1 to 3 substituents independently selected from halo or cyano, preferably fluoro. Within the groups in embodiment 28, in another group of compounds Ar is phenyl, 2-methylphenyl, 3-methylphenyl, 4-methylphenyl, 4-ethylphenyl, 3-isopropylphenyl, 4-ethoxyphenyl, 3-CF₃phenyl, 4-CF₃phenyl, 2-chlorophenyl, 3-chlorophenyl, 4-chlorophenyl, 4-chloromethylphenyl, 4-difluoromethylphenyl, 2-bromophenyl, 4-bromophenyl, 2-cyanophenyl, 3-cyanophenyl, 2-fluorophenyl, 3-fluorophenyl, 4-fluorophenyl, 4-isopropylphenyl, 3-bromophenyl, 4-methylsulfonylphenyl, 4-cyanophenyl, 4-tert-butylphenyl, 3-methoxyphenyl, 3-methoxyphenyl, 4-methoxyphenyl, 4-OCF₃phenyl, 2,3-dichlorophenyl, 3,4-dichlorophenyl, 3,5-dichlorophenyl, 2,4-dichlorophenyl, 2,5-dichlorophenyl, 2,6-dichlorophenyl, 2-chloro-4-methylsulfonylphenyl, 2,5-difluorophenyl, 2,6-difluorophenyl, 2,4-difluorophenyl, 3,4-difluorophenyl, 3,5-difluorophenyl, 3,4-dimethylphenyl, 4-fluoro-2-methylphenyl, 2-fluoro-5-methylphenyl, 5-fluoro-2-methylphenyl, 5-chloro-2-difluoromethoxyphenyl, 4-chloro-3-methylphenyl, 2,3-dimethylphenyl, 2,4-dimethylphenyl, 2,5-dimethylphenyl, 2-bromo-5-chlorophenyl, 3-bromo-4-methylphenyl, 2-bromo-4-methylphenyl, 3-bromo-2-methylphenyl, 4-fluoro-3-methoxyphenyl, 2-bromo-5-methoxyphenyl, 3-bromo-4-methoxyphenyl, 4-bromo-2-chlorophenyl, 3-bromo-4-fluorophenyl, 4-bromo-2-fluorophenyl, 4-bromo-3-methylphenyl, 4-bromo-2-methylphenyl, 4-bromo-3-fluorophenyl, 4-chloro-2-methoxyphenyl, 5-bromo-2-fluorophenyl, 5-bromo-2-methylphenyl, 5-chloro-2-methylphenyl, 5-chloro-2-trifluoromethylphenyl, 4-chloro-2-methylphenyl, 4-chloro-3-methylphenyl, 2-chloro-5-methoxyphenyl, 3-chloro-4-methoxyphenyl, 2-chloro-4-methoxyphenyl, 2-chloro-5-fluorophenyl, 3-chloro-4-fluorophenyl, 2-chloro-6-trifluoromethylphenyl, 2-chloro-5-iodophenyl, 4-chloro-2-hydroxyphenyl, 2-methoxy-4-methylphenyl, 2-methoxy-5-trifluoromethoxyphenyl, 2-methoxy-5-trifluoromethylphenyl, 2-chloro-6-difluoromethoxyphenyl, 5-chloro-2-propoxyphenyl, 2-methoxy-5-tert-butylphenyl, 4-chloro-2-fluorophenyl, 5-chloro-2-fluorophenyl, 4-cyano-2-fluorophenyl, 4-bromo-3-trifluoromethylphenyl, 2-fluoro-4-trifluoromethylphenyl, 3-cyano-4-isopropoxyphenyl, 2-fluoro-4-methylphenyl, 2-fluoro-4-methoxyphenyl, 4-fluoro-2-hydroxyphenyl, 4-chloro-2-trifluoromethylphenyl, 4-chloro-3-fluorophenyl, 2-chloro-5-trifluoromethylphenyl, 2,4-dimethoxyphenyl, 2,5-dimethoxyphenyl, 2-chloro-4-trifluoromethylphenyl, 3-cyano-4-fluorophenyl, 5-chloro-2-methoxyphenyl, 2-chloro-3,6-difluorophenyl, 2,3,5-trichlorophenyl, 2,6-difluoro-3-methylphenyl, 4-chloro-2,6-difluorophenyl, 2,4,6-trifluorophenyl, 2,4-difluoro-6-hydroxyphenyl, 2,4,5-trifluorophenyl, 2,4,6-trimethylphenyl, 2,3,4-trifluorophenyl, 4-chloro-2-5-dimethylphenyl, 3-chloro-5-fluoro-2-methylphenyl, 5-chloro-2,4-difluorophenyl, or 4-bromo-2,5-difluorophenyl. Within the groups in embodiment 28, in yet another group of compounds Ar is 5-chloro-2-fluorophenyl, 2,4-difluorophenyl, 2,5-difluorophenyl.

Embodiment 29

The compound or pharmaceutically acceptable salt of any of the previous embodiments 1-27 wherein Ar is $C_{1-9}$ heteroaryl optionally substituted with 1 to 3 substituents independently selected from $C_{1-6}$ alkyl, halo, hydroxy, $C_{1-6}$ alkoxy, $C_{1-6}$ haloalkyl, $C_{1-6}$ haloalkoxy, $C_{1-6}$ alkylsulphonyl, $C_{1-6}$ alkylcarbonyl, cyano, $C_{2-12}$ alkoxyalkyloxy, or $C_{1-6}$ hydroxyalkyloxy. Within the groups in embodiment 29, in one group of compounds Ar is monocyclic $C_{1-9}$ heteroaryl optionally substituted with 1 to 3 substituents independently selected from $C_{1-6}$ alkyl, halo, hydroxy, $C_{1-6}$ alkoxy, $C_{1-6}$ haloalkyl, $C_{1-6}$ haloalkoxy, $C_{1-6}$ alkylsulphonyl, $C_{1-6}$ alkylcarbonyl, cyano, $C_{2-12}$ alkoxyalkyloxy, or $C_{1-6}$ hydroxyalkyloxy. Within the groups in embodiment 29, in another group of compounds Ar is Ar is pyridine-2-yl, pyridine-3-yl, pyridine-4-yl, 2,5-dichlorothien-3-yl, benzofuran-3-yl, 2,5-difluoropyridin-3-yl, 2,5-dichloropyridin-4-yl, 5-chloro-2-fluoropyridin-2-yl, 3-fluoropyridin-2-yl, 3,6-dichloropyridin-2-yl, 5-methylisoxazol-3-yl, indol-5-yl, indol-6-yl, benzo[d][1,2,3]thiadiazol-5-yl, 3,5-dimethylisoxazol-4-yl, 5-chlorothien-2-yl, 5-bromothien-2-yl, 5-chloro-1,3-dimethylpyrazol-4-yl, 5-bromo-6-chloropyridin-3-yl, 3-methyl-[1,2,4]-oxadiazol-5-yl, thiazol-5-yl, 5-methyloxazol-2-yl, 3-fluoro-5-chloropyridin-2-yl, or 2-chloro-5-fluoropyridin-3-yl.

Embodiment 30

The compound or pharmaceutically acceptable salt of any of the previous embodiments 1-27 wherein Ar is Ar is $C_{3-7}$ heterocycloalkenyl optionally substituted with 1 to 3 substituents independently selected from $C_{1-6}$ alkyl, halo, hydroxy, $C_{1-6}$ alkoxy, $C_{1-6}$ haloalkyl, $C_{1-6}$ haloalkoxy, $C_{1-6}$ alkylsulphonyl, $C_{1-6}$ alkylcarbonyl, cyano, $C_{2-12}$ alkoxyalkyloxy, or $C_{1-6}$ hydroxyalkyloxy. Within the groups in embodiment 29, in one group of compounds Ar is of the formula:

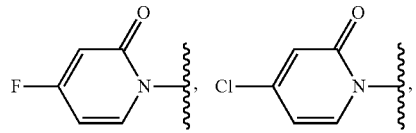

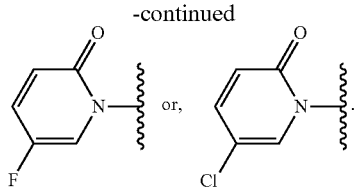

Embodiment 31

The compound or pharmaceutically acceptable salt of any of the previous embodiments 1-30 wherein $R^b$ and $R^c$ are hydrogen.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where $R^1$ is heterocycloamino attached to the core ring via nitrogen atom, $R^2$ is $NR^dR^e$, $R^b$, $R^c$, $R^3$, $R^4$, $R^5$, $R^6$, $X^1$, $X^2$, $X^3$, $X^4$, Ar, and Z are as defined in the Summary of the Invention can be prepared as illustrated and described in Scheme A below.

Scheme A

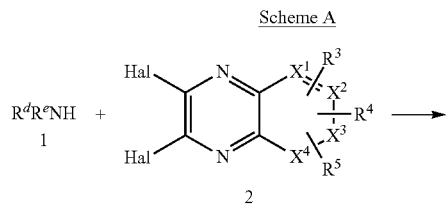

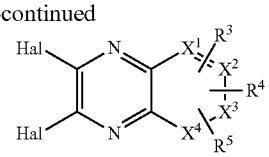

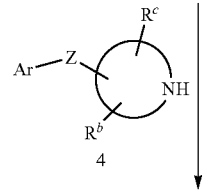

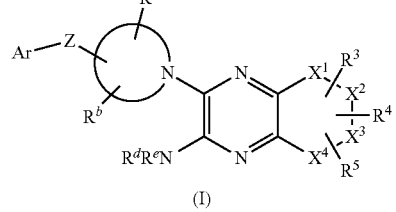

Treatment of a compound of formula 1 where $R^d$ and $R^e$ are defined in the Summary of the Invention with a compound of formula 2 where Hal is halo, $R^3$, $R^4$, $R^5$, $X^1$, $X^2$, $X^3$, and $X^4$ are as defined in the Summary of the Invention, provides a compound of formula 3. Compounds of formula 1 are either commercially available or can be ready prepared by methods well known in the art. The reaction is carried out in a suitable organic solvent like dioxane, ethanol, tetrahydrofuran, dimethyl sulfoxide, N,N-dimethylformamide and the like (with or without a base such as sodium hydride, diisopropylethylamine or triethylamine) and takes upon heating at a suitable temperature between 20 to 150° C. Compounds of formula 2 are either commercially available or can be readily prepared by methods well known in the art. For example, compounds of formula 2 where halo is chloro can be prepared by condensation of an aryl diamine with oxalic acid in a suitable aqueous acid, which upon treatment with a halogenating reagent such as thionyl chloride or phosphorous oxychloride and the like (with or without catalytic N,N-dimethylformamide) provides the compound of formula 2 were Hal is Cl. Compounds of formula 2 such as where $X^2$ or $X^3$ is nitrogen, as well as where $R^3$ or $R^4$ or $R^5$ is $C_{1-6}$ alkyl, cyano, and halo are commercially available.

Treatment of compound 3 with a heterocycloamino compound of formula 4 provides a compound of Formula (I). The reaction is carried out with or without base such as diisopropylethylamine and triethylamine, in a suitable organic solvent like dioxane, n-butanol, dimethyl sulfoxide and the like. Compounds of formula 4 are either commercially available or they can be readily prepared by methods well known in the art. For example, compounds of formula 4 where Z is oxygen can be prepared by Mitsunobu reaction between a piperidinol and an aryl alcohol. The reaction is usually carried out in the presence of a phosphine such as $PPh_3$, $PMe_3$, and the like and an activating reagent such as DEAD, DIAD and the like, in a suitable organic solvent such as tetrahydrofuran, toluene, dichloromethane, acetonitrile and the like. The reaction is usually carried out in the 0-80° C. temperature range.

Alternatively, a compound of formula 3 can be treated with piperazine which can be further modified by reductive amination, alkylation, arylation, amidation, sulfonylation and the like to provide a compound of Formula (I).

Compounds of Formula (I) can be converted to other compounds of Formula (I). For example, compounds of Formula (I) where Z is monosubstituted with fluorine can be prepared from the corresponding carbonyl by first reducing the carbonyl group to an alcohol group and then fluorination under conditions well known in the art. The reaction is typically carried out in the presence of a fluorinating agent such as DAST and the like, in a suitable solvent such as methanol and the like. The reaction is usually carried out in the −78 to 25° C. temperature range.

Alternatively, compounds of Formula (I) where Z is methylene can be prepared from the corresponding carbonyl compound by conditions well known in the art. The reaction is typically carried out in the presence of a reducing agent such as diisobutylaluminum hydride, borane-tetrahydrofuran, sodium borohydride and the like, in a suitable organic solvent such as dichloromethane, tetrahydrofuran, and the like.

Compounds of Formula (I) can also be prepared by reversing the order of addition of compounds of formula 1 and formula 4. Addition of compounds of formula 4 with compounds of formula 2 as defined in the Summary of the Invention, followed by addition of compounds of formula 1 as defined in the Summary of the Invention, provides a compound of Formula (I) with a different regiochemical outcome as that shown in Scheme A.

Detailed descriptions of some such transformations are provided in Working Examples below.

Alternatively, compounds of Formula (I) where $R^1$ is heterocycloamino attached to the core ring via carbon atom, $R^2$ is $NR^dR^e$, $R^b$, $R^c$, $R^3$, $R^4$, $R^5$, $R^6$, $X^1$, $X^2$, $X^3$, $X^4$, Ar, and Z are as defined in the Summary of the Invention, can be prepared as illustrated and described in Scheme B below.

Compounds of formula 6 can be prepared by reaction of a compound of formula 3 with a heterocycloaminoalkenyl of formula 5 where PG is a nitrogen protecting group. The reaction is carried out in the presence of a common palladium catalyst such as $Pd(PPh_3)_2Cl_2$, $Pd(PPh_3)_4$, $Pd_2dba_3$ and the like and a base such as $K_2C(O)_3$ and the like in a suitable organic solvent such as acetonitrile, dioxane, N,N-dimethylformamide and the like. The reaction is usually heated up to 70-175° C. Compounds of formula 5 such as tetrahydropyridine are commercially available.

Compounds of formula 7 can be prepared by hydrogenation of a compound of formula 6. The reaction is usually carried out in the presence of a common palladium catalyst such as Pd on carbon and the like under a hydrogen atmosphere in a suitable organic solvent such as methanol, ethanol and the like. Acidic hydrolysis of the carbamate group provides the compound in formula 7.

Compounds of formula 7 can be converted to compounds of Formula (I). For example, compounds of formula 7 can be subjected to alkylation, arylation, sulfonylation, reductive amination and the like under conditions well known in the art.

Utility

The GPR6 receptor exhibits high expression in the central nervous system (CNS) with minimal expression in peripheral tissues. GPR6 is highly selectively enriched in D2 receptor expressing MSNs in the striatum. The striatum plays a central role in modulating important behaviors including movement, reward, and motivational processes. GPR6 is GPCR that exhibits receptor signaling via the Gs pathway. Thus, GPR6 agonist activity results in an increase in intracellular cAMP levels whereas antagonists or inverse agonists cause a decrease in cAMP levels. GPR6 activity is therefore functionally opposed to D2 receptor signaling which operates via the Gi pathway i.e., an agonist decreases the level of intracellular cAMP. As such, compounds that modulate the activity of GPR6 have utility in a variety of neurological and psychiatric disorders. For example, the pathological hallmark of Parkinson disease (PD) is neuronal cell loss within the substantia nigra. Degeneration of the nigrostriatal pathway causes reduction in the striatal con-

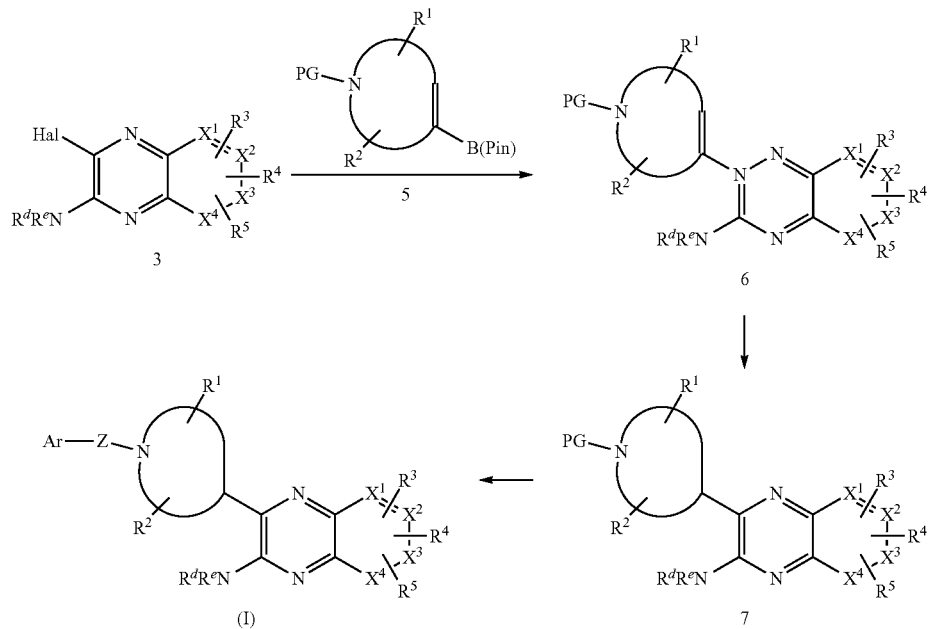

Scheme B centration of dopamine which results in motor and nonmotor clinical manifestations. The major striatal targets of dopaminergic innervation reside in the medium spiny neurons (MSNs) of the striatopallidal (indirect) and striatonigral (direct) output pathways. The MSNs of the direct output pathway express D1 dopamine receptors whereas those in the indirect pathway express D2 receptors.

About 75% of Parkinson's disease patients are treated with levodopa, a prodrug for dopamine discovered over 50 years ago (Dopamine Replacement Therapy). Levodopa has common serious side effects including induced dyskinesia (LID), impulsive control disorders (ICD), psychotic symptoms and sleep disturbances. LID is progressive (90% of PD patients develop LID within 10 yrs). Irreversible adaptations occur in D1 receptor signaling in MSNs in rodent models of LID including reduced desensitization leading to hypersensitivity in the direct pathway. Genetic inactivation of D1 but not D2 receptors abolishes LID in mice. However blockade of D1 receptor signaling does not affect the antiparkinsonian efficacy of L-DOPA. cAMP pathways modulated by D1/D2 dopamine receptors in MSN have been implicated in LID in PD. Dopamine D2 receptors in MSN are Gi coupled, inhibiting cAMP generation. Antagonism or inverse agonism of Gs coupled GPR6 should decrease cAMP in MSNs—a functional alternative to dopamine mediated activation of D2 receptors. As such, compounds that modulate the activity of GPR6 have utility in a variety of neurological and psychiatric disorders. For example movement disorders including Parkinson's disease and Huntington's disease either alone or in combination with other agents are approved for the treatment of Parkinson's disease including L-DOPA, dopaminergic agonists, MAO B inhibitors, DOPA decarboxylase inhibitors and C(O)MT inhibitors. Other potential disease indications that could be treated by modulation of GPR6 include drug addiction and eating disorders, cognitive disorders, schizophrenia, bipolar disorders, and depression.

Testing

The GPR6 inhibitory activity of the compounds of the present invention can be tested using the in vitro assay and in vivo assay described in working Example I and II below.

Administration and Pharmaceutical Composition

In general, the compounds of this invention will be administered in a therapeutically effective amount by any of the accepted modes of administration for agents that serve similar utilities. Therapeutically effective amounts of compounds of Formula (I) may range from about 0.01 to about 100 mg per kg patient body weight per day, which can be administered in single or multiple doses. Preferably, the dosage level will be about 0.1 to about 50 mg/kg per day; more preferably about 0.5 to about 10 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this invention, i.e., the active ingredient, will depend upon numerous factors such as the severity of the disease to be treated, the age and relative health of the subject, the potency of the compound utilized, the route and form of administration, and other factors.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aid administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention can be used. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In one embodiment, the compound of the present invention may be administered in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the compound of the present invention may be administered in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, PDE10 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazopam, lormetazepam, maprotiline, mecloqualone, melatonin, mephobarbital, meprobamate, methaqualone, midaflur, midazolam, nefazodone, nisobamate, nitrazopam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazopam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof In another embodiment, the compound of the present invention may be administered in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol) hydrochloride, C(O)MT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and prarnipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compound of the present invention may be administered in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compound of the present invention may be administered in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the compound of the present invention may be administered in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, adrenoreceptor antagonists, neurokinin-1 receptor antagonists, atypical anti-depressants, benzodiazepines, 5-HTA agonists or antagonists, especially 5-HTA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide, venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazopam and prazepam; buspirone, flesinoxan, gepirone and ipsapirone, and pharmaceutically acceptable salts thereof.

EXAMPLES

The following preparations of the intermediate (References) and compounds of Formula (I) (Examples) are given to enable those skilled in the art to more clearly understand and to practice the present invention. They should not be considered as limiting the scope of the invention, but merely as being illustrative and representative thereof

SYNTHETIC EXAMPLES

Reference A

Synthesis of
3-chloro-N-cyclopropylquinoxalin-2-amine

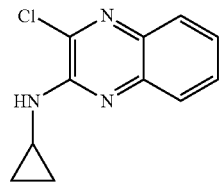 [SMILES: Clc1nc2ccccc2nc1NC1CC1]

A solution of 2,3-dichloroquinoxaline (400 mg, 2.010 mmol), cyclopropanamine (149 mg, 2.61 mmol) and N-ethyl-N-isopropylpropan-2-amine (526 µl, 3.01 mmol) in dioxane (2871 µl) was heated at 80° C. for 2 days. ISCO purification (10-40% EtOAc/hexanes) afforded the title compound as a light yellow solid.

Utilizing similar reaction conditions described above, following compounds were synthesized using commercially available amines and quinoxalines:

3-chloro-2-(cyclopropylamino)quinoxaline-6-carbonitrile; 3-chloro-N-cyclopropyl-6-fluoroquinoxalin-2-amine; 3-chloro-N-cyclopropyl-6,7-difluoroquinoxalin-2-amine; 3-chloro-2-(isopropylamino)quinoxaline-6-carbonitrile; 3-chloro-N-(2,2-difluoroethyl)pyrido-[3,4-b]pyrazin-2-amine; 3-chloro-N-cyclopropylpyrido[3,4-b]pyrazin-2-amine; 3,8-dichloro-N-cyclopropylpyrido[3,4-b]pyrazin-2-amine; 3-chloro-N-cyclopropyl-7-methylpyrido[3,4-b]pyrazin-2-amine; 3-chloro-N-cyclopropyl-5-methylpyrido[3,4-b]pyrazin-2-amine; 3-chloro-2-(cyclobutylamino)quinoxaline-6-carbonitrile; 3-chloro-2-((2-fluoroethyl)amino)-quinoxaline-6-carbonitrile; 3-chloro-N-(3-methoxypropyl)quinoxalin-2-amine; 3-chloro-2-((3,3,3-trifluoropropyl)amino)quinoxaline-6-carbonitrile; 6-bromo-3-chloro-N-cyclopropylquinoxalin-2-amine; 7-bromo-3-chloro-N-cyclopropylpyrido[3,4-b]pyrazin-2-amine, and 3,7-dichloro-N-cyclopropylpyrido[3,4-b]pyrazin-2-amine.

Reference B

Synthesis of 5-bromo-3-chloro-N-cyclopropylquinoxalin-2-amine and 8-bromo-3-chloro-N-cyclopropylquinoxalin-2-amine

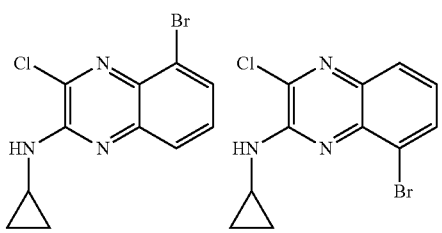

A solution of 5-bromo-2,3-dichloroquinoxaline (250 mg, 0.899 mmol), cyclopropanamine (71.7 µl, 1.034 mmol) and N-ethyl-N-isopropylpropan-2-amine (157 µl, 0.899 mmol) in dioxane (1285 µl) was heated at 80° C. overnight. ISCO purification (20-80% EtOAc/Hexanes) yielded both pure title compounds as yellow solids.

Reference C

Synthesis of
N-cyclopropyl-3-(piperazin-1-yl)quinoxalin-2-amine dihydrochloride

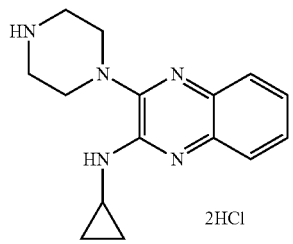 [SMILES: c1ccc2nc(N3CCNCC3)c(NC3CC3)nc2c1]

Step 1: tert-butyl 4-(3-(cyclopropylamino)quinoxalin-2-yl)piperazine-1-carboxylate A solution of 3-chloro-N-cyclopropylquinoxalin-2-amine (503 mg, 2.290 mmol), tert-butyl piperazine-1-carboxylate (640 mg, 3.43 mmol) and DIPEA (1200 µl, 6.87 mmol) in dioxane (4580 µl) was stirred at 140° C. overnight. ISCO purification (10-70% EtOAc/hexanes) afforded the title compound as an ivory solid.

Step 2:
N-cyclopropyl-3-(piperazin-1-yl)quinoxalin-2-amine dihydrochloride

A solution of tert-butyl 4-(3-(cyclopropylamino)quinoxalin-2-yl)piperazine-1-carboxylate (127 mg, 0.344 mmol) in dioxane (859 µl) was treated with HCl (859 µl, 3.44 mmol, 4 M in dioxane) at RT and the reaction stirred for 4 h. The solvent was removed under reduced pressure to afford the title compound as a tan solid.

Following the procedure described above, following compounds were synthesized using commercially available starting materials.

2-(cyclopropylamino)-3-(piperazin-1-yl)quinoxaline-6-carbonitrile; N-cyclopropyl-6-fluoro-3-(piperazin-1-yl)quinoxalin-2-amine; 3-(piperazin-1-yl)-N-(pyridin-3-yl)quinoxalin-2-amine; 2-(isopropylamino)-3-(piperazin-1-yl)quinoxaline-6-carbonitrile; 2-(cyclobutylamino)-3-(piperazin-1-yl)quinoxaline-6-carbonitrile; and N-cyclopropyl-6,7-difluoro-3-(piperazin-1-yl)quinoxalin-2-amine Reference D Synthesis of 2-chloro-3-(piperazin-1-yl)quinoxaline, hydrogen chloride salt

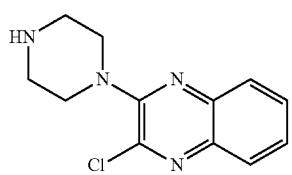 [SMILES: Clc1nc2ccccc2nc1N1CCNCC1]

Step 1: tert-butyl 4-(3-chloroquinoxalin-2-yl)piperazine-1-carboxylate

A solution of 2,3-dichloroquinoxaline (2 g, 10.05 mmol), tert-butyl piperazine-1-carboxylate (2.059 g, 11.05 mmol) and N-ethyl-N-isopropylpropan-2-amine (2.63 ml, 15.07 mmol) in dioxane (10.05 ml) was heated at 80° C. for 18 h. ISCO purification (5-10% EtOAc in hexanes) afforded the title compound as a yellow oil.

Step 2: 2-chloro-3-(piperazin-1-yl)quinoxaline, hydrogen chloride salt

A solution of tert-butyl 4-(3-chloroquinoxalin-2-yl)piperazine-1-carboxylate (243 mg, 0.697 mmol) in dioxane (1742 µl) was treated with HCl (1393 µl, 5.57 mmol, 4 M in dioxane) dropwise at RT and the resulting reaction mixture was stirred overnight. The solvent was removed under reduced pressure and the title compound was obtained as a yellow solid.

Reference E

Synthesis of 3-chloro-N-(pyridin-3-yl)quinoxalin-2-amine

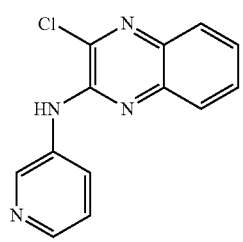 [SMILES: Clc1nc2ccccc2nc1Nc1cccnc1]

To a solution of 2,3-dichloroquinoxaline (10 g, 50.2 mmol) in ethanol (50 mL) was added pyridin-3-amine (4.73 g, 50.2 mmol). The reaction mixture was stirred at 20° C. for 2 h. The reaction mixture was poured into water and extracted with EtOAc. The organic layer was dried and concentrated under reduced pressure to yield the title compound as an orange-brown solid.

Reference F

Synthesis of 3-chloro-2-((6-methoxypyridin-3-yl)amino)quinoxaline-6-carbonitrile

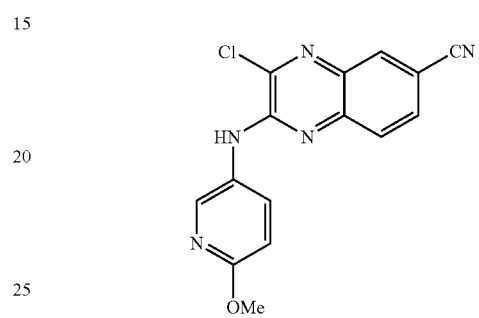

To a suspension of NaH (10.71 mg, 0.268 mmol, 60% in mineral oil) in THF (1116 µl) was added 6-methoxypyridin-3-amine (26.8 µl, 0.245 mmol). The mixture was stirred at RT for 30 min before 2,3-dichloroquinoxaline-6-carbonitrile (50 mg, 0.223 mmol) was added. The reaction mixture was stirred for 12 h at 70° C., then for 48 h at RT. ISCO purification (0-60% EtOAc/hexanes) afforded the title compound as a yellow solid.

Following the procedure described above, 3-chloro-2-(pyridin-3-ylamino)-quinoxaline-6-carbonitrile was synthesized.

Reference G

Synthesis of 3-chloro-N-(pyrazin-2-yl)quinoxalin-2-amine

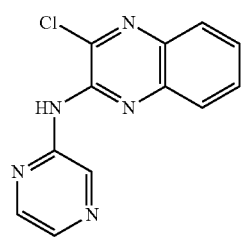 [SMILES: Clc1nc2ccccc2nc1Nc1cnccn1]

A suspension of 2,3-dichloroquinoxaline (200 mg, 1.005 mmol) and pyrazin-2-amine (191 mg, 2.010 mmol) in DMF (3 ml) was treated with NaH (80 mg, 2.010 mmol, 60% in mineral oil). Stirring was continued for 2 h at 15° C., then the reaction mixture was poured into water, extracted with EtOAc, dried over anhydrous sodium sulfate, filtered and concentrated to give the title compound. The crude material was used without further purification.

Following the procedure described above, following compounds were synthesized using commercially available starting materials.

3-chloro-N-(pyrimidin-4-yl)quinoxalin-2-amine; 3-chloro-N-(pyridazin-3-yl)quinoxalin-2-amine; 3-chloro-N-(1,2,4-triazin-3-yl)quinoxalin-2-amine; 3-chloro-N-(5,6-dimethyl-1,2,4-triazin-3-yl)quinoxalin-2-amine; 3-chloro-N-(pyridin-4-yl)quinoxalin-2-amine; 3-chloro-N-(pyridin-2-yl)quinoxalin-2-amine; N-(3-chloroquinoxalin-2-yl)-3,4-dimethylisoxazol-5-amine; and N-(3-chloroquinoxalin-2-yl)isoxazol-3-amine.

Reference H

Synthesis of 3-chloro-N-(2,2,2-trifluoroethyl)quinoxalin-2-amine

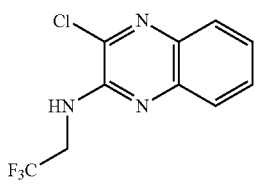 [SMILES: FC(F)(F)CNc1nc2ccccc2nc1Cl]

A suspension of Et$_3$N (0.420 ml, 3.01 mmol), 2,3-dichloroquinoxaline (200 mg, 1.005 mmol), and 2,2,2-trifluoroethanamine (199 mg, 2.010 mmol) in DMSO (5 ml) was heated at 120° C. under microwave irradiation for 1 h. The reaction mixture was concentrated under reduced pressure to give the title compound, which was used without further purification.

Following the procedure described above, 3-chloro-2-((2,2-difluoroethyl)amino)quinoxaline-6-carbonitrile was synthesized.

Reference I

Synthesis of 8-chloro-N-cyclopropyl-3-(piperazin-1-yl)pyrido[3,4-b]pyrazin-2-amine

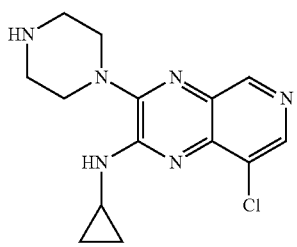 [SMILES: Clc1cncc2nc(N3CCNCC3)c(NC3CC3)nc12]

A mixture of 3,8-dichloro-N-cyclopropylpyrido[3,4-b]pyrazin-2-amine (100 mg, 0.392 mmol) and piperazine (338 mg, 3.92 mmol) in EtOH (10 ml) was heated at 40° C. for 3 h. The reaction was concentrated to dryness and partitioned between EtOAc and water. The insoluble material was collected by filtration then dried under vacuum to give the title compound as a tan solid.

Reference J

Synthesis of piperazin-1-yl(3-(trifluoromethyl)phenyl)methanone, hydrogen chloride salt

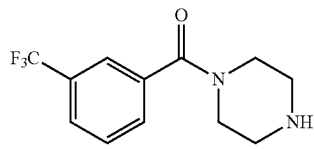 [SMILES: O=C(c1cccc(C(F)(F)F)c1)N1CCNCC1]

Step 1: tert-butyl 4-(3-(trifluoromethyl)benzoyl)piperazine-1-carboxylate

A solution of 3-(trifluoromethyl)benzoic acid (1.22 g, 6.44 mmol) and HATU (2.45 g, 6.44 mmol) in DMF (16.1 mL) and iPr$_2$NEt (16.1 mmol, 2.81 mL) was stirred at RT for 30 min, followed by the addition of tert-butyl piperazine-1-carboxylate (1.2 g, 6.44 mmol). The resulting reaction mixture was stirred at RT overnight. Purification by column chromatography (25% EtOAc/hexanes) afforded the title compound as a yellow solid.

Step 2: piperazin-1-yl(3-(trifluoromethyl)phenyl)methanone, hydrogen chloride salt A solution of tert-butyl 4-(3-(trifluoromethyl)benzoyl)piperazine-1-carboxylate (600 mg, 1.674 mmol) in dioxane (5.58 mL) was treated with HCl (3.35 mL, 13.39 mmol, 4 M in dioxane) at RT. After stirring for 12 h, the reaction mixture was diluted with hexanes and filtered. The solid was dissolved in MeOH and the solvent was removed under reduced pressure to afford the title compound as a white solid.

Following the procedure described above, following compounds were synthesized using commercially available carboxylic acids.

(4-(methylsulfonyl)phenyl)(piperazin-1-yl)methanone, hydrogen chloride salt; (2,5-dichlorophenyl)(piperazin-1-yl)methanone, hydrogen chloride salt; (2,5-dichlorophenyl)-(piperazin-1-yl)methanone, hydrogen chloride salt; (3-chloro-4-methoxyphenyl)(piperazin-1-yl)methanone, hydrogen chloride salt; (3,5-dichlorophenyl)(piperazin-1-yl)methanone, hydrogen chloride salt; (3-chlorophenyl)(piperazin-1-yl)methanone, hydrogen chloride salt; (2,3-dichlorophenyl)(piperazin-1-yl)methanone, hydrogen chloride salt; (5-methylisoxazol-3-yl)(piperazin-1-yl)methanone, hydrogen chloride salt; (4-chlorophenyl)(piperazin-1-yl)methanone, hydrogen chloride salt; and (4-chloro-2-fluorophenyl)(piperazin-1-yl)methanone hydrogen chloride salt.

Reference K

Synthesis of piperazin-1-yl(4-(trifluoromethyl)phenyl)methanone 2,2,2-trifluoroacetate

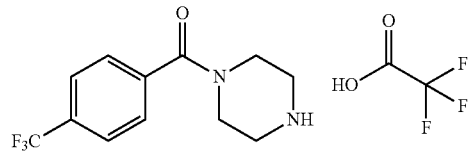

Step 1: tert-butyl 4-(4-(trifluoromethyl)benzoyl)piperazine-1-carboxylate 4-(Trifluoromethyl)benzoic acid (1.531 g, 8.05 mmol) and HATU (3.06 g, 8.05 mmol) were dissolved in DMF (20.1 mL) at RT, then iPr$_2$NEt (3.33 mL, 20.13 mmol) was added and the solution stirred for 30 min. tert-Butyl piperazine-1-carboxylate (1.5 g, 8.05 mmol) was then added and stirring continued for 16 h.

ISCO purification yielded the title compound as a yellow oil.

Step 2: piperazin-1-yl(4-(trifluoromethyl)phenyl)methanone 2,2,2-trifluoroacetate A solution of tert-butyl 4-(4-(trifluoromethyl)benzoyl)piperazine-1-carboxylate (1.78 g, 4.97 mmol) in DCM (9.9 mL) was treated with TFA (64.6 mmol, 5 mL) dropwise via syringe at RT. The resulting reaction mixture was stirred until complete by LCMS, then quenched with sat. NaHCO$_3$ and extracted with DCM. The organic layers were combined and dried over MgSO$_4$. Purification by column chromatography (15% MeOH/DCM) afforded the title compound as a yellow solid.

Reference L

Synthesis of 1-(pyridin-3-ylmethyl)piperazine dihydrochloride salt

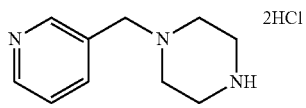 [SMILES: c1cncc(CN2CCNCC2)c1]

Step 1: tert-butyl 4-(pyridin-3-ylmethyl)piperazine-1-carboxylate

A solution of tert-butyl piperazine-1-carboxylate (306 mg, 1.643 mmol) and nicotinaldehyde (157 μl, 1.643 mmol) in DCE (5476 μl) was treated with sodium triacetoxyborohydride (487 mg, 2.300 mmol) at RT. The resulting reaction mixture was stirred at RT for 2 h. Purification by column chromatography (50% EtOAc/hexanes, then 10% MeOH/DCM) gave the title compound as a clear oil.

Step 2: 1-(pyridin-3-ylmethyl)piperazine dihydrochloride salt

A solution of tert-butyl 4-(pyridin-3-ylmethyl)piperazine-1-carboxylate (359 mg, 1.29 mmol) in dioxane (4.31 mL) was treated with HCl (2.58 mL, 10.35 mmol, 4 M in dioxane) dropwise at RT and the resulting reaction mixture was stirred for 18 h. After dilution with hexanes, the reaction mixture was filtered and the solid obtained was dissolved in MeOH. The solvent was removed under reduced pressure to afford the title compound as an ivory solid.

Following the procedure described above, following compounds were synthesized using commercially available aldehydes:

1-(pyridin-4-ylmethyl)piperazine, dihydrogen chloride salt; 1-(pyridin-2-ylmethyl)piperazine, dihydrogen chloride salt; 1-(3-bromobenzyl)piperazine, hydrogen chloride salt; 1-(5-chloro-2-(difluoromethoxy)benzyl)piperazine, hydrogen chloride salt; 1-(4-fluorobenzyl)piperazine, hydrogen chloride salt; 1-(2,5-dimethylbenzyl)piperazine, hydrogen chloride salt; 1-(2,4-difluorobenzyl)piperazine, hydrogen chloride salt; 1-(2,4,5-trifluorobenzyl)piperazine, hydrogen chloride salt; 1-(2,5-difluorobenzyl)piperazine, hydrogen chloride salt; 1-(5-chloro-2-fluorobenzyl)piperazine, hydrogen chloride salt; 1-(2,5-dichlorobenzyl)piperazine, hydrogen chloride salt; and 1-(2,6-dichlorobenzyl)piperazine, hydrogen chloride salt.

Reference M

Synthesis of (2-chloro-4-(methylsulfonyl)phenyl)(piperazin-1-yl)methanone, hydrogen chloride salt

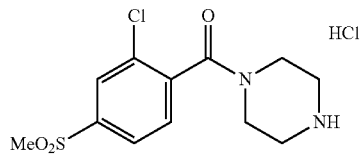 [SMILES: CS(=O)(=O)c1ccc(C(=O)N2CCNCC2)c(Cl)c1 ; Cl]

Step 1: tert-butyl 4-(2-chloro-4-(methylsulfonyl)benzoyl)piperazine-1-carboxylate A solution of 2-chloro-4-(methylsulfonyl)benzoic acid (550 mg, 2.344 mmol) in DCM (7813 μl) and DMF (2 drops) was treated with oxalyl chloride (411 μl, 4.69 mmol) at RT and the reaction mixture was stirred for 2 h. A solution of tert-butyl piperazine-1-carboxylate (960 mg, 5.16 mmol) and Et$_3$N (719 μl, 5.16 mmol) in DCM (4.6 mL) was cooled to 0° C. and the crude acid chloride solution was added dropwise. The reaction mixture was allowed to warm up to RT and stirred for 3 h. ISCO purification (75% EtOAc/hexanes) afforded the title compound as a white solid.

Step 2: (2-chloro-4-(methylsulfonyl)phenyl)(piperazin-1-yl)methanone, hydrogen chloride salt A solution of tert-butyl 4-(2-chloro-4-(methylsulfonyl)benzoyl)piperazine-1-carboxylate (581 mg, 1.442 mmol) in dioxane (4.81 mL) was treated with HCl (3605 μl, 14.42 mmol, 4 M in dioxane) and the resulting reaction mixture stirred at RT overnight. The solvent was removed to afford the title compound as a white solid.

Following the procedure described above, (3,6-dichloropyridin-2-yl)(piperazin-1-yl)methanone, dihydrogen chloride salt was synthesized using commercially available carboxylic acid.

Reference N

Synthesis of 4-(2,5-difluorophenoxyl)piperidine hydrochloride

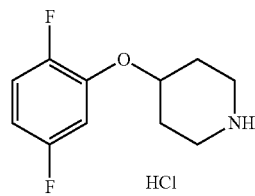 [SMILES: Fc1ccc(F)c(OC2CCNCC2)c1 ; Cl]

Step 1: tert-butyl 4-(2,5-difluorophenoxyl)piperidine-1-carboxylate

To a solution of tert-butyl 4-hydroxypiperidine-1-carboxylate (150 mg, 0.745 mmol) in THF (2484 µl) was added 2,5-difluorophenol (107 mg, 0.820 mmol) and triphenylphosphine (235 mg, 0.894 mmol). The mixture was cooled to 0° C. and DEAD (487 µl, 1.230 mmol, 40% wt in PhMe) was added dropwise. The mixture was then heated at 65° C. for 7 h then at RT for 18 h. ISCO purification (0-100% EtOAc/hexanes) yielded the title compound as a colorless oil.

Step 2: 4-(2,5-difluorophenoxyl)piperidine hydrochloride

To a solution of tert-butyl 4-(2,5-difluorophenoxyl)piperidine-1-carboxylate (71 mg, 0.227 mmol) in dioxane (755 µl) was added HCl (283 µl, 1.133 mmol, 4 M in dioxane). The mixture was stirred at RT for 16 h then concentrated under reduced pressure to afford the title compound as a white solid.

Following the procedure described above, following compounds were synthesized using commercially available aryl alcohols:
4-(2,4,6-trifluorophenoxyl)piperidine hydrochloride; 4-(5-chloro-2-fluorophenoxy)-piperidine hydrochloride; and 4-(4-chloro-2-fluorophenoxy)piperidine hydrochloride.

Reference O

Synthesis of (2-fluorophenyl)(piperidin-4-yl)methanone hydrochloride

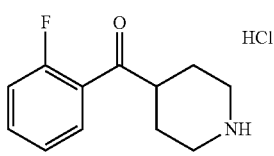 [SMILES: O=C(c1ccccc1F)C1CCNCC1 ; Cl]

Step 1: tert-butyl 4-(2-fluorobenzoyl)piperidine-1-carboxylate

To a −78° C. solution of 1-bromo-2-fluorobenzene (88 µl, 0.808 mmol) in THF (4080 µl) was added n-BuLi (1154 µl, 1.616 mmol, 1.4 M in PhMe) dropwise. After stirring at −78° C. for 15 min, a solution of tert-butyl 4-(methoxy(methyl)carbamoyl)piperidine-1-carboxylate (200 mg, 0.734 mmol) in THF (1 mL) was added dropwise. The ice bath was removed and the reaction mixture was warmed to RT then stirred for 2 h. The solution was cooled to −30° C. and sat. aq. NH₄Cl (10 mL) was added. Upon reaching RT, the solution was diluted with EtOAc and the organic layer was washed with H₂O. The solvents were removed under reduced pressure and then ISCO purification (0-100% EtOAc/hexanes) yielded the title compound as a yellow oil.

Step 2: (2-fluorophenyl)(piperidin-4-yl)methanone hydrochloride

To a solution of tert-butyl 4-(2-fluorobenzoyl)piperidine-1-carboxylate (125 mg, 0.407 mmol) in dioxane (1356 µl) was added HCl (508 µl, 2.033 mmol, 4 M in dioxane). The mixture was stirred at 45° C. for 2 h then the solvents were removed under reduced pressure to afford the title compound as a light yellow solid.

Following the procedure described above, following compounds were synthesized using commercially available aryl bromides:
(2-fluorophenyl)(piperidin-4-yl)methanone hydrochloride; (2,5-difluorophenyl)-(piperidin-4-yl)methanone hydrochloride; piperidin-4-yl(2,4,6-trifluorophenyl)methanone hydrochloride; (4-chloro-2,6-difluorophenyl)(piperidin-4-yl)methanone hydrochloride; (4-chloro-2-fluorophenyl)(piperidin-4-yl)methanone hydrochloride; (5-chloro-2-fluorophenyl)(piperidin-4-yl)methanone hydrochloride; and (2,4-difluorophenyl)(piperidin-4-yl)methanone hydrochloride; (2-methoxyphenyl)(piperidin-4-yl)methanone hydrochloride; (2-chlorophenyl)(piperidin-4-yl)methanone hydrochloride; phenyl(piperidin-4-yl)methanone hydrochloride; (2,3-difluorophenyl)(piperidin-4-yl)methanone hydrochloride; (3-chlorophenyl)(piperidin-4-yl)methanone hydrochloride; piperidin-4-yl(o-tolyl)methanone hydrochloride; (2,6-difluorophenyl)(piperidin-4-yl)methanone hydrochloride; (2-chloro-5-fluorophenyl)(piperidin-4-yl)methanone hydrochloride; (3-fluorophenyl)(piperidin-4-yl)methanone hydrochloride; piperidin-4-yl(thiophen-2-yl)methanone, hydrogen chloride salt; (2-chlorothiophen-3-yl)(piperidin-4-yl)methanone hydrochloride; piperidin-4-yl(thiophen-3-yl)methanone hydrochloride; 3-(piperidine-4-carbonyl)benzonitrile hydrochloride; (2-(methylthio)phenyl)(piperidin-4-yl)methanone hydrochloride; 4-fluoro-3-(piperidine-4-carbonyl)benzonitrile hydrochloride; (6-chloro-2,3-difluorophenyl)(piperidin-4-yl)methanone hydrochloride; (2-chloro-3-fluorophenyl)(piperidin-4-yl)methanone hydrochloride.

Reference P

Synthesis of (R/S)-4-((2,4-difluorophenyl)fluoromethyl)piperidine hydrochloride

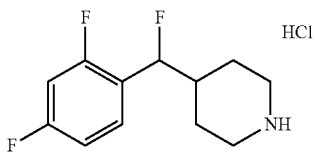 [SMILES: Fc1ccc(C(F)C2CCNCC2)c(F)c1 ; Cl]

Step 1: tert-butyl 4-((2,4-difluorophenyl)(hydroxy)methyl)piperidine-1-carboxylate To a 0° C. solution of tert-butyl 4-(2,4-difluorobenzoyl)piperidine-1-carboxylate (1.28 g, 3.93 mmol) in MeOH (15.74 ml) was added NaBH₄ (0.372 g, 9.84 mmol). The ice bath was removed and the reaction mixture stirred for 2 h at RT then was quenched with sat. aq. NH₄Cl. The organic layer was extracted with EtOAc, washed with H₂O and dried over MgSO₄. The solvent was removed under reduced pressure to yield the title compound as a white hygroscopic solid.

Step 2: tert-butyl 4-((2,4-difluorophenyl)fluoromethyl)piperidine-1-carboxylate To a −78° C. solution of tert-butyl 4-((2,4-difluorophenyl)(hydroxy)methyl)piperidine-1-carboxylate (200 mg, 0.611 mmol) in CH$_2$Cl$_2$ (3055 μl) was added DAST (242 μl, 1.833 mmol). The mixture was stirred at −78° C. for 30 min., then quenched with MeOH. ISCO purification (0-100% EtOAc/hexanes) afforded the title compound as a colorless oil.

Step 3: (R/S)-4-((2,4-difluorophenyl)fluoromethyl)piperidine hydrochloride

To a solution of tert-butyl 4-((2,4-difluorophenyl)fluoromethyl)piperidine-1-carboxylate (148 mg, 0.449 mmol) in dioxane (1498 μl) was added HCl (337 μl, 1.348 mmol, 4 M in dioxane). The mixture was heated at 45° C. for 16 h then concentrated under reduced pressure to yield the title compound as a white solid.

Note: Optically pure compounds were obtained by chiral SFC separation of racemic compound.

Following the procedure described above, (R/S)-4-(2,5-difluorophenyl)fluoromethyl)-piperidine hydrochloride was synthesized.

Reference Q

Synthesis of 4-(2,4-difluorophenyl)difluoromethyl)piperidine hydrochloride

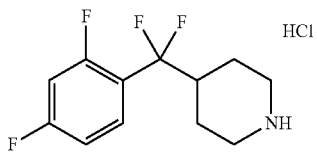

Step 1: tert-butyl 4-((2,4-difluorophenyl)difluoromethyl)piperidine-1-carboxylate To a solution of tert-butyl 4-(2,4-difluorobenzoyl)piperidine-1-carboxylate (7.7 g, 23.67 mmol) in DCM (100 ml) was added DAST (46.9 ml, 355 mmol). The reaction mixture was stirred at reflux for 2 days. Purification by column chromatography afforded the title compound.

Step 2: 4-((2,4-difluorophenyl)difluoromethyl)piperidine hydrochloride

To a solution of tert-butyl 4-((2,4-difluorophenyl)difluoromethyl)piperidine-1-carboxylate (2.6 g, 7.49 mmol) in DCM (10 mL) was added HCl (2.28 mL, 74.9 mmol). The mixture was stirred at −78° C. for 16 h then concentrated under reduced pressure to yield the title compound as a white solid.

Following the procedure described above, following compounds were synthesized using commercially available starting materials.

4-((2,5-difluorophenyl)difluoromethyl)piperidine hydrochloride; and 4-((5-chloro-2-fluorophenyl)difluoromethyl)piperidine hydrochloride.

Reference R

Synthesis of 4-fluoro-1-(piperidin-4-ylmethyl)pyridin-2(1H)-one, hydrogen chloride salt

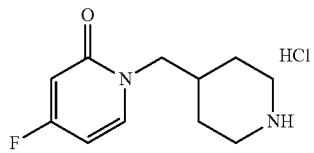 [SMILES: O=c1cc(F)ccn1CC1CCNCC1 ; Cl]

Step 1: tert-butyl 4-((4-fluoro-2-oxopyridin-1(2H)-yl)methyl)piperidine-1-carboxylate A solution of 4-fluoropyridin-2(1H)-one (112 mg, 0.990 mmol), tert-butyl 4-(bromomethyl)piperidine-1-carboxylate (276 mg, 0.990 mmol) and potassium carbonate (274 mg, 1.981 mmol) in dioxane (1981 μl) was stirred at 80° C. until complete by LCMS analysis. HPLC purification afforded the title compound as a white solid.

Step 2: 4-fluoro-1-(piperidin-4-ylmethyl)pyridin-2(1H)-one, hydrogen chloride salt A solution of tert-butyl 4-((4-fluoro-2-oxopyridin-1(2H)-yl)methyl)piperidine-1-carboxylate (100 mg, 0.322 mmol) in dioxane (644 μl) was treated with HCl (806 μl, 3.22 mmol, 4 M in dioxane) dropwise via syringe at RT and the resulting reaction mixture stirred for 3 h. The solvent was removed under reduced pressure to yield the title compound as a white solid.

Following the procedure described above, following compounds were synthesized using commercially available pyridinones:

4-chloro-1-(piperidin-4-ylmethyl)pyridin-2(1H)-one hydrochloride; 5-fluoro-1-(piperidin-4-ylmethyl)pyridin-2(1H)-one hydrochloride; and 5-chloro-1-(piperidin-4-ylmethyl)pyridin-2(1H)-one hydrochloride.

Reference S

Synthesis of 1-(1-(2,5-dichlorophenyl)ethyl)piperazine hydrochloride

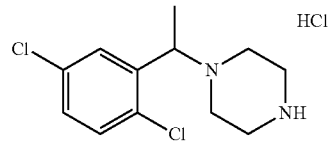 [SMILES: CC(c1cc(Cl)ccc1Cl)N1CCNCC1 ; Cl]

Step 1: tert-butyl 4-(1-(2,5-dichlorophenyl)ethyl)piperazine-1-carboxylate

A 10-mL screwtop vial containing tert-butyl piperazine-1-carboxylate (200 mg, 1.074 mmol), 1-(2,5-dichlorophenyl)ethanone (203 mg, 1.074 mmol), sodium triacetoxyborohydride (341 mg, 1.611 mmol), and acetic acid (92 μl, 1.611 mmol) in DCE (3579 μl) was stirred at RT overnight.

1 M KOH was added with rapid stirring for 30 min, then the reaction mixture was extracted with ether. The combined organic layer was washed with brine and the organic extracts were combined, filtered through MgSO₄, and concentrated to afford the title compound.

Step 2: 1-(1-(2,5-dichlorophenyl)ethyl)piperazine hydrochloride

A 10-mL screwtop vial containing tert-butyl 4-(1-(2,5-dichlorophenyl)ethyl)-piperazine-1-carboxylate (270 mg, 0.751 mmol) and HCl (1879 µl, 7.51 mmol, 4 M in dioxane) in DCM (2505 µl) was stirred overnight and concentrated under reduced pressure to give the title compound.

Reference T

Synthesis of N-(4-chlorophenyl)piperidin-4-amine dihydrochloride

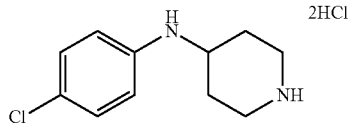 [SMILES: "2HCl" ; Clc1ccc(NC2CCNCC2)cc1]

Step 1: tert-butyl 4-((4-chlorophenyl)amino)piperidine-1-carboxylate

A 20-mL screwtop vial containing tert-butyl 4-oxopiperidine-1-carboxylate (500 mg, 2.509 mmol), acetic acid (287 µl, 5.02 mmol), and 4-chloroaniline (320 mg, 2.509 mmol) in DCE (6274 µl) was stirred for 10 min then sodium triacetoxyborohydride (745 mg, 3.51 mmol) was added and the reaction mixture was stirred overnight. ISCO purification (0-15% EtOAc/hexanes) afforded the title compound.

Step 2: N-(4-chlorophenyl)piperidin-4-amine dihydrochloride

A 5-mL screwtop vial containing tert-butyl 4-((4-chlorophenyl)amino)piperidine-1-carboxylate (150 mg, 0.483 mmol) was stirred in HCl (965 µl, 3.86 mmol, 4 M in dioxane) overnight. Concentration under reduced pressure gave the title compound.

Reference U

Synthesis of N-(2,4-difluorophenyl)piperidin-4-amine bis(2,2,2-trifluoroacetate)

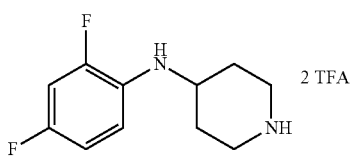 [SMILES: Fc1ccc(NC2CCNCC2)c(F)c1 ; "2 TFA"]

Step 1: tert-butyl 4-((2,4-difluorophenyl)amino) piperidine-1-carboxylate

A 10-mL screwtop vial containing 2,4-difluoroaniline (130 mg, 1.004 mmol), acetic acid (115 µl, 2.008 mmol), and tert-butyl 4-oxopiperidine-1-carboxylate (200 mg, 1.004 mmol) in DCE (2509 µl) was stirred for 10 min and then sodium triacetoxyborohydride (319 mg, 1.506 mmol) was added. After 2 h, the mixture was added to 1 M KOH, then the reaction mixture was extracted with ether. The combined organic layers were washed with brine, filtered through MgSO₄, and concentrated to afford the title compound.

Step 2: N-(2,4-difluorophenyl)piperidin-4-amine bis(2,2,2-trifluoroacetate)

A 50-mL round-bottomed flask containing tert-butyl 4-((2,4-difluorophenyl)amino)piperidine-1-carboxylate (314 mg, 1.005 mmol) in TFA (3 mL) was stirred at RT for 2 h. Concentration under reduced pressure yielded the title compound.

Reference V

Synthesis of 7-bromo-2,3-dichloropyrido[3,4-b]pyrazine

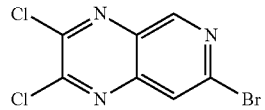 [SMILES: Clc1nc2cnc(Br)cc2nc1Cl]

Step 1: 7-bromopyrido[3,4-b]pyrazine-2,3(1H,4H)-dione hydrochloride

To a solution of 6-bromopyridine-3,4-diamine (467 mg, 2.484 mmol) in HCl (3726 µl, 14.90 mmol, 4 M aq) was added oxalic acid (257 mg, 2.86 mmol). The mixture was heated at 120° C. for 14 h then filtered, washed with cold water and dried under vacuum to yield the title compound as a tan solid.

Step 2: 7-bromo-2,3-dichloropyrido[3,4-b]pyrazine

To 7-bromopyrido[3,4-b]pyrazine-2,3(1H,4H)-dione hydrochloride (626 mg, 2.248 mmol) was added thionyl chloride (6070 µl, 83 mmol) and N,N-dimethylformamide (174 µl, 2.248 mmol). The reaction mixture was heated at 80° C. overnight then poured into ice water and filtered. The solid was dried under vacuum for 2 h to give the title compound as a pale solid that was used without further purification.

Reference W

Synthesis of 2,3,7-trichloropyrido[3,4-b]pyrazine

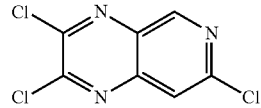 [SMILES: Clc1cc2nc(Cl)c(Cl)nc2cn1]

Step 1: 7-bromopyrido[3,4-b]pyrazine-2,3 (1H,4H)-dione hydrochloride

To a solution of 6-bromopyridine-3,4-diamine (467 mg, 2.484 mmol) in HCl (3726 µl, 14.90 mmol, 4 M aq) was added oxalic acid (257 mg, 2.86 mmol). The mixture was heated at 120° C. for 14 h then filtered, washed with cold water and dried under vacuum to yield the title compound as a tan solid.

Step 2: 2,3,7-trichloropyrido[3,4-b]pyrazine

To 7-bromopyrido[3,4-b]pyrazine-2,3(1H,4H)-dione hydrochloride (130 mg, 0.467 mmol) was added POCl$_3$ (1305 µl, 14.00 mmol) and N,N-dimethylformamide (36.1 µl, 0.467 mmol). The mixture was heated at 120° C. for 16 h then poured into ice water. The mixture was extracted with EtOAc, washed with water, dried over Na$_2$SO$_4$ and concentrated under reduced pressure. The crude material was dried under vacuum then used directly without further purification.

Reference X

Synthesis of 2-(cyclopropylamino)-3-(piperidin-4-yl)quinoxaline-6-carbonitrile

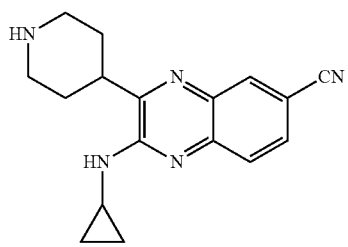 [SMILES: N#Cc1ccc2nc(NC3CC3)c(C3CCNCC3)nc2c1]

Step 1: tert-butyl 4-(7-cyano-3-(cyclopropylamino)quinoxalin-2-yl)-5,6-dihydropyridine-1(2H)-carboxylate A 10 mL microwave vial containing 3-chloro-2-(cyclopropylamino)quinoxaline-6-carbonitrile (200 mg, 0.817 mmol), tert-butyl 4-(4,4,5,5-tetramethyl-1,3,2-dioxaborolan-2-yl)-5,6-dihydropyridine-1(2H)-carboxylate (455 mg, 1.471 mmol), bis(triphenylphosphine)palladium(II) chloride (115 mg, 0.163 mmol), and potassium carbonate (339 mg, 2.452 mmol) in MeCN (4087 µl) was degassed with nitrogen for 10 min then heated to 150° C. for 1 h. Concentration under reduced pressure and ISCO purification (35% EtOAc/hexanes) gave the title compound.

Step 2: 2-(cyclopropylamino)-3-(1,2,3,6-tetrahydropyridin-4-yl)quinoxaline-6-carbonitrile dihydrochloride A 5 mL screwtop-vial containing tert-butyl 4-(7-cyano-3-(cyclopropylamino)quinoxalin-2-yl)-5,6-dihydropyridine-1(2H)-carboxylate (220 mg, 0.562 mmol) and HCl (2810 µl, 11.24 mmol, 4 M in dioxane) in CH$_2$Cl$_2$ (Volume: 562 µl) was stirred overnight and concentrated to yield the title compound.

Step 3: 2-(cyclopropylamino)-3-(piperidin-4-yl)quinoxaline-6-carbonitrile

To a 5 mL screw-top vial containing 2-(cyclopropylamino)-3-(1,2,3,6-tetrahydropyridin-4-yl)quinoxaline-6-carbonitrile dihydrochloride (18 mg, 0.049 mmol) and 10% palladium on carbon (5.26 mg, 0.049 mmol) in methanol (247 µl) was bubbled hydrogen under balloon pressure for 30 min. Filtration, concentration, and HPLC purification gave the title compound.

Reference Y

Synthesis of N-cyclopropyl-7-methyl-3-(piperidin-4-yl)pyrido[3,4-b]pyrazin-2-amine, 2,2,2-trifluoroacetic acid salt

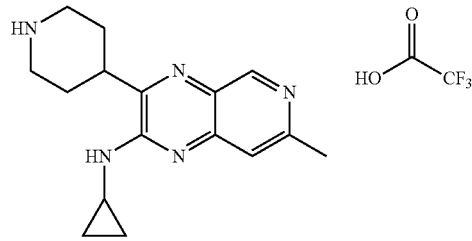 [SMILES: Cc1cc2nc(NC3CC3)c(C3CCNCC3)nc2cn1 ; O=C(O)C(F)(F)F]

Step 1: tert-butyl 4-(2-(cyclopropylamino)-7-methylpyrido[3,4-b]pyrazin-3-yl)-5,6-dihydropyridine-1(2H)-carboxylate A vial charged with 3-chloro-N-cyclopropyl-7-methylpyrido[3,4-b]pyrazin-2-amine (50 mg, 0.213 mmol), tert-butyl 4-(4,4,5,5-tetramethyl-1,3,2-dioxaborolan-2-yl)-5,6-dihydropyridine-1(2H)-carboxylate (119 mg, 0.383 mmol), potassium carbonate (88 mg, 0.639 mmol) and Pd(PPh$_3$)$_2$Cl$_2$ (29.9 mg, 0.043 mmol), was evacuated/refilled with nitrogen (3×). MeCN (1065 µl) was added to the reaction mixture and the vial was evacuated and refilled with nitrogen (3×). The resulting mixture was heated at 80° C. overnight. ISCO purification (0-5% MeOH/DCM) gave the title compound as an off-white solid.

Step 2: tert-butyl 4-(2-(cyclopropylamino)-7-methylpyrido[3,4-b]pyrazin-3-yl)piperidine-1-carboxylate, 2,2,2-trifluoroacetic acid salt A mixture of tert-butyl 4-(2-(cyclopropylamino)-7-methylpyrido[3,4-b]pyrazin-3-yl)-5,6-dihydropyridine-1(2H)-carboxylate (30 mg, 0.079 mmol) and 10% palladium on carbon (3 mg, 2.82 µmol) in MeOH (393 µl) was stirred under a hydrogen balloon at RT overnight. HPLC purification gave the title compound as an off-white solid.

Step 3: N-cyclopropyl-7-methyl-3-(piperidin-4-yl)pyrido[3,4-b]pyrazin-2-amine, 2,2,2-trifluoroacetic acid salt To a solution of tert-butyl 4-(2-(cyclopropylamino)-7-methylpyrido[3,4-b]pyrazin-3-yl)piperidine-1-carboxylate 2,2,2-trifluoroacetate (18 mg, 0.036 mmol) in DCM (0.3 ml) at 0° C. was added TFA (0.15 ml). The resulting solution was stirred at 0° C. for 2 h and then concentrated under reduced pressure to yield the title compound as a colorless oil.

Reference Z

Synthesis of N-cyclopropyl-3-(3-methylpiperazin-1-yl)quinoxalin-2-amine dihydrochloride

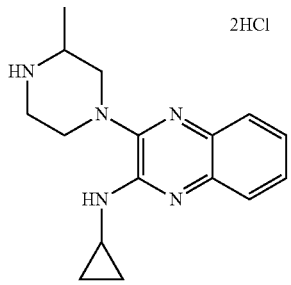 [SMILES: CC1CN(c2nc3ccccc3nc2NC2CC2)CCN1]

Step 1: tert-butyl 4-(3-(cyclopropylamino)quinoxalin-2-yl)-2-methylpiperazine-1-carboxylate To a solution of 3-chloro-N-cyclopropylquinoxalin-2-amine (100 mg, 0.455 mmol) in dioxane (455 µl) was added tert-butyl 2-methylpiperazine-1-carboxylate (137 mg, 0.683 mmol) and iPr$_2$EtN (119 µl, 0.683 mmol). The mixture was heated at 130° C. for 60 h. Purification by ISCO (0-60% EtOAc/Hexanes) yielded the title compound as a yellow oil.

Step 2: N-cyclopropyl-3-(3-methylpiperazin-1-yl)quinoxalin-2-amine dihydrochloride To a solution of tert-butyl 4-(3-(cyclopropylamino)quinoxalin-2-yl)-2-methylpiperazine-1-carboxylate (177 mg, 0.462 mmol) in dioxane (1539 µl) was added HCl (346 µl, 1.385 mmol, 4 M in dioxane). The mixture was heated at 75° C. for 20 h. The solvent was removed under reduced pressure to yield the title compound as a tan solid.

Synthesized by a similar procedure, using commercially available Boc-piperazines:
methyl 4-(3-(cyclopropylamino)quinoxalin-2-yl)piperazine-2-carboxylate dihydrochloride; N-cyclopropyl-3-(3-(methoxymethyl)piperazin-1-yl)quinoxalin-2-amine dihydrochloride; N-cyclopropyl-3-(3-isopropylpiperazin-1-yl)quinoxalin-2-amine dihydrochloride; N-cyclopropyl-3-(2-methylpiperazin-1-yl)quinoxalin-2-amine dihydrochloride; 3-(3-benzylpiperazin-1-yl)-N-cyclopropylquinoxalin-2-amine dihydrochloride

Reference AA

Synthesis of 1-(4-(piperidin-4-yloxy)phenyl)ethanone, hydrogen chloride salt

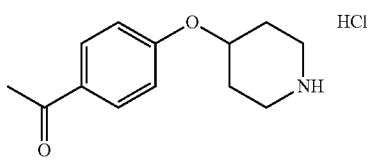 [SMILES: Cl ; CC(=O)c1ccc(OC2CCNCC2)cc1]

Step 1: tert-butyl 4-(4-acetylphenoxyl)piperidine-1-carboxylate

To a 20 mL screwtop vial containing tert-butyl 4-hydroxypiperidine-1-carboxylate (500 mg, 2.484 mmol), 1-(4-hydroxyphenyl)ethanone (372 mg, 2.73 mmol), and triphenylphosphine (782 mg, 2.98 mmol) in THF (8281 µl) was added DEAD (1475 µl, 3.73 mmol) dropwise and heated to 50° C. for 4 h. ISCO purification (0-100% hexanes/ethyl acetate) gave the title compound.

Step 2: 1-(4-(piperidin-4-yloxy)phenyl)ethanone, hydrogen chloride salt

To a 10 mL screwtop vial containing tert-butyl 4-(4-acetylphenoxyl)piperidine-1-carboxylate (580 mg, 1.816 mmol) and HCl (2270 µl, 9.08 mmol, 4 M in dioxane) in dioxane (3632 µl) was stirred for 2 h and concentrated to yield the title compound as a white solid.

Synthesized by a similar procedure, using commercially available phenols: N,N-dimethyl-4-(piperidin-4-yloxy)benzamide, hydrogen chloride salt; 4-(4-(methylthio)phenoxy)piperidine, hydrogen chloride salt; 4-(4-ethoxyphenoxyl)piperidine, hydrogen chloride salt

Reference AB

Synthesis of (2-fluoro-5-(methylthio)phenyl)(piperidin-4-yl)methanone, hydrogen chloride salt

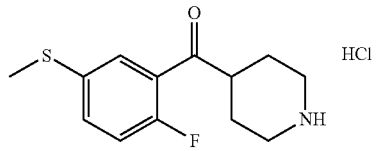 [SMILES: CSc1ccc(F)c(C(=O)C2CCNCC2)c1 ; Cl]

Step 1: tert-butyl 4-(2-fluoro-5-(methylthio)benzoyl)piperidine-1-carboxylate To a 50 mL round-bottomed flask containing (3-bromo-4-fluorophenyl)(methyl)sulfane (250 mg, 1.131 mmol) in THF (5654 µl) at −78° C. was added tert-butyllithium (1397 µl, 2.375 mmol) dropwise by syring-pump. After 10 min, tert-butyl 4-(methoxy(methyl)carbamoyl)piperidine-1-carboxylate (339 mg, 1.244 mmol) was added and the reaction mixture was warmed to RT then quenched with AcOH. ISCO purification (20% ethyl acetate in hexanes) gave the title compound.

Step 2: (2-fluoro-5-(methylthio)phenyl)(piperidin-4-yl)methanone, hydrogen chloride salt A 5 mL screwtop vial containing tert-butyl 4-(2-fluoro-5-(methylthio)benzoyl)piperidine-1-carboxylate (200 mg, 0.566 mmol) and HCl (2.122 mL, 8.49 mmol, 4 M in dioxane) in dioxane (1.132 mL) was stirred overnight. Concentration in vacuo yielded the title compound as a white solid. Synthesized by a similar procedure, using commercially available aryl bromides: 3-fluoro-4-(piperidin-4-yloxy)phenol, hydrogen chloride salt

Reference AC

Synthesis of 4-(2-fluoro-4-(2-fluoroethoxyl)phenoxy)piperidine, hydrogen chloride salt

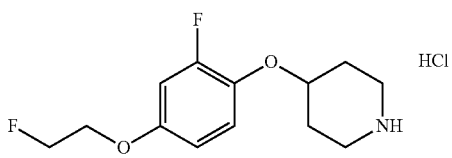 [SMILES: FCCOc1ccc(OC2CCNCC2)c(F)c1 ; Cl]

Step 1: tert-butyl 4-(2-fluoro-4-(2-fluoroethoxyl)phenoxy)piperidine-1-carboxylate A 5 mL screwtop vial containing tert-butyl 4-(2-fluoro-4-hydroxyphenoxy)piperidine-1-carboxylate (42 mg, 0.135 mmol) and sodium hydride (4.86 mg, 0.202 mmol, 60% dispersion in mineral oil) in DMF (674 µl) was stirred for 10 min then added 1-bromo-2-fluoroethane (30.2 µl, 0.405 mmol). After 2 h the reaction mixture was poured into water, extracted with ether (2×) and filtered through MgSO4, Concentration in vacuo yielded the title compound.

Step 2: 4-(2-fluoro-4-(2-fluoroethoxyl)phenoxy)piperidine, hydrogen chloride salt A 5 mL screwtop vial containing tert-butyl 4-(2-fluoro-4-(2-fluoroethoxyl)phenoxy)piperidine-1-carboxylate (45 mg, 0.126 mmol) and HCl (472 µl, 1.889 mmol, 4 M in dioxane) in dioxane (252 µl) was stirred overnight then concentrated to give the title compound.

Reference AD

Synthesis of 5-chloro-N-cyclopropyl-3-(4-(2-fluoro-4-methoxyphenoxy)piperidin-1-yl)pyrido[3,4-b]pyrazin-2-amine

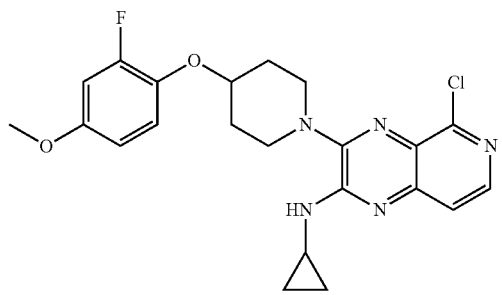 [SMILES: COc1ccc(OC2CCN(c3nc4c(Cl)nccc4nc3NC3CC3)CC2)c(F)c1]

Step 1: 5-bromopyrido[3,4-b]pyrazine-2,3(1H,4H)-dione

A solution of 1,2-di(1H-imidazol-1-yl)ethane-1,2-dione (1.456 g, 7.66 mmol) and 2-bromopyridine-3,4-diamine (1.2 g, 6.38 mmol) in DMF (21.27 ml) was stirred at RT overnight. The precipitate was filtered and washed with anhydrous THF to give the title compound as a grey solid.

Step 2: 2,3,5-trichloropyrido[3,4-b]pyrazine

To a flask containing 5-bromopyrido[3,4-b]pyrazine-2,3 (1H,4H)-dione (1.5 g, 6.20 mmol) was added sulfurous dichloride (16.74 ml, 229 mmol) and N,N-dimethylformamide (0.480 ml, 6.20 mmol). The mixture was heated at 78° C. overnight then water was added to quench the reaction. Filtration afforded the title compound as a light yellow solid.

Step 3: 3,5-dichloro-N-cyclopropylpyrido[3,4-b]pyrazin-2-amine

To a solution of 2,3,5-trichloropyrido[3,4-b]pyrazine (600 mg, 2.56 mmol) in DCM (12.8 mL) at 0° C. was slowly added N-ethyl-N-isopropylpropan-2-amine (1341 µl, 7.68 mmol) and cyclopropanamine (248 µl, 3.58 mmol). The reaction was stirred at 0° C. for 3 h. ISCO purification (0-100% EtOAc in hexanes) yielded the title compound as a white solid.

Step 4: 5-chloro-N-cyclopropyl-3-(4-(2-fluoro-4-methoxyphenoxy)piperidin-1-yl)pyrido[3,4-b]pyrazin-2-amine A solution of 3,5-dichloro-N-cyclopropylpyrido[3,4-b]pyrazin-2-amine (57 mg, 0.223 mmol), 4-(2-fluoro-4-methoxyphenoxy)piperidine, HCl (76 mg, 0.290 mmol, 4 M in dioxane) and N-ethyl-N-isopropylpropan-2-amine (156 µl, 0.894 mmol) in dioxane (745 µl) was heated at 60° C. for 2 h. ISCO purification (10-60% ethyl acetate in hexanes) gave the title compound as a white solid.

Synthesized by a similar procedure, using reference compound piperizines: 5-chloro-N-cyclopropyl-3-(4-(2,4-difluorophenoxyl)piperazin-1-yl)pyrido[3,4-b]pyrazin-2-amine; 5-chloro-N-cyclopropyl-3-(4-(2-fluoro-4-methoxyphenoxy)piperazin-1-yl)pyrido[3,4-b]pyrazin-2-amine

Reference AF

Synthesis of (5-(4-(2,4-difluorophenoxyl)piperidin-1-yl)-6-(isopropylamino)pyrazine-2,3-diyl)dimethanol

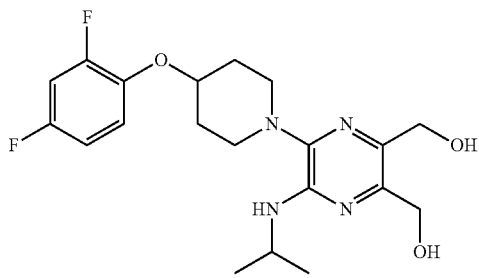 [SMILES: CC(C)Nc1nc(CO)c(CO)nc1N1CCC(Oc2ccc(F)cc2F)CC1]

Step 1: 5,6-dichloropyrazine-2,3-dicarboxylic acid dihydrochloride

A suspension of 2,3-dichloroquinoxaline (10 g, 50.2 mmol) in H₂O (500 mL) was heated to 95° C. with stirring and KMnO₄ (39.7 g, 251 mmol) in hot H₂O (600 mL) was added dropwise over 2 h. The reaction continued stirring for another 2 h, and then the solid MnO2 was removed by filtration from the hot suspension and washed twice with hot H₂O. The combined filtrate was concentrated to 100 mL, cooled to 0° C., and acidified with cold conc. HCl (pH<0). Filtration afforded the title compound as a colorless solid.

Step 2: dimethyl 5,6-dichloropyrazine-2,3-dicarboxylate

To a suspension of 5,6-dichloropyrazine-2,3-dicarboxylic acid dihydrochloride (310 mg, 1.000 mmol) in MeOH (3 ml) was added SOCl₂ (0.584 ml, 8.00 mmol), dropwise, at 0° C. The reaction mixture was allowed to stir at 60° C. for 3 h and was then concentrated to dryness. EtOAc was added and the suspension was filtered. The filtrate was concentrated in vacuo and purified by column chromatograph (petroleum ether in ethyl acetate=20:1, then 15:1) to give the title compound as a solid.

Step 3: dimethyl 5-(4-(2,4-difluorophenoxyl)piperidin-1-yl)-6-(isopropylamino)pyrazine-2,3-dicarboxylate A solution of dimethyl 5,6-dichloropyrazine-2,3-dicarboxylate (2 g, 7.55 mmol) in dioxane (7.55 ml) and DMF (7.55 ml) was treated with propan-2-amine (0.643 ml, 7.55 mmol) and DIPEA (3.29 ml, 18.86 mmol) and then stirred at RT overnight. Then, 4-(2,4-difluorophenoxyl)piperidine hydrochloride (1.884 g, 7.55 mmol), and DIPEA (3.29 ml, 18.86 mmol) were added and the resulting reaction mixture stirred at 90° C. for 8 h. ISCO purification gave dimethyl the title compound as a white solid.

Step 4: (5-(4-(2,4-difluorophenoxyl)piperidin-1-yl)-6-(isopropylamino)pyrazine-2,3-diyl)dimethanol To a solution of dimethyl 5-(4-(2,4-difluorophenoxyl)piperidin-1-yl)-6-(isopropylamino)pyrazine-2,3-dicarboxylate (2 g, 4.31 mmol) in THF (43.1 ml) at 0° C. was added Super-hydride (21.53 ml, 21.53 mmol) and the reaction was stirred at RT for 2 h. Then, the reaction was quenched with 1N HCl (pH=2-4). Saturated NaHCO₃ was added to adjust the pH to 8 and then the reaction mixture was extracted with ethyl acetate (30 mL×2). ISCO purification (10-80% ethyl acetate in hexanes) gave the title compound as a colorless oil.

Example 1

Synthesis of N-cyclopropyl-3-(4-(3-methylbenzyl)piperazin-1-yl)naphthalen-2-amine

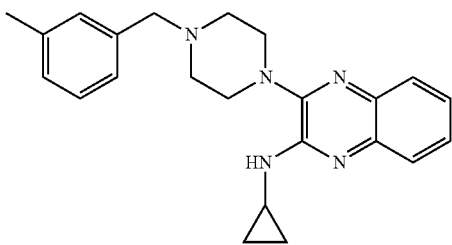 [SMILES: Cc1cccc(CN2CCN(c3nc4ccccc4nc3NC3CC3)CC2)c1]

A solution of 3-chloro-N-cyclopropylquinoxalin-2-amine (30 mg, 0.137 mmol), 1-(3-methylbenzyl)piperazine (39.0 mg, 0.205 mmol) and N-ethyl-N-isopropylpropan-2-amine (0.072 ml, 0.410 mmol) in dioxane (0.25 ml) was heated at 150° C. overnight. HPLC purification afforded the title compound as a white solid. MS (ESI, pos. ion) m/z: 374.3 (M+1)

Using similar reaction conditions as described above, and utilizing intermediates prepared as described above or commercially available piperazines and piperidines, following compounds were synthesized which were purified by either HPLC or ISCO:

N-cyclopropyl-3-(4-(3-methylbenzyl)piperazin-1-yl)quinoxalin-2-amine, 2,2,2-trifluoroacetic acid salt; N-cyclopropyl-3-(3-(thiazol-5-ylmethyl)piperidin-1-yl)quinoxalin-2-amine, 2,2,2-trifluoroacetic acid salt; 5-bromo-N-cyclopropyl-3-(4-(2,5-dichlorobenzyl)piperazin-1-yl)quinoxalin-2-amine; 8-bromo-N-cyclopropyl-3-(4-(2,5-dichlorobenzyl)piperazin-1-yl)quinoxalin-2-amine, 2,2,2-trifluoroacetic acid salt; N-cyclopropyl-2-(4-(3-methylbenzyl)piperazin-1-yl)pyrido[2,3-b]pyrazin-3-amine, 2,2,2-trifluoroacetic acid salt; N-cyclopropyl-2-(4-(2,5-dichlorobenzyl)piperazin-1-yl)pyrido[2,3-b]pyrazin-3-amine, 2,2,2-trifluoroacetic acid salt; 7-bromo-N-cyclopropyl-3-(4-(2,5-dichlorobenzyl)piperazin-1-yl)quinoxalin-2-amine, 2,2,2-trifluoroacetic acid salt; 6-bromo-N-cyclopropyl-3-(4-(2,5-dichlorobenzyl)piperazin-1-yl)quinoxalin-2-amine, 2,2,2-trifluoroacetic acid salt; mixture of N-cyclopropyl-3-(4-(2,5-dichlorobenzyl)piperazin-1-yl)-7-methoxyquinoxalin-2-amine, 2,2,2-trifluoroacetic acid salt and N-cyclopropyl-3-(4-(2,5-dichlorobenzyl)piperazin-1-yl)-7-methoxyquinoxalin-2-amine, 2,2,2-trifluoroacetic acid salt; mixture of N-cyclopropyl-3-(4-(2,5-dichlorobenzyl)piperazin-1-yl)-7-fluoroquinoxalin-2-amine and N-cyclopropyl-3-(4-(2,5-dichlorobenzyl)piperazin-1-yl)-7-fluoroquinoxalin-2-amine; 2-(cyclopropylamino)-3-(4-(2,5-dichlorobenzyl)piperazin-1-yl)quinoxaline-6-carbonitrile; 3-(4-(2,5-dichlorobenzyl)piperazin-1-yl)-N-(2-methoxyphenyl)quinoxalin-2-amine; 3-(4-(2,5-dichlorobenzyl)piperazin-1-yl)-N-(4-fluorophenyl)quinoxalin-2-amine; N-(4-bromophenyl)-3-(4-(2,5-dichlorobenzyl)piperazin-1-yl)quinoxalin-2-amine; N-cyclopropyl-3-(4-(2,5-dichlorobenzyl)piperazin-1-yl)-5,7-dimethylquinoxalin-2-amine; N-cyclopropyl-3-(4-(2,5-dichlorobenzyl)piperazin-1-yl)-6,8-dimethylquinoxalin-2-amine; 8-bromo-N-cyclopropyl-3-(4-(2,5-dichlorobenzyl)piperazin-1-yl)quinoxalin-2-amine, 2,2,2-trifluoroacetic acid salt; N-cyclopropyl-3-(4-(2,5-dichlorobenzyl)piperazin-1-yl)pyrido[3,4-b]pyrazin-2-amine, 2,2,2-trifluoroacetic acid salt; (4-chlorophenyl)(4-(2-(cyclopropylamino)pyrido[3,4-b]pyrazin-3-yl)piperazin-1-yl)methanone; N-cyclopropyl-3-(4-(2,5-difluorobenzyl)piperazin-1-yl)pyrido[3,4-b]pyrazin-2-amine, 2,2,2-trifluoroacetic acid salt; 2-(cyclopropylamino)-3-(4-(2,6-dichlorobenzyl)piperazin-1-yl)quinoxaline-6-carbonitrile, 2,2,2-trifluoroacetic acid salt; 3-(4-(2,5-dichlorobenzyl)piperazin-1-yl)-2-(pyridin-3-ylamino)quinoxaline-6-carbonitrile, 2,2,2-trifluoroacetic acid salt; 3-(4-(2,5-difluorobenzyl)piperazin-1-yl)-2-(pyridin-3-ylamino)quinoxaline-6-carbonitrile; 3-(4-(4-chlorobenzoyl)piperazin-1-yl)-2-(pyridin-3-ylamino)quinoxaline-6-carbonitrile; N-cyclopropyl-3-(4-(2,4-difluorobenzyl)piperidin-1-yl)pyrido[3,4-b]pyrazin-2-amine, 2,2,2-trifluoroacetic acid salt; 2-(cyclopropylamino)-3-(4-(2,4-difluorobenzyl)piperidin-1-yl)quinoxaline-6-carbonitrile, 2,2,2-trifluoroacetic acid salt; 7-bromo-N-cyclopropyl-3-(4-(2,4-difluorobenzyl)piperidin-1-yl)pyrido[3,4-b]pyrazin-2-amine, 2,2,2-trifluoroacetic acid salt; 7-chloro-N-cyclopropyl-3-(4-(2,4-difluorophenoxyl)piperidin-1-yl)pyrido[3,4-b]pyrazin-2-amine, 2,2,2-trifluoroacetic acid salt; 7-chloro-N-cyclopropyl-3-(4-((2,4-difluorophenyl)fluoromethyl)piperidin-1-yl)pyrido[3,4-b]pyrazin-2-amine, 2,2,2-trifluoroacetic acid salt; 3-(4-(2,4-difluorobenzyl)piperazin-1-yl)-2-((2,2-difluoroethyl)amino)quinoxaline-6-carbonitrile; 2-((2,2-difluoroethyl)amino)-3-(4-((2,4-difluorophenyl)fluoromethyl)piperidin-1-yl)quinoxaline-6-carbonitrile; 3-(4-(2,4-difluorobenzyl)

piperidin-1-yl)-2-((2,2-difluoroethyl)amino)quinoxaline-6-carbonitrile; 2-((2,2-difluoroethyl)amino)-3-(4-(2,4-difluorophenoxyl)piperidin-1-yl)quinoxaline-6-carbonitrile; 3-(4-(2,4-difluorobenzyl)piperidin-1-yl)-2-((2-methoxyethyl)amino)quinoxaline-6-carbonitrile; 3-(4-(2,4-difluorobenzyl)piperidin-1-yl)-N-(2-methoxyethyl)pyrido[3,4-b]pyrazin-2-amine, 2,2,2-trifluoroacetic acid salt; 3-(4-(2,4-difluorobenzyl)piperazin-1-yl)-N-(2-methoxyethyl)pyrido[3,4-b]pyrazin-2-amine, 2,2,2-trifluoroacetic acid salt; 3-(4-((2,4-difluorophenyl)fluoromethyl)piperidin-1-yl)-N-(2-methoxyethyl)pyrido[3,4-b]pyrazin-2-amine, 2,2,2-trifluoroacetic acid salt; 3-(4-(2,4-difluorobenzyl)piperazin-1-yl)-2-((2-methoxyethyl)amino)quinoxaline-6-carbonitrile; 3-(4-(2,4-difluorophenoxyl)piperidin-1-yl)-2-((2-methoxyethyl)amino)quinoxaline-6-carbonitrile; 3-(4-((2,4-difluorophenyl)fluoromethyl)piperidin-1-yl)-2-((2-methoxyethyl)amino)quinoxaline-6-carbonitrile; 3-(4-(2,4-difluorophenoxyl)piperidin-1-yl)-N-(2-methoxyethyl)pyrido[3,4-b]pyrazin-2-amine, 2,2,2-trifluoroacetic acid salt; N-cyclopropyl-3-(4((2,4-difluorophenyl)difluoromethyl)piperidin-1-yl)-5-methylpyrido[3,4-b]pyrazin-2-amine; 2-(cyclopropylamino)-3-(4-((2,4-difluorophenyl)difluoromethyl)piperidin-1-yl)quinoxaline-6-carbonitrile; N-cyclopropyl-3-(4-((2,4-difluorophenyl)difluoromethyl)piperidin-1-yl)pyrido[3,4-b]pyrazin-2-amine; N-cyclopropyl-3-(4-phenoxypiperidin-1-yl)quinoxalin-2-amine; 3-(4-(2,5-dichlorobenzyl)piperazin-1-yl)-N-(pyridin-3-yl)quinoxalin-2-amine; 3-(4-(2,5-difluorobenzyl)piperazin-1-yl)-2-((6-methoxypyridin-3-yl)amino)quinoxaline-6-carbonitrile, 2,2,2-trifluoroacetic acid salt; 3-(4-(2,4-difluorobenzyl)piperazin-1-yl)-N-(2,2-difluoroethyl)pyrido[3,4-b]pyrazin-2-amine, 2,2,2-trifluoroacetic acid salt; 3-(4-(5-chloro-2-fluorobenzyl)piperazin-1-yl)-N-(2,2-difluoroethyl)pyrido[3,4-b]pyrazin-2-amine, 2,2,2-trifluoroacetic acid salt; (4-chloro-2-fluorophenyl)(4-(2-((2,2-difluoroethyl)amino)pyrido[3,4-b]pyrazin-3-yl)piperazin-1-yl)methanone, 2,2,2-trifluoroacetic acid salt; N-(2,2-difluoroethyl)-3-(4-(2,4,5-trifluorobenzyl)piperazin-1-yl)pyrido[3,4-b]pyrazin-2-amine, 2,2,2-trifluoroacetic acid salt; 3-(4-(2,4-difluorobenzyl)piperazin-1-yl)-2-(pyridin-3-ylamino)quinoxaline-6-carbonitrile, 2,2,2-trifluoroacetic acid salt; 2-(pyridin-3-ylamino)-3-(4-(2,4,5-trifluorobenzyl)piperazin-1-yl)quinoxaline-6-carbonitrile, 2,2,2-trifluoroacetic acid salt; 3-(4-(4-chloro-2-fluorobenzoyl)piperazin-1-yl)-2-(pyridin-3-ylamino)quinoxaline-6-carbonitrile, 2,2,2-trifluoroacetic acid salt; 3-(4-(2,4-difluorobenzyl)piperidin-1-yl)-2-(pyridin-3-ylamino)quinoxaline-6-carbonitrile, 2,2,2-trifluoroacetic acid salt; 3-(4-(2-chlorophenoxyl)piperidin-1-yl)-N-cyclopropylpyrido[3,4-b]pyrazin-2-amine, 2,2,2-trifluoroacetic acid salt; N-cyclopropyl-3-(4-(2-fluorophenoxyl)piperidin-1-yl)pyrido[3,4-b]pyrazin-2-amine, 2,2,2-trifluoroacetic acid salt; N-cyclopropyl-3-(4-(3-fluorophenoxyl)piperidin-1-yl)pyrido[3,4-b]pyrazin-2-amine, 2,2,2-trifluoroacetic acid salt; (1-(2-(cyclopropylamino)pyrido[3,4-b]pyrazin-3-yl)piperidin-4-yl)(4-fluorophenyl)methanone, 2,2,2-trifluoroacetic acid salt; N-cyclopropyl-3-(4-(4-fluorobenzyl)piperidin-1-yl)pyrido[3,4-b]pyrazin-2-amine, 2,2,2-trifluoroacetic acid salt; (1-(2-(cyclopropylamino)pyrido[3,4-b]pyrazin-3-yl)piperidin-4-yl)(3,4-difluorophenyl)methanone, 2,2,2-trifluoroacetic acid salt; N-cyclopropyl-3-(4-((4-fluorophenyl)sulfonyl)piperidin-1-yl)pyrido[3,4-b]pyrazin-2-amine, 2,2,2-trifluoroacetic acid salt; 3-(4-(4-chlorobenzyl)piperidin-1-yl)-N-cyclopropylpyrido[3,4-b]pyrazin-2-amine, 2,2,2-trifluoroacetic acid salt; 3-(4-(4-chlorophenoxyl)piperidin-1-yl)-N-cyclopropylpyrido[3,4-b]pyrazin-2-amine, 2,2,2-trifluoroacetic acid salt; 3-(4-(3-chlorophenoxyl)piperidin-1-yl)-N-cyclopropylpyrido[3,4-b]pyrazin-2-amine, 2,2,2-trifluoroacetic acid salt; (4-chlorophenyl)(1-(2-(cyclopropylamino)pyrido[3,4-b]pyrazin-3-yl)piperidin-4-yl)methanone, 2,2,2-trifluoroacetic acid salt; N-cyclopropyl-3-(3-(4-fluorobenzyl)piperidin-1-yl)pyrido[3,4-b]pyrazin-2-amine, 2,2,2-trifluoroacetic acid salt; N-cyclopropyl-3-(4-(2,5-difluorophenoxyl)piperidin-1-yl)pyrido[3,4-b]pyrazin-2-amine, 2,2,2-trifluoroacetic acid salt; N-cyclopropyl-3-(4-(2,4,6-trifluorophenoxyl)piperidin-1-yl)pyrido[3,4-b]pyrazin-2-amine, 2,2,2-trifluoroacetic acid salt; N-cyclopropyl-3-(4-(4-fluorophenoxyl)piperidin-1-yl)pyrido[3,4-b]pyrazin-2-amine, 2,2,2-trifluoroacetic acid salt; N-cyclopropyl-3-(4-(2,4-difluorophenoxyl)piperidin-1-yl)pyrido[3,4-b]pyrazin-2-amine, 2,2,2-trifluoroacetic acid salt; (1-(2-(cyclopropylamino)pyrido[3,4-b]pyrazin-3-yl)piperidin-4-yl)(2-fluorophenyl)methanone, 2,2,2-trifluoroacetic acid salt; (1-(2-(cyclopropylamino)pyrido[3,4-b]pyrazin-3-yl)piperidin-4-yl)(2,5-difluorophenyl)methanone, 2,2,2-trifluoroacetic acid salt; 3-(4-(5-chloro-2-fluorophenoxy)piperidin-1-yl)-N-cyclopropylpyrido[3,4-b]pyrazin-2-amine, 2,2,2-trifluoroacetic acid salt; N-cyclopropyl-3-(4-phenoxypiperidin-1-yl)pyrido[3,4-b]pyrazin-2-amine, 2,2,2-trifluoroacetic acid salt; (1-(2-(cyclopropylamino)pyrido[3,4-b]pyrazin-3-yl)piperidin-4-yl)(2,4-difluorophenyl)methanone, 2,2,2-trifluoroacetic acid salt; 3-(4-(4-chloro-2-fluorophenoxy)piperidin-1-yl)-N-cyclopropylpyrido[3,4-b]pyrazin-2-amine, 2,2,2-trifluoroacetic acid salt; (1-(2-(cyclopropylamino)pyrido[3,4-b]pyrazin-3-yl)piperidin-4-yl)(2,4,6-trifluorophenyl)methanone, 2,2,2-trifluoroacetic acid salt; (4-chloro-2,6-difluorophenyl)(1-(2-(cyclopropylamino)pyrido[3,4-b]pyrazin-3-yl)piperidin-4-yl)methanone, 2,2,2-trifluoroacetic acid salt; (4-chloro-2-fluorophenyl)(1-(2-(cyclopropylamino)pyrido[3,4-b]pyrazin-3-yl)piperidin-4-yl)methanone, 2,2,2-trifluoroacetic acid salt; (5-chloro-2-fluorophenyl)(1-(2-(cyclopropylamino)pyrido[3,4-b]pyrazin-3-yl)piperidin-4-yl)methanone, 2,2,2-trifluoroacetic acid salt; 3-(4-(4-chloro-2-fluorophenoxy)piperidin-1-yl)-2-(cyclopropylamino)quinoxaline-6-carbonitrile, 2,2,2-trifluoroacetic acid salt; 3-(4-(4-chloro-2-fluorophenoxy)piperidin-1-yl)-2-(isopropylamino)quinoxaline-6-carbonitrile, 2,2,2-trifluoroacetic acid salt; 3-(4-(4-chloro-2-fluorophenoxy)piperidin-1-yl)-N-cyclopropyl-7-methylpyrido[3,4-b]pyrazin-2-amine, 2,2,2-trifluoroacetic acid salt; 2-(cyclopropylamino)-3-(4-(2,4-difluorophenoxyl)piperidin-1-yl)quinoxaline-6-carbonitrile, 2,2,2-trifluoroacetic acid salt; 3-(4-(5-chloro-2-fluorobenzoyl)piperidin-1-yl)-2-(cyclopropylamino)quinoxaline-6-carbonitrile, 2,2,2-trifluoroacetic acid salt; N-cyclopropyl-3-(4-(2,4-difluorobenzyl)piperidin-1-yl)-6,7-difluoroquinoxalin-2-amine, 2,2,2-trifluoroacetic acid salt; N-cyclopropyl-3-(4-(2,4-difluorobenzyl)piperidin-1-yl)-6-fluoroquinoxalin-2-amine, 2,2,2-trifluoroacetic acid salt; 2-(cyclopropylamino)-3-(4-((2,4-difluorophenyl)fluoromethyl)piperidin-1-yl)quinoxaline-6-carbonitrile, 2,2,2-trifluoroacetic acid salt; 3-(4-((2,4-difluorophenyl)fluoromethyl)piperidin-1-yl)-2-(isopropylamino)quinoxaline-6-carbonitrile, 2,2,2-trifluoroacetic acid salt; 3-(cyclopropylamino)-2-(4-((2,4-difluorophenyl)fluoromethyl)piperidin-1-yl)quinoxaline-6-carbonitrile, 2,2,2-trifluoroacetic acid salt; N-cyclopropyl-3-(4-((2,4-difluorophenyl)-fluoromethyl)piperidin-1-yl)-7-methylpyrido[3,4-b]pyrazin-2-amine, 2,2,2-trifluoroacetic acid salt; N-cyclopropyl-3-(4-((2,4-difluorophenyl)fluoromethyl)piperidin-1-yl)-5-methylpyrido[3,4-b]pyrazin-2-amine, 2,2,2-trifluoroacetic acid salt; N-cyclopropyl-3-(4-(2,4-difluorobenzyl)piperidin-1-yl)-5-methylpyrido[3,4-b]pyrazin-2-amine, 2,2,2-trifluoroacetic acid salt; N-cyclopropyl-3-(4-(2,4-difluorophenoxyl)piperidin-1-yl)-5-methylpyrido[3,4-b]pyrazin-2-amine, 2,2,2-trifluoroacetic acid salt; N-cyclopropyl-3-(4-(2,4-difluorophenoxy)piperidin-1-yl)-5-methylpyrido[3,4-b]pyrazin-2-amine, 2,2,2-trifluoroacetic acid salt; 3-(4-(4-chlorobenzoyl)piperazin-1-yl)-2-(cyclobutylamino)quinoxaline-6-carbonitrile; 3-(4-(4-chlorobenzoyl)piperazin-1-yl)-2-(isopropylamino)quinoxaline-6-carbonitrile; N-cyclopropyl-3-(4-(1-(2,5-dichlorophenyl)ethyl)piperazin-1-yl)quinoxalin-2-amine, 2,2,2-trifluoroacetic acid salt; 3-(4-((4-chlorophenyl)amino)

piperidin-1-yl)-N-cyclopropylquinoxalin-2-amine, 2,2,2-trifluoroacetic acid salt; N-cyclopropyl-3-(4-((2,4-difluorophenyl)amino)piperidin-1-yl)pyrido[3,4-b]pyrazin-2-amine, 2,2,2-trifluoroacetic acid salt; (4-(3-(cyclopropylamino)quinoxalin-2-yl)piperazin-1-yl)(3-(trifluoromethyl)phenyl)methanone, 2,2,2-trifluoroacetic acid salt; 3-(4-(3-chlorobenzyl)piperazin-1-yl)-N-cyclopropylquinoxalin-2-amine, 2,2,2-trifluoroacetic acid salt; (4-(3-(cyclopropylamino)quinoxalin-2-yl)piperazin-1-yl)(4-(methylsulfonyl)phenyl)methanone, 22,2,2-trifluoroacetic acid salt; (4-(3-(cyclopropylamino)quinoxalin-2-yl)piperazin-1-yl)(2,5-dichlorophenyl)methanone, 2,2,2-trifluoroacetic acid salt; (4-(3-(cyclopropylamino)quinoxalin-2-yl)piperazin-1-yl)(3,4-dichlorophenyl)methanone, 2,2,2-trifluoroacetic acid salt; (3-chloro-4-methoxyphenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(3,5-dichlorophenyl)methanone, 2,2,2-trifluoroacetic acid salt; (3-chlorophenyl)(4-(3-(cyclopropylamino)quinoxalin-2-yl)piperazin-1-yl)methanone, 2,2,2-trifluoroacetic acid salt; N-cyclopropyl-3-(4-(pyridin-3-ylmethyl)piperazin-1-yl)quinoxalin-2-amine, 22,2,2-trifluoroacetic acid salt; (4-(3-(cyclopropylamino)quinoxalin-2-yl)piperazin-1-yl)(2,3-dichlorophenyl)methanone, 2,2,2-trifluoroacetic acid salt; N-cyclopropyl-3-(4-((5-methyloxazol-2-yl)methyl)piperidin-1-yl)quinoxalin-2-amine, 2,2,2-trifluoroacetic acid salt; N-cyclopropyl-3-(4-(pyridin-4-ylmethyl)piperazin-1-yl)quinoxalin-2-amine, 22,2,2-trifluoroacetic acid salt; N-cyclopropyl-3-(4-((3-methyl-1,2,4-oxadiazol-5-yl)methyl)piperidin-1-yl)quinoxalin-2-amine, 2,2,2-trifluoroacetic acid salt; N-cyclopropyl-3-(4-(pyridin-2-ylmethyl)piperazin-1-yl)quinoxalin-2-amine, 22,2,2-trifluoroacetic acid salt; (4-(3-(cyclopropylamino)quinoxalin-2-yl)piperazin-1-yl)(4-(trifluoromethyl)phenyl)methanone, 2,2,2-trifluoroacetic acid salt; N-cyclopropyl-3-(4-(2,4-dichlorobenzyl)piperazin-1-yl)quinoxalin-2-amine, 2,2,2-trifluoroacetic acid salt; N-cyclopropyl-3-(4-(2,6-dichlorobenzyl)piperazin-1-yl)quinoxalin-2-amine, 2,2,2-trifluoroacetic acid salt; 3-(4-(3-bromobenzyl)piperazin-1-yl)-N-cyclopropylquinoxalin-2-amine; 3-(4-(2,5-dichlorobenzyl)piperazin-1-yl)-N-(3-methoxypropyl)quinoxalin-2-amine; (2-chloro-4-(methylsulfonyl)phenyl)(4-(3-(cyclopropylamino)quinoxalin-2-yl)piperazin-1-yl)methanone; (4-(3-(cyclopropylamino)quinoxalin-2-yl)piperazin-1-yl)(3,6-dichloropyridin-2-yl)methanone; (4-(3-(cyclopropylamino)quinoxalin-2-yl)piperazin-1-yl)(5-methylisoxazol-3-yl)methanone; (4-chlorophenyl)(4-(3-(cyclopropylamino)-6,7-difluoroquinoxalin-2-yl)piperazin-1-yl)methanone; (4-(2-(cyclopropylamino)pyrido[3,4-b]pyrazin-3-yl)piperazin-1-yl)(4-(trifluoromethyl)phenyl)methanone, 2,2,2-trifluoroacetic acid salt; 3-(4-(5-chloro-2-(difluoromethoxy)benzyl)piperazin-1-yl)-N-cyclopropylpyrido[3,4-b]pyrazin-2-amine, 2,2,2-trifluoroacetic acid salt; N-cyclopropyl-3-(4-(4-fluorobenzyl)piperazin-1-yl)pyrido[3,4-b]pyrazin-2-amine, 2,2,2-trifluoroacetic acid salt; N-cyclopropyl-3-(4-(2,6-dichlorobenzyl)piperazin-1-yl)pyrido[3,4-b]pyrazin-2-amine, 2,2,2-trifluoroacetic acid salt; N-cyclopropyl-3-(4-(2,5-dimethylbenzyl)piperazin-1-yl)pyrido[3,4-b]pyrazin-2-amine, 2,2,2-trifluoroacetic acid salt; 2-(cyclopropylamino)-3-(4-(2,4-difluorobenzyl)piperazin-1-yl)quinoxaline-6-carbonitrile, 2,2,2-trifluoroacetic acid salt; 2-(cyclopropylamino)-3-(4-(2,4,5-trifluorobenzyl)piperazin-1-yl)quinoxaline-6-carbonitrile, 2,2,2-trifluoroacetic acid salt; 3-(4-(5-chloro-2-fluorobenzyl)piperazin-1-yl)-2-(cyclopropylamino)quinoxaline-6-carbonitrile, 2,2,2-trifluoroacetic acid salt; (1-(2-(cyclopropylamino)-7-methylpyrido[3,4-b]pyrazin-3-yl)piperidin-4-yl)(2,5-difluorophenyl)methanone, 2,2,2-trifluoroacetic acid salt; N-cyclopropyl-3-(4-(2,4-difluorophenoxyl)piperidin-1-yl)-7-methylpyrido[3,4-b]pyrazin-2-amine,2,2,2-trifluoroacetic acid salt; 3-(4-(2,4-difluorobenzyl)piperidin-1-yl)-2-(isopropylamino)quinoxaline-6-carbonitrile; 2-(cyclobutylamino)-3-(4-(2,4-difluorobenzyl)piperidin-1-yl)quinoxaline-6-carbonitrile; 2-(cyclopropylamino)-3-(4-((2,5-difluorophenyl)fluoromethyl)piperidin-1-yl)quinoxaline-6-carbonitrile, 2,2,2-trifluoroacetic acid salt; 2-(cyclopropylamino)-3-(4-((4-fluoro-2-oxopyridin-1(2H)-yl)methyl)piperidin-1-yl)quinoxaline-6-carbonitrile, 2,2,2-trifluoroacetic acid salt; 2-(cyclopropylamino)-3-(4-(2,5-difluorobenzoyl)piperidin-1-yl)quinoxaline-6-carbonitrile, 2,2,2-trifluoroacetic acid salt; 1-((1-(2-(cyclopropylamino)-7-methylpyrido[3,4-b]pyrazin-3-yl)piperidin-4-yl)methyl)-4-fluoropyridin-2(1H)-one, 2,2,2-trifluoroacetic acid salt; 2-(cyclobutylamino)-3-(4-((2,5-difluorophenyl)fluoromethyl)piperidin-1-yl)quinoxaline-6-carbonitrile, 2,2,2-trifluoroacetic acid salt; 3-(cyclopropylamino)-2-(4-((2,5-difluorophenyl)fluoromethyl)piperidin-1-yl)quinoxaline-6-carbonitrile, 2,2,2-trifluoroacetic acid salt; 3-(4-((2,5-difluorophenyl)fluoromethyl)piperidin-1-yl)-2-(isopropylamino)quinoxaline-6-carbonitrile, 2,2,2-trifluoroacetic acid salt; 8-chloro-N-cyclopropyl-3-(4-((2,5-difluorophenyl)-fluoromethyl)piperidin-1-yl)pyrido[3,4-b]pyrazin-2-amine, 2,2,2-trifluoroacetic acid salt; 6-bromo-N-cyclopropyl-3-(4-(2,4-difluorobenzyl)piperidin-1-yl)quinoxalin-2-amine, 2,2,2-trifluoroacetic acid salt; 3-(4-(2,4-difluorobenzyl)piperidin-1-yl)-2-((3,3,3-trifluoropropyl)-amino)quinoxaline-6-carbonitrile, 2,2,2-trifluoroacetic acid salt; 3-(4-((2,5-difluorophenyl)-fluoromethyl)piperidin-1-yl)-2-((3,3,3-trifluoropropyl)amino)quinoxaline-6-carbonitrile, 2,2,2-trifluoroacetic acid salt; 3-(4-(2,4-difluorophenoxyl)piperidin-1-yl)-2-((3,3,3-trifluoropropyl)amino)quinoxaline-6-carbonitrile, 2,2,2-trifluoroacetic acid salt; 3-(4-(2,5-difluorobenzyl)piperazin-1-yl)-2-((3,3,3-trifluoropropyl)amino)quinoxaline-6-carbonitrile, 2,2,2-trifluoroacetic acid salt; 3-(4-(2,4-difluorobenzyl)piperazin-1-yl)-2-((3,3,3-trifluoropropyl)amino)quinoxaline-6-carbonitrile, 2,2,2-trifluoroacetic acid salt; 6-bromo-N-cyclopropyl-3-(4-(2,5-difluorobenzyl)piperazin-1-yl)quinoxalin-2-amine, 2,2,2-trifluoroacetic acid salt; 6-bromo-3-(4-(5-chloro-2-fluorobenzyl)piperazin-1-yl)-N-cyclopropylquinoxalin-2-amine, 2,2,2-trifluoroacetic acid salt; 6-bromo-N-cyclopropyl-3-(4-(2,4-difluorobenzyl)piperazin-1-yl)quinoxalin-2-amine, 2,2,2-trifluoroacetic acid salt; 6-bromo-N-cyclopropyl-3-(4-((2,5-difluorophenyl)fluoromethyl)piperidin-1-yl)quinoxalin-2-amine, 2,2,2-trifluoroacetic acid salt; 6-bromo-N-cyclopropyl-3-(4-(2,4-difluorophenoxyl)piperidin-1-yl)quinoxalin-2-amine, 2,2,2-trifluoroacetic acid salt; 7-bromo-N-cyclopropyl-3-(4-((2,4-difluorophenyl)fluoromethyl)piperidin-1-yl)pyrido[3,4-b]pyrazin-2-amine, 2,2,2-trifluoroacetic acid salt; 7-bromo-N-cyclopropyl-3-(4-(2,4-difluorobenzyl)-piperazin-1-yl)pyrido[3,4-b]pyrazin-2-amine, 2,2,2-trifluoroacetic acid salt; 3-(4-((4-chloro-2-oxopyridin-1(2H)-yl)methyl)piperidin-1-yl)-2-(cyclopropylamino)-quinoxaline-6-carbonitrile; 1-((1-(2-(cyclopropylamino)-5-methylpyrido[3,4-b]pyrazin-3-yl)piperidin-4-yl)methyl)-5-fluoropyridin-2(1H)-one; 4-chloro-1-((1-(2-(cyclopropylamino)-5-methylpyrido[3,4-b]pyrazin-3-yl)piperidin-4-yl)methyl)pyridin-2(1H)-one; 2-(cyclopropylamino)-3-(4-((5-fluoro-2-oxopyridin-1(2H)-yl)methyl)piperidin-1-yl)quinoxaline-6-carbonitrile; 1-((1-(2-(cyclopropylamino)pyrido[3,4-b]pyrazin-3-yl)piperidin-4-yl)methyl)-4-fluoropyridin-2(1H)-one; 1-((1-(2-(cyclopropylamino)-5-methylpyrido[3,4-b]pyrazin-3-yl)piperidin-4-yl)methyl)-4-fluoropyridin-2(1H)-one; 5-chloro-1-((1-(2-(cyclopropylamino)-pyrido[3,4-b]pyrazin-3-yl)piperidin-4-yl)methyl)pyridin-2(1H)-one; 3-(4-((5-chloro-2-fluorophenyl)difluoromethyl)piperidin-1-yl)-2-(cyclopropylamino)quinoxaline-6-carbonitrile; 3-(4-((5-chloro-2-fluorophenyl)difluoromethyl)piperidin-1-yl)-N-cyclopropyl-7-methylpyrido[3,4-b]pyrazin-2-amine; 3-(4-((5-chloro-2-oxopyridin-1(2H)-yl)methyl)piperidin-1-yl)-2-(cyclopropylamino)quinoxaline-6-carbonitrile; 3-(4-((5-chloro-2- fluorophenyl)difluoromethyl)piperidin-1-yl)-N- cyclopropyl-5-methylpyrido[3,4-b]pyrazin-2-amine; 5-chloro-1-((1-(2-(cyclopropylamino)-5-methylpyrido[3,4-b]pyrazin-3-yl)piperidin-4-yl)methyl)pyridin-2(1H)-one; 5-chloro-1-((1-(2-(cyclopropylamino)-7-methylpyrido[3,4-b]pyrazin-3-yl)piperidin-4-yl)methyl)pyridin-2(1H)-one; 3-(4-((5-chloro-2-fluorophenyl)difluoromethyl)-piperidin-1-yl)-N-cyclopropylpyrido[3,4-b]pyrazin-2-amine; N-cyclopropyl-3-(4-((2,5-difluorophenyl)difluoromethyl)piperidin-1-yl)pyrido[3,4-b]pyrazin-2-amine; N-cyclopropyl-3-(4-((2,5-difluorophenyl)difluoromethyl)piperidin-1-yl)-7-methylpyrido[3,4-b]pyrazin-2-amine; N-cyclopropyl-3-(4-((2,5-difluorophenyl)-difluoromethyl)piperidin-1-yl)-5-methylpyrido[3,4-b]pyrazin-2-amine; 2-(cyclopropylamino)-3-(4-((2,5-difluorophenyl)difluoromethyl)piperidin-1-yl)quinoxaline-6-carbonitrile, and 7-chloro-N-cyclopropyl-3-(4-(2,4-difluorobenzyl)piperidin-1-yl)pyrido[3,4-b]pyrazin-2-amine; N-cyclopropyl-3-(4-(pyridin-3-yloxy)piperidin-1-yl)pyrido[3,4-b]pyrazin-2-amine; N-cyclopropyl-3-(4-(4-methoxyphenoxyl)piperidin-1-yl)pyrido[3,4-b]pyrazin-2-amine; N-cyclopropyl-3-(4-(pyridin-2-yloxy)piperidin-1-yl)pyrido[3,4-b]pyrazin-2-amine; N-cyclopropyl-3-(4-(pyridin-4-yloxy)piperidin-1-yl)pyrido[3,4-b]pyrazin-2-amine; (1-(2-(cyclopropylamino)pyrido[3,4-b]pyrazin-3-yl)piperidin-4-yl)(2-methoxyphenyl)methanone, 2,2,2-trifluoroacetic acid salt; 4-((1-(2-(cyclopropylamino)pyrido[3,4-b]pyrazin-3-yl)piperidin-4-yl)oxy)benzonitrile; (2-chlorophenyl)(1-(2-(cyclopropylamino)pyrido[3,4-b]pyrazin-3-yl)piperidin-4-yl)methanone, 2,2,2-trifluoroacetic acid salt; N-cyclopropyl-3-(4-(3-methoxyphenoxyl)piperidin-1-yl)pyrido[3,4-b]pyrazin-2-amine, 2,2,2-trifluoroacetic acid salt; N-cyclopropyl-3-(4-(2-methoxyphenoxyl)piperidin-1-yl)pyrido[3,4-b]pyrazin-2-amine, 2,2,2-trifluoroacetic acid salt; (1-(2-(cyclopropylamino)pyrido[3,4-b]pyrazin-3-yl)piperidin-4-yl)(phenyl)methanone; (1-(2-(cyclopropylamino)pyrido[3,4-b]pyrazin-3-yl)piperidin-4-yl)(2,3-difluorophenyl)methanone, 2,2,2-trifluoroacetic acid salt; (3-chlorophenyl)(1-(2-(cyclopropylamino)pyrido[3,4-b]pyrazin-3-yl)piperidin-4-yl)methanone; 3-((1-(2-(cyclopropylamino)pyrido[3,4-b]pyrazin-3-yl)piperidin-4-yl)oxy)benzonitrile; (1-(2-(cyclopropylamino)pyrido[3,4-b]pyrazin-3-yl)piperidin-4-yl)(3-methoxyphenyl)methanone; (1-(2-(cyclopropylamino)pyrido[3,4-b]pyrazin-3-yl)piperidin-4-yl)(o-tolyl)methanone, 2,2,2-trifluoroacetic acid salt; (1-(2-(cyclopropylamino)pyrido[3,4-b]pyrazin-3-yl)piperidin-4-yl)(2,6-difluorophenyl)methanone, 2,2,2-trifluoroacetic acid salt; (2-chloro-5-fluorophenyl)(1-(2-(cyclopropylamino)pyrido[3,4-b]pyrazin-3-yl)piperidin-4-yl)methanone, 2,2,2-trifluoroacetic acid salt; (1-(2-(cyclopropylamino)pyrido[3,4-b]pyrazin-3-yl)piperidin-4-yl)(3-fluorophenyl)methanone, 2,2,2-trifluoroacetic acid salt; 1-(4-((1-(2-(cyclopropylamino)pyrido[3,4-b]pyrazin-3-yl)piperidin-4-yl)oxy)phenyl)ethanone, 2,2,2-trifluoroacetic acid salt; 4-((1-(2-(cyclopropylamino)pyrido[3,4-b]pyrazin-3-yl)piperidin-4-yl)oxy)-N,N-dimethylbenzamide, 2,2,2-trifluoroacetic acid salt; N-cyclopropyl-3-(4-(4-(methylthio)phenoxy)piperidin-1-yl)pyrido[3,4-b]pyrazin-2-amine, 2,2,2-trifluoroacetic acid salt; (1-(2-(cyclopropylamino)pyrido[3,4-b]pyrazin-3-yl)piperidin-4-yl)(2-fluoro-5-(methylthio)phenyl)methanone, 2,2,2-trifluoroacetic acid salt; N-cyclopropyl-3-(4-(4-ethoxyphenoxyl)piperidin-1-yl)pyrido[3,4-b]pyrazin-2-amine, 2,2,2-trifluoroacetic acid salt; N-cyclopropyl-3-(4-(2-fluoro-4-(2-fluoroethoxyl)phenoxy)piperidin-1-yl)pyrido[3,4-b]pyrazin-2-amine, 2,2,2-trifluoroacetic acid salt; 4-((1-(2-(cyclopropylamino)pyrido[3,4-b]pyrazin-3-yl)piperidin-4-yl)oxy)-3-fluorophenol, 2,2,2-trifluoroacetic acid salt; (6-chloro-2,3-difluorophenyl)(1-(2-(cyclopropylamino)pyrido[3,4-b]pyrazin-3-yl)piperidin-4-yl)methanone, 2,2,2-trifluoroacetic acid salt; N-cyclopropyl-3-(4-(2-fluoro-4-methoxyphenoxy)piperidin-1-yl)pyrido[3,4-b]pyrazin-2-amine, 2,2,2-trifluoroacetic acid salt; (2-chloro-3-fluorophenyl)(1-(2-(cyclopropylamino)pyrido[3,4-b]pyrazin-3-yl)piperidin-4-yl)methanone, hydrogen chloride salt; (2-chlorothiophen-3-yl)(1-(2-(cyclopropylamino)pyrido[3,4-b]pyrazin-3-yl)piperidin-4-yl)methanone, hydrogen chloride salt; (1-(2-(cyclopropylamino)pyrido[3,4-b]pyrazin-3-yl)piperidin-4-yl)(thiophen-2-yl)methanone, 2,2,2-trifluoroacetic acid salt; 3-(1-(2-(cyclopropylamino)pyrido[3,4-b]pyrazin-3-yl)piperidine-4-carbonyl)benzonitrile, hydrogen chloride salt; (1-(2-(cyclopropylamino)pyrido[3,4-b]pyrazin-3-yl)piperidin-4-yl)(2-(methylthio)phenyl)methanone, 2,2,2-trifluoroacetic acid salt; (1-(2-(cyclopropylamino)pyrido[3,4-b]pyrazin-3-yl)piperidin-4-yl)(thiophen-3-yl)methanone, 2,2,2-trifluoroacetic acid salt; 3-(1-(2-(cyclopropylamino)pyrido[3,4-b]pyrazin-3-yl)piperidine-4-carbonyl)-4-fluorobenzonitrile, 2,2,2-trifluoroacetic acid salt; 3-(4-(2-fluoro-4-methoxyphenoxy)piperidin-1-yl)-N-isopropylpyrido[3,4-b]pyrazin-2-amine, 2,2,2-trifluoroacetic acid salt; 3-(4-(2,4-difluorophenoxyl)piperidin-1-yl)-N-isopropylpyrido[3,4-b]pyrazin-2-amine, 2,2,2-trifluoroacetic acid salt; 3-(4-((2,4-difluorophenyl)fluoromethyl)piperidin-1-yl)-N-isopropylpyrido[3,4-b]pyrazin-2-amine, 2,2,2-trifluoroacetic acid salt; N-ethyl-3-(4-(2-fluoro-4-methoxyphenoxy)piperidin-1-yl)pyrido[3,4-b]pyrazin-2-amine, 2,2,2-trifluoroacetic acid salt; 2-((1-(2-(cyclopropylamino)pyrido[3,4-b]pyrazin-3-yl)piperidin-4-yl)oxy)benzonitrile; (2-chloro-6-fluorophenyl)(1-(2-(cyclopropylamino)pyrido[3,4-b]pyrazin-3-yl)piperidin-4-yl)methanone; (2-(cyclopropylamino)pyrido[3,4-b]pyrazin-3-yl)(4-(2-fluoro-4-methoxyphenoxy)piperidin-1-yl)methanone, 2,2,2-trifluoroacetic acid salt; N-cyclopropyl-3-(4-((4-fluorophenyl)sulfonyl)piperidin-1-yl)-7-methylpyrido[3,4-b]pyrazin-2-amine 2,2,2-trifluoroacetate Example 2

Synthesis of 3-(4-(2,5-dichlorobenzyl)piperazin-1-yl)-N-(pyrazin-2-yl)quinoxalin-2-amine, 2,2,2-trifluoroacetic acid salt

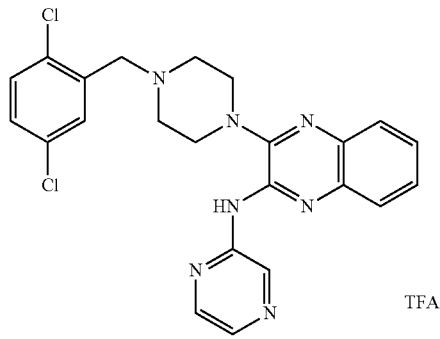 [SMILES: Clc1ccc(Cl)c(CN2CCN(c3nc4ccccc4nc3Nc3cnccn3)CC2)c1]

3-Chloro-N-(pyrazin-2-yl)quinoxalin-2-amine (210 mg, 0.815 mmol) and 1-(2,5-dichlorobenzyl)piperazine (220 mg, 0.896 mmol) were added to n-BuOH (0.8 ml). After stirring for 2 h at 90° C., the reaction mixture was purified by HPLC to yield the title compound as a yellow solid. MS (ESI, pos. ion) m/z: 466.0 (M+1)

Utilizing similar reaction conditions as described above, following compounds were synthesized:
3-(4-(2,5-dichlorobenzyl)piperazin-1-yl)-N-(pyrimidin-4-yl)quinoxalin-2-amine, 2,2,2-trifluoroacetic acid salt; 3-(4-(2,5-dichlorobenzyl)piperazin-1-yl)-N-(pyridazin-3-yl)quinoxalin-2-amine, 2,2,2-trifluoroacetic acid salt; 3-(4-(2,5-dichlorobenzyl)piperazin-1-yl)-N-(1,2,4-triazin-3-yl)quinoxalin-2-amine, 2,2,2-trifluoroacetic acid salt; 3-(4-(2, 5-dichlorobenzyl)piperazin-1-yl)-N-(5,6-dimethyl-1,2,4-triazin-3-yl)quinoxalin-2-amine, 2,2,2-trifluoroacetic acid salt; N-(3-(4-(2,5-dichlorobenzyl)piperazin-1-yl)quinoxalin-2-yl)-3,4-dimethylisoxazol-5-amine, 2,2,2-trifluoroacetic acid salt; 3-(4-(2,5-dichlorobenzyl)piperazin-1-yl)-N-(pyridin-4-yl)quinoxalin-2-amine, 2,2,2-trifluoroacetic acid salt; 3-(4-(2,5-dichlorobenzyl)piperazin-1-yl)-N-(pyridin-2-yl)quinoxalin-2-amine, 2,2,2-trifluoroacetic acid salt; 3-(4-(2,5-dichlorobenzyl)piperazin-1-yl)-N-(2,2,2-trifluoroethyl)quinoxalin-2-amine, 2,2,2-trifluoroacetic acid salt; and 2-(cyclobutylamino)-3-(4-(2,5-dichlorobenzyl)piperazin-1-yl)quinoxaline-6-carbonitrile, 2,2,2-trifluoroacetic acid salt.

Example 3

Synthesis of 3-(4-(4-chlorobenzoyl)piperazin-1-yl)-2-((2-fluoroethyl)amino)quinoxaline-6-carbonitrile, 2,2,2-trifluoroacetic acid salt

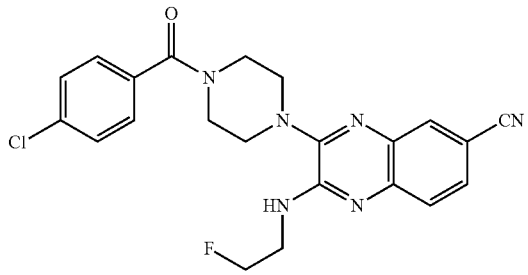 [SMILES: N#Cc1ccc2nc(NCCF)c(N3CCN(C(=O)c4ccc(Cl)cc4)CC3)nc2c1]

A suspension of 3-chloro-2-((2,2-difluoroethyl)amino)quinoxaline-6-carbonitrile (50 mg, 0.186 mmol), (4-chlorophenyl)(piperazin-1-yl)methanone hydrochloride (72.9 mg, 0.279 mmol) and DIPEA (0.098 ml, 0.558 mmol) in DMSO (1 ml) was stirred at RT for 16 h. After HPLC purification, most of MeCN was removed under reduced pressure. The resulting suspension was neutralized with solid Na₂CO₃ and extracted with EtOAc. The organic layer was dried over Na₂SO₄ and concentrated to afford the title compound as a yellow solid. MS (ESI, pos. ion) m/z: 438.8 (M+1)

Utilizing similar reaction conditions described above, following compounds were synthesized:

3-(4-(2,5-dichlorobenzyl)piperazin-1-yl)-2-((2,2-difluoroethyl)amino)quinoxaline-6-carbonitrile; 3-(4-(4-chlorobenzoyl)piperazin-1-yl)-2-((2,2-difluoroethyl)amino)quinoxaline-6-carbonitrile; 3-(4-(2,5-dichlorobenzyl)piperazin-1-yl)-2-(isoxazol-3-ylamino)quinoxaline-6-carbonitrile, 2,2,2-trifluoroacetic acid salt; 3-(4-(4-chlorobenzoyl)piperazin-1-yl)-2-(isoxazol-3-ylamino)quinoxaline-6-carbonitrile, 2,2,2-trifluoroacetic acid salt; 3-(4-(2,5-dichlorobenzyl)piperazin-1-yl)-2-((2-fluoroethyl)amino)quinoxaline-6-carbonitrile, 2,2,2-trifluoroacetic acid salt; 3-(4-(2,5-difluorobenzyl)piperazin-1-yl)-2-((2-fluoroethyl)amino)quinoxaline-6-carbonitrile, 2,2,2-trifluoroacetic acid salt; 3-(4-(2,5-difluorobenzyl)piperazin-1-yl)-2-((2,2-difluoroethyl)amino)quinoxaline-6-carbonitrile, 2,2,2-trifluoroacetic acid salt; 3-(4-(2,5-difluorobenzyl)piperazin-1-yl)-2-(isoxazol-3-ylamino)quinoxaline-6-carbonitrile.

Example 4

Synthesis of benzofuran-3-yl(4-(3-(cyclopropylamino)quinoxalin-2-yl)piperazin-1-yl)methanone

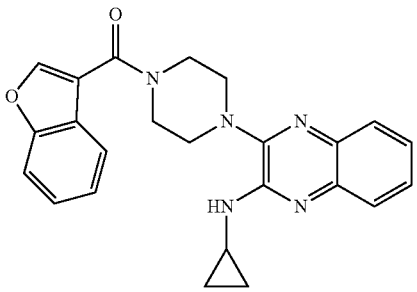 [SMILES: O=C(c1coc2ccccc12)N1CCN(c2nc3ccccc3nc2NC2CC2)CC1]

To a 1-dram vial was added benzofuran-3-carboxylic acid (11.84 mg, 0.073 mmol), HATU (27.8 mg, 0.073 mmol), and iPr₂EtN (44.7 µl, 0.256 mmol) in DMF (365 µl). After stirring at RT for 30 min, N-cyclopropyl-3-(piperazin-1-yl)quinoxalin-2-amine, 2HCl (25 mg, 0.073 mmol) was added. The reaction mixture was stirred for 3 h and then HPLC purification yielded the title compound as a colorless oil. MS (ESI, pos. ion) m/z: 414.3 (M+1)

Utilizing similar reaction conditions described above, following compounds were synthesized:

(4-(3-(cyclopropylamino)quinoxalin-2-yl)piperazin-1-yl)(3,4-dimethylphenyl-)methanone, 2,2,2-trifluoroacetic acid salt; (4-(3-(cyclopropylamino)quinoxalin-2-yl)piperazin-1-yl)(2,4-dichlorophenyl)methanone, 2,2,2-trifluoroacetic acid salt; 4-(4-(3-(cyclopropylamino)quinoxalin-2-yl)piperazine-1-carbonyl)benzonitrile, 2,2,2-trifluoroacetic acid salt; (4-(3-(cyclopropylamino)quinoxalin-2-yl)piperazin-1-yl)(4-ethylphenyl)methanone, 2,2,2-trifluoroacetic acid salt; (4-(3-(cyclopropylamino)quinoxalin-2-yl)piperazin-1-yl)(2,5-difluorophenyl)methanone, 2,2,2-trifluoroacetic acid salt; (4-(3-(cyclopropylamino)-quinoxalin-2-yl)piperazin-1-yl)(naphthalen-2-yl)methanone, 2,2,2-trifluoroacetic acid salt; (2-bromo-5-methoxyphenyl)(4-(3-(cyclopropylamino)quinoxalin-2-yl)piperazin-1-yl)methanone, 2,2,2-trifluoroacetic acid salt; (3-bromo-4-methoxyphenyl)(4-(3-(cyclopropylamino)quinoxalin-2-yl)piperazin-1-yl)methanone, 2,2,2-trifluoroacetic acid salt; (4-bromo-2-chlorophenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(5-fluoro-2-methylphenyl)methanone, 2,2,2-trifluoroacetic acid salt; (3-bromo-4-fluorophenyl)(4-(3-(cyclopropylamino)quinoxalin-2-yl)piperazin-1-yl)methanone, 2,2,2-trifluoroacetic acid salt; (4-bromo-2-fluorophenyl)(4-(3-(cyclopropylamino)quinoxalin-2-yl)piperazin-1-yl)methanone, 2,2,2-trifluoroacetic acid salt; (5-bromo-2-fluorophenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(4-ethoxyphenyl)methanone, 2,2,2-trifluoroacetic acid salt; (4-(3-(cyclopropylamino)quinoxalin-2-yl)piperazin-1-yl)(3-isopropylphenyl)methanone, 2,2,2-trifluoroacetic acid salt; (4-(3-(cyclopropylamino)-quinoxalin-2-yl)piperazin-1-yl)(4-isopropylphenyl)methanone, 2,2,2-trifluoroacetic acid salt; (4-bromo-2-methylphenyl)(4-(3-(cyclopropylamino)quinoxalin-2-yl)piperazin-1-yl)methanone, 2,2,2-trifluoroacetic acid salt; (2-chloro-3,6-difluorophenyl)(4-(3-(cyclopropylamino)quinoxalin-2-yl)piperazin-1-yl)methanone, 2,2,2-trifluoroacetic acid salt; (2-chloro-5-iodophenyl)(4-(3-(cyclopropylamino)quinoxalin-2-yl)piperazin-1-yl)methanone, 2,2,2-trifluoroacetic acid salt; (5-bromo-2-methylphenyl)(4-(3-(cyclopropylamino)-quinoxalin-2-yl)piperazin-1-yl)methanone, 2,2,2-trifluoroacetic acid salt; (4-(3-(cyclopropylamino)quinoxalin-2-yl)piperazin-1-yl)(4-(trifluoromethoxy)phenyl)methanone, 2,2,2-trifluoroacetic acid salt; (4-(3-(cyclopropylamino)quinoxalin-2-yl)piperazin-1-yl)(1H-indol-6-yl)methanone, 2,2,2-trifluoroacetic acid salt; (5-chloro-2-methylphenyl)(4-(3-(cyclopropylamino)quinoxalin-2-yl)piperazin-1-yl)methanone, 2,2,2-trifluoroacetic acid salt; (4-chloro-2-methylphenyl)(4-(3-(cyclopropylamino)quinoxalin-2-yl)piperazin-1-yl) methanone, 2,2,2-trifluoroacetic acid salt; (4-(3-(cyclopropylamino)quinoxalin-2-yl)piperazin-1-yl)(2,4-dimethylphenyl)methanone, 2,2,2-trifluoroacetic acid salt; (2-chloro-5-methoxyphenyl)(4-(3-(cyclopropylamino)quinoxalin-2-yl)piperazin-1-yl)methanone, 2,2,2-trifluoroacetic acid salt; 5-(4-(3-(cyclopropylamino)quinoxalin-2-yl)piperazine-1-carbonyl)-2-isopropoxybenzonitrile, 2,2,2-trifluoroacetic acid salt; (4-(3-(cyclopropylamino)quinoxalin-2-yl)piperazin-1-yl)(2-methoxy-5-(trifluoromethoxy)phenyl)methanone, 2,2,2-trifluoroacetic acid salt; (4-(3-(cyclopropylamino)quinoxalin-2-yl)piperazin-1-yl)(2,3,5-trichlorophenyl)-methanone, 2,2,2-trifluoroacetic acid salt; (2-chloro-6-(trifluoromethyl)phenyl)(4-(3-(cyclopropylamino)quinoxalin-2-yl)piperazin-1-yl)methanone, 2,2,2-trifluoroacetic acid salt; (4-(chloromethyl)phenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(1H-indol-5-yl)methanone, 2,2,2-trifluoroacetic acid salt; (4-bromo-3-methylphenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(4-fluoro-3-methoxyphenyl)methanone, 2,2,2-trifluoroacetic acid salt; (3-bromo-4-methylphenyl)(4-(3-(cyclopropylamino)quinoxalin-2-yl)piperazin-1-yl) methanone, 2,2,2-trifluoroacetic acid salt; (4-chloro-3-methylphenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(4-fluoro-2-methylphenyl)methanone; (3-bromo-2-methylphenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(3,5-difluorophenyl)methanone, 2,2,2-trifluoroacetic acid salt; (4-bromophenyl)(4-(3-(cyclopropylamino)quinoxalin-2-yl)piperazin-1-yl)methanone, 2,2,2-trifluoroacetic acid salt; 3-(4-(3-(cyclopropylamino)-quinoxalin-2-yl)piperazine-1-carbonyl)benzonitrile, 2,2,2-trifluoroacetic acid salt; (3-bromophenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(2,6-dichlorophenyl)methanone, 2,2,2-trifluoroacetic acid salt; (2-bromo-4-methylphenyl)(4-(3-(cyclopropylamino)quinoxalin-2-yl)piperazin-1-yl)methanone, 2,2,2-trifluoroacetic acid salt; 4-(4-(3-(cyclopropylamino)quinoxalin-2-yl)piperazine-1-carbonyl)-3-fluorobenzonitrile, 2,2,2-trifluoroacetic acid salt; benzo[d][1,2,3]thiadiazol-5-yl(4-(3-(cyclopropylamino)-quinoxalin-2-yl)piperazin-1-yl) methanone, 2,2,2-trifluoroacetic acid salt; (2-chloro-5-fluorophenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(2-methoxy-5-(trifluoromethyl)phenyl)methanone, 2,2,2-trifluoroacetic acid salt; (4-bromo-3-(trifluoromethyl)phenyl)(4-(3-(cyclopropylamino)quinoxalin-2-yl)piperazin-1-yl)methanone; (4-chloro-3-methylphenyl)(4-(3-(pyridin-3-ylamino)quinoxalin-2-yl)piperazin-1-yl)methanone, 2,2,2-trifluoroacetic acid salt; (3-bromo-4-fluorophenyl)(4-(3-(cyclopropylamino)-6,7-difluoroquinoxalin-2-yl)piperazin-1-yl)methanone, 2,2,2-trifluoroacetic acid salt; 3-(4-(3-bromo-4-fluorobenzoyl)piperazin-1-yl)-2-(cyclopropylamino)quinoxaline-6-carbonitrile, 2,2,2-trifluoroacetic acid salt; 3-(4-(3-bromo-4-fluorobenzoyl)piperazin-1-yl)-2-(isopropylamino)quinoxaline-6-carbonitrile, 2,2,2-trifluoroacetic acid salt; 3-(4-(3-bromo-4-fluorobenzoyl)piperazin-1-yl)-2-(cyclobutylamino)-quinoxaline-6-carbonitrile, 2,2,2-trifluoroacetic acid salt; (4-chlorophenyl)(4-(3-(cyclopropylamino)quinoxalin-2-yl)piperazin-1-yl)methanone, 2,2,2-trifluoroacetic acid salt; (2-chlorophenyl)(4-(3-(cyclopropylamino)quinoxalin-2-yl)piperazin-1-yl)methanone, 2,2,2-trifluoroacetic acid salt; (4-(3-(cyclopropylamino)quinoxalin-2-yl)piperazin-1-yl)(m-tolyl)methanone, 2,2,2-trifluoroacetic acid salt; (4-(3-(cyclopropylamino)quinoxalin-2-yl)piperazin-1-yl)(2,5-dichlorothiophen-3-yl)methanone; (4-(2-(cyclopropylamino)pyrido-[3,4-b]pyrazin-3-yl)piperazin-1-yl)(4-(difluoromethyl)phenyl)methanone, 2,2,2-trifluoroacetic acid salt; (4-chloro-3-fluorophenyl)(4-(2-(cyclopropylamino)pyrido[3,4-b]pyrazin-3-yl)piperazin-1-yl)methanone, 2,2,2-trifluoroacetic acid salt; (4-(2-(cyclopropylamino)pyrido[3,4-b]pyrazin-3-yl)piperazin-1-yl)(3,4-difluorophenyl)methanone, 2,2,2-trifluoroacetic acid salt; (3-chloro-4-fluorophenyl)(4-(2-(cyclopropylamino)pyrido[3,4-b]pyrazin-3-yl)piperazin-1-yl)methanone, 2,2,2-trifluoroacetic acid salt; (4-chloro-2-fluorophenyl)(4-(2-(cyclopropylamino)pyrido[3,4-b]pyrazin-3-yl)piperazin-1-yl) methanone, 2,2,2-trifluoroacetic acid salt; (2-chloro-4-fluorophenyl)(4-(2-(cyclopropylamino)pyrido[3,4-b]pyrazin-3-yl)piperazin-1-yl)methanone, 2,2,2-trifluoroacetic acid salt; (4-chloro-2-hydroxyphenyl)(4-(2-(cyclopropylamino)pyrido[3,4-b]pyrazin-3-yl)piperazin-1-yl)methanone, 2,2,2-trifluoroacetic acid salt; (4-chloro-2-methoxyphenyl)(4-(2-(cyclopropylamino)pyrido[3,4-b]pyrazin-3-yl)piperazin-1-yl)methanone, 2,2,2-trifluoroacetic acid salt; 3-(1-(4-chlorobenzoyl)piperidin-4-yl)-2-(cyclopropylamino)quinoxaline-6-carbonitrile, 2,2,2-trifluoroacetic acid salt; (4-(3-(cyclopropylamino)quinoxalin-2-yl)-3-methylpiperazin-1-yl)(2,5-dichlorophenyl)methanone, 2,2,2-trifluoroacetic acid salt.

Example 5

Synthesis of cyclohexyl(4-(3-(cyclopropylamino)quinoxalin-2-yl)piperazin-1-yl)methanone

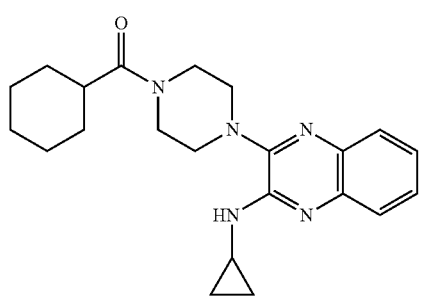 [SMILES: O=C(C1CCCCC1)N1CCN(c2nc3ccccc3nc2NC2CC2)CC1]

A solution of N-cyclopropyl-3-(piperazin-1-yl)quinoxalin-2-amine dihydrochloride (50 mg, 0.146 mmol) and Et₃N (30.5 µl, 0.219 mmol) in DCM (365 µl) was treated with cyclohexanecarbonyl chloride (23.93 µl, 0.175 mmol) dropwise via syringe at RT. The resulting reaction mixture was stirred for 2 h. ISCO purification (40% EtOAc/Hexanes) afforded the title compound as a light-yellow solid. MS (ESI, pos. ion) m/z: 380.3 (M+1)

Example 6

Synthesis of 3-(4-(4-chlorobenzoyl)piperazin-1-yl)-2-(cyclopropylamino)quinoxaline-6-carbonitrile

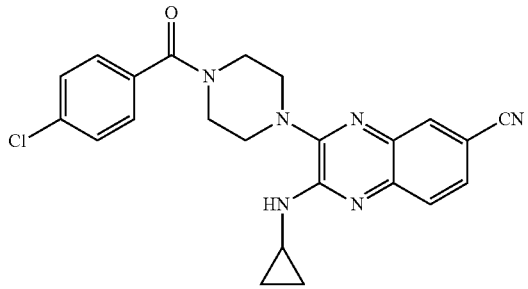 [SMILES: N#Cc1ccc2nc(NC3CC3)c(N3CCN(C(=O)c4ccc(Cl)cc4)CC3)nc2c1]

To a solution of 4-chlorobenzoic acid (6.39 mg, 0.041 mmol) in CH₂Cl₂ (136 µl) was added 3 drops DMF and oxalyl chloride (5.36 µl, 0.061 mmol). The reaction mixture was allowed to stir at RT for 60 min then added to a solution of 2-(cyclopropylamino)-3-(piperazin-1-yl)quinoxaline-6-carbonitrile, 2HCl (15 mg, 0.041 mmol) and triethylamine (19.92 µl, 0.143 mmol) in CH₂Cl₂ (200 µl). The reaction mixture was allowed to stir at RT for 2 h. ISCO purification (0-100% EtOAc/Hexanes) yielded the title compound as a yellow oil. MS (ESI, pos. ion) m/z: 433.3 (M+1)

Utilizing similar reaction conditions described above, following compounds were synthesized:

(4-chlorophenyl)(4-(3-(cyclopropylamino)-7-fluoroquinoxalin-2-yl)piperazin-1-yl)methanone; (4-chlorophenyl)(4-(3-(pyridin-3-ylamino)quinoxalin-2-yl)piperazin-1-yl)methanone, 2,2,2-trifluoroacetic acid salt; (4-bromo-3-fluorophenyl)(4-(3-(cyclopropylamino)-7-fluoroquinoxalin-2-yl)piperazin-1-yl)methanone; 2-(cyclopropylamino)-3-(4-(2,5-dichloroisonicotinoyl)piperazin-1-yl)quinoxaline-6-carbonitrile; 2-(cyclopropylamino)-3-(4-(2,5-dichloronicotinoyl)piperazin-1-yl)quinoxaline-6-carbonitrile, 2,2,2-trifluoroacetic acid salt; (4-(2-(cyclopropylamino)pyrido[3,4-b]pyrazin-3-yl)piperazin-1-yl)(2-fluoro-4-(trifluoromethyl)phenyl)methanone, 2,2,2-trifluoroacetic acid salt; (5-chloro-3-fluoropyridin-2-yl)(4-(2-(cyclopropylamino)pyrido[3,4-b]pyrazin-3-yl)piperazin-1-yl)methanone, 2,2,2-trifluoroacetic acid salt; (4-(2-(cyclopropylamino)-pyrido[3,4-b]pyrazin-3-yl)piperazin-1-yl)(2-fluoro-4-methylphenyl)methanone, 2,2,2-trifluoroacetic acid salt; (4-(2-(cyclopropylamino)pyrido[3,4-b]pyrazin-3-yl)piperazin-1-yl)(2-fluoro-4-methoxyphenyl)methanone, 2,2,2-trifluoroacetic acid salt; (4-chloro-2-methylphenyl)(4-(2-(cyclopropylamino)pyrido[3,4-b]pyrazin-3-yl)piperazin-1-yl)methanone, 2,2,2-trifluoroacetic acid salt; 4-(4-(2-(cyclopropylamino)pyrido[3,4-b]pyrazin-3-yl)piperazine-1-carbonyl)-3-fluorobenzonitrile, 2,2,2-trifluoroacetic acid salt; (4-(2-(cyclopropylamino)pyrido[3,4-b]pyrazin-3-yl)piperazin-1-yl)(4-fluoro-2-hydroxyphenyl)-methanone, 2,2,2-trifluoroacetic acid salt; (4-chloro-2,6-difluorophenyl)(4-(2-(cyclopropylamino)pyrido[3,4-b]pyrazin-3-yl)piperazin-1-yl)methanone, 2,2,2-trifluoroacetic acid salt; (4-(2-(cyclopropylamino)pyrido[3,4-b]pyrazin-3-yl)piperazin-1-yl)(3-fluoropyridin-2-yl)methanone, 2,2,2-trifluoroacetic acid salt; (4-chloro-2-(trifluoromethyl)phenyl)(4-(2-(cyclopropylamino)pyrido[3,4-b]pyrazin-3-yl)piperazin-1-yl)methanone, 2,2,2-trifluoroacetic acid salt; (4-(2-(cyclopropylamino)pyrido[3,4-b]pyrazin-3-yl)piperazin-1-yl)(2,4,6-trifluorophenyl)methanone, 2,2,2-trifluoroacetic acid salt; and (4-(2-(cyclopropylamino)-pyrido[3,4-b]pyrazin-3-yl)piperazin-1-yl)(2,4-difluoro-6-hydroxyphenyl)methanone, 2,2,2-trifluoroacetic acid salt.

Example 7

Synthesis of 3-(4-(benzofuran-3-ylmethyl)piperazin-1-yl)-N-cyclopropylquinoxalin-2-amine

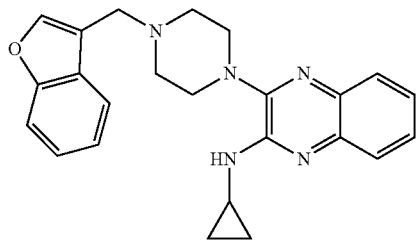 [SMILES: c1ccc2nc(N3CCN(Cc4coc5ccccc45)CC3)c(NC3CC3)nc2c1]

To a solution of benzofuran-3-yl(4-(3-(cyclopropylamino)quinoxalin-2-yl)piperazin-1-yl)methanone, TFA (8 mg, 0.015 mmol) in THF (152 µl) was added triethylamine (2.114 µl, 0.015 mmol). The mixture was cooled to 0° C. and BH₃-THF (76 µl, 0.076 mmol, 1 M in THF) was added. The reaction mixture was stirred at RT for 18 h. ISCO purification (0-60% EtOAc/Hexanes) yielded the title compound as a yellow oil. MS (ESI, pos. ion) m/z: 400.3 (M+1)

Utilizing similar reaction conditions described above, following compounds were synthesized:

N-cyclopropyl-3-(4-((2,5-dichlorothiophen-3-yl)methyl)piperazin-1-yl)quinoxalin-2-amine, 2,2,2-trifluoroacetic acid salt; N-cyclopropyl-3-(4-((3,6-dichloropyridin-2-yl)methyl)piperazin-1-yl)quinoxalin-2-amine, 2,2,2-trifluoroacetic acid salt; 3-(4-(cyclohexylmethyl)piperazin-1-yl)-N-cyclopropylquinoxalin-2-amine; 3-(4-(2-chloro-4-(methylsulfonyl)benzyl)piperazin-1-yl)-N-cyclopropylquinoxalin-2-amine, 2,2,2-trifluoroacetic acid salt; N-cyclopropyl-3-(4-((5-methylisoxazol-3-yl)methyl)piperazin-1-yl)quinoxalin-2-amine, 2,2,2-trifluoroacetic acid salt; and 3-(4-(3-chlorobenzyl)piperazin-1-yl)-N-cyclopropyl-6,7-difluoroquinoxalin-2-amine, 2,2,2-trifluoroacetic acid salt.

Example 8

Synthesis of N-cyclopropyl-3-(4-(5-fluoro-2-methylbenzyl)piperazin-1-yl)quinoxalin-2-amine, 2,2,2-trifluoroacetic acid salt

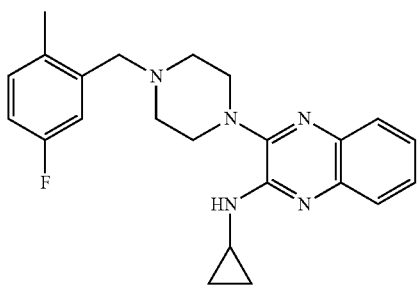 [SMILES: Cc1ccc(F)cc1CN1CCN(c2nc3ccccc3nc2NC2CC2)CC1]

To a solution of (4-(3-(cyclopropylamino)quinoxalin-2-yl)piperazin-1-yl)(5-fluoro-2-methylphenyl)methanone 2,2,2-trifluoroacetate (65 mg, 0.125 mmol) in THF (1 ml) was added diisobutylaluminum hydride (142 mg, 1.001 mmol, 1 M in hexanes) at RT. The reaction mixture was stirred at RT for 16 h. HPLC purification afforded the title compound as a white solid. MS (ESI, pos. ion) m/z: 391.9 (M+1)

Utilizing similar reaction conditions described above, following compounds were synthesized:
N-cyclopropyl-3-(4-(4-fluoro-2-methylbenzyl)piperazin-1-yl)quinoxalin-2-amine, 2,2,2-trifluoroacetic acid salt; 3-(4-(4-chloro-3-methylbenzyl)piperazin-1-yl)-N-cyclopropylquinoxalin-2-amine, 2,2,2-trifluoroacetic acid salt; 3-(4-(2-bromo-5-methoxybenzyl)piperazin-1-yl)-N-cyclopropylquinoxalin-2-amine, 2,2,2-trifluoroacetic acid salt; 3-(4-(3-bromo-4-methoxybenzyl)piperazin-1-yl)-N-cyclopropylquinoxalin-2-amine, 2,2,2-trifluoroacetic acid salt; 3-(4-(4-bromo-2-chlorobenzyl)piperazin-1-yl)-N-cyclopropylquinoxalin-2-amine, 2,2,2-trifluoroacetic acid salt; 3-(4-(3-bromo-4-fluorobenzyl)piperazin-1-yl)-N-cyclopropylquinoxalin-2-amine, 2,2,2-trifluoroacetic acid salt; 3-(4-(4-bromo-2-fluorobenzyl)piperazin-1-yl)-N-cyclopropylquinoxalin-2-amine, 2,2,2-trifluoroacetic acid salt; 3-(4-(5-bromo-2-fluorobenzyl)piperazin-1-yl)-N-cyclopropylquinoxalin-2-amine, 2,2,2-trifluoroacetic acid salt; 3-(4-(5-bromo-2-methylbenzyl)piperazin-1-yl)-N-cyclopropylquinoxalin-2-amine, 2,2,2-trifluoroacetic acid salt; 3-(4-((1H-indol-6-yl)methyl)piperazin-1-yl)-N-cyclopropylquinoxalin-2-amine, 2,2,2-trifluoroacetic acid salt; 3-(4-(5-chloro-2-methylbenzyl)piperazin-1-yl)-N-cyclopropylquinoxalin-2-amine, 2,2,2-trifluoroacetic acid salt; 3-(4-(4-chloro-2-methylbenzyl)piperazin-1-yl)-N-cyclopropylquinoxalin-2-amine, 2,2,2-trifluoroacetic acid salt; 3-(4-(2-chloro-3,6-difluorobenzyl)-piperazin-1-yl)-N-cyclopropylquinoxalin-2-amine, 2,2,2-trifluoroacetic acid salt; 3-(4-(2-chloro-5-methoxybenzyl)piperazin-1-yl)-N-cyclopropylquinoxalin-2-amine, 2,2,2-trifluoroacetic acid salt; 3-(4-(2-chloro-6-(trifluoromethyl)benzyl)piperazin-1-yl)-N-cyclopropylquinoxalin-2-amine, 2,2,2-trifluoroacetic acid salt; N-cyclopropyl-3-(4-(3-isopropylbenzyl)piperazin-1-yl)quinoxalin-2-amine, 2,2,2-trifluoroacetic acid salt; 3-(4-(3-chloro-4-methoxybenzyl)piperazin-1-yl)-N-cyclopropylquinoxalin-2-amine, 2,2,2-trifluoroacetic acid salt; 3-(4-(4-bromo-3-methylbenzyl)piperazin-1-yl)-N-cyclopropylquinoxalin-2-amine, 2,2,2-trifluoroacetic acid salt; 3-(4-(4-bromo-2-methylbenzyl)piperazin-1-yl)-N-cyclopropylquinoxalin-2-amine, 2,2,2-trifluoroacetic acid salt; 3-(4-(2-chloro-5-iodobenzyl)piperazin-1-yl)-N-cyclopropylquinoxalin-2-amine, 2,2,2-trifluoroacetic acid salt; N-cyclopropyl-3-(4-(2-methoxy-5-(trifluoromethoxy)benzyl)-piperazin-1-yl)quinoxalin-2-amine, 2,2,2-trifluoroacetic acid salt; N-cyclopropyl-3-(4-(2,3,5-trichlorobenzyl)piperazin-1-yl)quinoxalin-2-amine, 2,2,2-trifluoroacetic acid salt; 3-(4-((2-chloro-5-fluoropyridin-3-yl)methyl)piperazin-1-yl)-N-cyclopropylquinoxalin-2-amine, 2,2,2-trifluoroacetic acid salt; 3-(4-(2-bromo-5-chlorobenzyl)piperazin-1-yl)-N-cyclopropylquinoxalin-2-amine, 2,2,2-trifluoroacetic acid salt; 3-(4-(5-chloro-2-(trifluoromethyl)-benzyl)piperazin-1-yl)-N-cyclopropylquinoxalin-2-amine, 2,2,2-trifluoroacetic acid salt; N-cyclopropyl-3-(4-(2,6-difluoro-3-methylbenzyl)piperazin-1-yl)quinoxalin-2-amine, 2,2,2-trifluoroacetic acid salt; and N-cyclopropyl-3-(4-(2-methoxy-5-(trifluoromethyl)benzyl)piperazin-1-yl)quinoxalin-2-amine, 2,2,2-trifluoroacetic acid salt.

Example 9

Synthesis of N-cyclopentyl-3-(4-(2,5-dichlorobenzyl)piperazin-1-yl)quinoxalin-2-amine

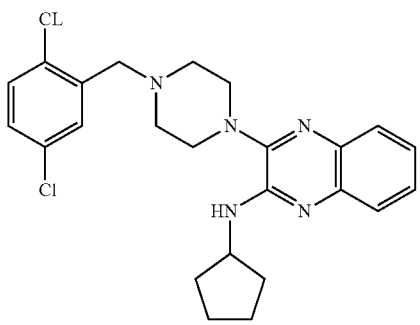

A solution of (4-(3-(cyclopentylamino)quinoxalin-2-yl)piperazin-1-yl)(2,5-dichlorophenyl)methanone (16 mg, 0.034 mmol) in THF (0.35 mL) and DCM (0.35 mL) was added trifluoromethanesulfonic acid anhydride (0.017 mL, 0.102 mmol) at RT and the resulting reaction mixture stirred for 1 h. NaBH$_4$ (3.86 mg, 0.102 mmol) was then added in one portion and stirring continued at RT for 1 h. HPLC purification afforded the title compound as a white solid. MS (ESI, pos. ion) m/z: 456.2 (M+1)

Utilizing similar reaction conditions described above, following compounds were synthesized:
3-(4-(2,5-dichlorobenzyl)piperazin-1-yl)-N-phenylquinoxalin-2-amine, 2,2,2-trifluoroacetic acid salt; N-cyclopropyl-3-(4-(3-(trifluoromethyl)benzyl)piperazin-1-yl)quinoxalin-2-amine, 2,2,2-trifluoroacetic acid salt; 3-(4-(4-chlorobenzyl)piperazin-1-yl)-N-cyclopropylquinoxalin-2-amine, 2,2,2-trifluoroacetic acid salt; 3-(4-(2-chlorobenzyl)-piperazin-1-yl)-N-cyclopropylquinoxalin-2-amine, 2,2,2-trifluoroacetic acid salt; N-cyclopropyl-3-(4-(4-(methylsulfonyl)benzyl)piperazin-1-yl)quinoxalin-2-amine, 22,2,2-trifluoroacetic acid salt; N-cyclopropyl-3-(4-(2,5-dichlorobenzyl)piperazin-1-yl)quinoxalin-2-amine, 2,2,2-trifluoroacetic acid salt; N-cyclopropyl-3-(4-(4-(trifluoromethyl)-benzyl)piperazin-1-yl)quinoxalin-2-amine, 2,2,2-trifluoroacetic acid salt; N-cyclopropyl-3-(4-(2,3-dichlorobenzyl)piperazin-1-yl)quinoxalin-2-amine, 2,2,2-trifluoroacetic acid salt Example 10

Synthesis of 3-(4-(3-chlorobenzyl)piperazin-1-yl)-2-(cyclopropylamino)quinoxaline-6-carbonitrile

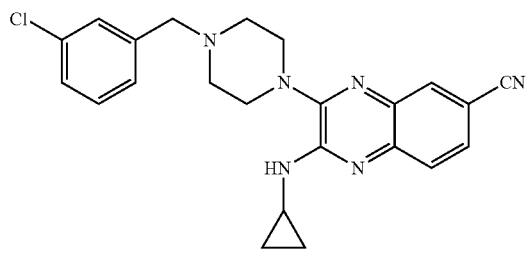 [SMILES: N#Cc1ccc2nc(NC3CC3)c(N3CCN(Cc4cccc(Cl)c4)CC3)nc2c1]

To a solution of 2-(cyclopropylamino)-3-(piperazin-1-yl) quinoxaline-6-carbonitrile, 2HCl (15 mg, 0.041 mmol) and triethylamine (11.38 µl, 0.082 mmol) in DCE (204 µl) was added 3-chlorobenzaldehyde (4.63 µl, 0.041 mmol) then sodium triacetoxyborohydride (12.12 mg, 0.057 mmol). The reaction mixture was stirred at RT for 2 h. ISCO purification (0-100% EtOAc/Hexanes) afforded the title compound as a colorless oil. MS (ESI, pos. ion) m/z: 419.3 (M+1)

Utilizing similar reaction conditions described above, following compounds were synthesized and purified by either HPLC or ISCO):

N-cyclopropyl-3-(4-(2,5-difluorobenzyl)piperazin-1-yl)-6-fluoroquinoxalin-2-amine; 2-(cyclopropylamino)-3-(4-(4-fluorobenzyl)piperazin-1-yl)quinoxaline-6-carbonitrile; 8-chloro-3-(4-(5-chloro-2-fluorobenzyl)piperazin-1-yl)-N-cyclopropylpyrido[3,4-b]pyrazin-2-amine, 2,2,2-trifluoroacetic acid salt; 8-chloro-N-cyclopropyl-3-(4-(2,5-difluorobenzyl)-piperazin-1-yl)pyrido[3,4-b]pyrazin-2-amine, 2,2,2-trifluoroacetic acid salt; 8-chloro-N-cyclopropyl-3-(4-(2,4-difluorobenzyl)piperazin-1-yl)pyrido[3,4-b]pyrazin-2-amine, 2,2,2-trifluoroacetic acid salt; 8-chloro-N-cyclopropyl-3-(4-(2,4,5-trifluorobenzyl)piperazin-1-yl)pyrido[3,4-b]pyrazin-2-amine, 2,2,2-trifluoroacetic acid salt; 2-(4-(2,5-difluorobenzyl)piperazin-1-yl)-N-(pyridin-3-yl)pyrido[3,4-b]pyrazin-3-amine, 2,2,2-trifluoroacetic acid salt; 7-bromo-N-cyclopropyl-2-(piperazin-1-yl)pyrido[3,4-b]pyrazin-3-amine 2,2,2-trifluoroacetate; 3-(4-(5-chloro-2-propoxybenzyl)piperazin-1-yl)-N-cyclopropylpyrido[3,4-b] pyrazin-2-amine, 2,2,2-trifluoroacetic acid salt; 3-(4-(5-(tert-butyl)-2-methoxybenzyl)piperazin-1-yl)-N-cyclopropylpyrido[3,4-b]pyrazin-2-amine, 2,2,2-trifluoroacetic acid salt; N-cyclopropyl-3-(4-(2,6-difluorobenzyl)piperazin-1-yl)pyrido[3,4-b]pyrazin-2-amine, 2,2,2-trifluoroacetic acid salt; 3-(4-(3-chloro-4-fluorobenzyl)piperazin-1-yl)-N-cyclopropylpyrido[3,4-b] pyrazin-2-amine, 2,2,2-trifluoroacetic acid salt; N-cyclopropyl-3-(4-(2,4,5-trifluorobenzyl)piperazin-1-yl) pyrido[3,4-b]pyrazin-2-amine, 2,2,2-trifluoroacetic acid salt; 3-(4-(4-chloro-3-fluorobenzyl)piperazin-1-yl)-N-cyclopropylpyrido[3,4-b]pyrazin-2-amine, 2,2,2-trifluoroacetic acid salt; N-cyclopropyl-3-(4-(3,4-difluorobenzyl) piperazin-1-yl)pyrido[3,4-b]pyrazin-2-amine, 2,2,2-trifluoroacetic acid salt; N-cyclopropyl-3-(4-(2,4-difluorobenzyl)piperazin-1-yl)pyrido[3,4-b]pyrazin-2-amine, 2,2,2-trifluoroacetic acid salt; 3-(4-(5-chloro-2-fluorobenzyl)piperazin-1-yl)-N-cyclopropylpyrido[3,4-b] pyrazin-2-amine, and 2,2,2-trifluoroacetic acid salt; 3-(4-(2-chloro-5-fluorobenzyl)piperazin-1-yl)-N-cyclopropylpyrido [3,4-b]pyrazin-2-amine, 2,2,2-trifluoroacetic acid salt; 2-(cyclopropylamino)-3-(1-(2,5-dichlorobenzyl)piperidin-4-yl)quinoxaline-6-carbonitrile, 2,2,2-trifluoroacetic acid salt; 2-(cyclopropylamino)-3-(1-(2,5-difluorobenzyl)piperidin-4-yl)quinoxaline-6-carbonitrile, 2,2,2-trifluoroacetic acid salt; N-cyclopropyl-3-(1-(2,4-difluorobenzyl)piperidin-4-yl)-7-methylpyrido[3,4-b]pyrazin-2-amine, 2,2,2-trifluoroacetic acid salt; N-cyclopropyl-3-(4-(2,5-dichlorobenzyl)-2-methylpiperazin-1-yl)quinoxalin-2-amine; methyl 4-(3-(cyclopropylamino)quinoxalin-2-yl)-1-(2,5-dichlorobenzyl) piperazine-2-carboxylate; N-cyclopropyl-3-(4-(2,5-dichlorobenzyl)-3-isopropylpiperazin-1-yl)quinoxalin-2-amine; N-cyclopropyl-3-(4-(2,5-dichlorobenzyl)-3-methylpiperazin-1-yl)quinoxalin-2-amine, 2,2,2-trifluoroacetic acid salt; N-cyclopropyl-3-(4-(2,5-dichlorobenzyl)-3-(methoxymethyl)piperazin-1-yl) quinoxalin-2-amine; 3-(3-benzyl-4-(2,5-dichlorobenzyl) piperazin-1-yl)-N-cyclopropylquinoxalin-2-amine, 2,2,2-trifluoroacetic acid salt.

Example 11

Synthesis of 2,2,2-trifluoroacetic acid, N-cyclopropyl-3-(4-(3,4-dimethylbenzyl)piperazin-1-yl)quinoxalin-2-amine salt

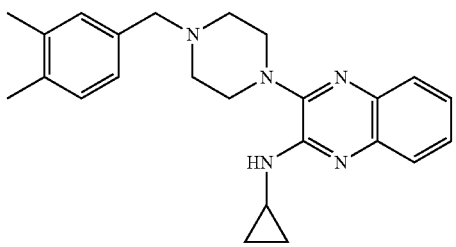 [SMILES: Cc1ccc(CN2CCN(c3nc4ccccc4nc3NC3CC3)CC2)cc1C]

A mixture of N-cyclopropyl-3-(piperazin-1-yl)quinoxalin-2-amine hydrochloride (100 mg, 0.327 mmol), 4-(chloromethyl)-1,2-dimethylbenzene (152 mg, 0.981 mmol) and Et₃N (0.137 ml, 0.981 mmol) was stirred in DMF (3 ml) at 50° C. for 16 h. HPLC purification yielded the title compound as a yellow oil. MS (ESI, pos. ion) m/z: 388.1 (M+1)

Utilizing similar reaction conditions described above, following compounds were synthesized:

4-((4-(3-(cyclopropylamino)quinoxalin-2-yl)piperazin-1-yl)methyl)benzonitrile, 2,2,2-trifluoroacetic acid salt; N-cyclopropyl-3-(4-(4-ethylbenzyl)piperazin-1-yl)quinoxalin-2-amine, 2,2,2-trifluoroacetic acid salt; N-cyclopropyl-3-(4-(3,4-dichlorobenzyl)piperazin-1-yl)quinoxalin-2-amine, 2,2,2-trifluoroacetic acid salt; N-cyclopropyl-3-(4-(2,5-difluorobenzyl)piperazin-1-yl)quinoxalin-2-amine, 2,2,2-trifluoroacetic acid salt; N-cyclopropyl-3-(4-(naphthalen-2-ylmethyl)piperazin-1-yl)quinoxalin-2-amine, 2,2,2-trifluoroacetic acid salt; 3-(4-(4-bromobenzyl)piperazin-1-yl)-N-cyclopropylquinoxalin-2-amine, 2,2,2-trifluoroacetic acid salt; 3-((4-(3-(cyclopropylamino)quinoxalin-2-yl)piperazin-1-yl)methyl)benzonitrile, 2,2,2-trifluoroacetic acid salt; N-cyclopropyl-3-(4-(4-fluorobenzyl)piperazin-1-yl) quinoxalin-2-amine, 2,2,2-trifluoroacetic acid salt; N-cyclopropyl-3-(4-(4-isopropylbenzyl)piperazin-1-yl)quinoxalin-2-amine, 2,2,2-trifluoroacetic acid salt; N-cyclopropyl-3-(4-(3,5-difluorobenzyl)piperazin-1-yl)quinoxalin-2-amine, 2,2,2-trifluoroacetic acid salt; N-cyclopropyl-3-(4-(2,3-dimethylbenzyl)piperazin-1-yl)quinoxalin-2-amine, 2,2,2-trifluoroacetic acid salt; N-cyclopropyl-3-(4-(2,4-dimethylbenzyl)piperazin-1-yl)quinoxalin-2-amine, 2,2,2-trifluoroacetic acid salt; 3-(4-(2-chloro-5-fluorobenzyl)-piperazin-1-yl)-N-cyclopropylquinoxalin-2-amine, 2,2,2-trifluoroacetic acid salt; N-cyclopropyl-3-(4-(2,5-difluorobenzyl)piperazin-1-yl)-6,7-difluoroquinoxalin-2-amine, 2,2,2-trifluoroacetic acid salt; 3-(4-(2,5-difluorobenzyl)piperazin-1-yl)-N-(pyridin-3-yl)quinoxalin-2-amine, 2,2,2-trifluoroacetic acid salt; 2-(cyclopropylamino)-3-(4-(2,5-difluorobenzyl)-piperazin-1-yl)quinoxaline-6-carbonitrile, 2,2,2-trifluoroacetic acid salt; 3-(4-(2,5-dichlorobenzyl)piperazin-1-yl)-2-(isopropylamino)quinoxaline-6-carbonitrile, 2,2,2-trifluoroacetic acid salt; 3-(4-(2,5-difluorobenzyl)piperazin-1-yl)-2-(isopropylamino)-quinoxaline-6-carbonitrile, 2,2,2-trifluoroacetic acid salt; 2-(cyclobutylamino)-3-(4-(2,5-difluorobenzyl) piperazin-1-yl)quinoxaline-6-carbonitrile, 2,2,2-trifluoroacetic acid salt.

Example 12

Synthesis of N-cyclopropyl-3-(4-(3-methylbenzyl)piperazin-1-yl)pyrido[2,3-b]pyrazin-2-amine

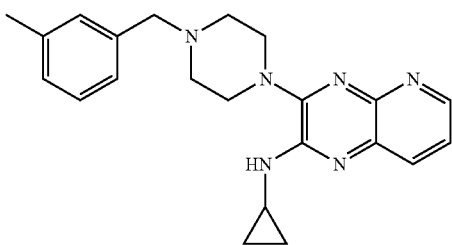

Step 1: 2-chloro-3-(4-(3-methylbenzyl)piperazin-1-yl)pyrido[2,3-b]pyrazine

To a solution of 2,3-dichloropyrido[2,3-b]pyrazine (100 mg, 0.50 mmol) in dioxane (0.5 mL) was added dropwise a solution of 1-(3-methylbenzyl)piperazine (100 mg, 0.525 mmol) in dioxane (1.0 mL), followed by N-ethyl-N-isopropylpropan-2-amine (0.096 mL, 0.550 mmol). The resulting solution was stirred at RT overnight. Column chromatography purification yielded the title compound as a brown oil.

Step 2: N-cyclopropyl-3-(4-(3-methylbenzyl)piperazin-1-yl)pyrido[2,3-b]pyrazin-2-amine A solution of 2-chloro-3-(4-(3-methylbenzyl)piperazin-1-yl)pyrido[2,3-b]pyrazine (34.5 mg, 0.097 mmol), cyclopropanamine (7.79 mg, 0.136 mmol) and DIPEA (0.026 mL, 0.146 mmol) in dioxane (0.3 mL) was heated at 100° C. for 8 h. Column chromatography purification gave the title compound as a colorless oil. MS (ESI, pos. ion) m/z: 375.3 (M+1)

Utilizing similar reaction conditions described above, following compounds were synthesized and purified by either HPLC or ISCO:
3-(4-(3-chlorobenzyl)piperazin-1-yl)-N-(4-fluorophenyl)quinoxalin-2-amine, 2,2,2-trifluoroacetic acid salt; (4-(3-(cyclopentylamino)quinoxalin-2-yl)piperazin-1-yl)(2,5-dichlorophenyl)methanone, 2,2,2-trifluoroacetic acid salt; (2,5-dichlorophenyl)(4-(3-(phenylamino)quinoxalin-2-yl)piperazin-1-yl)methanone, 2,2,2-trifluoroacetic acid salt; N-(cyclopropylmethyl)-3-(4-(2,5-dichlorobenzyl)piperazin-1-yl)quinoxalin-2-amine, 2,2,2-trifluoroacetic acid salt; 3-(4-(2,5-dichlorobenzyl)piperazin-1-yl)-N-(3-methoxyphenyl)-quinoxalin-2-amine; 3-(4-(2,5-dichlorobenzyl)piperazin-1-yl)-N-(4-methoxyphenyl)-quinoxalin-2-amine; 4-((3-(4-(2,5-dichlorobenzyl)piperazin-1-yl)quinoxalin-2-yl)amino)benzonitrile; N-cyclopropyl-3-(4-(2,5-dichlorobenzyl)piperazin-1-yl)pyrido[2,3-b]pyrazin-2-amine; 3-(cyclopropylamino)-2-(4-(2,5-dichlorobenzyl)piperazin-1-yl)quinoxaline-6-carbonitrile, 2,2,2-trifluoroacetic acid salt; N-cyclopropyl-2-(4-(2,5-difluorobenzyl)piperazin-1-yl)pyrido[3,4-b]pyrazin-3-amine, 2,2,2-trifluoroacetic acid salt; N-cyclopropyl-2-(4-(2,5-dichlorobenzyl)piperazin-1-yl)pyrido[3,4-b]pyrazin-3-amine, 2,2,2-trifluoroacetic acid salt; 2-(4-(4-chlorobenzoyl)piperazin-1-yl)-3-(cyclopropylamino)-quinoxaline-6-carbonitrile, 2,2,2-trifluoroacetic acid salt; (4-chlorophenyl)(4-(3-(cyclopropylamino)pyrido[3,4-b]pyrazin-2-yl)piperazin-1-yl)methanone, 2,2,2-trifluoroacetic acid salt; 3-(cyclopropylamino)-2-(4-(2,5-difluorobenzyl)piperazin-1-yl)quinoxaline-6-carbonitrile, 2,2,2-trifluoroacetic acid salt; 3-(cyclopropylamino)-2-(4-((4-fluorophenyl)-sulfonyl)piperazin-1-yl)quinoxaline-6-carbonitrile, 2,2,2-trifluoroacetic acid salt; 3-(cyclopropylamino)-2-(4-((4-fluorophenyl)sulfonyl)piperazin-1-yl)quinoxaline-6-carbonitrile, 2,2,2-trifluoroacetic acid salt; N-cyclopropyl-2-(4-(2,4,5-trifluorobenzyl)-piperazin-1-yl)pyrido[3,4-b]pyrazin-3-amine, 2,2,2-trifluoroacetic acid salt; N-cyclopropyl-2-(4-(2,4-difluorobenzyl)piperazin-1-yl)pyrido[3,4-b]pyrazin-3-amine, 2,2,2-trifluoroacetic acid salt; 2-(4-(2,4-difluorobenzyl)piperazin-1-yl)-N-(2,2-difluoroethyl)pyrido[3,4-b]pyrazin-3-amine, 2,2,2-trifluoroacetic acid salt; N-(2,2-difluoroethyl)-2-(4-(2,4,5-trifluorobenzyl)-piperazin-1-yl)pyrido[3,4-b]pyrazin-3-amine, 2,2,2-trifluoroacetic acid salt; N-cyclopropyl-2-(4-(2,4-difluorobenzyl)piperidin-1-yl)pyrido[3,4-b]pyrazin-3-amine, 2,2,2-trifluoroacetic acid salt; 2-(4-(2,4-difluorobenzyl)piperidin-1-yl)-N-(2,2-difluoroethyl)pyrido[3,4-b]pyrazin-3-amine; N-cyclopropyl-2-(4-(2,4-difluorobenzyl)piperidin-1-yl)-7-methylpyrido[3,4-b]-pyrazin-3-amine, 2,2,2-trifluoroacetic acid salt; 3-(cyclopropylamino)-2-(4-(2,4-difluorobenzyl)piperazin-1-yl)quinoxaline-6-carbonitrile, 2,2,2-trifluoroacetic acid salt; 2-(4-(5-chloro-2-fluorobenzyl)piperazin-1-yl)-3-(cyclopropylamino)quinoxaline-6-carbonitrile, 2,2,2-trifluoroacetic acid salt; 3-(cyclopropylamino)-2-(4-(2,4,5-trifluorobenzyl)piperazin-1-yl)quinoxaline-6-carbonitrile, 2,2,2-trifluoroacetic acid salt; and 2-(4-(4-chloro-2-fluorophenoxy)piperidin-1-yl)-3-(cyclopropylamino)quinoxaline-6-carbonitrile, 2,2,2-trifluoroacetic acid salt.

Example 13

Synthesis of N-(4-bromophenyl)-3-(4-(3-chlorobenzyl)piperazin-1-yl)quinoxalin-2-amine, 2,2,2-trifluoroacetic acid salt

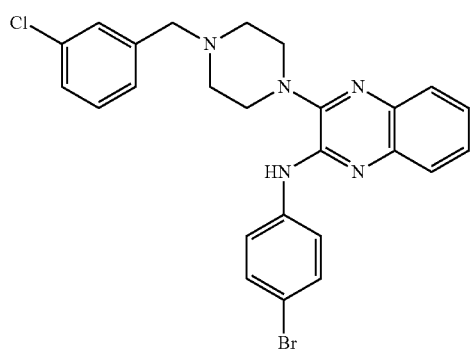 [SMILES: Clc1cccc(CN2CCN(c3nc4ccccc4nc3Nc3ccc(Br)cc3)CC2)c1]

A solution of DIPEA (0.026 ml, 0.151 mmol), 1-(3-chlorobenzyl)piperazine (19.06 mg, 0.090 mmol) and 2,3-dichloroquinoxaline (20 mg, 0.100 mmol) in dioxane (0.2 mL) was heated at 60° C. for 6 h. Then DIPEA (0.026 ml, 0.151 mmol) and 4-bromoaniline (25.9 mg, 0.151 mmol) were added. The resulting solution was stirred at 180° C. overnight. HPLC purification gave the title compound as a yellow solid. MS (ESI, pos. ion) m/z: 509.2 (M+1)

Utilizing similar reaction conditions described above, 2-(4-(3-chlorobenzyl)piperazin-1-yl)-N-phenylpyrido[2,3-b]pyrazin-3-amine, 2,2,2-trifluoroacetic acid salt was synthesized.

Example 14

Synthesis of 3-(4-(3-chlorobenzyl)piperazin-1-yl)-N-phenylpyrido[2,3-b]pyrazin-2-amine, 2,2,2-trifluoroacetic acid salt

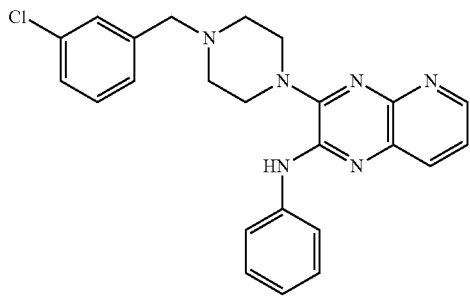 [SMILES: Clc1cccc(CN2CCN(c3nc4ncccc4nc3Nc3ccccc3)CC2)c1]

To a solution of 2,3-dichloropyrido[2,3-b]pyrazine (20 mg, 0.100 mmol) in dioxane (0.3 mL) was added aniline (9.78 mg, 0.105 mmol) and N-ethyl-N-isopropylpropan-2-amine (38.8 mg, 0.30 mmol). The reaction mixture was heated at 150° C. overnight, then 1-(3-chlorobenzyl)piperazine (31.6 mg, 0.150 mmol) was added. The resulting solution was heated at 150° C. overnight. HPLC purification afforded the title compound as a yellow solid. MS (ESI, pos. ion) m/z: 431.2 (M+1)

Utilizing similar reaction conditions described above, following compounds were synthesized:
3-(4-(3-chlorobenzyl)piperazin-1-yl)-N-phenylquinoxalin-2-amine, 2,2,2-trifluoroacetic acid salt; 3-(4-(3-chlorobenzyl)piperazin-1-yl)-N-(4-(trifluoromethoxy)-phenyl)quinoxalin-2-amine, 2,2,2-trifluoroacetic acid salt; 3-(4-(3-chlorobenzyl)piperazin-1-yl)-N-(4-propylphenyl)quinoxalin-2-amine, 2,2,2-trifluoroacetic acid salt; 3-(4-(3-chlorobenzyl)piperazin-1-yl)-N-(p-tolyl)quinoxalin-2-amine, 2,2,2-trifluoroacetic acid salt; 3-(4-(3-chlorobenzyl)piperazin-1-yl)-N-(4-methoxyphenyl)quinoxalin-2-amine, 2,2,2-trifluoroacetic acid salt; 3-(4-(3-chlorobenzyl)piperazin-1-yl)-N-(2-methoxyphenyl)-quinoxalin-2-amine, 2,2,2-trifluoroacetic acid salt; 3-(4-(3-chlorobenzyl)piperazin-1-yl)-N-(3-methoxyphenyl)quinoxalin-2-amine, 2,2,2-trifluoroacetic acid salt; N-(4-(tert-butyl)phenyl)-3-(4-(3-chlorobenzyl)piperazin-1-yl)quinoxalin-2-amine, 2,2,2-trifluoroacetic acid salt; and 3-(4-(3-chlorobenzyl)piperazin-1-yl)-N-(4-isopropoxyphenyl)quinoxalin-2-amine, 2,2,2-trifluoroacetic acid salt.

Example 15

Synthesis of 3-(4-(2,5-dichlorobenzyl)piperazin-1-yl)-N-(pyridin-3-yl)pyrido[2,3-b]pyrazin-2-amine, 2,2,2-trifluoroacetic acid salt

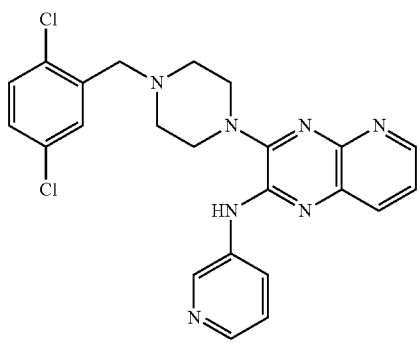 [SMILES: Clc1ccc(Cl)c(CN2CCN(c3nc4ncccc4nc3Nc3cccnc3)CC2)c1]

Step 1: 2-chloro-3-(4-(2,5-dichlorobenzyl)piperazin-1-yl)pyrido[2,3-b]pyrazine

To a solution of 2,3-dichloropyrido[2,3-b]pyrazine (21 mg, 0.105 mmol) and 1-(2,5-dichlorobenzyl)piperazine, HCl (31.0 mg, 0.110 mmol) in dioxane (350 μl) was added N-ethyl-N-isopropylpropan-2-amine (56.8 μl, 0.325 mmol) dropwise at RT. The resulting mixture was stirred at RT overnight and HPLC purification yielded the title compound as a yellow solid.

Step 2: 3-(4-(2,5-dichlorobenzyl)piperazin-1-yl)-N-(pyridin-3-yl)pyrido[2,3-b]pyrazin-2-amine, 2,2,2-trifluoroacetic acid salt A mixture of 2-chloro-3-(4-(2,5-dichlorobenzyl)piperazin-1-yl)pyrido[2,3-b]pyrazine (25 mg, 0.061 mmol), pyridin-3-amine (7.48 mg, 0.080 mmol) and NaH (9.79 mg, 0.245 mmol, 60% in mineral oil) in THF (266 μL) was stirred at RT for 3 h. After quenching with methanol (0.5 mL), HPLC purification afforded the title compound as a yellow solid. MS (ESI, pos. ion) m/z: 466.2 (M+1)

Utilizing similar reaction conditions described above, following compounds were synthesized:
2-(4-(2,5-dichlorobenzyl)piperazin-1-yl)-3-(pyridin-3-ylamino)quinoxaline-6-carbonitrile; mixture of 3-(4-(2,5-dichlorobenzyl)piperazin-1-yl)-6-fluoro-N-(pyridin-3-yl)quinoxalin-2-amine, 2,2,2-trifluoroacetic acid salt and 3-(4-(2,5-dichlorobenzyl)piperazin-1-yl)-7-fluoro-N-(pyridin-3-yl)quinoxalin-2-amine, 2,2,2-trifluoroacetic acid salt; N-(pyridin-3-yl)-2-(4-(2,4,5-trifluorobenzyl)piperazin-1-yl)pyrido[3,4-b]pyrazin-3-amine, 2,2,2-trifluoroacetic acid salt; and 2-(4-(2,4-difluorobenzyl)piperazin-1-yl)-N-(pyridin-3-yl)pyrido[3,4-b]pyrazin-3-amine

Example 16

Synthesis of 2-(cyclopropylamino)-3-(4-(2,5-dichlorobenzyl)piperazin-1-yl)quinoxaline-5-carbonitrile, 2,2,2-trifluoroacetic acid salt

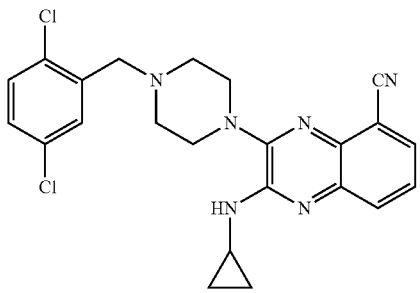 [SMILES: N#Cc1cccc2nc(NC3CC3)c(N3CCN(Cc4cc(Cl)ccc4Cl)CC3)nc12]

A vial containing 5-bromo-N-cyclopropyl-3-(4-(2,5-dichlorobenzyl)piperazin-1-yl)quinoxalin-2-amine (20 mg, 0.039 mmol), dicyanozinc (2.78 mg, 0.024 mmol), Pd$_2$(dba)$_3$ (1.805 mg, 1.971 μmol) and dppf (2.186 mg, 3.94 μmol) in anhydrous NMP (0.3 mL) was evacuated and purged with N$_2$ (3×). The resulting mixture was heated at 120° C. for 2 h. HPLC purification gave the title compound as a grey solid. MS (ESI, pos. ion) m/z: 453.3 (M+1)

Utilizing similar reaction conditions described above, following compounds were synthesized:
3-(cyclopropylamino)-2-(4-(2,5-dichlorobenzyl)piperazin-1-yl)quinoxaline-5-carbonitrile, 2,2,2-trifluoroacetic acid salt; 2-(cyclopropylamino)-3-(4-(2,4-difluorobenzyl)piperidin-1-yl)pyrido[3,4-b]pyrazine-7-carbonitrile; and 3-(cyclopropylamino)-2-(4-(2,4-difluorobenzyl)piperazin-1-yl)pyrido[3,4-b]pyrazine-7-carbonitrile, 2,2,2-trifluoroacetic acid salt.

Example 17

Synthesis of N-cyclopropyl-3-(4-(2,4-difluorobenzyl)piperazin-1-yl)pyrazino[2,3-d]pyridazin-2-amine, 2,2,2-trifluoroacetic acid salt

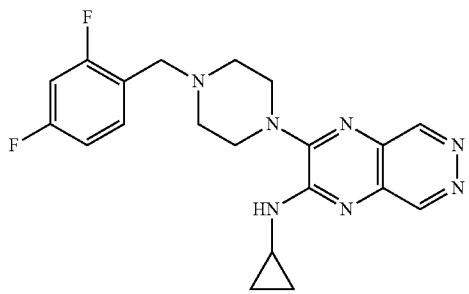 [SMILES: Fc1ccc(CN2CCN(c3nc4cnncc4nc3NC3CC3)CC2)c(F)c1]

Step 1: pyrazino[2,3-d]pyridazine-2,3(1H,4H)-dione

A solution of pyridazine-4,5-diamine (200 mg, 1.816 mmol), oxalic acid (196 mg, 2.179 mmol) and aq hydrogen chloride (2.7 mL, 10.90 mmol, 4.0N) was heated at reflux for 20 h. The reaction mixture was cooled to RT and the resulting precipitate was filtered, washed with water and dried under vacuum to afford the title compound as a white solid.

Step 2: 2,3-dichloropyrazino[2,3-d]pyridazine

A solution of pyrazino[2,3-d]pyridazine-2,3(1H,4H)-dione hydrochloride (300 mg, 1.496 mmol) in phosphoryl trichloride (1812 µl, 19.44 mmol) was heated at 120° C. overnight. Removal of the excess $POCl_3$ under reduced pressure gave the title compound as a black sticky oil, which was used directly in the next step without further purification.

Step 3: N-cyclopropyl-3-(4-(2,4-difluorobenzyl)piperazin-1-yl)pyrazino[2,3-d]pyridazin-2-amine, 2,2,2-trifluoroacetic acid salt To a solution of 2,3-dichloropyrazino[2,3-d]pyridazine hydrochloride (48 mg, 0.202 mmol) in DCM (1.0 mL) at 0° C. was added N-ethyl-N-isopropylpropan-2-amine (177 µl, 1.011 mmol) dropwise, followed by slow addition of cyclopropanamine (11.19 µl, 0.162 mmol). The reaction mixture was stirred at 0° C. for 20 min and then 1-(2,4-difluorobenzyl)piperazine hydrochloride (75 mg, 0.303 mmol) and DIPEA (0.2 mL) were added and stirring continued at 0° C. for 30 min. HPLC purification afforded the title compound as a light yellow solid. MS (ESI, pos. ion) m/z: 398.3 (M+1)

Utilizing similar reaction conditions described above, N-cyclopropyl-3-(4-(2,4-difluorobenzyl)piperidin-1-yl)pyrazino[2,3-d]pyridazin-2-amine, 2,2,2-trifluoroacetic acid salt was synthesized.

Example 18

Synthesis of N-cyclopropyl-3-(4-(2,5-difluorobenzyl)piperidin-1-yl)pyrido[3,4-b]pyrazin-2-amine, 2,2,2-trifluoroacetic acid salt

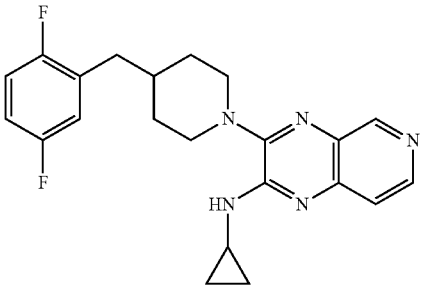 [SMILES: Fc1ccc(F)c(CC2CCN(c3nc4cnccc4nc3NC3CC3)CC2)c1]

Step 1: tert-butyl 4-(2,5-difluorobenzylidene)piperidine-1-carboxylate

To a solution of tert-butyl 4-oxopiperidine-1-carboxylate (64.1 mg, 0.322 mmol) in THF (1.6 mL) at −78° C. was added LiHMDS (386 µl, 0.386 mmol, 1.0N in MeOt-Bu). After the reaction mixture was stirred at −78° C. for 30 min, a solution of tert-butyl 4-oxopiperidine-1-carboxylate (64.1 mg, 0.322 mmol) in THF (0.3 mL) was added. The reaction mixture was allowed to warm to RT and and stirred for 48 h. Column chromatography purification gave the title compound as a white solid.

Step 2: 4-(2,5-difluorobenzylidene)piperidine

To a solution of tert-butyl 4-(2,5-difluorobenzylidene)piperidine-1-carboxylate (20 mg, 0.065 mmol) in DCM (0.6 ml) at 0° C. was added TFA (0.3 mL, 3.89 mmol) and stirring continued at 0° C. for 2 h. Removal of the solvent yielded the title compound as a colorless oil, which was used directly in the next step without further purification.

Step 3: N-cyclopropyl-3-(4-(2,5-difluorobenzylidene)piperidin-1-yl)pyrido[3,4-b]pyrazin-2-amine A solution of 3-chloro-N-cyclopropylpyrido[3,4-b]pyrazin-2-amine (127 mg, 0.574 mmol), 4-(2,5-difluorobenzylidene)piperidine (100 mg, 0.478 mmol) and DIPEA (167 µl, 0.956 mmol) in dioxane (0.8 mL) was heated at 80° C. for 8 h. HPLC purification afforded the title compound.

Step 4: N-cyclopropyl-3-(4-(2,5-difluorobenzyl)piperidin-1-yl)pyrido[3,4-b]pyrazin-2-amine, 2,2,2-trifluoroacetic acid salt To a solution of N-cyclopropyl-3-(4-(2,5-difluorobenzylidene)piperidin-1-yl)pyrido[3,4-b]pyrazin-2-amine 2,2,2-trifluoroacetate (21.2 mg, 0.042 mmol) in MeOH (209 µl) was added 10% Pd/C (4 mg, 3.76 µmol). The reaction mixture was stirred under a $H_2$ atmosphere overnight. HPLC purification yielded the title compound as a light yellow solid. MS (ESI, pos. ion) m/z: 396.3 (M+1)

Example 19

Synthesis of N-cyclopropyl-3-(4-(2,4-difluorobenzyl)piperidin-1-yl)-7-methoxypyrido[3,4-b]pyrazin-2-amine, 2,2,2-trifluoroacetic acid salt

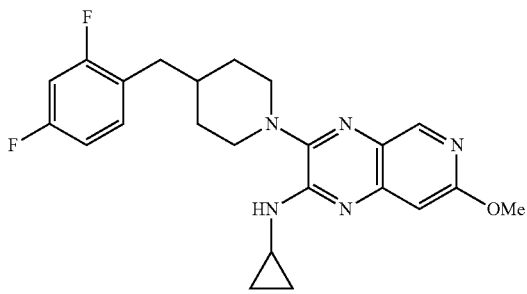 [SMILES: COc1cc2nc(NC3CC3)c(N3CCC(Cc4ccc(F)cc4F)CC3)nc2cn1]

A vial charged with 7-chloro-N-cyclopropyl-3-(4-(2,4-difluorobenzyl)piperidin-1-yl)pyrido[3,4-b]pyrazin-2-amine (15 mg, 0.035 mmol), Pd$_2$(dba)$_3$ (2.56 mg, 2.79 μmol), and Cs$_2$CO$_3$ (11.37 mg, 0.035 mmol) was evacuated and purged with N$_2$ (3×). After MeOH (0.3 ml) was added, the mixture was again evacuated and purged with N$_2$ (2×) and then heated at 100° C. overnight. HPLC purification gave the title compound as a grey solid. MS (ESI, pos. ion) m/z: 426.3 (M+1)

Example 20

Synthesis of 2-(cyclopropylamino)-3-(4-(2,4-difluorobenzyl)piperidin-1-yl)pyrido[3,4-b]pyrazin-7-ol, 2,2,2-trifluoroacetic acid salt

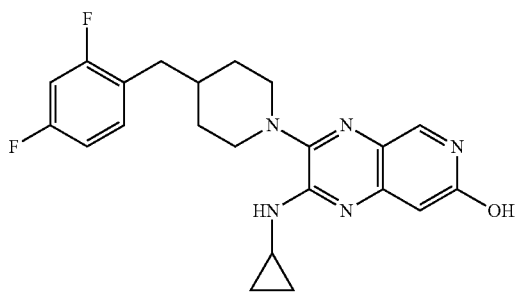 [SMILES: Oc1cc2nc(NC3CC3)c(N3CCC(Cc4ccc(F)cc4F)CC3)nc2cn1]

A vial charged with 7-chloro-N-cyclopropyl-3-(4-(2,4-difluorobenzyl)piperidin-1-yl)pyrido[3,4-b]pyrazin-2-amine (25 mg, 0.058 mmol), Pd$_2$(dba)$_3$ (4.26 mg, 4.65 μmol), potassium trimethylsilanolate (22.38 mg, 0.174 mmol) and cesium carbonate (18.95 mg, 0.058 mmol) was evacuated and purged with N$_2$ (3×). After DMF (0.29 mL) was added, the mixture was again evacuated and purged with N$_2$ (2×) and then heated at 110° C. overnight. HPLC purification yielded the title compound as a yellow solid. MS (ESI, pos. ion) m/z: 412.3 (M+1)

Example 21

Synthesis of 2-(cyclopropylamino)-3-(4-(phenylsulfonyl)piperazin-1-yl)quinoxaline-6-carbonitrile

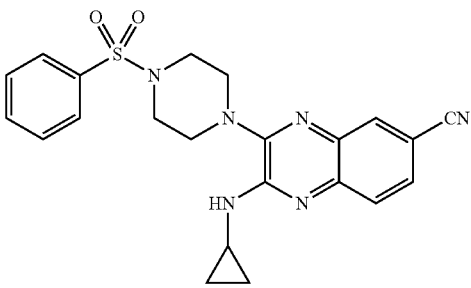 [SMILES: N#Cc1ccc2nc(NC3CC3)c(N3CCN(S(=O)(=O)c4ccccc4)CC3)nc2c1]

To a solution of 2-(cyclopropylamino)-3-(piperazin-1-yl)quinoxaline-6-carbonitrile, 2HCl (15 mg, 0.041 mmol) in CH$_2$Cl$_2$ (204 μl) was added triethylamine (17.08 μl, 0.123 mmol). After stirring for 10 min, benzenesulfonyl chloride (6.27 μl, 0.049 mmol) was added and the reaction mixture was stirred at RT for 2 h. ISCO purification (0-60% EtOAc/Hexanes) afforded the title compound as a white solid. MS (ESI, pos. ion) m/z: 435.3 (M+1)

Utilizing similar reaction conditions described above, following compounds were synthesized and purified by either ISCO or HPLC:

3-(4-(phenylsulfonyl)piperazin-1-yl)-N-(pyridin-3-yl)quinoxalin-2-amine; N-cyclopropyl-6-fluoro-3-(4-(phenylsulfonyl)piperazin-1-yl)quinoxalin-2-amine; 3-(4-((3-chlorophenyl)sulfonyl)piperazin-1-yl)-2-(cyclopropylamino)quinoxaline-6-carbonitrile; 3-(4-((3-chlorophenyl)sulfonyl)piperazin-1-yl)-N-cyclopropyl-6-fluoroquinoxalin-2-amine; 2-(cyclopropylamino)-3-(4-((2,5-dichlorophenyl)sulfonyl)piperazin-1-yl)quinoxaline-6-carbonitrile; 2-(cyclopropylamino)-3-(4-(o-tolylsulfonyl)piperazin-1-yl)quinoxaline-6-carbonitrile; 2-(cyclopropylamino)-3-(4-(m-tolylsulfonyl)piperazin-1-yl)quinoxaline-6-carbonitrile; 2-(cyclopropylamino)-3-(4-tosylpiperazin-1-yl)quinoxaline-6-carbonitrile; 3-(4-((2-bromophenyl)sulfonyl)piperazin-1-yl)-2-(cyclopropylamino)quinoxaline-6-carbonitrile; 3-(4-((3-bromophenyl)sulfonyl)piperazin-1-yl)-2-(cyclopropylamino)quinoxaline-6-carbonitrile; 3-(4-((4-bromophenyl)sulfonyl)piperazin-1-yl)-2-(cyclopropylamino)-quinoxaline-6-carbonitrile; N-cyclopropyl-3-(4-((4-fluorophenyl)sulfonyl)piperazin-1-yl)pyrido[3,4-b]pyrazin-2-amine, 2,2,2-trifluoroacetic acid salt; N-cyclopropyl-2-(4-((4-fluorophenyl)sulfonyl)piperazin-1-yl)pyrido[3,4-b]pyrazin-3-amine, 2,2,2-trifluoroacetic acid salt; 2-(cyclopropylamino)-3-(4-((3,5-dimethylisoxazol-4-yl)sulfonyl)piperazin-1-yl)quinoxaline-6-carbonitrile, 2,2,2-trifluoroacetic acid salt; 2-(cyclopropylamino)-3-(4-((2,5-dimethylphenyl)sulfonyl)piperazin-1-yl)quinoxaline-6-carbonitrile, 2,2,2-trifluoroacetic acid salt; 2-(cyclopropylamino)-3-(4-((4-methoxyphenyl)sulfonyl)piperazin-1-yl)quinoxaline-6-carbonitrile, 2,2,2-trifluoroacetic acid salt; 2-(cyclopropylamino)-3-(4-((2-methoxyphenyl)sulfonyl)piperazin-1-yl)quinoxaline-6-carbonitrile, 2,2,2-trifluoroacetic acid salt; 2-(cyclopropylamino)-3-(4-((3-methoxyphenyl)sulfonyl)piperazin-1-yl)quinoxaline-6-carbonitrile, 2,2,2-trifluoroacetic acid salt; 3-(4-((5-chlorothiophen-2-yl)sulfonyl)piperazin-1-yl)-2-(cyclopropylamino)quinoxaline-6-carbonitrile, 2,2,2-trifluoroacetic acid salt; 2-(cyclopropylamino)-3-(4-

(mesitylsulfonyl)piperazin-1-yl)quinoxaline-6-carbonitrile, 2,2,2-trifluoroacetic acid salt; 2-(cyclopropylamino)-3-(4-((2-methoxy-4-methylphenyl)sulfonyl)-piperazin-1-yl)quinoxaline-6-carbonitrile, 2,2,2-trifluoroacetic acid salt; 3-(4-((5-chloro-1,3-dimethyl-1H-pyrazol-4-yl)sulfonyl)piperazin-1-yl)-2-(cyclopropylamino)quinoxaline-6-carbonitrile, 2,2,2-trifluoroacetic acid salt; 2-(cyclopropylamino)-3-(4-((2,3,4-trifluorophenyl)sulfonyl)piperazin-1-yl)quinoxaline-6-carbonitrile, 2,2,2-trifluoroacetic acid salt; 3-(4-((4-(tert-butyl)phenyl)sulfonyl)piperazin-1-yl)-2-(cyclopropylamino)quinoxaline-6-carbonitrile, 2,2,2-trifluoroacetic acid salt; 3-(4-((4-chloro-2,5-dimethylphenyl)-sulfonyl)piperazin-1-yl)-2-(cyclopropylamino)quinoxaline-6-carbonitrile, 2,2,2-trifluoroacetic acid salt; 3-(4-((3-chloro-5-fluoro-2-methylphenyl)sulfonyl)piperazin-1-yl)-2-(cyclopropylamino)quinoxaline-6-carbonitrile, 2,2,2-trifluoroacetic acid salt; 2-(cyclopropylamino)-3-(4-((4-(trifluoromethoxy)phenyl)sulfonyl)piperazin-1-yl)quinoxaline-6-carbonitrile, 2,2,2-trifluoroacetic acid salt; 3-(4-((5-bromothiophen-2-yl)sulfonyl)piperazin-1-yl)-2-(cyclopropylamino)quinoxaline-6-carbonitrile, 2,2,2-trifluoroacetic acid salt; 3-(4-((4-bromo-2-fluorophenyl)sulfonyl)piperazin-1-yl)-2-(cyclopropylamino)quinoxaline-6-carbonitrile, 2,2,2-trifluoroacetic acid salt; 3-(4-((2-chloro-5-(trifluoromethyl)phenyl)-sulfonyl)piperazin-1-yl)-2-(cyclopropylamino)quinoxaline-6-carbonitrile, 2,2,2-trifluoroacetic acid salt; 3-(4-((4-bromo-2-chlorophenyl)sulfonyl)piperazin-1-yl)-2-(cyclopropylamino)quinoxaline-6-carbonitrile, 2,2,2-trifluoroacetic acid salt; 2-(cyclopropylamino)-3-(4-((4-ethylphenyl)sulfonyl)piperazin-1-yl)quinoxaline-6-carbonitrile, 2,2,2-trifluoroacetic acid salt; 2-(cyclopropylamino)-3-(4-((2-fluoro-5-methylphenyl)sulfonyl)piperazin-1-yl)quinoxaline-6-carbonitrile, 2,2,2-trifluoroacetic acid salt; 2-(cyclopropylamino)-3-(4-((3,4-difluorophenyl)sulfonyl)piperazin-1-yl)quinoxaline-6-carbonitrile, 2,2,2-trifluoroacetic acid salt; 2-(cyclopropylamino)-3-(4-((2,5-dimethoxyphenyl)sulfonyl)piperazin-1-yl)quinoxaline-6-carbonitrile, 2,2,2-trifluoroacetic acid salt; 3-(4-((2-chloro-4-(trifluoromethyl)phenyl)sulfonyl)piperazin-1-yl)-2-(cyclopropylamino)quinoxaline-6-carbonitrile, 2,2,2-trifluoroacetic acid salt; 3-(4-((3-cyano-4-fluorophenyl)sulfonyl)piperazin-1-yl)-2-(cyclopropylamino)quinoxaline-6-carbonitrile, 2,2,2-trifluoroacetic acid salt; 3-(4-((5-chloro-2-methoxyphenyl)sulfonyl)piperazin-1-yl)-2-(cyclopropylamino)quinoxaline-6-carbonitrile, 2,2,2-trifluoroacetic acid salt; 3-(4-((5-chloro-2,4-difluorophenyl)sulfonyl)piperazin-1-yl)-2-(cyclopropylamino)quinoxaline-6-carbonitrile, 2,2,2-trifluoroacetic acid salt; 3-(4-((5-bromo-6-chloropyridin-3-yl)sulfonyl)piperazin-1-yl)-2-(cyclopropylamino)quinoxaline-6-carbonitrile, 2,2,2-trifluoroacetic acid salt; 3-(4-((4-bromo-2,5-difluorophenyl)sulfonyl)piperazin-1-yl)-2-(cyclopropylamino)quinoxaline-6-carbonitrile, 2,2,2-trifluoroacetic acid salt; 2-(cyclopropylamino)-3-(4-((2,4-dimethoxyphenyl)sulfonyl)piperazin-1-yl)quinoxaline-6-carbonitrile; N-cyclopropyl-3-(4-(phenylsulfonyl)piperazin-1-yl)quinoxalin-2-amine; N-cyclopropyl-3-(4-((4-(trifluoromethoxy)phenyl)sulfonyl)piperazin-1-yl)quinoxalin-2-amine; 3-(4-(cyclopentylsulfonyl)piperazin-1-yl)-N-cyclopropylquinoxalin-2-amine; 3-(4-((4-chlorophenyl)sulfonyl)piperazin-1-yl)-2-(cyclopropylamino)quinoxaline-6-carbonitrile, 2,2,2-trifluoroacetic acid salt; 2-(cyclopropylamino)-3-(4-((3-fluorophenyl)sulfonyl)-piperazin-1-yl)quinoxaline-6-carbonitrile, 2,2,2-trifluoroacetic acid salt; 2-(cyclopropylamino)-3-(4-((2-fluorophenyl)sulfonyl)piperazin-1-yl)quinoxaline-6-carbonitrile, 2,2,2-trifluoroacetic acid salt; 3-(4-((2-chlorophenyl)sulfonyl)piperazin-1-yl)-2-(cyclopropylamino)quinoxaline-6-carbonitrile, 2,2,2-trifluoroacetic acid salt; 2-(cyclopropylamino)-3-(4-((4-fluorophenyl)sulfonyl)piperazin-1-yl)quinoxaline-6-carbonitrile, 2,2,2-trifluoroacetic acid salt; 3-(4-((2-cyanophenyl)sulfonyl)piperazin-1-yl)-2-(cyclopropylamino)quinoxaline-6-carbonitrile, 2,2,2-trifluoroacetic acid salt; 3-(4-((3-cyanophenyl)sulfonyl)piperazin-1-yl)-2-(cyclopropylamino)quinoxaline-6-carbonitrile, 2,2,2-trifluoroacetic acid salt; 3-(4-((4-cyanophenyl)sulfonyl)piperazin-1-yl)-2-(cyclopropylamino)quinoxaline-6-carbonitrile, 2,2,2-trifluoroacetic acid salt; and N-cyclopropyl-3-(4-((4-(trifluoromethyl)phenyl)sulfonyl)piperazin-1-yl)pyrido[3,4-b]pyrazin-2-amine, 2,2,2-trifluoroacetic acid salt.

Example 22

Synthesis of N-cyclopropyl-3-(4-phenethylpiperazin-1-yl)quinoxalin-2-amine

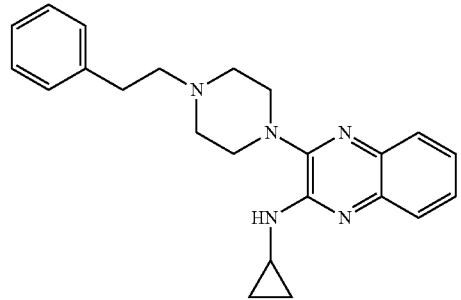 [SMILES: c1ccc(CCN2CCN(c3nc4ccccc4nc3NC3CC3)CC2)cc1]

Step 1: 1-(4-(3-(cyclopropylamino)quinoxalin-2-yl)piperazin-1-yl)-2-phenylethanone To a solution of 2-phenylacetic acid (11.93 mg, 0.088 mmol) in CH$_2$Cl$_2$ (438 µl) was added DMF (3 drops) and oxalyl chloride (11.51 µl, 0.131 mmol), then the mixture was allowed to stir for 60 min. The acid chloride was added to a solution of N-cyclopropyl-3-(piperazin-1-yl)quinoxalin-2-amine, 2HCl (30 mg, 0.088 mmol) and triethylamine (36.7 µl, 0.263 mmol) in CH$_2$Cl$_2$ (400 µl). The reaction mixture was allowed to stir at RT for 2 h. ISCO purification (0-100% EtOAc/Hexanes) yielded the title compound as a yellow oil.

Step 2: N-cyclopropyl-3-(4-phenethylpiperazin-1-yl)quinoxalin-2-amine

To a solution of 1-(4-(3-(cyclopropylamino)quinoxalin-2-yl)piperazin-1-yl)-2-phenylethanone (5 mg, 0.013 mmol) in THF (43.0 µl) was added BH$_3$-THF (64.5 µl, 0.065 mmol, 1 M in THF). The mixture was stirred at RT for 16 h. ISCO purification (0-80% EtOAc/Hexanes) afforded the title compound as a yellow oil. MS (ESI, pos. ion) m/z: 374.3 (M+1)

Utilizing similar reaction conditions described above, following compounds were synthesized and purified by either HPLC or ISCO:

3-(4-(4-chlorophenethyl)piperazin-1-yl)-N-cyclopropylquinoxalin-2-amine; N-cyclopropyl-3-(4-(4-methoxyphenethyl)piperazin-1-yl)quinoxalin-2-amine; N-cyclopropyl-3-(4-(2,5-dichlorophenethyl)piperazin-1-yl)quinoxalin-2-amine

Example 23

Synthesis of 3-(4-benzylpiperidin-1-yl)-N-phenylquinoxalin-2-amine, 2,2,2-trifluoroacetic acid salt

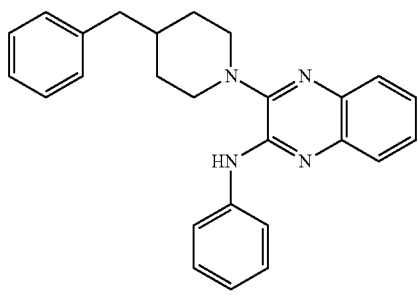 [SMILES: c1ccc(CC2CCN(c3nc4ccccc4nc3Nc3ccccc3)CC2)cc1]

Step 1: 2-(4-benzylpiperidin-1-yl)-3-chloroquinoxaline

A solution of 2,3-dichloroquinoxaline (1 g, 5.02 mmol) and EtOH (25 ml) was treated with 4-benzylpiperidine (1.233 g, 7.03 mmol). The reaction mixture was stirred at 15° C. for 15 h. The solvent was removed under reduced pressure to give the title compound, which was used for the next step without further purification.

Step 2: 3-(4-benzylpiperidin-1-yl)-N-phenylquinoxalin-2-amine, 2,2,2-trifluoroacetic acid salt 2-(4-Benzylpiperidin-1-yl)-3-chloroquinoxaline (200 mg, 0.592 mmol) and aniline (55.1 mg, 0.592 mmol) was stirred in n-BuOH (0.6 ml) at 90° C. for 16 h. The solvent was removed under reduced pressure and HPLC purification afforded the title compound as a yellow solid.

Utilizing similar reaction conditions described above, following compounds were synthesized:

N-(3-bromophenyl)-3-(4-(3-chlorobenzyl)piperazin-1-yl)quinoxalin-2-amine, 2,2,2-trifluoroacetic acid salt; N-(2-bromophenyl)-3-(4-(3-chlorobenzyl)piperazin-1-yl)quinoxalin-2-amine, 2,2,2-trifluoroacetic acid salt; 3-(4-(3-chlorobenzyl)piperazin-1-yl)-N-(pyridin-3-yl)quinoxalin-2-amine, 2,2,2-trifluoroacetic acid salt; 3-(4-(3-chlorobenzyl)piperazin-1-yl)-N-(pyridin-4-yl)quinoxalin-2-amine, 2,2,2-trifluoroacetic acid salt; N-(3-(4-(3-chlorobenzyl)piperazin-1-yl)quinoxalin-2-yl)-1,3,4-thiadiazol-2-amine, 2,2,2-trifluoroacetic acid salt; N-(3-(4-(3-chlorobenzyl)piperazin-1-yl)quinoxalin-2-yl)thiazol-2-amine, 2,2,2-trifluoroacetic acid salt; 3-(4-(3-chlorobenzyl)piperazin-1-yl)-N-(pyrimidin-2-yl)quinoxalin-2-amine, 2,2,2-trifluoroacetic acid salt; and 3-(4-(3-chlorobenzyl)piperazin-1-yl)-N-(pyrimidin-5-yl)quinoxalin-2-amine, 2,2,2-trifluoroacetic acid salt.

Example 24

Synthesis of 3-(4-(2,5-dichlorobenzyl)piperazin-1-yl)-N-isobutylquinoxalin-2-amine, 2,2,2-trifluoroacetic acid salt

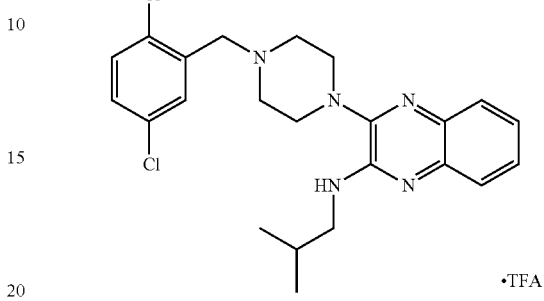

Step 1: 2-chloro-3-(4-(2,5-dichlorobenzyl)piperazin-1-yl)quinoxaline

A suspension of 2-chloro-3-(piperazin-1-yl)quinoxaline (2.5 g, 10.05 mmol), 1,4-dichloro-2-(chloromethyl)benzene (2.358 g, 12.06 mmol) and Et₃N (4.20 ml, 30.2 mmol) in DMF (20 ml) was stirred at RT for 16 h. The reaction mixture was poured into water and extracted with EtOAc. The organic phase was dried, concentrated, and chromatographed on silica gel to give the title compound.

Step 2: 3-(4-(2,5-dichlorobenzyl)piperazin-1-yl)-N-isobutylquinoxalin-2-amine, 2,2,2-trifluoroacetic acid salt A suspension of 2-chloro-3-(4-(2,5-dichlorobenzyl)piperazin-1-yl)quinoxaline (50 mg, 0.123 mmol) and 2-methylpropan-1-amine (90 mg, 1.226 mmol) was heated in n-BuOH (1 ml) at 130° C. under microwave irradiation for 1 h. HPLC purification afforded the title compound as a white solid. MS (ESI, pos. ion) m/z: 444.0 (M+1)

Utilizing similar reaction conditions described above, following compounds were synthesized using commercially available amines:

3-(4-(2,5-dichlorobenzyl)piperazin-1-yl)-N-isopropylquinoxalin-2-amine, 2,2,2-trifluoroacetic acid salt; 3-(4-(2,5-dichlorobenzyl)piperazin-1-yl)-N-(2-ethylbutyl)quinoxalin-2-amine, 2,2,2-trifluoroacetic acid salt; 3-(4-(2,5-dichlorobenzyl)piperazin-1-yl)-N-(4-methylpentan-2-yl)quinoxalin-2-amine, 2,2,2-trifluoroacetic acid salt; 3-(4-(2,5-dichlorobenzyl)piperazin-1-yl)-N-neopentylquinoxalin-2-amine, 2,2,2-trifluoroacetic acid salt; 3-(4-(2,5-dichlorobenzyl)piperazin-1-yl)-N-isopentylquinoxalin-2-amine, 2,2,2-trifluoroacetic acid salt; N-(sec-butyl)-3-(4-(2,5-dichlorobenzyl)piperazin-1-yl)quinoxalin-2-amine, 2,2,2-trifluoroacetic acid salt; 3-(4-(2,5-dichlorobenzyl)piperazin-1-yl)-N-propylquinoxalin-2-amine, 2,2,2-trifluoroacetic acid salt; 3-(4-(2,5-dichlorobenzyl)piperazin-1-yl)-N-(2-methoxyethyl)quinoxalin-2-amine, 2,2,2-trifluoroacetic acid salt; N-cyclobutyl-3-(4-(2,5-dichlorobenzyl)piperazin-1-yl)quinoxalin-2-amine, 2,2,2-trifluoroacetic acid salt; N-(tert-butyl)-3-(4-(2,5-dichlorobenzyl)piperazin-1-yl)quinoxalin-2-amine, 2,2,2-trifluoroacetic acid salt; 3-(4-(2,5-dichlorobenzyl)piperazin-1-yl)-N-(3,3-dimethylbutyl)quinoxalin-2-amine, 2,2,2-trifluoroacetic acid salt; 3-(4-(2, 5-dichlorobenzyl)piperazin-1-yl)-N-(2-ethoxyethyl)-quinoxalin-2-amine, 2,2,2-trifluoroacetic acid salt; 3-(4-(2,5-dichlorobenzyl)piperazin-1-yl)-N-(2-isopropoxyethyl) quinoxalin-2-amine, 2,2,2-trifluoroacetic acid salt; 3-(4-(2,5-dichlorobenzyl)piperazin-1-yl)-N-(3-ethoxypropyl) quinoxalin-2-amine, 2,2,2-trifluoroacetic acid salt; N-cyclohexyl-3-(4-((2,5-dichlorobenzyl)piperazin-1-yl)quinoxalin-2-amine, 2,2,2-trifluoroacetic acid salt; 3-(4-(2,5-dichlorobenzyl)piperazin-1-yl)-N-(tetrahydro-2H-pyran-4-yl)quinoxalin-2-amine, 2,2,2-trifluoroacetic acid salt; and (R)-2-((3-(4-(2,5-dichlorobenzyl)-piperazin-1-yl)quinoxalin-2-yl)amino)propan-1-ol, 2,2,2-trifluoroacetic acid salt Example 25

Synthesis of (R/S)—N-cyclopropyl-3-(4-((2,4-difluorophenyl)fluoromethyl)piperidin-1-yl)pyrido[3,4-b]pyrazin-2-amine

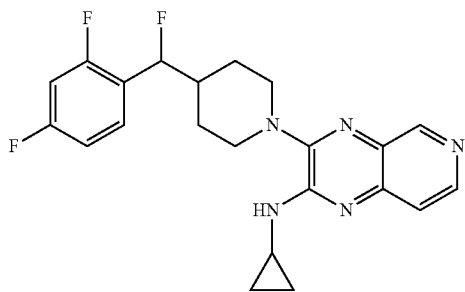 [SMILES: Fc1ccc(C(F)C2CCN(c3nc4cnccc4nc3NC3CC3)CC2)c(F)c1]

Step 1: (1-(2-(cyclopropylamino)pyrido[3,4-b]pyrazin-3-yl)piperidin-4-yl)(2,4-difluorophenyl)methanol To a solution of (1-(2-(cyclopropylamino)pyrido[3,4-b]pyrazin-3-yl)piperidin-4-yl)(2,4-difluorophenyl)methanone, TFA (50 mg, 0.096 mmol) in MeOH (478 µl) was added NaBH₄ (10.84 mg, 0.287 mmol). The mixture was stirred at RT for 2 h then purified by ISCO (0-100% EtOAc/hexanes) to yield the title compound as a colorless oil.

Step 2: (R/S)—N-cyclopropyl-3-(4-((2,4-difluorophenyl)fluoromethyl)piperidin-1-yl)pyrido[3,4-b]pyrazin-2-amine To a −78° C. solution of (1-(2-(cyclopropylamino)pyrido[3,4-b]pyrazin-3-yl)piperidin-4-yl)(2,4-difluorophenyl)methanol (7 mg, 0.017 mmol) in CH₂Cl₂ (85 µl) was added DAST (6.74 µl, 0.051 mmol). The reaction mixture was stirred for 30 min then quenched with a few drops of MeOH. ISCO purification (0-100% EtOAc/hexanes) yielded the title compound as a colorless oil. MS (ESI, pos. ion) m/z: 414.3 (M+1)

Note: Optically pure final compounds were obtained by chiral SFC separation of racemic compound.

Utilizing similar reaction conditions described above, following compounds were synthesized:

(R/S)—N-cyclopropyl-3-(4-(fluoro (4-fluorophenyl) methyl)piperidin-1-yl)pyrido[3,4-b]pyrazin-2-amine; (R/S)-3-(4-((5-chloro-2-fluorophenyl)fluoromethyl)piperidin-1-yl)-N-cyclopropylpyrido[3,4-b]pyrazin-2-amine; (R/S)—N-cyclopropyl-3-(4-((2,5-difluorophenyl)-fluoromethyl) piperidin-1-yl)-7-methylpyrido[3,4-b]pyrazin-2-amine; and (R/S)—N-cyclopropyl-3-(4-((2,5-difluorophenyl)fluoromethyl)piperidin-1-yl)pyrido[3,4-b]pyrazin-2-amine Example 26

Synthesis of (S)—N-cyclopropyl-3-(4-((2,4-difluorophenyl)fluoromethyl)piperidin-1-yl)-7-methylpyrido[3,4-b]pyrazin-2-amine 2,2,2-trifluoroacetate

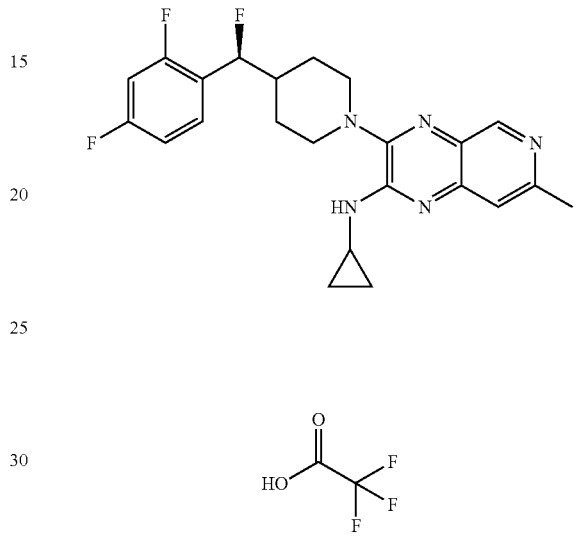

To a solution of 3-chloro-N-cyclopropyl-7-methylpyrido [3,4-b]pyrazin-2-amine (10 mg, 0.043 mmol) in dioxane (85 µl) was added (S)-4-((2,4-difluorophenyl)fluoromethyl)piperidine, HCl (14.72 mg, 0.055 mmol) and iPr₂EtN (29.8 µl, 0.170 mmol). The mixture was heated at 80° C. for 2 h. HPLC purification afforded the title compound as a yellow oil. MS (ESI, pos. ion) m/z: 428.3 (M+1)

Utilizing similar reaction conditions described above, following compounds were synthesized using chiral intermediate compounds: (R)—N-cyclopropyl-3-(4-((2,4-difluorophenyl)-fluoromethyl)piperidin-1-yl)-7-methylpyrido[3,4-b]pyrazin-2-amine, 2,2,2-trifluoroacetic acid salt; (S)-2-(cyclopropylamino)-3-(4-((2,4-difluorophenyl)fluoromethyl)-piperidin-1-yl)quinoxaline-6-carbonitrile, 2,2,2-trifluoroacetic acid salt; (S)—N-cyclopropyl-3-(4-((2,4-difluorophenyl)fluoromethyl) piperidin-1-yl)-5-methylpyrido[3,4-b]pyrazin-2-amine, 2,2,2-trifluoroacetic acid salt; (S)—N-cyclopropyl-3-(4-((2,4-difluorophenyl)fluoromethyl)piperidin-1-yl)pyrido[3,4-b] pyrazin-2-amine, 2,2,2-trifluoroacetic acid salt; (R)-2-(cyclopropylamino)-3-(4-((2,4-difluorophenyl) fluoromethyl)piperidin-1-yl)quinoxaline-6-carbonitrile, 2,2,2-trifluoroacetic acid salt; (R)-7-chloro-N-cyclopropyl-3-(4-((2,4-difluorophenyl)-fluoromethyl)piperidin-1-yl)pyrido[3,4-b]pyrazin-2-amine, 2,2,2-trifluoroacetic acid salt; and (S)-7-chloro-N-cyclopropyl-3-(4-((2,4-difluorophenyl) fluoromethyl)piperidin-1-yl)pyrido[3,4-b]pyrazin-2-amine, 2,2,2-trifluoroacetic acid salt.

Example 27

Synthesis of (R/S)-3-(4-(1-(5-chloro-2-fluorophenyl)-1-fluoroethyl)piperidin-1-yl)-N-cyclopropylpyrido[3,4-b]pyrazin-2-amine

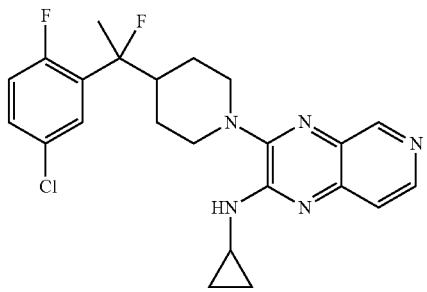 [SMILES: CC(F)(c1cc(Cl)ccc1F)C1CCN(c2nc3cnccc3nc2NC2CC2)CC1]

Step 1: 1-(5-chloro-2-fluorophenyl)-1-(1-(2-(cyclopropylamino)pyrido[3,4-b]pyrazin-3-yl)piperidin-4-yl)ethanol To a −78° C. solution of (5-chloro-2-fluorophenyl)(1-(2-(cyclopropylamino)-pyrido[3,4-b]pyrazin-3-yl)piperidin-4-yl)methanone, TFA (18 mg, 0.033 mmol) in THF (167 μl) was added methyl magnesium bromide (33.3 μl, 0.100 mmol, 3 M in Et₂O). The mixture was stirred at −78° C. for 1 h then RT for 1 h. A few drops of H₂O were added to quench the reaction, which was then filtered through a syringe filter and the solvents were removed under reduced pressure to yield the title compound as a tan solid.

Step 2: (R/S)-3-(4-(1-(5-chloro-2-fluorophenyl)-1-fluoroethyl)piperidin-1-yl)-N-cyclopropylpyrido[3,4-b]pyrazin-2-amine To a −78° C. solution of 1-(5-chloro-2-fluorophenyl)-1-(1-(2-(cyclopropylamino)-pyrido[3,4-b]pyrazin-3-yl)piperidin-4-yl)ethanol (13 mg, 0.029 mmol) in CH₂Cl₂ (147 μl) was added DAST (11.66 μl, 0.088 mmol). The mixture was stirred at −78° C. for 30 min then warmed to 10° C. and added another 3 eq DAST (11.66 μl, 0.088 mmol). The reaction mixture was quenched with a few drops of H₂O and ISCO purification (30-100% EtOAc/hexanes) afforded the title compound as a colorless oil. MS (ESI, pos. ion) m/z: 444.2 (M+1)

Example 28

Synthesis of (R/S)-3-(4-((2,5-difluorophenyl)fluoromethyl)piperidin-1-yl)-2-(isopropylamino)quinoxaline-6-carbonitrile, 2,2,2-trifluoroacetic acid salt

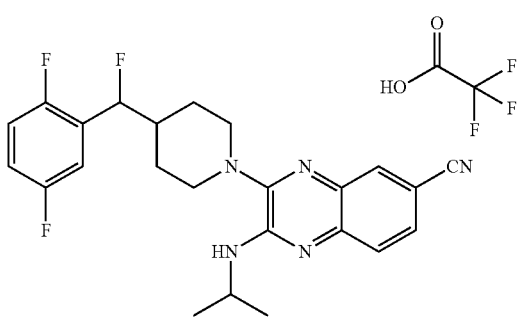

A solution of (R/S)-4-((2,5-difluorophenyl)fluoromethyl)piperidine hydrochloride (28 mg, 0.105 mmol) and 3-chloro-2-(isopropylamino)quinoxaline-6-carbonitrile (20 mg, 0.081 mmol) in dioxane (162 μl) and DIPEA (42.5 μl, 0.243 mmol) was stirred at 75° C. for 3 h. HPLC purification afforded the title compound as an ivory solid. MS (ESI, pos. ion) m/z: 440.3 (M+1)

Note: Optically pure final compounds were obtained by chiral SFC separation of racemic compound.

Utilizing similar reaction conditions described above, following compounds were synthesized:
(R/S)-2-(cyclopropylamino)-3-(4-((2,4-difluorophenyl)fluoromethyl)piperidin-1-yl)quinoxaline-6-carbonitrile;
(R/S)-3-(4-((2,4-difluorophenyl)fluoromethyl)piperidin-1-yl)-2-(isopropylamino)quinoxaline-6-carbonitrile; and
(R/S)-3-(cyclopropylamino)-2-(4-((2,4-difluorophenyl)fluoromethyl)piperidin-1-yl)quinoxaline-6-carbonitrile.

Example 29

Synthesis of (S)-2-(cyclopropylamino)-3-(4-((2,4-difluorophenyl)fluoromethyl)piperidin-1-yl)pyrido[3,4-b]pyrazine-7-carbonitrile

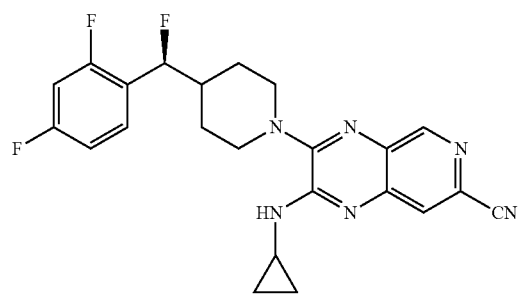 [SMILES: N#Cc1cc2nc(NC3CC3)c(N3CCC([C@H](F)c4ccc(F)cc4F)CC3)nc2cn1]

Step 1: 7-bromo-3-chloro-N-cyclopropylpyrido[3,4-b]pyrazin-2-amine

To solution of 7-bromo-2,3-dichloropyrido[3,4-b]pyrazine (90 mg, 0.323 mmol) in DCM (1613 μl) at 0° C. was added a solution of cyclopropanamine (26.8 μl, 0.387 mmol) in DCM (0.2 mL), followed by the addition of DIPEA (169 μl, 0.968 mmol). The resulting solution was stirred at 0° C. for 2 h. ISCO purification (0-50% EtOAc/Hexanes) gave the title compound as an off-white solid.

Step 2: (S)-7-bromo-N-cyclopropyl-3-(4-((2,4-difluorophenyl)fluoromethyl)piperidin-1-yl)pyrido[3,4-b]pyrazin-2-amine A mixture of 7-bromo-3-chloro-N-cyclopropylpyrido[3,4-b]pyrazin-2-amine (30 mg, 0.100 mmol), (S)-4-((2,4-difluorophenyl)fluoromethyl)piperidine, HCl (31.9 mg, 0.120 mmol) and DIPEA (0.052 ml, 0.300 mmol) in dioxane (0.3 ml) was heated at 80° C. for 8 h. Silica gel column chromatography purification gave the title compound as a white solid.

Step 3: (S)-2-(cyclopropylamino)-3-(4-((2,4-difluorophenyl)fluoromethyl)piperidin-1-yl)pyrido[3,4-b]pyrazine-7-carbonitrile To a vial was added (S)-7-bromo-N-cyclopropyl-3-(4-((2,4-difluorophenyl)-fluoromethyl)piperidin-1- yl)pyrido[3,4- b]pyrazin-2-amine (25 mg, 0.051 mmol), Pd$_2$(dba)$_3$ (2.325 mg, 2.54 μmol), dicyanozinc (3.58 mg, 0.030 mmol) and dppf (2.82 mg, 5.08 μmol) in NMP (508 μl). The vial was evacuated and filled with N$_2$ (3×) then heated at 120° C. for 2 h. HPLC and ISCO purification afforded the title compound as a white solid. MS (ESI, pos. ion) m/z: 439.2 (M+1)

Utilizing similar reaction conditions described above, using reference compounds, the following compounds were synthesized: (R)-2-(cyclopropylamino)-3-(4-((2,4-difluorophenyl)fluoromethyl)piperidin-1-yl)pyrido[3,4-b]pyrazine-7-carbonitrile; 3-(4-(2-fluoro-4-methoxyphenoxy)piperidin-1-yl)-2-(isopropylamino)pyrido[3,4-b]pyrazine-7-carbonitrile, 2,2,2-trifluoroacetic acid salt; 3-(4-(2,5-difluorobenzoyl)piperidin-1-yl)-2-(isopropylamino)pyrido[3,4-b]pyrazine-7-carbonitrile, 2,2,2-trifluoroacetic acid salt; 3-(4-(2-fluoro-4-methoxybenzyl)piperidin-1-yl)-2-(isopropylamino)pyrido[3,4-b]pyrazine-7-carbonitrile, 2,2,2-trifluoroacetic acid salt; 2-((2,2-difluoroethyl)amino)-3-(4-(2,4-difluorophenoxyl)piperidin-1-yl)pyrido[3,4-b]pyrazine-7-carbonitrile, 2,2,2-trifluoroacetic acid salt; 2-(tert-butylamino)-3-(4-(2,4-difluorophenoxyl)piperidin-1-yl)pyrido[3,4-b]pyrazine-7-carbonitrile Example 30

Synthesis of (S)-3-(cyclopropylamino)-2-(4-((2,4-difluorophenyl)fluoromethyl)piperidin-1-yl)pyrido[3,4-b]pyrazine-7-carbonitrile

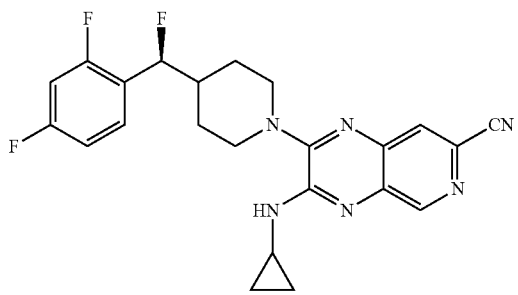 [SMILES: N#Cc1cc2nc(N3CCC([C@H](F)c4ccc(F)cc4F)CC3)c(NC3CC3)nc2cn1]

Step 1: (S)-7-bromo-3-chloro-2-(4-((2,4-difluorophenyl)fluoromethyl)piperidin-1-yl)pyrido[3,4-b]pyrazine To a mixture of 7-bromo-2,3-dichloropyrido[3,4-b]pyrazine (30 mg, 0.108 mmol) in DCM (1 ml) at 0° C. was added (S)-4-((2,4-difluorophenyl)fluoromethyl)piperidine, HCl (31.4 mg, 0.118 mmol), followed by addition of N-ethyl-N-isopropylpropan-2-amine (0.056 ml, 0.323 mmol). The resulting mixture was stirred at 0° C. for 2 h. ISCO purification gave the title compound as a yellow solid.

Step 2: (S)-7-bromo-N-cyclopropyl-2-(4-((2,4-difluorophenyl)fluoromethyl)piperidin-1-yl)pyrido[3,4-b]pyrazin-3-amine A solution of (S)-7-bromo-3-chloro-2-(4-((2,4-difluorophenyl)fluoromethyl)piperidin-1-yl)pyrido[3,4-b]pyrazine (40 g, 85 mmol), cyclopropanamine (38.7 g, 678 mmol) and DIPEA (22.22 ml, 127 mmol) in dioxane (0.3 ml) was heated at 80° C. for 24 h. Silica gel column chromatography purification gave the title compound as a white solid.

Step 3: (S)-3-(cyclopropylamino)-2-(4-((2,4-difluorophenyl)fluoromethyl)piperidin-1-yl)pyrido[3,4-b]pyrazine-7-carbonitrile To a vial was added (S)-7-bromo-N-cyclopropyl-2-(4-((2,4-difluorophenyl)-fluoromethyl)piperidin-1-yl)pyrido[3,4-b]pyrazin-3-amine (17 mg, 0.035 mmol), Pd$_2$(dba)$_3$ (1.581 mg, 1.726 μmol), dicyanozinc (2.433 mg, 0.021 mmol) and dppf (1.914 mg, 3.45 μmol) in NMP (345 μl). The vial was evacuated and filled with N$_2$ (3×) then heated at 120° C. for 2 h. HPLC and ISCO purification afforded the title compound as a white solid. MS (ESI, pos. ion) m/z: 439.2 (M+1).

Utilizing similar reaction conditions described above, (R)-3-(cyclopropylamino)-2-(4-((2,4-difluorophenyl)-fluoromethyl)piperidin-1-yl)pyrido[3,4-b]pyrazine-7-carbonitrile was synthesized.

Example 31

Synthesis of 2,2,2-trifluoroacetic acid, 1-(4-((1-(2-(cyclopropylamino)pyrido[3,4-b]pyrazin-3-yl)piperidin-4-yl)oxy)phenyl)ethanol salt

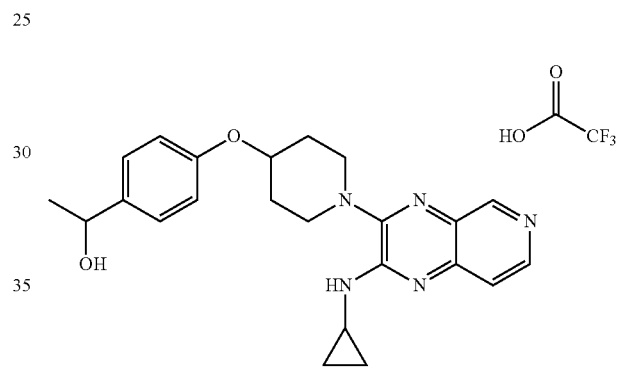

A 5 mL screwtop vial containing 1-(4-((1-(2-(cyclopropylamino)pyrido[3,4-b]pyrazin-3-yl)piperidin-4-yl)oxy)phenyl)ethanone 2,2,2-trifluoroacetate (130 mg, 0.251 mmol) and sodium tetrahydroborate (28.5 mg, 0.754 mmol) in MeOH (1256 μl) was stirred for 30 min. HPLC purification afforded the title compound as a clear oil. MS (ESI, pos. ion) m/z: 406.3 (M+1).

Example 32

Synthesis of 2-(4-(4-chloro-2-fluorophenoxy)piperidin-1-yl)-3-(isopropylamino)quinoxaline-6-carbonitrile

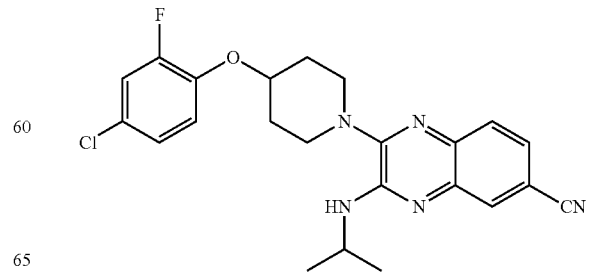

Step 1: 3-chloro-2-(4-(4-chloro-2-fluorophenoxy) piperidin-1-yl)quinoxaline-6-carbonitrile To a solution of 2,3-dichloroquinoxaline-6-carbonitrile (400 mg, 1.785 mmol) and 4-(4-chloro-2-fluorophenoxy) piperidine (615 mg, 2.68 mmol) in dichloromethane (40 ml) was added triethylamine (0.025 ml, 0.179 mmol), which was stirred at 20° C. for 6 h. Water was added and the reaction was extracted with dichloromethane (2×) and the combined organic layers were concentrated. Purification by column chromatography (PE:EtOAc=50:1) afforded the title compound as a yellow solid.

Step 2: 2-(4-(4-chloro-2-fluorophenoxy)piperidin-1-yl)-3-(isopropylamino)quinoxaline-6-carbonitrile To a solution of 3-chloro-2-(4-(4-chloro-2-fluorophenoxy)piperidin-1-yl)quinoxaline-6-carbonitrile (100 mg, 0.240 mmol) in DMSO (10 ml) was added triethylamine (0.033 ml, 0.240 mmol) and propan-2-amine (142 mg, 2.397 mmol), which was stirred at 120° C. for 16 h. HPLC purification afforded the title compound as a yellow solid. MS (ESI, pos. ion) m/z: 439.8 (M+1).

Utilizing similar reaction conditions described above, 2-(4-(2-chloro-5-(isopropylamino)benzoyl)piperidin-1-yl)-3-(isopropylamino)quinoxaline-6-carbonitrile was synthesized.

Example 33

Synthesis of 3-(4-(2,4-difluorophenoxyl)piperidin-1-yl)-2-(isopropylamino)-N,N-dimethylpyrido[3,4-b]pyrazine-7-carboxamide, 2,2,2-trifluoroacetic acid salt

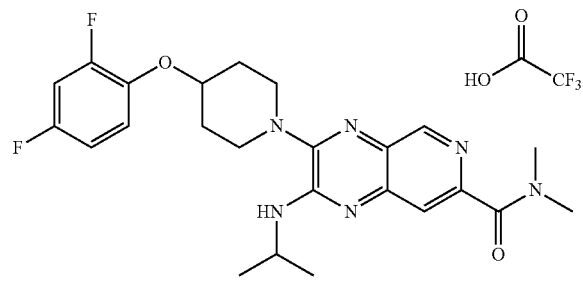 [SMILES: CC(C)Nc1nc2cc(C(=O)N(C)C)ncc2nc1N1CCC(Oc2ccc(F)cc2F)CC1 ; O=C(O)C(F)(F)F]

Step 1: 7-bromo-3-(4-(2,4-difluorophenoxyl)piperidin-1-yl)-N-isopropylpyrido[3,4-b]pyrazin-2-amine A solution of 4-(2,4-difluorophenoxyl)piperidine hydrochloride (150 mg, 0.599 mmol) and 7-bromo-3-chloro-N-isopropylpyrido[3,4-b]pyrazin-2-amine (139 mg, 0.461 mmol) in dioxane (922 μl) and DIPEA (242 μl, 1.383 mmol) was stirred at 90° C. for 4 h. ISCO purification (40% EtOAc in hexanes) afforded the title compound as an orange solid.

Step 2: 3-(4-(2,4-difluorophenoxyl)piperidin-1-yl)-2-(isopropylamino)-N,N-dimethylpyrido[3,4-b]pyrazine-7-carboxamide, 2,2,2-trifluoroacetic acid salt A solution of 7-bromo-3-(4-(2,4-difluorophenoxyl)piperidin-1-yl)-N-isopropylpyrido[3,4-b]pyrazin-2-amine (30 mg, 0.063 mmol), phenyl formate (13.68 μl, 0.125 mmol), diacetoxypalladium (2.82 mg, 0.013 mmol), (9,9-dimethyl-9H-xanthene-4,5-diyl)bis(diphenylphosphine) (14.52 mg, 0.025 mmol) and triethylamine (17.48 μl, 0.125 mmol) in MeCN (314 μl) was stirred at 80° C. overnight. Dimethylamine (157 μl, 0.314 mmol) was then added and stirring continued at 80° C. for 1 h. HPLC purification afforded the title compound as a yellow solid. MS (ESI, pos. ion) m/z: 471.3 (M+1).

Utilizing similar reaction conditions described above, the following compounds were synthesized: 3-(4-(4-chloro-2-fluorophenoxy)piperidin-1-yl)-2-(isopropylamino)-N,N-dimethylpyrido[3,4-b]pyrazine-7-carboxamide, 2,2,2-trifluoroacetic acid salt; 3-(4-(2,4-difluorobenzyl)piperazin-1-yl)-2-(isopropylamino)-N,N-dimethylpyrido[3,4-b]pyrazine-7-carboxamide, 2,2,2-trifluoroacetic acid salt; 3-(4-(2,5-difluorobenzoyl)piperidin-1-yl)-2-(isopropylamino)-N,N-dimethylpyrido[3,4-b]pyrazine-7-carboxamide, 2,2,2-trifluoroacetic acid salt; (S)-2-(cyclopropylamino)-3-(4-((2,4-difluorophenyl)fluoromethyl)piperidin-1-yl)-N,N-dimethylpyrido[3,4-b]pyrazine-7-carboxamide, 2,2,2-trifluoroacetic acid salt; (R)-2-(cyclopropylamino)-3-(4-((2,4-difluorophenyl)fluoromethyl)piperidin-1-yl)-N,N-dimethylpyrido[3,4-b]pyrazine-7-carboxamide, 2,2,2-trifluoroacetic acid salt; (S)-2-(cyclopropylamino)-3-(4-((2,4-difluorophenyl)fluoromethyl)piperidin-1-yl)pyrido[3,4-b]pyrazin-7-yl)(morpholino)methanone, 2,2,2-trifluoroacetic acid salt; (R)-(2-(cyclopropylamino)-3-(4-((2,4-difluorophenyl)fluoromethyl)piperidin-1-yl)pyrido[3,4-b]pyrazin-7-yl)(morpholino)methanone, 2,2,2-trifluoroacetic acid salt; (2-(cyclopropylamino)-3-(4-(2-fluoro-4-methoxyphenoxy)piperidin-1-yl)pyrido[3,4-b]pyrazin-7-yl)(4-methylpiperazin-1-yl)methanone; 2,2,2-trifluoroacetic acid salt; (2-(cyclopropylamino)-3-(4-(2,4-difluorobenzyl)piperazin-1-yl)pyrido[3,4-b]pyrazin-7-yl)(morpholino)methanone, 2,2,2-trifluoroacetic acid salt; 2-(cyclopropylamino)-3-(4-(2-fluoro-4-methoxybenzyl)piperazin-1-yl)-N,N-dimethylpyrido[3,4-b]pyrazine-7-carboxamide, 2,2,2-trifluoroacetic acid salt; 2-((2,2-difluoroethyl)amino)-3-(4-(2,4-difluorophenoxyl)piperidin-1-yl)-N,N-dimethylpyrido[3,4-b]pyrazine-7-carboxamide, 2,2,2-trifluoroacetic acid salt; 2-(cyclopropylamino)-3-(4-(2,4-difluorophenoxyl)piperidin-1-yl)-N,N-dimethylpyrido[3,4-b]pyrazine-7-carboxamide;

Example 34

Synthesis of 3-(4-(2-fluoro-4-methoxyphenoxy) piperidin-1-yl)-N-isopropylpyrazino[2,3-d] pyridazin-2-amine, 2,2,2-trifluoroacetic acid salt

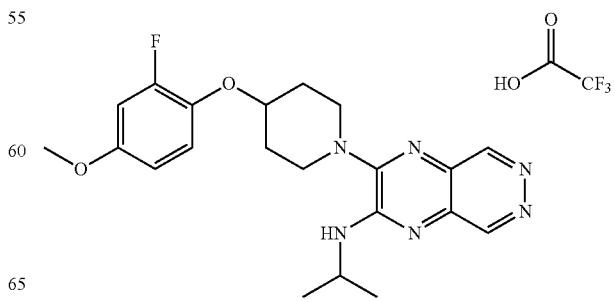

Step 1: pyrazino[2,3-d]pyridazine-2,3(1H,4H)-dione

A mixture of pyridazine-4,5-diamine (4 g, 36.3 mmol) and di(1H-imidazol-1-yl)methanone (7.07 g, 43.6 mmol) in DMF (145 ml) was heated at 75° C. for 16 h. Then 60 mL THF was added and the reaction mixture was stirred at RT for 1 h. Filtration, followed by wash with THF, gave the title compound as a grey powder. The material was used directly in the next step without further purification.

Step 2: 2,3-dichloropyrazino[2,3-d]pyridazine

A mixture of pyrazino[2,3-d]pyridazine-2,3(1H,4H)-dione (1 g, 6.09 mmol) in phosphoryl trichloride (22.72 ml, 244 mmol) was heated at 133° C. for 24 h. After removal of $POCl_3$ in vacuo, ice was added to the reaction flask. Then, 120 mL cold ethyl acetate was added and the mixture was made basic with sat. $NaHCO_3$ while at 0° C. After filtration, the organic layer was quickly separated and dried with $Na_2SO_4$. After the drying agent was filtered off, the filtrate was used immediately in the next step without further purification.

Step 3: 3-chloro-N-isopropylpyrazino[2,3-d]pyridazin-2-amine

Half of the above ethyl acetate solution was transferred to a reaction flask at 0° C., then propan-2-amine (0.052 ml, 0.607 mmol) and DIPEA (0.530 ml, 3.03 mmol) was added. The reaction mixture was stirred at 0° C. for 15 min and then used in the next step without purification.

Step 4: 3-(4-(2-fluoro-4-methoxyphenoxy)piperidin-1-yl)-N-isopropylpyrazino[2,3-d]pyridazin-2-amine, 2,2,2-trifluoroacetic acid salt Half of the reaction solution was transferred to a reaction flask at 0° C., and then 4-(2-fluoro-4-methoxyphenoxy)piperidine, HCl (0.199 g, 0.760 mmol) and N-ethyl-N-isopropylpropan-2-amine (0.265 ml, 1.520 mmol) were added. The reaction mixture was stirred at 0° C. for 1 h and at RT for 2 h. HPLC purification afforded the title compound as a brown solid. MS (ESI, pos. ion) m/z: 413.4 (M+1).

Utilizing similar reaction conditions described above, the following compounds were synthesized: (S)—N-cyclopropyl-3-(4-((2,4-difluorophenyl)fluoromethyl)piperidin-1-yl)pyrazino[2,3-d]pyridazin-2-amine, 2,2,2-trifluoroacetic acid salt; N-cyclopropyl-3-(4-(2-fluoro-4-methoxyphenoxy)piperidin-1-yl)pyrazino[2,3-d]pyridazin-2-amine, 2,2,2-trifluoroacetic acid salt; (R)—N-cyclopropyl-3-(4-((2,4-difluorophenyl)fluoromethyl)piperidin-1-yl)pyrazino[2,3-d]pyridazin-2-amine, 2,2,2-trifluoroacetic acid salt; N-cyclopropyl-3-(4-(2-fluoro-4-(methylthio)phenoxy)piperidin-1-yl)pyrazino[2,3-d]pyridazin-2-amine, 2,2,2-trifluoroacetic acid salt; N-cyclopropyl-3-(4-(2,4-difluorophenoxy)piperidin-1-yl)pyrazino[2,3-d]pyridazin-2-amine, 2,2,2-trifluoroacetic acid salt; 4-((1-(3-(cyclopropylamino)pyrazino[2,3-d]pyridazin-2-yl)piperidin-4-yl)oxy)-3-fluorophenol; 3-(4-(2,4-difluorophenoxy)piperidin-1-yl)-N-isopropylpyrazino[2,3-d]pyridazin-2-amine, 2,2,2-trifluoroacetic acid salt; 3-(4-((2,4-difluorophenyl)fluoromethyl)piperidin-1-yl)-N-isopropylpyrazino[2,3-d]pyridazin-2-amine, 2,2,2-trifluoroacetic acid salt; (S)—N-(sec-butyl)-3-(4-(2-fluoro-4-methoxyphenoxy)piperidin-1-yl)pyrazino[2,3-d]pyridazin-2-amine, 2,2,2-trifluoroacetic acid salt; (R)—N-(sec-butyl)-3-(4-(2-fluoro-4-methoxyphenoxy)piperidin-1-yl)pyrazino[2,3-d]pyridazin-2-amine, 2,2,2-trifluoroacetic acid salt; 3-fluoro-4-((1-(3-(isopropylamino)pyrazino[2,3-d]pyridazin-2-yl)piperidin-4-yl)oxy)benzonitrile, 2,2,2-trifluoroacetic acid salt; (R)-3-(4-((2,4-difluorophenyl)fluoromethyl)piperidin-1-yl)-N-isopropylpyrazino[2,3-d]pyridazin-2-amine, 2,2,2-trifluoroacetic acid salt; (2-fluoro-4-methoxyphenyl)(1-(3-(isopropylamino)pyrazino[2,3-d]pyridazin-2-yl)piperidin-4-yl)methanone, 2,2,2-trifluoroacetic acid salt; 3-(4-(2-fluoro-4-methoxybenzyl)piperidin-1-yl)-N-isopropylpyrazino[2,3-d]pyridazin-2-amine, 2,2,2-trifluoroacetic acid salt; 3-(4-(4-chloro-2-fluorophenoxy)piperidin-1-yl)-N-isopropylpyrazino[2,3-d]pyridazin-2-amine, 2,2,2-trifluoroacetic acid salt; 3-(4-((R)-(2,4-difluorophenyl)fluoromethyl)piperidin-1-yl)-N-((1R,2R)-2-methylcyclopropyl)pyrazino[2,3-d]pyridazin-2-amine, 2,2,2-trifluoroacetic acid salt; 3-(4-(2,4-difluorobenzyl)piperazin-1-yl)-N-isopropylpyrazino[2,3-d]pyridazin-2-amine 2,2,2-trifluoroacetate; N-isopropyl-3-(4-(3-methoxyphenoxyl)piperidin-1-yl)pyrazino[2,3-d]pyridazin-2-amine 2,2,2-trifluoroacetate; 3-(4-(4-chloro-2-fluorophenoxy)piperidin-1-yl)-N-cyclopropylpyrazino[2,3-d]pyridazin-2-amine 2,2,2-trifluoroacetate; 3-(4-(2-fluoro-4-(fluoromethoxy)phenoxy)piperidin-1-yl)-N-isopropylpyrazino[2,3-d]pyridazin-2-amine.

Example 35

Synthesis of 2-(cyclopropylamino)-3-(4-(2-fluoro-4-methoxyphenoxy)piperidin-1-yl)-N,N-dimethylpyrido[3,4-b]pyrazine-5-carboxamide

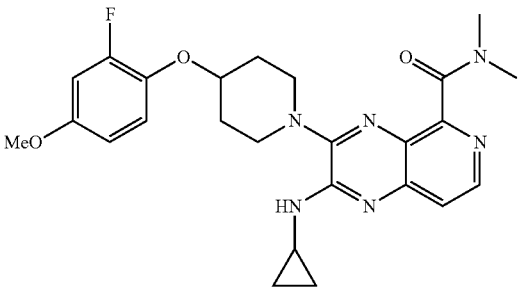 [SMILES: COc1ccc(OC2CCN(c3nc4c(C(=O)N(C)C)nccc4nc3NC3CC3)CC2)c(F)c1]

A vial was charged with 5-chloro-N-cyclopropyl-3-(4-(2-fluoro-4-methoxyphenoxy)piperidin-1-yl)pyrido[3,4-b]pyrazin-2-amine (40 mg, 0.090 mmol), diacetoxypalladium (4.05 mg, 0.018 mmol), (9,9-dimethyl-9H-xanthene-4,5-diyl)bis(diphenylphosphine) (20.86 mg, 0.036 mmol), phenyl formate (22.01 mg, 0.180 mmol) and triethylamine (24.91 µl, 0.180 mmol). The vial was purged with nitrogen and MeCN (410 µl) was added. The mixture was heated at 100° C. for 14 h. Then, dimethylamine (225 µl, 0.451 mmol) in THF was added and the mixture was stirred at RT for 2 h. HPLC purification afforded the title compound as a yellow solid. MS (ESI, pos. ion) m/z: 481.4 (M+1).

Utilizing similar reaction conditions described above, and using commercially available amines, the following compounds were synthesized: (2-(cyclopropylamino)-3-(4-(2-fluoro-4-methoxyphenoxy)piperidin-1-yl)pyrido[3,4-b]pyrazin-5-yl)(morpholino)methanone, 2,2,2-trifluoroacetic acid salt; azetidin-1-yl(2-(cyclopropylamino)-3-(4-(2-fluoro-4-methoxyphenoxy)piperidin-1-yl)pyrido[3,4-b]pyrazin-5-yl)methanone, 2,2,2-trifluoroacetic acid salt.

Example 36

Synthesis of 2-(cyclopropylamino)-3-(4-(2-fluoro-4-methoxyphenoxy)piperidin-1-yl)pyrido[3,4-b]pyrazine-5-carbonitrile, 2,2,2-trifluoroacetic acid salt

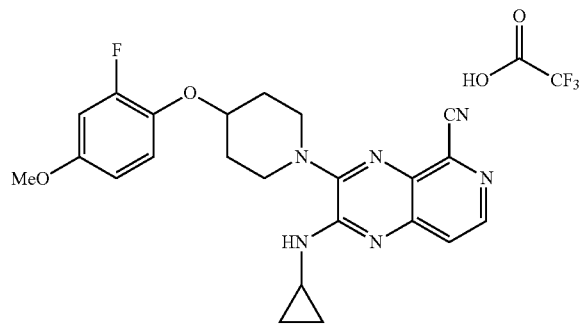

To a vial was added 5-chloro-N-cyclopropyl-3-(4-(2-fluoro-4-methoxyphenoxy)piperidin-1-yl)pyrido[3,4-b]pyrazin-2-amine (22 mg, 0.050 mmol), dicyanozinc (5.82 mg, 0.050 mmol), zinc (2.59 mg, 0.040 mmol), bis(2,2,2-trifluoroacetyl)palladium (4.47 mg, 0.015 mmol) and [1,1'-binaphthalen]-2-yldi-tert-butylphosphine (11.85 mg, 0.030 mmol). After purging with nitrogen for 2 min, NMP (248 µl) was added. The resulting reaction mixture was heated at 100° C. overnight. HPLC purification yielded the title compound as a light yellow film. MS (ESI, pos. ion) m/z: 435.3 (M+1).

Utilizing similar reaction conditions described above, and using reference compounds, the following compounds were synthesized: 2-(cyclopropylamino)-3-(4-(2,4-difluorobenzyl)piperazin-1-yl)pyrido[3,4-b]pyrazine-5-carbonitrile, 2,2,2-trifluoroacetic acid salt; 2-(cyclopropylamino)-3-(4-(2-fluoro-4-methoxybenzyl)piperazin-1-yl)pyrido[3,4-b]pyrazine-5-carbonitrile, 2,2,2-trifluoroacetic acid salt.

Example 37

Synthesis of N-cyclopropyl-3-(4-(2-fluoro-4-methoxyphenoxy)piperidin-1-yl)-5-morpholinopyrido[3,4-b]pyrazin-2-amine, 2,2,2-trifluoroacetic acid salt

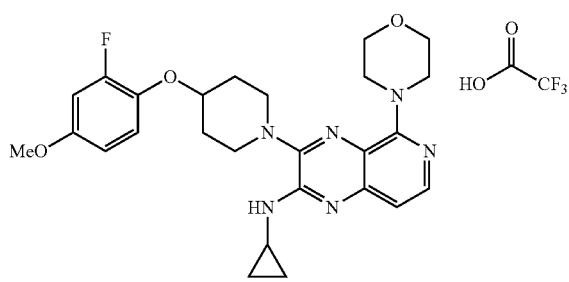

A solution of 5-chloro-N-cyclopropyl-3-(4-(2-fluoro-4-methoxyphenoxy)piperidin-1-yl)pyrido[3,4-b]pyrazin-2-amine (13 mg, 0.029 mmol), morpholine (3.83 µl, 0.044 mmol) and DIPEA (0.015 ml, 0.088 mmol) in dioxane (0.25 ml) was heated at 150° C. overnight. HPLC purification gave the title compound as white solid. MS (ESI, pos. ion) m/z: 495.4 (M+1).

Utilizing similar reaction conditions described above, and using commercially available amines, the following compounds were synthesized: N2-cyclopropyl-3-(4-(2-fluoro-4-methoxyphenoxy)piperidin-1-yl)-N5,N5-dimethylpyrido[3,4-b]pyrazine-2,5-diamine, 2,2,2-trifluoroacetic acid salt.

Example 38

Synthesis of 2-(4-(2,4-difluorophenoxyl)piperidin-1-yl)-N-isopropylpyrido[3,4-b]pyrazin-3-amine

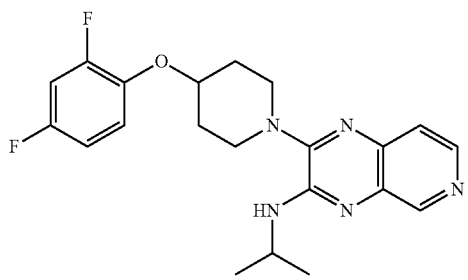 [SMILES: CC(C)Nc1nc2cnccc2nc1N1CCC(Oc2ccc(F)cc2F)CC1]

Step 1: 3-chloro-2-(4-(2,4-difluorophenoxyl)piperidin-1-yl)pyrido[3,4-b]pyrazine A 500 mL round bottom flask equipped with a stir bar, septum, and N2 inlet was charged with 2,3-dichloropyrido[3,4-b]pyrazine (9.0 g, 36.0 mmol), 4-(2,4-difluorophenoxyl)piperidine hydrochloride (9.44 g, 37.8 mmol), and DCM (90 ml) to furnish an orange suspension. Next, N-ethyl-N-isopropylpropan-2-amine (18.81 ml, 108 mmol) was added to the flask over 2 min at 0° C. The reaction mixture was stirred at 0° C. for 3 h under nitrogen to furnish an orange suspension. The reaction mixture was partitioned between saturated aqueous NH4Cl (100 mL), EtOAc (500 mL), MeOH (50 mL) and H2O (25 mL) to furnish two layers. The layers were separated and the aqueous phase was washed with EtOAc (2×100 mL). MeOH (10 mL) was added during each phase separation. The organic extracts were combined, washed with saturated NaHCO3 (100 mL), brine (100 mL), dried over Na2SO4, filtered, rinsed with EtOAc, and dried in vacuo. Purification by silica gel column (10-50% EtOAc in hexanes) provided the title compound as a yellow-orange solid.

Step 2: 2-(4-(2,4-difluorophenoxyl)piperidin-1-yl)-3-fluoropyrido[3,4-b]pyrazine To a vial charged with 3-chloro-2-(4-(2,4-difluorophenoxyl)piperidin-1-yl)pyrido[3,4-b]pyrazine (1.0 g, 2.65 mmol) and potassium fluoride (0.200 g, 3.45 mmol) was added DMSO (5.0 mL) in one portion at 23° C. The mixture was stirred at 23° C. for 2 h to furnish an orange suspension. The crude reaction mixture was used in the next step without further workup or purification.

Step 3: 2-(4-(2,4-difluorophenoxyl)piperidin-1-yl)-N-isopropylpyrido[3,4-b]pyrazin-3-amine To the crude reaction mixture of 2-(4-(2,4-difluorophenoxyl)piperidin-1-yl)-3-fluoropyrido[3,4-b]pyrazine was added N-ethyl-N-isopropylpropan-2-amine (0.924 mL, 5.31 mmol) and propan-2-amine (0.684 mL, 7.96 mmol) at 23° C.

to furnish a red solution. The reaction mixture was stirred at 23° C. for 20 h. The reaction mixture was diluted with H2O (20 mL) and stirred for 15 min at 23° C. to furnish an orange suspension. The resulting solid was filtered, rinsed with H2O and dried in vacuo. Purification on silica gel (0-100% ethyl acetate in heptanes) provided the title compound as a light yellow solid. MS (ESI, pos. ion) m/z: 400.0 (M+1).

Utilizing similar reaction conditions described above, and using commercially available amines, the following compound was synthesized: N-cyclobutyl-2-(4-(2,4-difluorophenoxyl)piperidin-1-yl)pyrido[3,4-b]pyrazin-3-amine.

Example 39

Synthesis of 3-(4-(2,4-difluorophenoxyl)piperidin-1-yl)-N-isopropyl-5,8-dimethylpyrazino[2,3-d]pyridazin-2-amine 2,2,2-trifluoroacetate

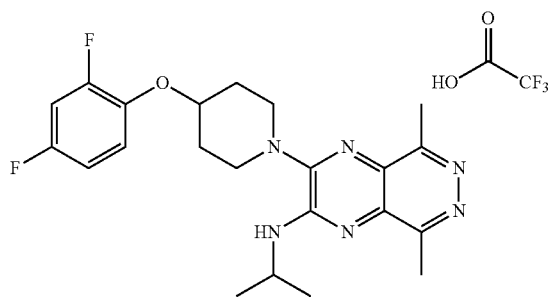

Step 1: 5-(4-(2,4-difluorophenoxyl)piperidin-1-yl)-6-(isopropylamino)pyrazine-2,3-dicarbaldehyde A solution of (5-(4-(2,4-difluorophenoxyl)piperidin-1-yl)-6-(isopropylamino)pyrazine-2,3-diyl)dimethanol (100 mg, 0.245 mmol) and Dess-Martin Periodinane (260 mg, 0.612 mmol) in DCM (2448 μl) was stirred at RT for 3 h. The reaction mixture was quenched with 2 mL sat. Na2S2O4 and sat. NaHCO3 and stirred at RT for 15 min. ISCO purification gave the title compound as a yellow solid.

Step 2: 1,1'-(5-(4-(2,4-difluorophenoxyl)piperidin-1-yl)-6-(isopropylamino)pyrazine-2,3-diyl)diethanol To a solution of 5-(4-(2,4-difluorophenoxyl)piperidin-1-yl)-6-(isopropylamino)pyrazine-2,3-dicarbaldehyde (32 mg, 0.079 mmol) in degassed THF (1 mL) at −78° C. was added methylmagnesium bromide (0.198 mL, 0.277 mmol, 1.4 M in toluene). The reaction was stirred at −78° C. for 2 h then ethyl acetate (3 mL) was added, followed by sat. NaHCO3 (3 mL). The mixture was allowed to warm to RT then the aqueous layer was extracted with ethyl acetate (5 mL×2). ISCO purification (0-100% ethyl acetate in heptanes) gave the title compound as a yellow oil.

Step 3: 3-(4-(2,4-difluorophenoxyl)piperidin-1-yl)-N-isopropyl-5,8-dimethylpyrazino[2,3-d]pyridazin-2-amine 2,2,2-trifluoroacetate A solution of 1,1'-(5-(4-(2,4-difluorophenoxyl)piperidin-1-yl)-6-(isopropylamino)pyrazine-2,3-diyl)diethanol (13 mg, 0.030 mmol) and Dess-Martin Periodinane (29.1 mg, 0.069 mmol) in DCM (298 μl) was stirred at RT for 5 h. Then, 3 drops of NH2NH2—H2O were added to the reaction mixture and stirring continued for 1 h. HPLC purification gave the title compound as a brown solid. MS (ESI, pos. ion) m/z: 428.9 (M+1).

Example 40

Synthesis of 3-(4-(2,4-difluorophenoxyl)piperidin-1-yl)-N-isopropyl-8-methylpyrazino[2,3-d]pyridazin-2-amine

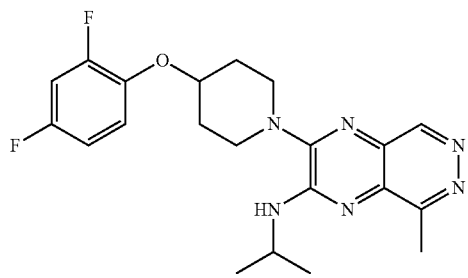 [SMILES: Cc1nncc2nc(N3CCC(Oc4ccc(F)cc4F)CC3)c(NC(C)C)nc12]

Step 1: (3-(((tert-butyldimethylsilyl)oxy)methyl)-5-(4-(2,4-difluorophenoxyl)piperidin-1-yl)-6-(isopropylamino)pyrazin-2-yl)methanol and (3-(((tert-butyldimethylsilyl)oxy)methyl)-6-(4-(2,4-difluorophenoxyl)piperidin-1-yl)-5-(isopropylamino)pyrazin-2-yl)methanol To a solution of (5-(4-(2,4-difluorophenoxyl)piperidin-1-yl)-6-(isopropylamino)pyrazine-2,3-diyl)dimethanol (800 mg, 1.959 mmol) in DCM (9793 μl) at 0° C. was added DIPEA (513 μl, 2.94 mmol), followed a solution of TBS-Cl (310 mg, 2.057 mmol) in DCM (3 mL), and one crystal of DMAP. The reaction was stirred at 0° C. for 3 h and then RT overnight. ISCO purification (0-50% ethyl acetate in heptane) gave a mixture of the title compounds as a colorless oil.

Step 2: 3-(((tert-butyldimethylsilyl)oxy)methyl)-5-(4-(2,4-difluorophenoxyl)piperidin-1-yl)-6-(isopropylamino)pyrazine-2-carbaldehyde and 3-(((tert-butyldimethylsilyl)oxy)methyl)-6-(4-(2,4-difluorophenoxyl)piperidin-1-yl)-5-(isopropylamino)pyrazine-2-carbaldehyde A solution of (3-(((tert-butyldimethylsilyl)oxy)methyl)-5-(4-(2,4-difluorophenoxyl)piperidin-1-yl)-6-(isopropylamino)pyrazin-2-yl)methanol (598 mg, 1.144 mmol, as a mixture of regioisomers) and Dess-Martin Periodinane (728 mg, 1.716 mmol) in DCM (11.4 mL) was stirred at RT for 3 h. Then, sat. NaHCO3 (10 mL) and sat. Na2S2O3 (10 mL) were added and the resulting mixture was stirred vigorously for 15 min. The organic phase was extracted with ethyl acetate (10 mL×2). ISCO purification (0-100% ethyl acetate in heptane) gave a mixture of the title compounds as a light yellow oil.

Step 3: 1-(3-(((tert-butyldimethylsilyl)oxy)methyl)-5-(4-(2,4-difluorophenoxyl)piperidin-1-yl)-6-(isopropylamino)pyrazin-2-yl)ethanol and 1-(3-(((tert-butyldimethylsilyl)oxy)methyl)-6-(4-(2,4-difluorophenoxyl)piperidin-1-yl)-5-(isopropylamino)pyrazin-2-yl)ethanol To a solution of 3-(((tert-butyldimethylsilyl)oxy)methyl)-6-(4-(2,4-difluorophenoxyl)piperidin-1-yl)-5-(isopropylamino)pyrazine-2-carbaldehyde (241 mg, 0.463 mmol, as a mixture of regioisomers) in THF (4628 µl) at −78° C. was added methylmagnesium bromide (827 µl, 1.157 mmol, 1.4 M in toluene). The resulting solution was stirred at −78° C. for 1 h and warmed up to 0° C. for 30 min. 1N HCl was added to quench the reaction and the mixture was extracted with ethyl acetate (15 mL×2). ISCO purification (0-60% ethyl acetate in heptane) gave a mixture of the title compounds as a light yellow oil.

Step 4: 1-(5-(4-(2,4-difluorophenoxyl)piperidin-1-yl)-3-(hydroxymethyl)-6-(isopropylamino)pyrazin-2-yl)ethanol and 1-(6-(4-(2,4-difluorophenoxyl)piperidin-1-yl)-3-(hydroxymethyl)-5-(isopropylamino) pyrazin-2-yl)ethanol To a solution of 1-(3-(((tert-butyldimethylsilyl)oxy) methyl)-5-(4-(2,4-difluorophenoxyl)piperidin-1-yl)-6-(isopropylamino)pyrazin-2-yl)ethanol (137 mg, 0.255 mmol, as a mixture of regioisomers) in THF (2552 µl) was added TBAF (306 µl, 0.306 mmol) at RT. The reaction was stirred for 1 h then quenched with sat. NaHCO$_3$ (3 mL) and water (3 mL). The mixture was extracted with ethyl acetate (10 mL×2).

ISCO purification gave a mixture of the title compounds as a yellow oil.

Step 5: 3-(4-(2,4-difluorophenoxyl)piperidin-1-yl)-N-isopropyl-5-methylpyrazino[2,3-d]pyridazin-2-amine and 3-(4-(2,4-difluorophenoxyl)piperidin-1-yl)-N-isopropyl-8-methylpyrazino[2,3-d]pyridazin-2-amine A solution of 1-(5-(4-(2,4-difluorophenoxyl)piperidin-1-yl)-3-(hydroxymethyl)-6-(isopropylamino)pyrazin-2-yl) ethanol (31 mg, 0.073 mmol, as a mixture of regioisomers) and Dess-Martin Periodinane (78 mg, 0.183 mmol) in DCM (734 µl) was stirred at RT for 4 h. Then, 5-6 drops of NH$_2$NH$_2$—H$_2$O was added at 0° C. and the reaction mixture was stirred at RT for 1 h. HPLC purification gave the isolated title compounds. MS (ESI, pos. ion) m/z: 415.0 (M+1).

BIOLOGICAL EXAMPLES

Example I

Inhibition of cAMP Activity of GPR6 In Vitro Assay

This cell based assay measures the ability of compounds to inhibit the constitutive cAMP activity of GPR6 receptor expressed in CHO-K1 cells. CHO cells were stably expressed with GPR6 receptor, whose expression is controlled by a tetracycline inducable element. The cells were cultured in medium containing F12K, 10% FBS, 1% Penn/Strep, 200 ug/mL Hygromycin. GPR6 receptor expression was induced for 20 hrs with 1 µg/ml doxycycline (sigma D9891) in growth media. After addition of doxycycline cells were plated at a density of 250-500 cells per well in half-volume black clear bottom plates (Costar) and place in an incubator (37°, 5% C(O)2) for 20 hours prior to cAMP assays.

Culture media was removed from cells and they were washed with 50 µL of Ringer's Buffer (MgCl2 0.047 mg/mL, NaH2PO4 0.18 mg/mL, Na2HPO4 0.1 mg/mL, KCl 0.34 mg/mL, NaHC(O)3 1.26 mg/mL, D-glucose 1.8 mg/mL, NaCl 7 mg/mL; pH=7.4). Compounds suspended in DMSO were diluted in Ringer's Buffer containing 0.5% fatty acid free BSA and incubated on cells for 45 min at 37° and 5% C(O)2. After incubation cells were incubated for 10 min at room temp with Eu-cAMP tracer solution from a Perkin Elmer Lance HTRF UltracAMP assay kit (TRF0264). Then ULight™-anti-cAMP solution from the Lance HTRF kit was added and incubated on a shaker at room temp for 1 hour prior to HTRF detection in a BMG PolarStar Omega.

IC$_{50}$ curves were generated with a four-parameter logistic equation using GraphPad Prism 5.03. The specific compounds of this invention had an IC$_{50}$ value of less than about 100 micromolar.

In approximate IC$_{50}$ value of a representative number of compounds of Formula (I) in this assay is provided in the table below.

| Cpd no. | IC$_{50}$ (um) | Cpd no. | IC$_{50}$ (um) | Cpd no. | IC$_{50}$ (um) | Cpd no. | IC$_{50}$ (um) |
|---|---|---|---|---|---|---|---|
| Compound Table 1 | | | | | | | |
| 1 | 17.687 | 53 | 1.20 | 126 | 46.99 | 230 | 0.80 |
| 2 | 45.394 | 58 | 5.53 | 133 | 0.032 | 239 | 4.74 |
| 3 | 24.575 | 59 | 0.25 | 134 | 1.64 | 240 | 4.59 |
| 5 | 40.644 | 63 | 1.13 | 154 | 0.72 | 241 | 0.65 |
| 9 | 10.07 | 66 | 1.94 | 157 | 105.44 | 247 | 1.49 |
| 17 | 25.90 | 67 | 1.03 | 158 | 0.44 | 248 | 1.85 |
| 20 | 69.18 | 75 | 21.78 | 162 | 4.63 | 251 | 4.34 |
| 21 | 3.03 | 81 | 4.58 | 167 | 3.33 | 252 | 2.54 |
| 22 | 7.67 | 85 | 7.55 | 170 | 4.07 | 256 | 0.38 |
| 30 | 26.24 | 89 | 4.78 | 171 | 1.57 | 257 | 0.31 |
| 31 | 6.14 | 95 | 22.16 | 172 | 2.34 | 263 | 0.12 |
| 33 | 2.16 | 98 | 3.21 | 174 | 1.67 | 265 | 0.30 |
| 38 | 5.73 | 99 | 6.03 | 177 | 17.82 | 280 | 0.45 |
| 39 | 6.15 | 100 | 3.96 | 194 | 3.64 | 281 | 0.96 |
| 42 | 3.16 | 103 | 5.31 | 211 | 9.44 | 282 | 4.29 |
| 45 | 2.34 | 105 | 5.66 | 214 | 1.47 | 283 | 0.42 |
| 46 | 4.82 | 110 | 6.03 | 221 | 20.42 | 285 | 1.36 |
| 47 | 3.36 | 111 | 3.31 | 223 | 5.62 | 288 | 2.65 |
| 292 | 0.056 | 115 | 3.98 | 226 | 0.57 | 289 | 0.27 |
| 302 | 0.34 | 122 | 10.30 | 227 | 3.29 | 291 | 0.14 |
| 306 | 0.38 | 426 | 0.027 | 415 | 0.064 | 484 | 0.029 |
| 315 | 0.05 | 427 | 0.078 | 416 | 1.51 | 486 | 0.098 |
| 329 | 1.30 | 428 | 0.02 | 421 | 8.39 | 488 | 0.029 |
| 330 | 0.029 | 430 | 1.10 | 424 | 0.31 | 489 | 0.007 |
| 333 | 0.097 | 431 | 0.17 | 493 | 0.009 | 520 | 0.030 |
| 336 | 0.96 | 444 | 0.20 | 494 | 0.002 | 523 | 0.34 |
| 340 | 15.43 | 447 | 0.035 | 495 | 0.018 | 524 | 0.015 |
| 351 | 0.062 | 452 | 0.021 | 498 | 0.006 | 525 | 0.029 |
| 363 | 0.23 | 461 | 0.020 | 500 | 0.16 | 526 | 0.67 |
| 369 | 0.40 | 465 | 0.011 | 502 | 1.43 | 532 | 0.38 |
| 392 | 0.26 | 469 | 0.09 | 504 | 0.082 | 536 | 0.93 |
| 400 | 0.39 | 471 | 0.075 | 509 | 0.049 | 539 | 0.77 |
| 413 | 0.019 | 476 | 0.015 | 513 | 0.071 | 540 | 0.046 |
| 414 | 0.39 | 479 | 0.14 | 516 | 0.029 | 545 | 0.045 |
| 550 | 0.017 | 480 | 0.072 | 518 | 0.024 | 547 | 0.016 |
| 551 | 0.045 | 481 | 0.024 | 519 | 0.25 | 549 | 0.011 |
| 552 | 0.024 | 554 | 0.19 | 557 | 1.92 | 558 | 1.94 |
| 559 | 0.067 | 564 | 11 | 565 | 15.37 | 567 | 5.78 |
| 569 | 0.062 | 568 | 2.18 | 571 | 3.90 | 572 | 0.021 |
| 573 | 2.8 | 574 | 4.81 | 575 | 6.75 | 576 | 2.883 |
| 577 | 4.9 | 578 | 7.21 | 579 | 0.01 | 580 | 0.008 |
| 581 | 0.006 | 582 | 0.007 | 584 | 1.74 | 585 | 6.04 |
| 586 | 2.29 | 587 | 0.078 | 588 | 2.74 | 589 | 0.069 |
| 591 | 0.022 | 592 | 0.026 | 593 | 0.023 | 594 | 0.031 |
| 595 | 0.478 | 596 | 0.026 | 597 | 0.089 | 599 | 0.005 |
| 600 | 0.02 | 601 | 0.022 | 602 | 0.146 | 603 | 1.023 |
| 604 | 0.054 | 605 | 0.036 | 606 | 0.054 | 607 | 0.043 |
| 608 | 0.717 | 609 | 0.051 | 610 | 1.572 | 611 | 0.044 |
| 612 | 0.114 | 613 | 0.092 | 614 | 0.066 | 615 | 0.088 |
| 616 | 0.939 | 617 | 0.054 | 618 | 0.012 | 619 | 0.014 |
| 620 | 0.018 | 621 | 0.021 | 622 | 0.029 | 623 | 0.039 |
| 625 | 0.006 | 626 | 0.09 | 627 | 0.051 | 628 | 0.276 |
| 629 | 0.008 | 630 | 0.007 | 631 | 0.006 | 632 | 0.028 |

-continued

| Cpd no. | IC$_{50}$ (um) | Cpd no. | IC$_{50}$ (um) | Cpd no. | IC$_{50}$ (um) | Cpd no. | IC$_{50}$ (um) |
|---|---|---|---|---|---|---|---|
| 633 | 0.004 | 634 | 0.006 | 635 | 0.04 | 636 | 0.016 |
| 637 | 0.026 | 638 | 0.021 | 639 | 0.03 | 640 | 0.072 |
| 641 | 0.014 | 642 | 0.054 | 643 | 0.015 | 644 | 0.007 |
| 645 | 0.145 | 646 | 0.538 | 648 | 0.065 | 649 | 0.044 |
| 650 | 1.00 | 651 | 0.06 | 652 | 0.031 | 653 | 0.093 |
| 654 | 0.03 | 655 | 0.02 | 656 | 0.014 | 657 | 0.008 |
| Compound Table 2 | | | | | | | |
| 3 | 0.84 | 8 | 79.62 | 9 | 17.7 | | |
| 6 | 0.53 | 7 | 6.64 | | | | |

Example II

Haloperidol-Induced Catalepsy

In Vivo Rodent Parkinson's Disease Model

The motor symptoms of Parkinson's disease include akinesia, bradykinesia, rigidity, tremor and postural abnormalities and are associated with the loss of nigral dopaminergic cells and a decline in striatal dopamine levels. Administration of haloperidol to rodents leads to a transient parkinsonian-like state that is reversed by the administration of L-Dopa (Duty, S.; Jenner, P. Br. *J. Pharmacol.* (2011), 164, 1357-1391) and other drugs that have been clinically validated for the treatment of Parkinson's disease. Haloperidol antagonizes dopamine D2 and, to a lesser extent, D1 receptors in medium spiny neurons that comprise the indirect and direct pathways of the motor circuit respectively. The resultant block of striatal dopamine transmission results in abnormal downstream firing within the basal ganglia circuits that is manifest as symptoms of muscle rigidity and catalepsy. Catalepsy has been postulated to reflect the clinical features of Parkinson's disease, whereby patients experience an inability of to initiate movements.

Male Sprague-Dawley rats (Charles River, Calco, Italy) weighing 175-200 g are used. Alternatively, male C57B16 mice weighing 25-35 g were used. The cataleptic state was induced by the subcutaneous administration of the dopamine receptor antagonist haloperidol (0.3 mg/kg, sc), 90 min before testing the animals on the vertical grid test. For this test, the rats or mice were placed on the wire mesh cover of a 25 cm×43 cm plexiglass cage placed at an angle of about 70 degrees with the bench table. The subject was placed on the grid with all four legs abducted and extended ("frog posture"). The use of such an unnatural posture is essential for the specificity of this test for catalepsy. The time span from placement of the paws until the first complete removal of one paw (descent latency) was measured maximally for 120 sec for rats. For mice, the front paws of a mouse was placed on a horizontal metal bar raised 2" above a Plexiglas platform and time was recorded for up to 30 seconds per trial. The test ended when the animal's front paws returned to the platform or after 30 seconds. The test was repeated three times and the average of the three trials was reported as the intensity index of catalepsy.

Catalepsy was measured 30 min, 120 min, and/or 240 min after dosing the subjects a 0.3 mg/kg i.p. dose of haloperidol along with the GPR6 modulator test compound. Test compound plasma and brain levels were determined by collected tissue samples at the end of the experiment, which was either at the 120 or 240 min time point. A representative number of compounds of the invention were administered in a dose range from 0.1 to 100 mg/kg i.p, sc or po in conjunction with haloperidol. The A2a antagonist KW6002 (istradefylline) was dosed at 0.6 mg/kg i.p. as a positive control. The compounds of the invention produced reversal of haloperidol-induced catalepsy. The results of a representative no. of compounds of this invention in this assay are disclosed in the table below.

| Cpd No. | Species | Dose (mpk) | Route | % reversal 30 min | % reversal 120 min |
|---|---|---|---|---|---|
| 33 | mouse | 30 | ip | 48.1 | 41.4 |
| 53 | " | 30 | ip | 13.6 | 15.4 |
| 59 | " | 10 | ip | 42 | 18.8 |
| 59 | " | 30 | ip | 27.4 | 15.7 |
| 50 | " | 30 | ip | 40.4 | 29.6 |
| 415 | rat | 10 | sc | 36.9 | 25.1 |

FORMULATION EXAMPLES

The following are representative pharmaceutical formulations containing a compound of Formula (I).

Tablet Formulation

The following ingredients are mixed intimately and pressed into single scored tablets.

| Ingredient | Quantity per tablet mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this invention | 200 |
| lactose spray dried | 148 |
| magnesium stearate | 2 |

Injectable Formulation

Compound of the invention (e.g., compound 1) in 2% HPMC, 1% Tween 80 in DI water, pH 2.2 with MSA, q.s. to at least 20 mg/mL.

What is claimed is:
1. A compound of the formula:

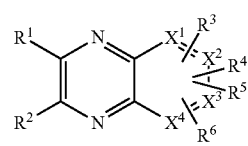

wherein:

R$^1$ is a heterocycloamino ring substituted with R$^a$, R$^b$, and R$^c$ wherein:

R$^a$ is —Z—Ar where Z is C$_{1-6}$ alkylene, C$_{1-6}$ haloalkylene, —O—, —C(O)—, —NH—, or —S(O)n— wherein n is 0, 1, or 2; and Ar is C$_{3-10}$ cycloalkyl, C$_{3-7}$ heterocycloalkyl, C$_{3-7}$ heterocycloalkenyl, C$_{6-10}$ aryl, or C$_{1-9}$ heteroaryl wherein C$_{3-10}$ cycloalkyl, C$_{3-7}$ heterocycloalkenyl, C$_{3-7}$ heterocycloalkyl, C$_{6-10}$ aryl, and C$_{1-9}$ heteroaryl are optionally substituted with 1 to 3 substituents independently selected from C$_{1-6}$ alkyl, halo, hydroxy, oxo, C$_{1-6}$ alkoxy, C$_{1-6}$ thioalkoxy, C$_{1-6}$ haloalkyl, C$_{1-6}$ hydroxyalkyl, C$_{1-6}$ haloalkoxy, C$_{1-6}$ alkylcarbonyl, C$_{1-6}$ alkylsulphonyl, cyano, C$_{2-12}$ alkoxyalkyloxy, C$_{1-9}$ amide, or C$_{1-6}$ hydroxyalkyloxy; and R$^b$ and R$^c$ are independently hydrogen, C$_{1-6}$ alkyl, hydroxy, or halo;

R$^2$ is —OR$^e$ or —NR$^d$R$^e$ wherein R$^d$ is hydrogen or C$_{1-6}$ alkyl and R$^e$ is C$_{1-6}$ alkyl, C$_{1-6}$ haloalkyl, C$_{1-6}$ hydroxyalkyl, C$_{2-12}$ alkoxyalkyl, C$_{1-12}$ aminoalkyl, C$_{3-10}$ cycloalkyl, C$_{4-16}$ cycloalkylalkyl, C$_{6-10}$ aryl, C$_{1-9}$ heteroaryl, C$_{3-7}$ heterocyclyl, or C$_{3-7}$ heterocycloalkenyl wherein C$_{6-10}$ aryl, C$_{1-9}$ heteroaryl, C$_{3-7}$ heterocyclyl, and C$_{3-7}$ heterocycloalkenyl are optionally substituted with 1 to 3 substituents independently selected from C$_{1-6}$ alkyl, halo, hydroxy, oxo, C$_{1-6}$ alkoxy, C$_{1-6}$ haloalkyl or C$_{1-6}$ haloalkoxy, or cyano;

all X$^1$-X$^4$ are carbon or one or two of X$^1$-X$^4$ are N and the rest of X$^1$-X$^4$ are carbon;

R$^3$, R$^4$, R$^5$, and R$^6$ are independently absent, hydrogen, C$_{1-6}$ alkyl, halo, hydroxy, C$_{1-6}$ alkoxy, C$_{1-6}$ alkoxycarbonyl, C$_{1-6}$ haloalkyl, C$_{1-6}$ haloalkoxy, C$_{1-9}$ amide, C$_{3-7}$ heterocyclyl, C$_{1-8}$ alkylamino, or cyano;

or a pharmaceutically acceptable salt thereof.

2. The compound of claim 1 wherein R$^1$ is piperidinyl.

3. The compound of claim 1 wherein R$^1$ is piperazinyl.

4. The compound of claim 3 wherein Z is C$_{1-6}$ alkylene.

5. The compound of claim 3 wherein Z is —C(O)—.

6. The compound of claim 4 wherein Ar is C$_{6-10}$ aryl optionally substituted with 1 to 3 substituents independently selected from C$_{1-6}$ alkyl, halo, hydroxy, oxo, C$_{1-6}$ alkoxy, C$_{1-6}$ haloalkyl, C$_{1-6}$ haloalkoxy, C$_{1-6}$ alkylcarbonyl, C$_{1-6}$ alkylsulphonyl, cyano, C$_{2-12}$ alkoxyalkyloxy, C$_{1-9}$ amide, or C$_{1-6}$ hydroxyalkyloxy.

7. The compound of claim 4 wherein Ar is C$_{1-9}$ heteroaryl optionally substituted with 1 to 3 substituents independently selected from C$_{1-6}$ alkyl, halo, hydroxy, oxo, C$_{1-6}$ alkoxy, C$_{1-6}$ haloalkyl, C$_{1-6}$ haloalkoxy, C$_{1-6}$ alkylcarbonyl, C$_{1-6}$ alkylsulphonyl, cyano, C$_{2-12}$ alkoxyalkyloxy, C$_{1-9}$ amide, or C$_{1-6}$ hydroxyalkyloxy.

8. The compound of claim 1 wherein R$^2$ is —NR$^d$R$^e$ wherein R$^d$ is hydrogen and R$^e$ is C$_{1-6}$ alkyl or C$_{3-10}$ cycloalkyl.

9. The compound of claim 1 wherein all X$^1$-X$^4$ are carbon.

10. The compound of claim 6 wherein all X$^1$-X$^4$ are carbon.

11. The compound of claim 1 wherein all X$^1$, X$^3$, X$^4$ are carbon, R$^6$ is absent, and X$^2$ is N.

12. The compound of claim 1 wherein all X$^1$, X$^2$, X$^4$ are carbon, R$^6$ is absent, and X$^3$ is N.

13. The compound of claim 1 wherein all X$^1$ and X$^4$ are carbon, R$^5$ and R$^6$ are absent, and X$^2$ and X$^3$ are N.

14. The compound of claim 1, which is selected from the group consisting of:
- N-cyclopropyl-3-(4-(3-methylbenzyl)piperazin-1-yl)quinoxalin-2-amine;
- (4-(3-(cyclopropylamino)quinoxalin-2-yl)piperazin-1-yl)(2,5-dichlorophenyl)methanone
- 2-(4-(3-chlorobenzyl)piperazin-1-yl)-N-phenylpyrido[2,3-b]pyrazin-3-amine;
- 3-(4-(4-bromobenzyl)piperazin-1-yl)-N-cyclopropylquinoxalin-2-amine;
- (4-(3-(cyclopropylamino)quinoxalin-2-yl)piperazin-1-yl)(3-isopropylphenyl)methanone;
- N-cyclopropyl-3-(4-(2,5-dichlorophenethyl)piperazin-1-yl)quinoxalin-2-amine;
- 3-(4-((2-chloro-5-(trifluoromethyl)phenyl)sulfonyl)piperazin-1-yl)-2-(cyclopropylamino)quinoxaline-6-carbonitrile;
- (4-chloro-2,6-difluorophenyl)(1-(2-(cyclopropylamino)pyrido[3,4-b]pyrazin-3-yl)piperidin-4-yl)methanone;
- (S)-2-(cyclopropylamino)-3-(4-((2,4-difluorophenyl)fluoromethyl)piperidin-1-yl)quinoxaline-6-carbonitrile;
- (1-(2-(cyclopropylamino)pyrido[3,4-b]pyrazin-3-yl)piperidin-4-yl)(pyrrolidin-1-yl)methanone;
- N-cyclobutyl-2-(4-(2,4-difluorophenoxy)piperidin-1-yl)pyrido[3,4-b]pyrazin-3-amine; and
- a pharmaceutically acceptable salt of any one of the above-mentioned compounds.

15. The compound of claim 1, which is N-cyclopropyl-3-(4-(2,4-difluorobenzyl) piperidin-1-yl)-5-methylpyrido[3,4-b]pyrazin-2-amine or a pharmaceutically acceptable salt thereof.

16. The compound of claim 1, which is (R)-N-cyclopropyl-3-(4-((2,4-difluorophenyl) fluoromethyl)piperidin-1-yl)-7-methylpyrido[3,4-b]pyrazin-2-amine or a pharmaceutically acceptable salt thereof.

17. The compound of claim 1, which is 2-(cyclopropylamino)-3-(4-(2,4-difluorophenoxy) piperidin-1-yl)-N,N-dimethylpyrido[3,4-b]pyrazine-7-carboxamide or a pharmaceutically acceptable salt thereof.

18. The compound of claim 1, which is 3-(4-(2-fluoro-4-methoxyphenoxy) piperidin-1-yl)-N-i sopropylpyrazino[2,3-d]pyridazin-2-amine or a pharmaceutically acceptable salt thereof.

19. The compound of claim 1, which is 3-(4-(4-chloro-2-fluorophenoxy) piperidin-1-yl)-2-(isopropylamino)-N,N-dimethylpyrido[3,4-b]pyrazine-7-carboxamide or a pharmaceutically acceptable salt thereof.

20. The compound of claim 1, which is 3-(4-(2,4-difluorophenoxy)piperidin-1-yl)-N-isopropylpyrazino [2,3-d]pyridazin-2-amine or a pharmaceutically acceptable salt thereof.

21. A pharmaceutical composition comprising a compound as defined in claim 1 or a pharmaceutically acceptable salt thereof and a pharmaceutically acceptable excipient.

* * * * *